US012806025B2

(12) United States Patent
Ginn et al.

(10) Patent No.: US 12,806,025 B2
(45) Date of Patent: Nov. 24, 2026

(54) SYSTEMS FOR SACROILIAC (SI) JOINT STABILIZATION

(71) Applicant: Tenon Medical, Inc., Los Gatos, CA (US)

(72) Inventors: Richard S Ginn, Gilroy, CA (US); Richard Brown, Colorado Springs, CO (US); Daren Stewart, Belmont, CA (US); Jeffrey Monroe, Phoenix, AZ (US)

(73) Assignee: Tenon Medical, Inc., Los Gatos, CA (US)

(*) Notice: Subject to any disclaimer, the term of this patent is extended or adjusted under 35 U.S.C. 154(b) by 510 days.

(21) Appl. No.: 18/240,197

(22) Filed: Aug. 30, 2023

(65) Prior Publication Data

US 2023/0404762 A1 Dec. 21, 2023

Related U.S. Application Data

(63) Continuation-in-part of application No. 17/903,527, filed on Sep. 6, 2022, now Pat. No. 12,544,231, which
(Continued)

(51) Int. Cl.
*A61F 2/30* (2006.01)
*A61B 5/055* (2006.01)
(Continued)

(52) U.S. Cl.
CPC .......... *A61F 2/30988* (2013.01); *A61B 5/055* (2013.01); *A61B 5/062* (2013.01);
(Continued)

(58) Field of Classification Search
CPC ....... A61F 2002/30995; A61F 2/30988; A61B 17/17; A61B 17/1757
See application file for complete search history.

(56) References Cited

U.S. PATENT DOCUMENTS 6,063,088 A * 5/2000 Winslow ............... A61F 2/4611
606/279
8,496,665 B2 * 7/2013 Cavallazzi ........... A61B 17/808
408/241 B (Continued)

*Primary Examiner* — Lynnsy M Summitt
(74) *Attorney, Agent, or Firm* — Francis Law Group

(57) ABSTRACT

Systems are described for conducting minimally invasive medical interventions utilizing instruments and assemblies thereof to stabilize and/or fixate a dysfunctional sacroiliac (SI) joint. The systems include a drill guide having a bone dislodging member adapted to create a pilot SI joint opening in the dysfunctional SI joint through an incision comprising a length no greater than 3.0 cm; portions of the pilot SI joint opening being disposed in the sacrum and ilium bone structures. The drill guide includes a tri-mode fixation system adapted to position and stabilize the drill guide during creation of the pilot SI joint opening in the dysfunctional SI joint and delivery of the SI joint prosthesis therein. The systems also include a SI joint prosthesis configured to be inserted into the pilot SI joint opening of the dysfunctional SI joint, a prosthesis deployment assembly configured to engage the SI joint prosthesis and advance the SI joint prosthesis into the dysfunctional SI joint, and a bone harvesting assembly adapted to extract and collect dislodge bone material from the bone dislodging member after creation of the pilot SI joint opening.

9 Claims, 78 Drawing Sheets

Related U.S. Application Data is a continuation of application No. 17/833,960, filed on Jun. 7, 2022, now Pat. No. 12,582,528, which is a continuation-in-part of application No. 17/833,098, filed on Jun. 6, 2022, now Pat. No. 12,551,348, which is a continuation of application No. 17/749,199, filed on May 20, 2022, now Pat. No. 12,465,491, which is a continuation-in-part of application No. 17/740,568, filed on May 10, 2022, now Pat. No. 12,472,069, which is a continuation-in-part of application No. 17/463,779, filed on Sep. 1, 2021, now Pat. No. 12,427,027, which is a continuation-in-part of application No. 13/857,977, filed on Apr. 5, 2013, now Pat. No. 11,273,042, which is a continuation of application No. 13/192,289, filed on Jul. 27, 2011, now abandoned.

(60) Provisional application No. 61/368,233, filed on Jul. 27, 2010.

(51) Int. Cl.

| | |
|---|---|
| ***A61B 5/06*** | (2006.01) |
| ***A61B 6/00*** | (2006.01) |
| ***A61B 6/03*** | (2006.01) |
| ***A61B 8/08*** | (2006.01) |
| ***A61B 17/16*** | (2006.01) |
| ***A61B 17/70*** | (2006.01) |
| ***A61B 17/88*** | (2006.01) |
| ***A61B 34/20*** | (2016.01) |
| ***A61F 2/44*** | (2006.01) |
| ***A61F 2/46*** | (2006.01) |

(52) U.S. Cl.

CPC .............. *A61B 6/032* (2013.01); *A61B 6/485* (2013.01); *A61B 8/0841* (2013.01); *A61B 17/1604* (2013.01); *A61B 17/1664* (2013.01); *A61B 17/1671* (2013.01); *A61B 17/70* (2013.01); *A61B 17/7055* (2013.01); *A61B 17/7074* (2013.01); *A61B 17/8858* (2013.01); *A61B 34/20* (2016.02); *A61F 2/4455* (2013.01); *A61F 2/4601* (2013.01); *A61F 2/4611* (2013.01); *A61B 2576/00* (2013.01); *A61F 2002/30121* (2013.01); *A61F 2002/30123* (2013.01); *A61F 2002/30166* (2013.01); *A61F 2002/30593* (2013.01); *A61F 2002/30995* (2013.01)

(56) References Cited

U.S. PATENT DOCUMENTS

| | | | | |
|---|---|---|---|---|
| 9,566,103 | B2 * | 2/2017 | Mayer | A61B 17/17 |
| 9,615,856 | B2 * | 4/2017 | Arnett | A61B 17/0642 |
| 2008/0287955 | A1 | 11/2008 | Michelson | |
| 2012/0283837 | A1 * | 11/2012 | Bae | A61F 2/447 623/17.16 |
| 2012/0296428 | A1 * | 11/2012 | Donner | A61B 17/7043 623/17.11 |
| 2014/0142700 | A1 | 5/2014 | Donner et al. | |
| 2016/0310197 | A1 * | 10/2016 | Black | A61B 17/92 |
| 2018/0036017 | A1 | 2/2018 | Donner et al. | |
| 2022/0071644 | A1 | 3/2022 | Donner et al. | |
| 2023/0181324 | A1 | 6/2023 | Ginn et al. | |

* cited by examiner

SYSTEMS FOR SACROILIAC (SI) JOINT STABILIZATION

CROSS-REFERENCES TO RELATED APPLICATIONS

This application is a continuation-in-part of U.S. patent application Ser. No. 17/903,527, filed on Sep. 6, 2022, which is a continuation-in-part of U.S. patent application Ser. No. 17/833,960, filed on Jun. 7, 2022, which is a continuation-in-part of U.S. patent application Ser. No. 17/833,098, filed on Jun. 6, 2022, which is a continuation of U.S. patent application Ser. No. 17/749,199, filed on May 20, 2022, which is a continuation-in-part application of U.S. patent application Ser. No. 17/740,568, filed on May 10, 2022, which is a continuation-in-part application of U.S. patent application Ser. No. 17/463,779, filed on Sep. 1, 2021, which is a continuation-in part of U.S. patent application Ser. No. 13/857,977, filed on Apr. 5, 2013, now U.S. Pat. No. 11,273,042, which is a continuation application of U.S. patent application Ser. No. 13/192,289, filed Jul. 27, 2011, now abandoned, which claims the benefit of U.S. provisional patent application Ser. No. 61/368,233, filed on Jul. 27, 2010.

FIELD OF THE INVENTION

The present invention relates to systems, apparatus and methods for treating dysfunctional bone structures. More particularly, the present invention relates to systems, apparatus and methods for stabilizing dysfunctional sacroiliac (SI) joints

BACKGROUND OF THE INVENTION

As is well known in the art, the sacroiliac (SI) joint 6 comprises a diarthrodial synovial joint, which, as illustrated in FIG. 1A, is defined by the interface between the articular surfaces of the sacrum 2 and the ilium 4. Thus, the SI joint 6 is defined by (and, hence, comprises) portions of the sacrum 2 and ilium 4.

As further illustrated in FIG. 1B, the SI joint 6 generally comprises the shape of an inverted capital letter "L" (denoted "13") lying on its side (rather than a triangle), where the long arm of the inverted "L" 15 (i.e., SI joint 6) is oriented along the posterior wall of the pelvis 11 (denoted "25" in FIG. 1A) and is also oriented relatively straight through its entire course.

The sacral floor (denoted "21" in FIG. 1C), which is defined by the region between the anterior sacral promontory 19*a* and the apex 19*b* of the sacrum 2, generally slopes downward and laterally at an approximately 30% grade relative to the cephalocaudal axis 27.

As illustrated in FIGS. 1B and 1C, the short arm of the inverted "L" (denoted "17") is generally oriented parallel to the transverse plane of the L5-S1 lumbosacral joint and limited superiorly by the sacral ala (denoted "23" in FIG. 1C).

The apex of the inverted "L" (denoted "29" in FIG. 1B) is positioned below the S2 segment region of the sacrum 2 (denoted "S2") proximate to the S3 segment region of the sacrum 2 (denoted "S3").

As illustrated in FIG. 1D, the SI joint further comprises a SI joint dorsal recess or gap 7 that is disposed between the sacrum 2 and ilium 4 proximate the S2 segment region of the sacrum 2.

As is well known in the art, the SI joint further comprises articular cartilage, i.e., hyaline and fibrocartilage, and a strong, extensive ligamentous architecture, which stabilizes the SI joint.

Generally, the articular surfaces of the sacrum 2 and the ilium 4 that define the SI joint 6 comprise cortical bone 8, which is more compact, dense and hard relative to softer trabecular bone 10, which, as further illustrated in FIG. 1A, is disposed in the interior regions of the sacrum and ilium 2, 4.

The SI Joint is distinguished from other synovial joints by the atypical articulation of the different articular surfaces of the sacrum and ilium; the articular surface of the sacrum comprising hyaline cartilage and the articular surface of the ilium comprising substantially stronger fibrocartilage.

As is further well known in the art, the primary plane of motion of the SI joint is anterior-posterior along a transverse axis. The terms often employed to describe the relative motion of the sacrum and ilium are nutation, which refers to anterior-inferior movement of the sacrum while the coccyx (denoted "3" in FIGS. 1A and 1D) moves posteriorly relative to the ilium, and counternutation, which refers to posterior-superior movement of the sacrum while the coccyx moves anteriorly relative to the ilium.

In most healthy individuals, the SI joint range of motion in flexion-extension is approximately 3°, approximately 1.5° in axial rotation, and approximately 0.8° in lateral bending.

As is well established, the SI joint performs several seminal biomechanical functions. The primary functions of the SI joint are to attenuate loads exerted on the upper body and to distribute the loads to the lower extremities. The SI joint also functions as a shock absorber for loads exerted on spine.

As is also well established, the noted loads and, hence, forces exerted on the SI joint can adversely affect the biomechanical functions of the SI joint, which can, and often will, result in SI joint dysfunction—an often-overlooked musculoskeletal pathology associated with lower back pain.

Indeed, SI joint dysfunction is estimated to be the primary cause of lower back pain in 15-30% of subjects afflicted with such pain. However, lower back pain associated with SI joint dysfunction is suspected to be far more common than most healthcare providers realize, since such pain is often associated with other skeletal and musculoskeletal dysfunctions.

SI joint dysfunction, and pain associated therewith, can be caused by various SI joint abnormalities and/or disorders, including traumatic fracture dislocation of the pelvis, degenerative arthritis, sacroiliitis, i.e., an inflammation or degenerative condition of the sacroiliac joint; osteitis condensans ilii, and other degenerative conditions of the SI joint structures and associated structures.

Various non-surgical methods, such as administration of pharmacological agents, e.g., the corticosteroid prednisone, and surgical methods and devices, i.e., SI joint prostheses, have been developed and employed to treat SI joint dysfunction and the pain associated therewith.

The most common approach employed to treat SI joint dysfunctions (when non-surgical treatments fail to ameliorate pain associated therewith), at present, is SI joint stabilization, i.e., reinforcing or modulating articulation by and between the sacrum and ilium, via surgical intervention.

SI joint stabilization typically comprises surgical placement of a bone structure prosthesis proximate to or in a dysfunctional SI joint and is generally characterized by the direction of access to the dysfunctional SI joint, e.g., lateral.

Although several conventional SI joint stabilization surgical methods and associated bone structure prostheses have effectively ameliorated pain associated with SI joint dysfunction, there remains many disadvantages associated with the conventional surgical methods and associated bone structure prostheses.

A major disadvantage associated with many conventional SI joint stabilization surgical methods is that the surgeon is required to make a substantial incision in and through the skin and tissues of a subject to access the dysfunctional SI joint. Often referred to as "open surgery" methods, these surgical methods have the attendant disadvantages of requiring general anesthesia and often involve increased operative time, pain, hospitalization, and recovery time due to the extensive soft tissue damage. There is also an increased probability of post-surgical complication associated with open surgery methods, such as nosocomial infection.

Minimally-invasive systems and methods for SI joint stabilization have thus been developed to address the noted disadvantages associated with open surgery methods. Although conventional minimally-invasive SI joint stabilization systems and methods, such as the systems and methods disclosed in U.S. Pub. No. 2009/0076551 to Petersen, have garnered some success in relieving pain associated with SI joint dysfunction and have effectively addressed many of the disadvantages associated with open surgery systems and methods, there similarly remains many disadvantages associated with conventional minimally-invasive SI joint stabilization systems and methods.

A major disadvantage associated with many conventional minimally-invasive SI joint stabilization methods is that such methods are difficult to perform and the associated surgical systems often require extensive, system-specific surgical training and experience. Indeed, it has been found that, notwithstanding the level of surgical training and experience that a surgeon may possess, when such conventional minimally-invasive SI joint stabilization systems and methods are employed, there is still a substantial incidence of damage to the lumbosacral neurovascular structures proximate to the SI joint.

A further disadvantage associated with most conventional minimally-invasive SI joint stabilization methods is that the creation of pilot openings in the SI joint are necessary for placement of a SI joint prostheses and proper alignment is often very difficult to achieve. Further, current conventional tooling systems that are employed to create the pilot openings are often complex and difficult to use.

A further disadvantage associated with many conventional minimally-invasive SI joint stabilization systems and methods is that they comprise anterior or lateral approaches to the dysfunctional SI joint and, hence, muscles, e.g., gluteal aponeurotic fascia and gluteus medius, and ligaments are typically disrupted, and nerves and blood vessels are susceptible to damage during placement of a bone structure prosthesis in a dysfunctional SI joint.

Further, some conventional minimally-invasive SI joint stabilization methods are particularly prone to failure due to the structure of SI joint prostheses and/or failure of the prostheses to effectively engage the SI joint structures, e.g., articular surfaces of the sacrum and/or ilium.

Illustrative are the SI joint prostheses disclosed in U.S. Pat. No. 8,951,254 to Mayer, et al.

The SI joint prostheses disclosed in U.S. Pat. No. 8,951,254 comprise polymer coated multi-piece structures and, hence, among other disadvantages, do not possess the necessary structural integrity to effectively stabilize a dysfunction SI joint when implanted therein.

A further disadvantage associated with the SI joint prostheses disclosed in U.S. Pat. No. 8,951,254 is that the polymer coatings are substantially immunogenic and will induce an adverse immune response when the prostheses are implanted in a dysfunctional SI joint. As is well established, the adverse immune response can, and often will, prevent healing and osteogenic processes, e.g., remodeling of damaged osseous tissue and regeneration of new osseous tissue.

It would thus be desirable to provide SI joint stabilization methods, systems and apparatus, which substantially reduce or eliminate the disadvantages associated with conventional SI joint stabilization methods, systems and apparatus.

It is therefore an object of the invention to provide improved SI joint stabilization methods, systems and apparatus, which substantially reduce or eliminate the disadvantages associated with conventional SI joint stabilization methods, systems and apparatus.

It is another object of the invention to provide improved minimally-invasive SI joint stabilization systems and apparatus, and methods of using same, that facilitate posterior placement of prostheses in and, thereby, effective stabilization of dysfunctional SI joints.

It is another object of the invention to provide improved minimally-invasive SI joint stabilization systems and apparatus, including prostheses, which, when employed to stabilize dysfunctional SI joints, disrupt less tissue and muscle, and avoid nerves and large blood vessels.

It is another object of the invention to provide improved minimally-invasive SI joint stabilization systems and apparatus, including prostheses, which effectively ameliorate pain associated with SI joint dysfunction.

It is another object of the invention to provide improved SI joint prostheses that provide secure engagement to SI joint structures.

It is another object of the invention to provide improved SI joint prostheses that possess optimal structural properties to effectively stabilize dysfunctional SI joints.

It is yet another object of the invention to provide improved SI joint prostheses that facilitate remodeling of damaged osseous tissue and regeneration of new osseous tissue and osseous tissue structures.

It is another object of the invention to provide improved minimally-invasive SI joint stabilization systems and apparatus adapted to create pilot openings in dysfunctional SI joints for placement of SI joint prostheses therein via a minimal incision.

It is another object of the invention to provide improved minimally-invasive SI joint stabilization systems adapted to create pilot openings in dysfunctional SI joints for placement of SI joint prostheses therein, which provide optimal direct visualization of the bone dislodging member thereof and the pilot opening during and after creation of the pilot openings.

It is another object of the invention to provide improved minimally-invasive SI joint stabilization systems adapted to create pilot openings in dysfunctional SI joints that comprise means for retracting and collecting bone material, i.e., autograft bone material, directly from the bone dislodging member after creation of pilot openings (and portions thereof) for subsequent formation of an osteogenic composition and/or direct delivery to prostheses.

It is another object of the invention to provide improved minimally-invasive SI joint stabilization systems that readily receive and properly guide SI joint prostheses into dysfunctional SI joints.

SUMMARY OF THE INVENTION

The present invention is directed to minimally-invasive methods, systems and apparatus for stabilizing dysfunctional SI joints.

In one embodiment, there is thus provided a minimally-invasive system for stabilizing a dysfunctional SI joint comprising:

a tool assembly adapted to create a pilot SI joint opening in the dysfunctional SI joint, a SI joint prosthesis and a prosthesis deployment assembly, the SI joint prosthesis comprising a first cross-sectional shape, the tool assembly comprising a guide pin adapted to be positioned in the dysfunctional SI joint and a drill guide assembly adapted to create the pilot SI joint opening in the dysfunctional SI joint through an incision comprising a length no greater than 3.0 cm, the drill guide assembly comprising a drill guide, a drill guide insert, a bone dislodging member, a plurality of Kirschner-wires (K-wires), and first and second drill guide fixation sub-systems, the drill guide insert comprising a second cross-sectional shape, the bone dislodging member adapted to dislodge portions of bone in a first bone structure of the dysfunctional SI joint and create a first portion of the pilot SI joint opening in the first bone structure and dislodge portions of bone in a second bone structure of the dysfunctional SI joint and create a second portion of the pilot SI joint opening in the second bone structure, the drill guide comprising a proximal end and a distal end, the distal end of the drill guide comprising a base, the drill guide further comprising a plurality of K-wire lumens extending from the proximal end of the drill guide to the distal end of the drill guide, the plurality of K-wire lumens adapted to receive the plurality of Kirschner-wires (K-wires) therein, the first drill guide fixation sub-system comprising the plurality of K-wires, the K-wires adapted to pierce and engage first and second bone structures of the dysfunctional SI joint, the second drill guide fixation sub-system comprising a K-wire pin member and a temporary fixation pin, the K-wire pin member and the temporary fixation pin adapted to pierce and engage the first and second bone structures of the dysfunctional SI joint, the drill guide further comprising a prosthesis internal access opening, the prosthesis internal access opening comprising a third cross-sectional shape that corresponds to the first cross-sectional shape of the SI joint prosthesis and the second cross-sectional shape of the drill guide insert, the drill guide insert comprising a guide pin lumen, a first lobe portion and a second lobe portion, the guide pin lumen adapted to receive the guide pin therein, the first lobe portion of the drill guide insert comprising a first drill guide lumen, the second lobe portion of the drill guide insert comprising a second drill guide lumen, the first and second drill guide lumens of the drill guide insert adapted to receive the K-wire pin member, the temporary fixation pin, and the bone dislodging member therein, the tool assembly further comprising a bone harvester assembly adapted to extract and collect dislodged bone material from the bone dislodging member after creation of the first portion of the pilot SI joint opening in the first bone structure of the dysfunctional SI joint and the second portion of the pilot SI joint opening in the second bone structure of the dysfunctional SI joint, the SI joint prosthesis configured and adapted to be inserted into and through the prosthesis internal access opening of the drill guide and into the pilot SI joint opening in a posterior trajectory, the prosthesis deployment assembly configured and adapted to engage the SI joint prosthesis and guide the SI joint prosthesis into and through the prosthesis internal access opening of the drill guide and into the pilot SI joint opening.

In some embodiments of the invention, the drill guide further comprises a plurality of anchor members extending from the base of the drill guide.

In a preferred embodiment, the first drill guide fixation sub-system is operable when the plurality of K-wires is received in the plurality of K-wire lumens in the drill guide and engage the first and second bone structures of the dysfunctional SI joint.

In a preferred embodiment, the second drill guide fixation sub-system is operable when the K-wire pin member is received in the first drill guide lumen of the drill guide insert and engages the first bone structure of the dysfunctional SI joint, and when the K-wire pin member is received in the second drill guide lumen of the drill guide insert and engages the second bone structure of the dysfunctional SI joint.

In a preferred embodiment, the second drill guide fixation sub-system further operable when the temporary fixation pin is received in the first drill guide lumen of the drill guide insert and engages the first bone structure of the dysfunctional SI joint, and when the temporary fixation pin is received in the second drill guide lumen of the drill guide insert and engages the second bone structure of the dysfunctional SI joint In a preferred embodiment of the invention, the tool assembly is adapted to access the dysfunctional SI joint in a posterior trajectory.

In a preferred embodiment, the bone dislodging member comprises a drill bit.

In a preferred embodiment, the drill bit comprises a plurality of graduated markings reflecting a first depth of the drill bit into the first bone structure when the first portion of the pilot SI joint opening is the created in the first bone structure and a second depth of the drill bit into the second bone structure when the second portion of the pilot SI joint opening is the created in the second bone structure.

In a preferred embodiment, the graduated markings are directly visible when the first portion of the pilot SI joint opening is created in the first bone structure with the drill bit and when the second portion of the pilot SI joint opening is created in the second bone structure with the drill bit.

In a preferred embodiment, the SI joint prosthesis comprises a first elongated section, a second elongated section, and a bridge section disposed between and connected to the first and second elongated sections, the first elongated section sized and configured to be inserted into the first portion of the pilot SI joint opening in the first bone structure of the dysfunctional SI joint when the SI joint prosthesis is advanced into the dysfunctional SI joint in a posterior trajectory, the second elongated section sized and configured to be inserted into the second portion of the pilot SI joint opening in the second bone structure of the dysfunctional SI joint when the SI joint prosthesis is advanced into the dysfunctional SI joint in a posterior trajectory, the bridge section comprising a bridge section proximal end and a bridge section distal end disposed opposite the bridge section proximal end and proximate the prosthesis distal end, the bridge section distal end comprising a first tapered region configured and adapted to disrupt at least articular cartilage and cortical bone.

In some embodiments, the SI joint prosthesis comprises a hollow structure.

In some embodiments, the bridge section comprises a hollow or open structure.

In some embodiments, the bridge section comprises a plurality of apertures and/or slots.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1A:
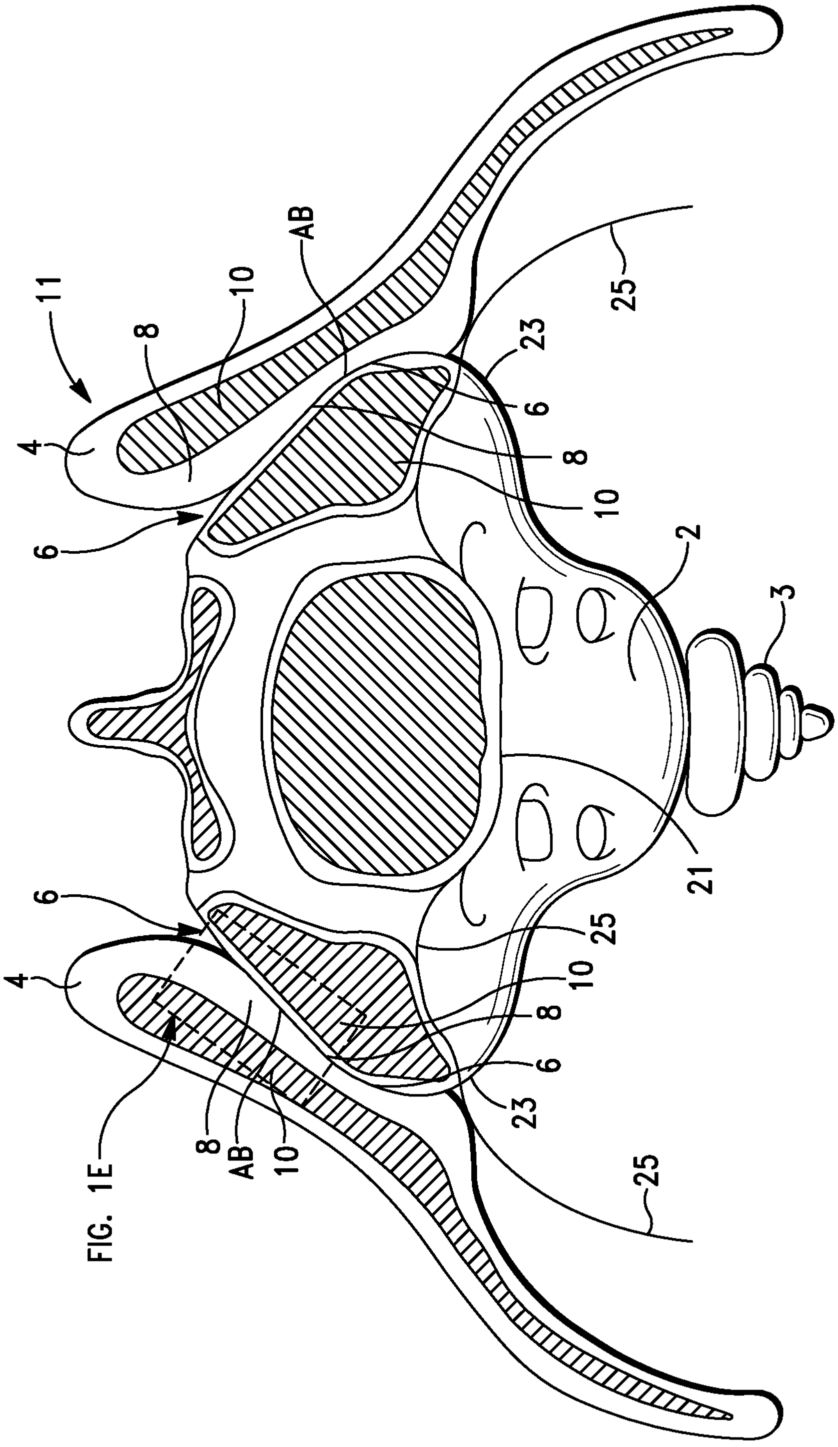
FIG. 1A is a schematic illustration of a human pelvic region from an anteroposterior (AP) perspective showing the SI joints thereof.
Figure 1B:
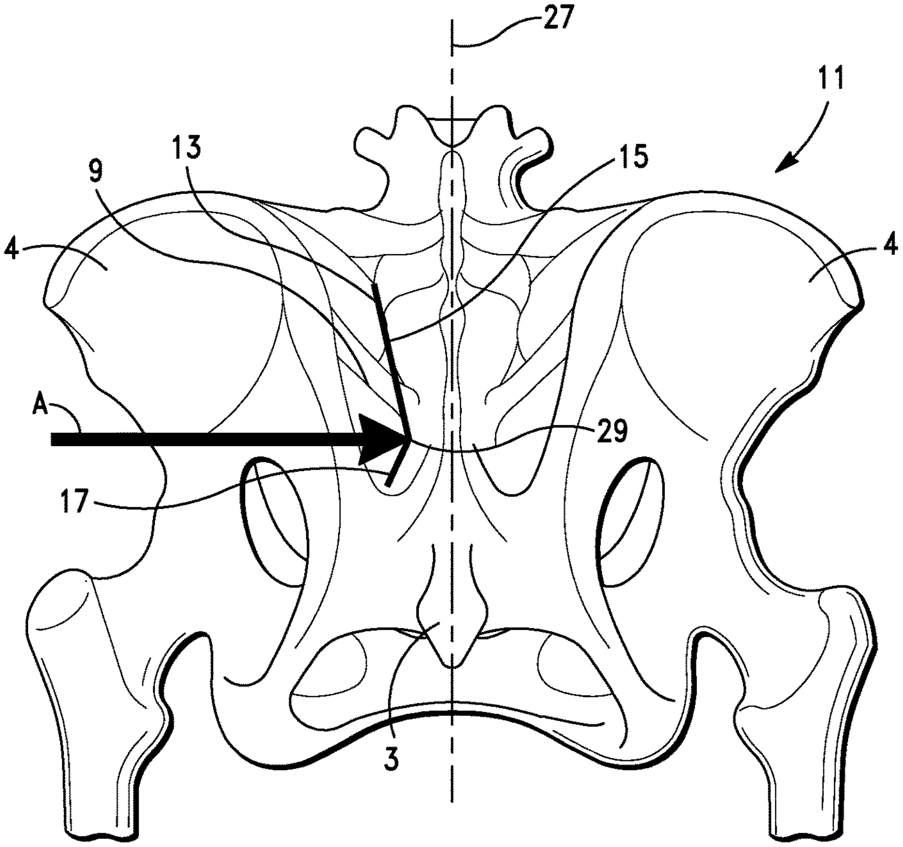
FIG. 1B is another schematic illustration of a human pelvic region from a posterior perspective showing the adjoining sacrum and ilium bone structures, and ligamentous structures thereof.

Before describing the present invention in detail, it is to be understood that this invention is not limited to particularly exemplified systems, apparatus, structures or methods as such may, of course, vary. Thus, although a number of systems, apparatus, structures and methods similar or equivalent to those described herein can be used in the practice of the present invention, the preferred systems, apparatus, structures and methods are described herein.

It is also to be understood that, although the present invention is described and illustrated in connection with sacroiliac (SI) joint stabilization, fixation and fusion procedures, the invention is not limited to such procedures. According to the invention, the systems, apparatus and methods of the invention can also be employed to stabilize and/or fuse other articulating bone structures, including, without limitation, vertebrae, tarsal bones and the like.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms “a”, “an” and “the” include plural referents unless the content clearly dictates otherwise. Thus, for example, reference to “an incision” includes two or more incisions and the like.

Further, ranges can be expressed herein as from “about” or “approximately” one particular value, and/or to “about” or “approximately” another particular value. When such a range is expressed, another embodiment includes from the one particular value and/or to the other particular value. Similarly, when values are expressed as approximations, by use of the antecedent “about” or “approximately”, it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as “about” or “approximately” that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

DEFINITIONS

The terms "bone" and "bone structure" are used interchangeably herein, and mean and include any skeletal member or structure that comprises osseous tissue. The terms "bone" and "bone structure" thus mean and include complete and partial skeletal members or bone structures, including articulating and non-articulating bone structures, (e.g., vertebrae, sacrum, ilium, femur, etc.) and portions thereof.

The terms "sacroiliac joint", "SI joint", "sacroiliac junction" and "SI junction" are used interchangeably herein, and mean and include any region proximate to articulating regions of the sacrum and ilium bone structures and, hence, a junction between and defined by sacrum and ilium bone structures. The terms "sacroiliac joint" and "SI joint" thus mean and include a "bone" and "bone structure".

The term "dysfunctional" as used in connection with a bone structure, means and includes a physiological abnormality, disorder or impairment of a bone structure. The term "dysfunctional" as used in connection with a SI joint thus means and includes, without limitation, a traumatic fracture dislocation of the pelvis, degenerative arthritis, sacroiliitis, i.e., an inflammation or degenerative condition of the SI joint; osteitis condensans ilii, and other degenerative conditions of SI joint bone structures.

The terms "fusion" and "arthrodesis" are used interchangeably herein in connection with bone structures, and mean and include partial or complete immobilization of adjacent bone structures.

The term "stabilization", as used herein, means and includes reinforcing bone structures or sections thereof, e.g., modulating motion of adjacent articular bone structures; particularly, the sacrum and ilium bone structures. The term "stabilization", thus, in some instances, means and includes fusion and arthrodesis of adjacent bone structures.

The term "prosthesis", as used herein in connection with bone structures, means and includes a system or apparatus configured and adapted to stabilize bone structures. The term "prosthesis" thus includes a system or apparatus adapted to modulate motion of articulating bone structures; particularly, sacrum and ilium bone structures.

The term "inferior-posterior", as used herein in connection with the trajectory of a single-member and multi-member bone structure prosthesis of the invention to a SI joint, means a posterior trajectory to a SI joint through the axial and sagittal planes of the ilium and sacrum bone structures and lower than the dorsal recess of the joint.

The term "transfixed", as used herein in connection with the single-member and multi-member bone structure prostheses of the invention, means engagement of the bone structure prostheses to the ilium and sacrum bone structures, and the interface or joint therebetween.

The term "biodegradable", as used herein, means the ability of a material; particularly, a polymer or adhesive, to breakdown and be absorbed within the physiological environment of a SI joint and/or a structure associated therewith, including sacrum and ilium bone structures, by one or more physical, chemical, or cellular processes.

Biodegradable polymers, according to the invention, thus include, without limitation, polylactide polymers (PLA), copolymers of lactic and glycolic acids, including poly(lactic-co-glycolic) acid (PLGA) and poly(ε-caprolactone-co-L-lactic) acid (PCL-LA); glycine/PLA co-polymers, polyethylene oxide (PEO)/PLA block copolymers, acetylated polyvinyl alcohol (PVA)/polycaprolactone copolymers, poly(glycerol sebacate) (PGS) and its derivatives, including poly(glycerol-co-sebacate acrylate) (PGSA); poly(polyol sebacate) (PPS), poly(xylitol sebacate) (PXS), poly(xylitol glutamate sebacate) (PXGS), hydroxybutyrate-hydroxyvalerate copolymers, polyesters such as, but not limited to, aspartic acid and different aliphatic diols; poly(alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA); aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like.

Biodegradable adhesives, according to the invention, thus include, without limitation, poly(glycerol-co-sebacate acrylate) (PGSA), poly(L-glutamic acid)-based compositions, poly(γ-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol, and combinations thereof; fibrin-based compositions, collagen-based compositions, including collagen/poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and OctylSeal); poly(ethylene glycol) (PEG) based compositions, including FocalSeal®, Progel™, Duraseal™, DuraSeal™ Xact, Coseal® and ReSure Sealant; polysaccharide-based compositions, polypeptide-based compositions, and combinations thereof.

The term "osteogenic composition", as used herein, means and includes an agent or composition that induces or modulates an osteogenic physiological or biological process, or cellular activity, e.g., induces proliferation, and/or growth and/or remodeling and/or regeneration of bone or osseous tissue.

The term "osteogenic composition" thus means and includes, without limitation, the following osteogenic materials and compositions comprising same: demineralized bone matrix, autograft bone material, allograft bone material, xenograft bone material, polymethyl-methacrylate, calcium-based bone material, including hydroxyapatite (HA) and tricalcium phosphate; and combinations or mixtures thereof.

The term "osteogenic composition" also means and includes, without limitation, the following polymer materials and compositions comprising same: poly(glycerol sebacate) (PGS), poly(glycerol-co-sebacate) acrylate (PGSA) and co-polymers, such as poly(glycerol sebacate)-co-poly(ethylene glycol) (PGS-PEG); and/or composites thereof, e.g., PGS-hydroxyapatite (HA) composites and PGS-poly(ε-caprolactone) (PGS-PCL) composites.

The term "osteogenic composition" also means and includes, without limitation, acellular extracellular matrix (ECM) derived from mammalian tissue sources.

The term "osteogenic composition" thus means and includes, without limitation, acellular ECM derived from bone or osseous tissue, small intestine submucosa (SIS), epithelium of mesodermal origin, i.e., mesothelial tissue, placental tissue, omentum tissue, and combinations thereof.

The terms "biologically active agent" and "biologically active composition" are used interchangeably herein, and mean and include agent or composition that induces or modulates a physiological or biological process, or cellular activity, e.g., induces proliferation, and/or growth and/or regeneration of tissue, including osseous tissue.

The terms "biologically active agent" and "biologically active composition", as used herein, thus include agents and compositions that can be varied in kind or amount to provide a therapeutic level effective to mediate the formation or healing of osseous tissue, cartilage and connective tissue, e.g., tendons and ligaments. The term "biologically active composition", in some instances, thus means and includes an "osteogenic composition."

The terms "biologically active agent" and "biologically active composition" thus mean and include, without limitation, the following bone morphogenic proteins (BMPs) and compositions comprising same: BMP-1, BMP2a, BMP2b, BMP3, BMP4, BMP5, BMP6, BMP7 (also referred to as osteogenic protein 1 (OP-1)), and BMP8a.

The terms "biologically active agent" and "biologically active composition" also mean and include, without limitation, the following biological agents and compositions comprising same: platelet derived growth factor (PDGF), an insulin-like growth factor (IGF), including IGF-1 and IGF-2; basic fibroblast growth factor (bFGF) (also referred to as FGF2), a transforming growth factor-β (TGF-β), including, TGF-β1 and TGF-β2; a growth hormone (GH), parathyroid hormone (PTH, including PTH1-34), transforming growth factor-α (TGF-α), granulocyte/macrophage colony stimulating factor (GM-CSF), epidermal growth factor (EGF), growth and differentiation factor-5 (GDF-5), vascular endothelial growth factor (VEGF), angiogenin, angiopoietin-1, del-1, follistatin, granulocyte colony-stimulating factor (G-CSF), hepatocyte growth factor/scatter factor (HGF/SF), interleukin-8 (IL-8), interleukin-10 (IL-10), leptin, midkine, placental growth factor, platelet-derived endothelial cell growth factor (PD-ECGF), platelet-derived growth factor-BB (PDGF-BB), pleiotrophin (PTN), progranulin, proliferin, a matrix metalloproteinase (MMP), angiopoietin 1 (ang1), angiopoietin 2 (ang2), and delta-like ligand 4 (DLL4).

The terms "biologically active agent" and "biologically active composition" also mean and include, without limitation, the following cells and compositions comprising same: bone marrow-derived progenitor cells, bone marrow stromal cells (BMSCs), osteoprogenitor cells, osteoblasts, osteocytes, osteoclasts, committed or partially committed cells from the osteogenic or chondrogenic lineage, hematopoietic stem cells, chondrocytes, chondrogenic progenitor cells (CPCs), mesenchymal stem cells (MSCs), and embryonic stem cells.

The terms "pharmacological agent" and "active agent" are used interchangeably herein, and mean and include an agent, drug, compound, composition or mixture thereof, including its formulation, which provides some therapeutic, often beneficial, effect. This includes any physiologically or pharmacologically active substance (or composition comprising same) that produces a localized or systemic effect or effects in animals, including warm blooded mammals.

The terms "pharmacological agent" and "active agent" thus mean and include, without limitation, the following osteoinductive agents and compositions comprising same: icaritin, tumor necrosis factor alpha (TNF-α) inhibitors, including etanercept and infliximab; disease-modifying antirheumatic drugs (DMARDs), including methotrexate and hydroxychloroquine; antibiotics, anti-viral agents, steroidal anti-inflammatories, non-steroidal anti-inflammatories, antithrombotic agents, including anti-coagulants and anti-platelet agents; and vasodilating agents.

The terms "pharmacological agent" and "active agent" further mean and include, without limitation, the following antibiotics and compositions comprising same: penicillin, carboxypenicillins, such as ticarcillin; tetracyclines, such as minocycline; gentamicin, vancomycin, ciprofloxacin, amikacin, aminoglycosides, cephalosporins, clindamycin, erythromycin, fluoroquinolones, macrolides, azolides, metronidazole, trimethoprim-sulfamethoxazole, polymyxin B, oxytetracycline, tobramycin, cefazolin, and rifampin.

The terms "anti-inflammatory" and "anti-inflammatory agent" are also used interchangeably herein, and mean and include a "pharmacological agent", which, when a therapeutically effective amount is administered to a subject, prevents or treats bodily tissue inflammation, i.e., the protective tissue response to injury or destruction of tissues, which serves to destroy, dilute, or wall off both the injurious agent and the injured tissues.

Anti-inflammatory agents thus include, without limitation, dexamethasone, betamethasone, prednisone, prednisolone, methylprednisolone sodium succinate, methylprednisolone, cortisone, ketorolac, diclofenac, and ibuprofen.

The term "pharmacological composition", as used herein, means and includes a composition comprising a "pharmacological agent" and "active agent".

The term "therapeutically effective", as used herein, means that the amount of the "pharmacological agent" and/or "pharmacological composition" and/or "biologically active agent" and/or "biologically active composition" administered is of sufficient quantity to induce a physiological reaction, preferably, a positive or desirable physiological reaction in a subject.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "one embodiment", "one aspect", and "an embodiment" and "an aspect", as used herein, means that a particular feature, structure, or characteristic described in connection with the embodiment may be included in at least one embodiment and not that any particular embodiment is required to have a particular feature, structure or characteristic described herein unless set forth in the claim.

The phrase "in one embodiment" or similar phrases employed herein do not limit the inclusion of a particular element of the invention to a single embodiment. The element may thus be included in other, or all embodiments discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present invention is directed to minimally-invasive systems, apparatus and methods for stabilizing dysfunctional SI joints.

As also indicated above, although the present invention is described and illustrated in connection with sacroiliac (SI) joint stabilization, fixation and fusion procedures, the invention is not limited to such procedures. According to the invention, the systems, apparatus and methods of the invention can also be employed to stabilize and/or fuse other articulating bone structures, including, without limitation, vertebrae, tarsal bones, and the like.

In some embodiments of the invention, there are thus provided SI joint stabilizing apparatus, referred to hereinafter as "SI joint stabilization prostheses", that are configured and adapted to stabilize dysfunctional SI joints. The SI joint prostheses are also configured to be implanted in the dysfunctional SI joint via a minimally-invasive system and, hence, minimally-invasively.

Figure 1C:
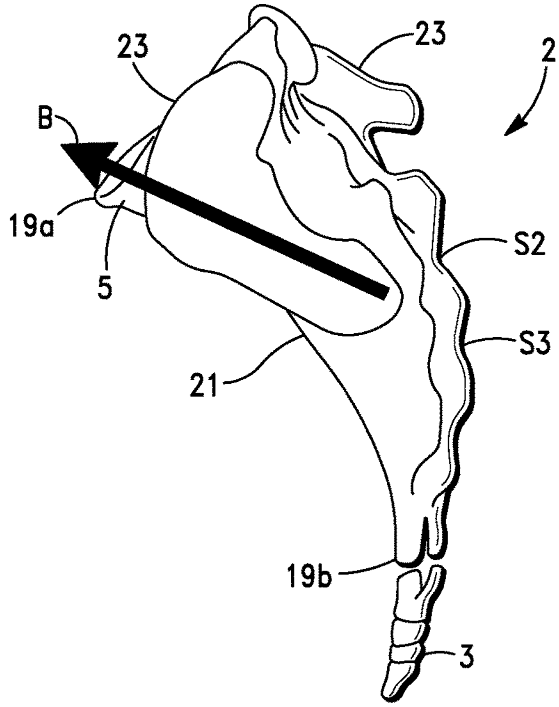
FIG. 1C is a schematic illustration of the sacrum and coccyx from a lateral perspective showing the sacral promontory and the articular surface of sacrum.
Figure 1D:
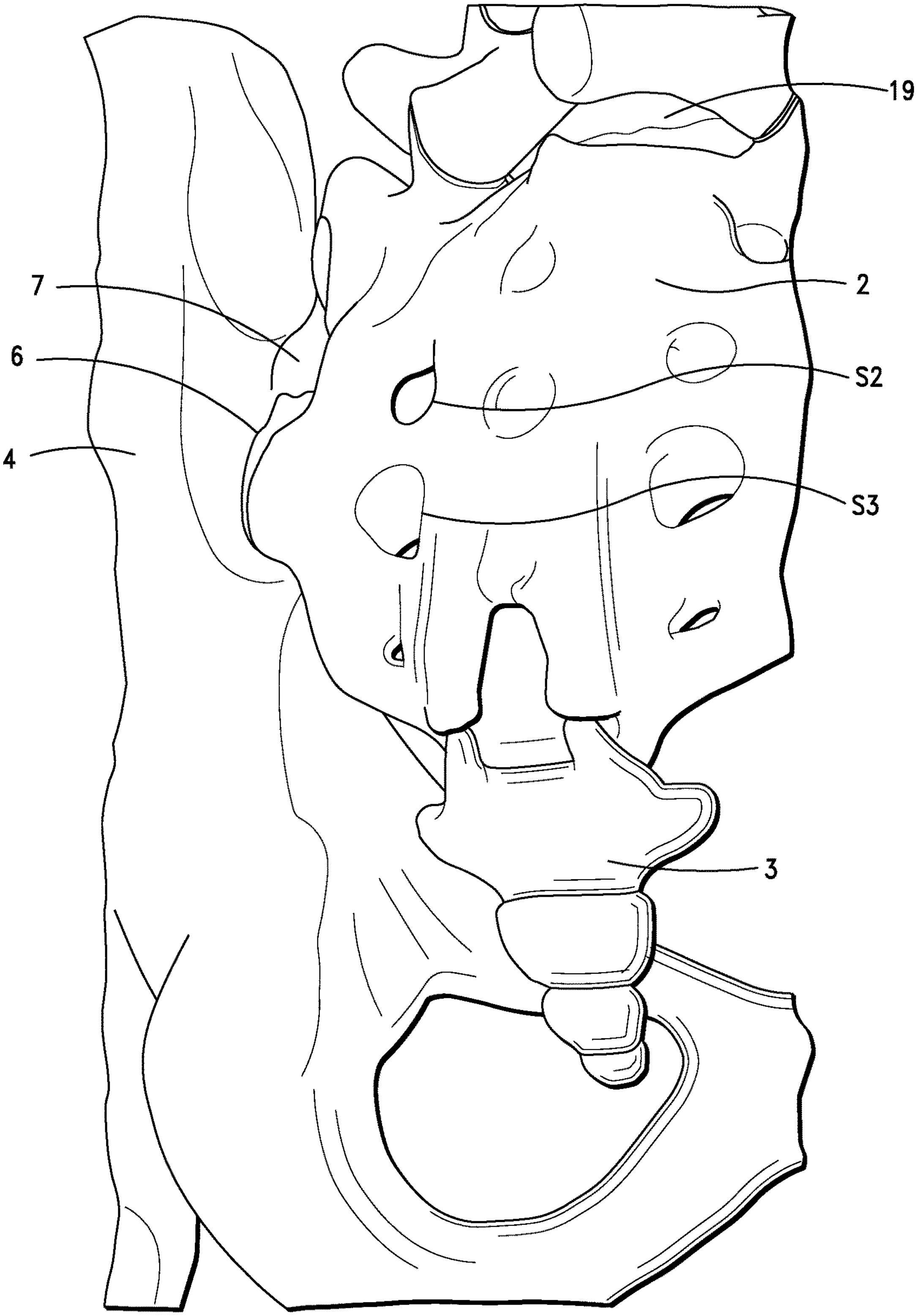
FIG. 1D is another schematic illustration of a human pelvic region from a posterior inferior perspective showing the adjoining sacrum and ilium bone structures of an SI joint, and an SI joint dorsal recess between the sacrum and ilium bone structures.

As discussed in detail herein, the minimally-invasive systems of the invention (also referred to herein as "minimally-invasive SI joint stabilization systems") are configured and adapted to advance the SI joint prostheses into dysfunctional SI joints in a posterior trajectory, more preferably, an inferior-posterior trajectory, such as illustrated in FIG. 1C and denoted by arrow "B", which results in enhanced stabilization of the dysfunctional SI joints.

As indicated above, SI joint stabilization (and, hence, treatment), including minimally-invasive SI joint stabilization, typically comprises surgical placement of a bone structure prosthesis proximate to or in a dysfunctional SI joint via anterior or lateral trajectories.

From the perspective of FIG. 1A, an anterior approach to the SI joint 6 shown in FIG. 1A (and, hence, a dysfunctional SI joint) would be substantially perpendicular to the page upon which FIG. 1A is printed.

More recently, a posterior trajectory has been employed to advance a bone structure prosthesis proximate to and in a dysfunctional SI joint.

Figure 1E:
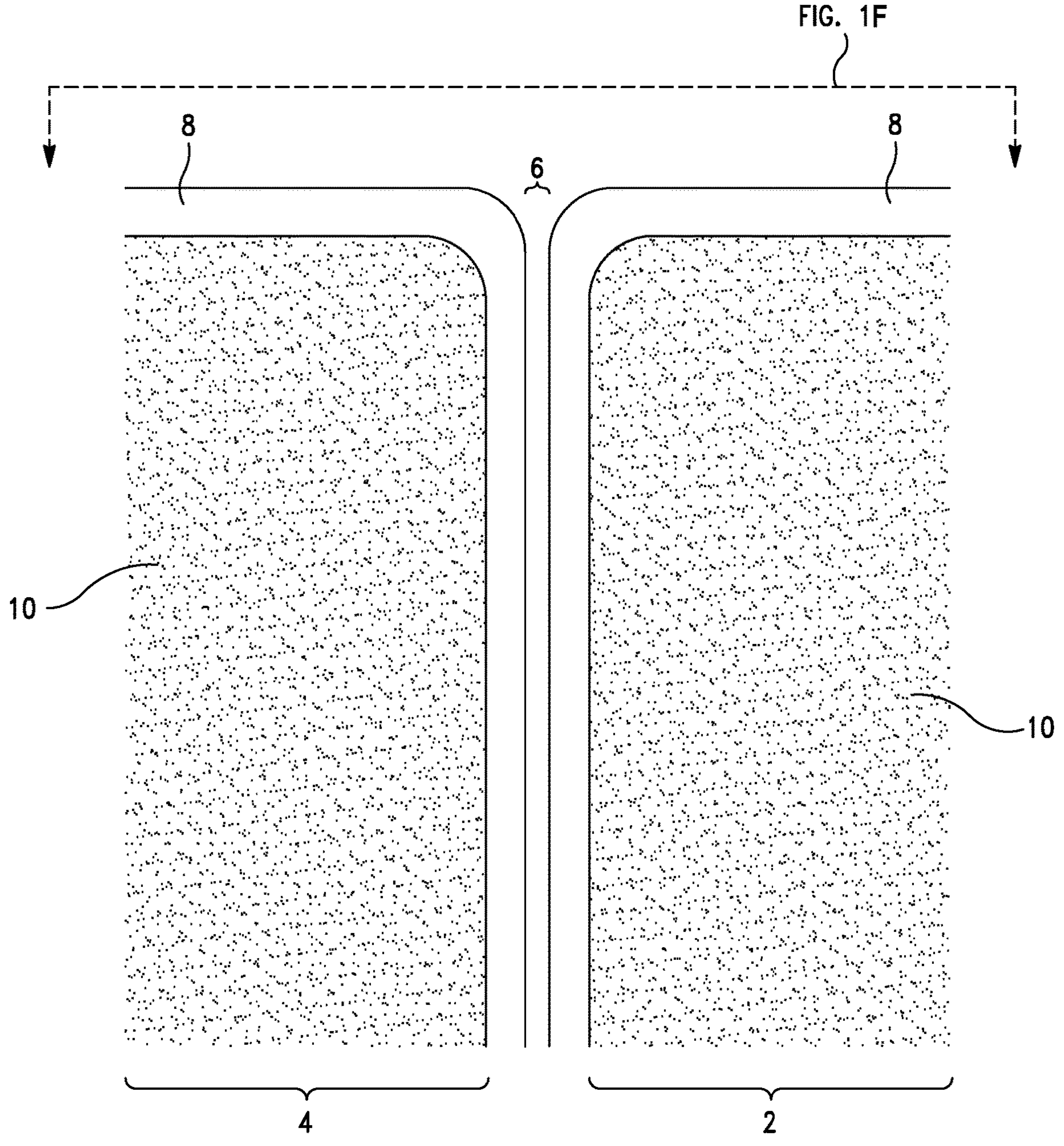
FIG. 1E is an illustration of a SI joint from a superior perspective showing the adjoining sacrum and ilium articular surfaces.

Referring now to FIG. 1E, there is shown an illustration of a SI joint 6 and surrounding structures. For illustrative simplicity, a uniform layer of cortical bone 8 is shown adjacent a deeper layer of trabecular bone 10 on both of the depicted sacrum 2 and ilium 4 structures. However, in actuality, such layers are far less uniform and homogeneous.

Figure 1F:
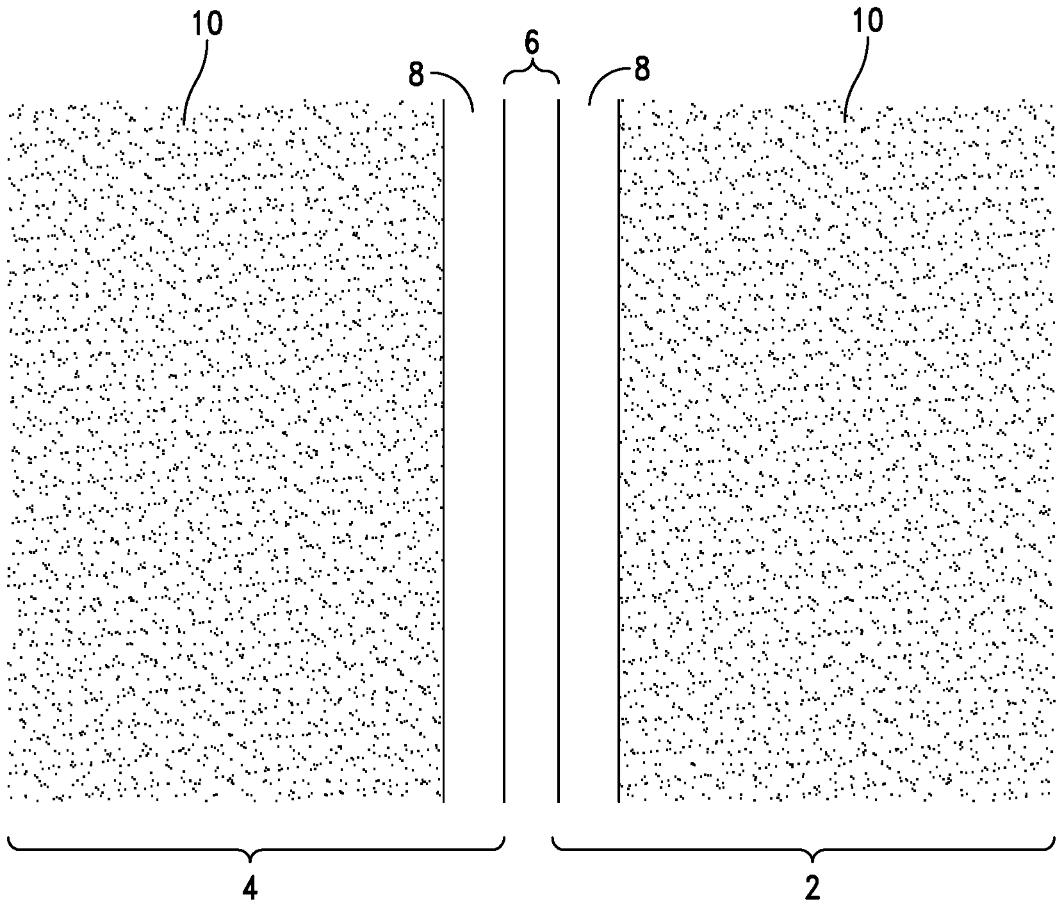
FIG. 1F is another illustration of a SI joint from a posterior perspective showing the adjoining sacrum and ilium articular surfaces.
Figure 1G:
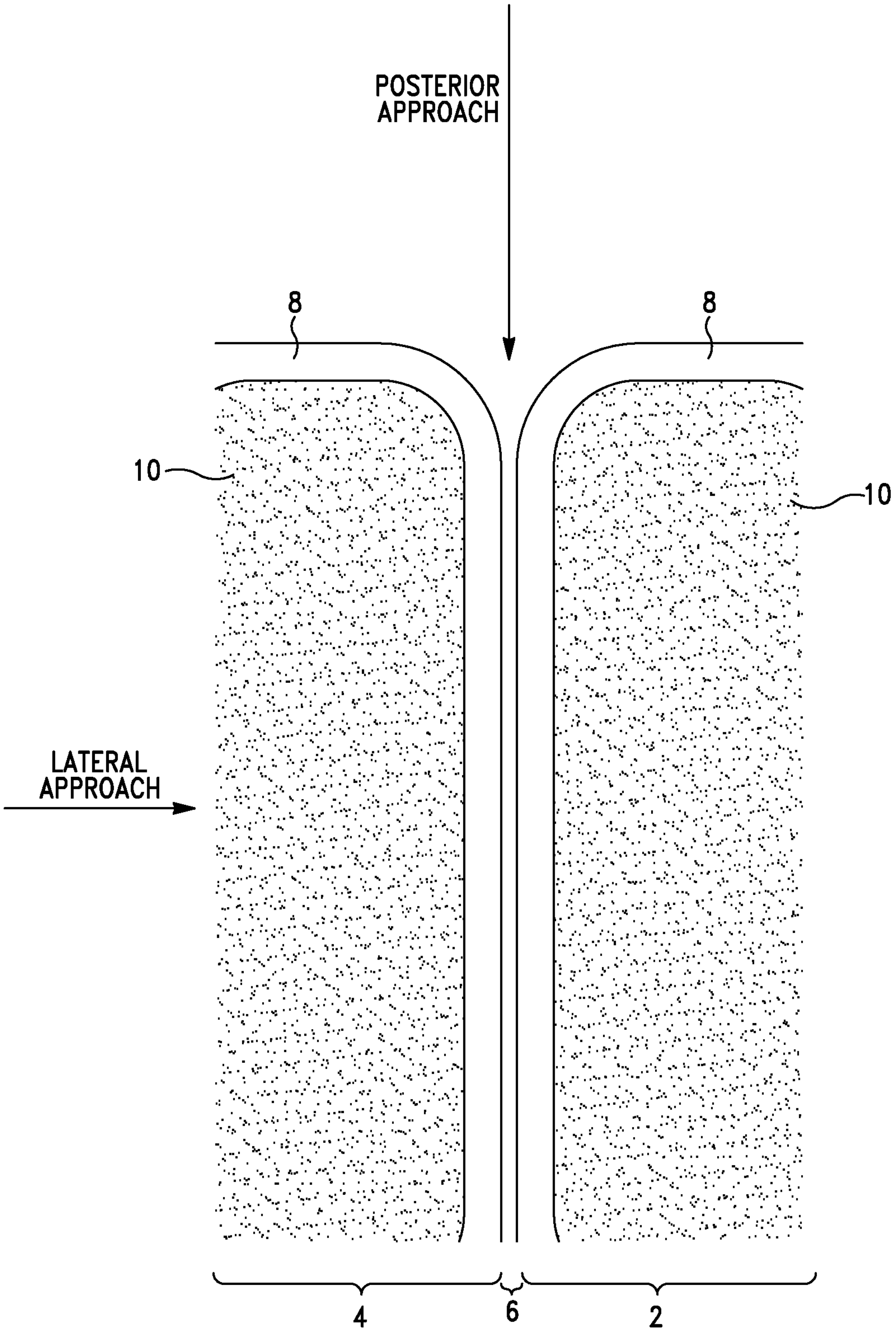
FIG. 1G is a further illustration of the SI joint shown in FIG. 1F showing lateral and posterior approaches to the SI joint, in accordance with the invention.

Referring now to FIG. 1F, there is shown a view of the same structure from a different posterior perspective. From the perspective of FIG. 1F, a posterior approach or trajectory to the SI joint 6 (and, hence, a dysfunctional SI joint) would be substantially perpendicular to the page upon which FIG. 1F is printed. Indeed, referring to FIG. 1G, a variation similar to that depicted in FIG. 1E is illustrated, showing an approximate approach vector for a lateral trajectory to the SI joint 6 versus a posterior trajectory, using the orientation paradigms introduced in FIGS. 1A and 1F-1G. Such paradigms are used to illustrate various embodiments of the subject invention in various figures that follow FIGS. 1A and 1F-1G.

As indicated above, a major disadvantage associated with many conventional anterior and lateral trajectories of a bone structure prosthesis to a dysfunctional SI joint is that muscles and ligaments are typically disrupted and often damaged. Nerves and blood vessels are also susceptible to damage during such SI joint stabilization methods.

In contrast, posterior delivery; particularly, inferior-posterior delivery, of the SI joint prostheses of the invention to a dysfunctional SI joint is much less invasive. Indeed, less tissue and fewer muscles are disrupted, and nerves and large blood vessels are avoided. The SI joint prostheses are also transfixed to optimal regions of cortical bone proximate a dysfunctional SI joint and, thereby, provide superior arthrodesis of the dysfunctional SI joint.

In a preferred embodiment of the invention, the SI joint stabilization systems of the invention generally comprise (i) a tool assembly configured and adapted to access the target dysfunctional SI joint via a posterior approach and create at least one pre-determined opening in the dysfunctional SI joint (referred to herein after as a "pilot SI joint opening"), (ii) a SI joint prosthesis configured and adapted to be inserted into the pilot SI joint opening created by the tool assembly, and (iii) a prosthesis deployment assembly configured and adapted to engage the SI joint prosthesis and advance the SI joint prosthesis into the dysfunctional SI joint.

Tool Assemblies

In a preferred embodiment of the invention, the tool assembly comprises an elongated guide pin (referred to as a "guide probe" in Co-pending U.S. application Ser. No. 17/463,779) and a drill guide assembly.

Figure 2B:
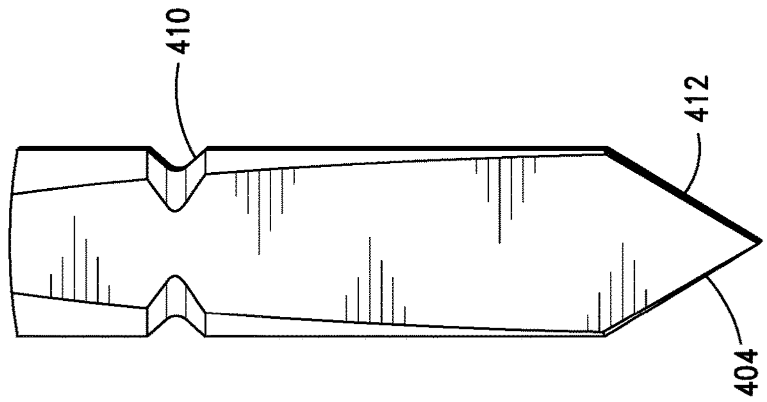
FIG. 2B is a partial side plan view of the guide pin shown in FIG. 2A showing a guide pin marking, in accordance with the invention.
Figure 2A:
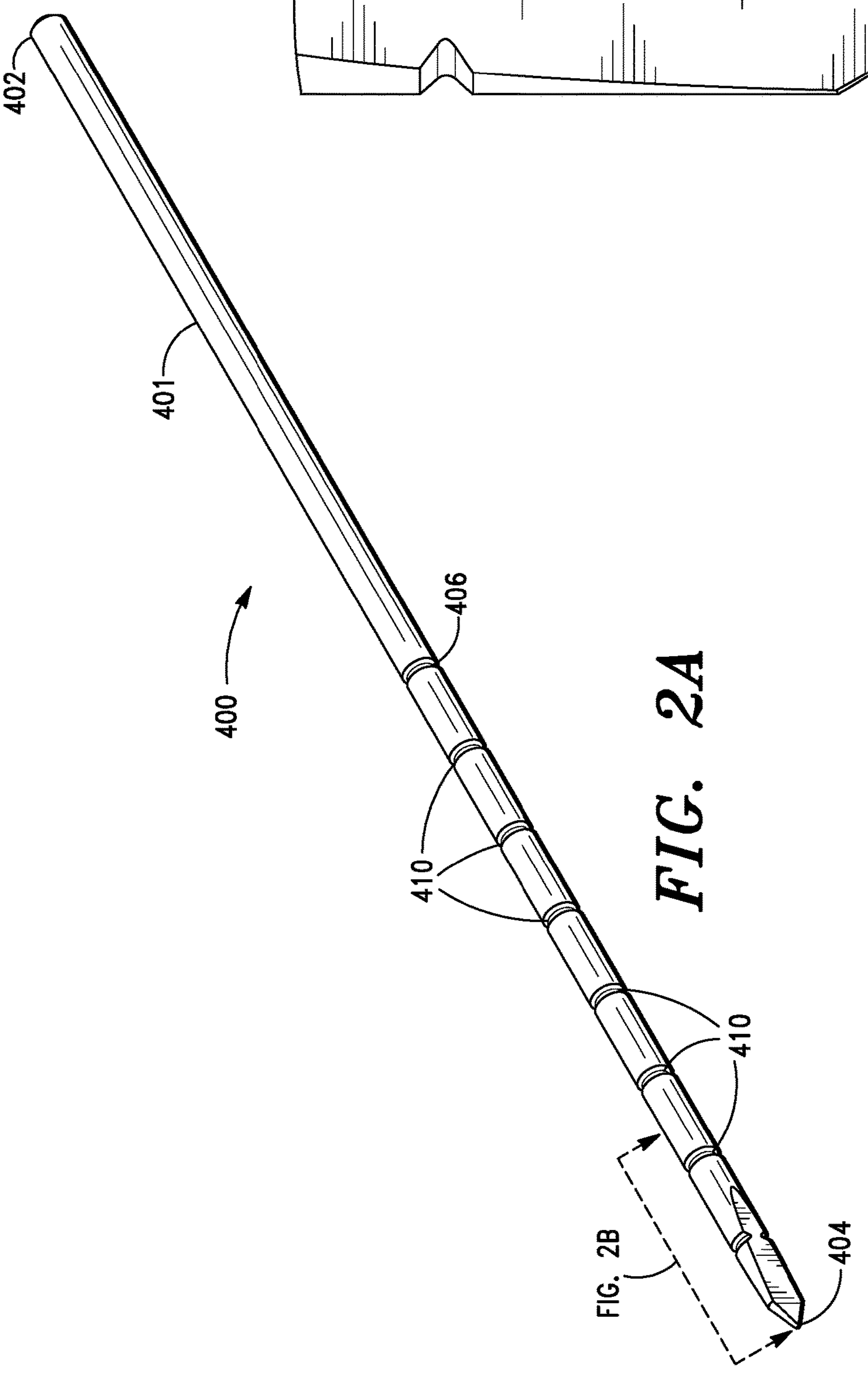
FIG. 2A is a perspective view of one embodiment of a guide pin, in accordance with the invention.

Referring now to FIG. 2A, there is shown a preferred embodiment of a guide pin of the invention (denoted "400").

As discussed in detail below, the guide pin 400 is sized and configured to be positioned in a dysfunctional SI joint and, when positioned therein, function as (i) a guide for the drill guide assembly, i.e. drill guide thereof, and, thereby, positioning of the pilot SI joint opening(s) created by the drill guide assembly, (ii) a landmark for the SI joint prosthesis to be disposed in the dysfunctional SI joint, and (iii) in some embodiments, a guide for the prosthesis deployment assembly and, hence, SI joint prosthesis engaged thereto into the pilot SI joint opening created by the drill guide assembly and, thereby, positioning of the SI joint prosthesis in the dysfunctional SI joint.

As illustrated in FIG. 2A, the guide pin 400 comprises an elongated graduated wire or rod structure 401 comprising proximal and distal ends 402, 404 and a plurality of spaced guide pin markings 410 that extend from the distal end 404 of the guide pin 400 to preferably at least the mid-region 406 of the guide pin 401.

According to the invention, the guide pin markings 410 can comprise various distinguishable surface markings, symbols, lines and/or structural patterns and arrangements, which preferably are readily detectable and, hence, readable via a conventional image capture apparatus, such as a fluoroscope and radiography system.

As illustrated in FIG. 2B, in a preferred embodiment of the invention, the guide pin markings 410 comprise a plurality of graduated or spaced grooves or depressions in the wire structure 401. According to the invention, any number of spaced grooves, i.e., markings 410, can be employed on the wire structure 401 and, hence, guide pin 400 and can be spaced apart at any desired dimension.

As illustrated in FIG. 2A, in a preferred embodiment of the invention, the guide pin 400 includes eight (8) grooves, i.e., markings 410, which are uniformly spaced approximately 10.0 mm apart.

As further illustrated in FIGS. 2A and 2B, in a preferred embodiment, the distal end 404 of the guide pin 400 comprises a pointed configuration 412 to facilitate entry of the distal end 404 of the guide pin 400 into and through tissue, articular cartilage, and SI joint bone structures.

Figure 3A:
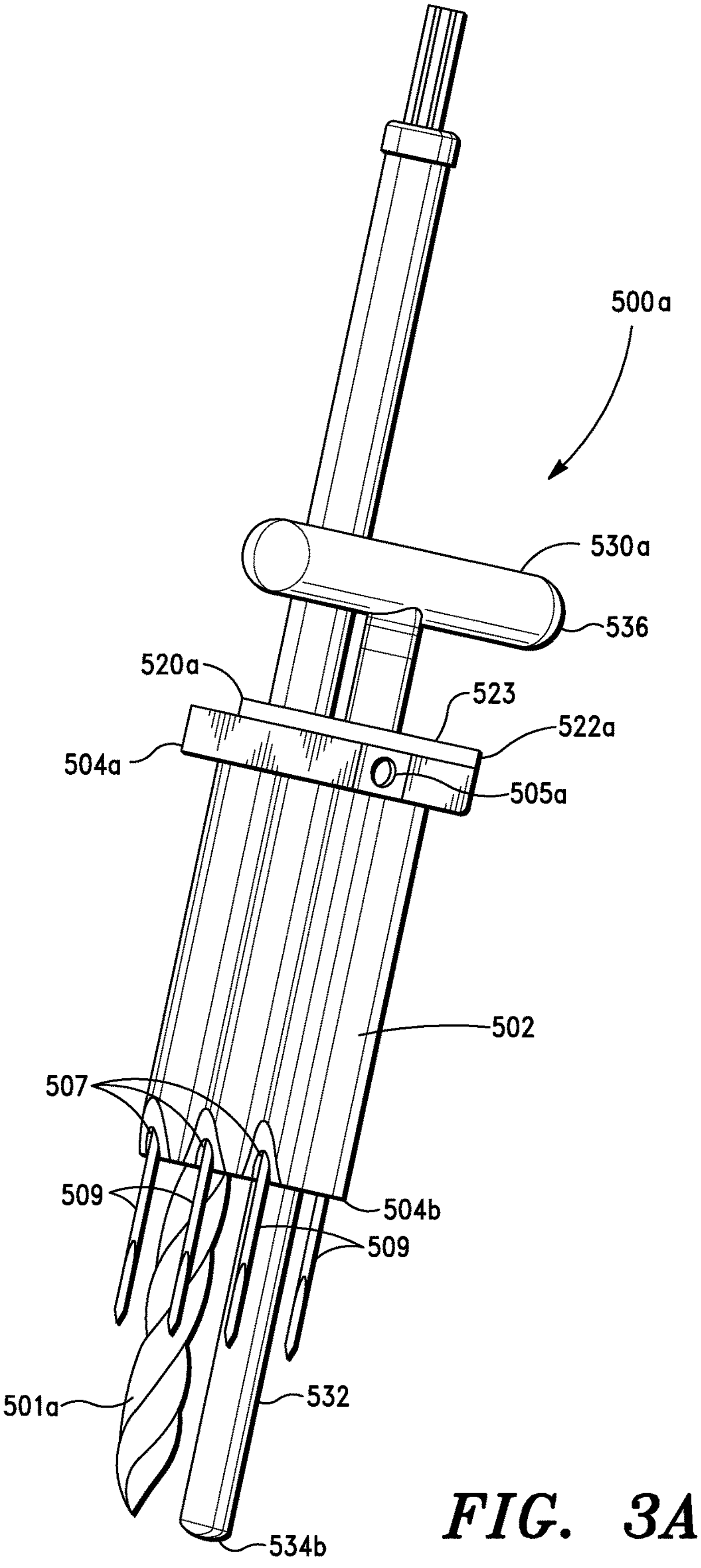
FIG. 3A is a perspective view of one embodiment of a drill guide assembly, in accordance with the invention.

Referring now to FIG. 3A, there is shown one embodiment of a drill guide assembly 500*a* of the invention.

According to the invention, the drill guide assembly 500*a* is configured and adapted to create pre-determined pilot SI joint openings in a SI joint; particularly, a dysfunctional SI joint, to accommodate placement of a SI joint prosthesis of the invention therein.

As illustrated in FIG. 3A, the drill guide assembly 500*a* generally comprises an access sleeve 502, a drill guide 520*a*, a bone dislodging apparatus 501*a*, and a drill alignment pin 530*a*.

Figure 3B:
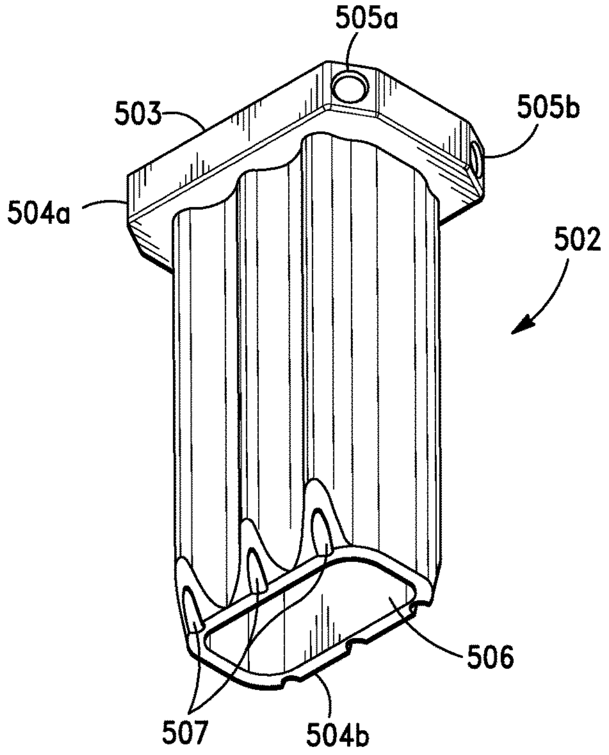
FIG. 3B is a perspective view of the access sleeve of the drill guide assembly shown in FIG. 3A, in accordance with the invention.
Figure 3C:
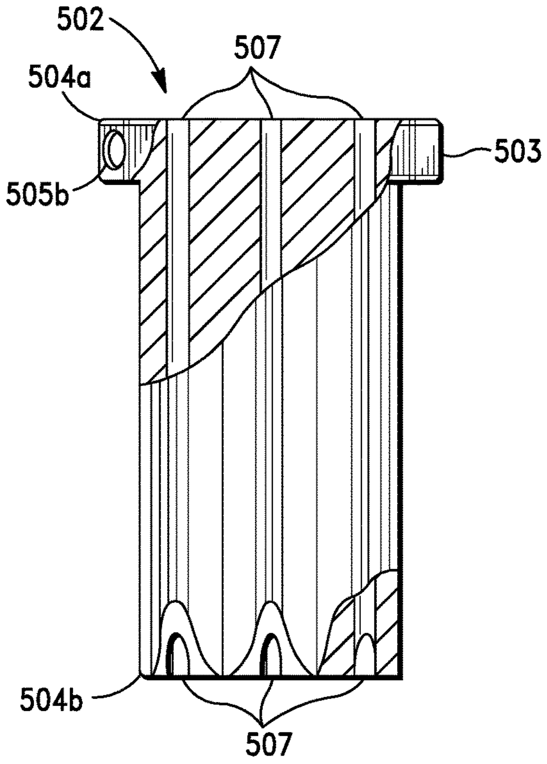
FIG. 3C is a front partial sectional plan view of the access sleeve shown in FIG. 3B, in accordance with the invention.
Figure 3D:
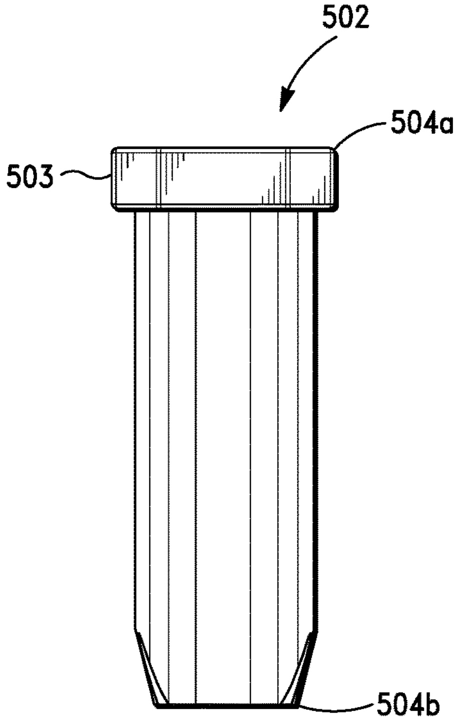
FIG. 3D is a right-side plan view of the access sleeve shown in FIG. 3B, in accordance with the invention.
Figure 3E:
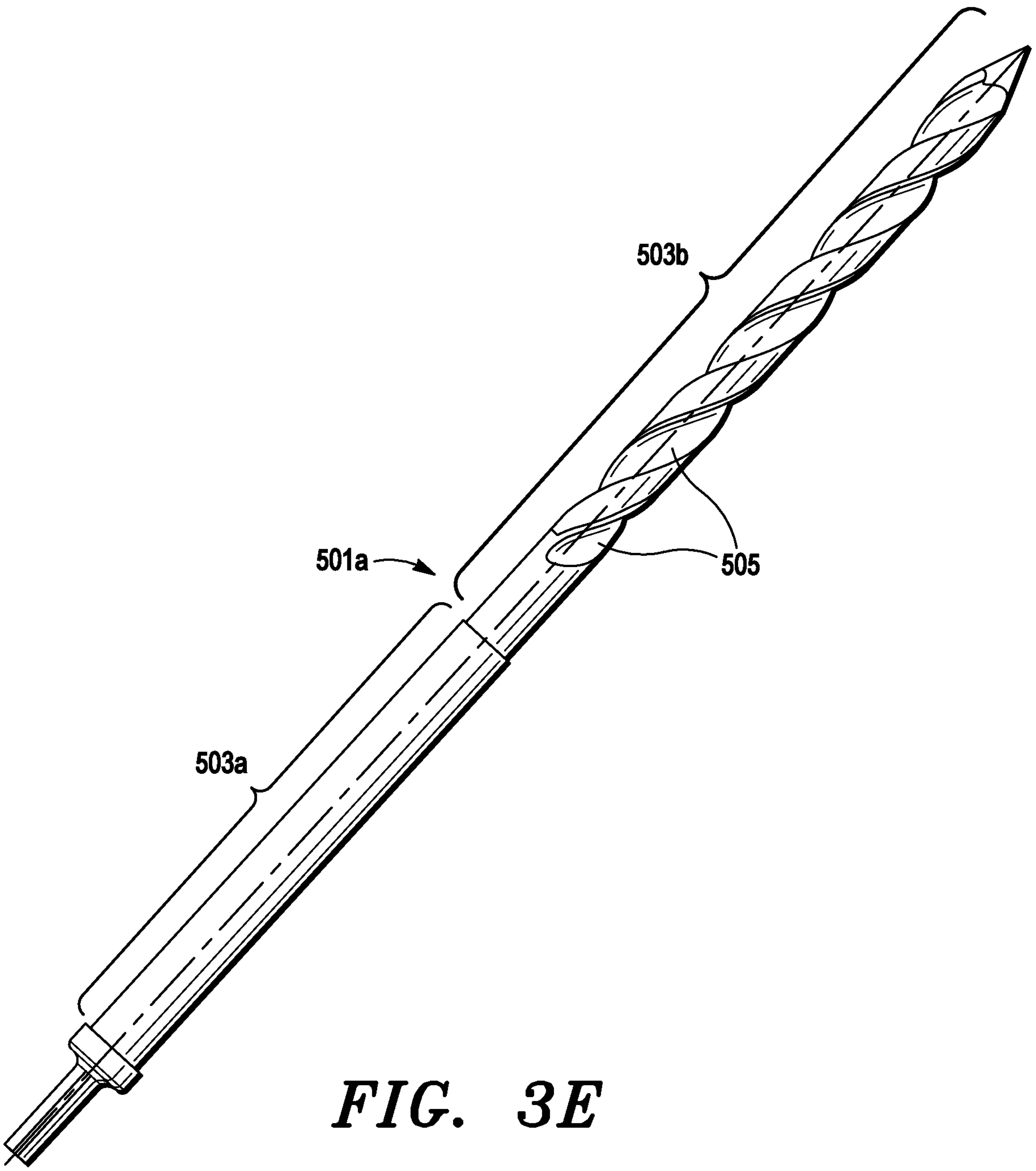
FIG. 3E is a perspective view of one embodiment of a bone dislodging apparatus, i.e., drill bit, in accordance with the invention.

In a preferred embodiment of the invention, the bone dislodging apparatus preferably comprises a conventional drill bit 501*a*, which, as illustrated in FIG. 3E, comprises an elongated rod or shaft structure having a proximal end region 503*a* and a bone dislodging end region 503*b*.

As discussed in detail in Co-pending U.S. application Ser. Nos. 17/463,779 and 17/972,785, and illustrated in FIGS. 3B-3D, the access sleeve 502 comprises proximal and distal ends 504*a*, 504*b*, an internal opening 506 that extends from the proximal end 504*a* to the distal end 504*b* of the access sleeve 502, and a plurality of Kirschner wire (K-wire) lumens 507, which, as illustrated in FIG. 3A, are sized and configured to receive and position K-wires 509 or similar pin structures therein.

As further illustrated in FIG. 3A, in a preferred embodiment, the access sleeve internal opening 506 is sized and configured to receive and position the drill guide 520*a* therein.

As further illustrated in FIGS. 3B and 3D, the proximal end 504*a* of the access sleeve 502 comprises a planar region 503, which, as illustrated in FIG. 3A, is configured to seat the proximal end 522*a* of the drill guide 520*a* (discussed below) thereon.

In a preferred embodiment, as additionally shown in FIGS. 3B and 3D, the proximal end 504*a* of the access sleeve 502, i.e., planar region 503, further comprises two (2) threaded holes 505*a*, 505*b*, which are preferably disposed on opposing edge regions of the planar region 503.

According to the invention, the threaded holes 505*a*, 505*b* are sized and configured to receive the threaded end 514 of the access sleeve handle 510*a*, discussed below.

Figure 3G:
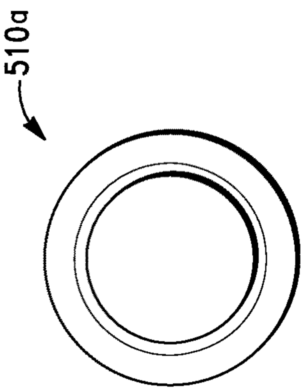
FIG. 3G is an end plan view of the access sleeve handle shown in FIG. 3F, in accordance with the invention.
Figure 3F:
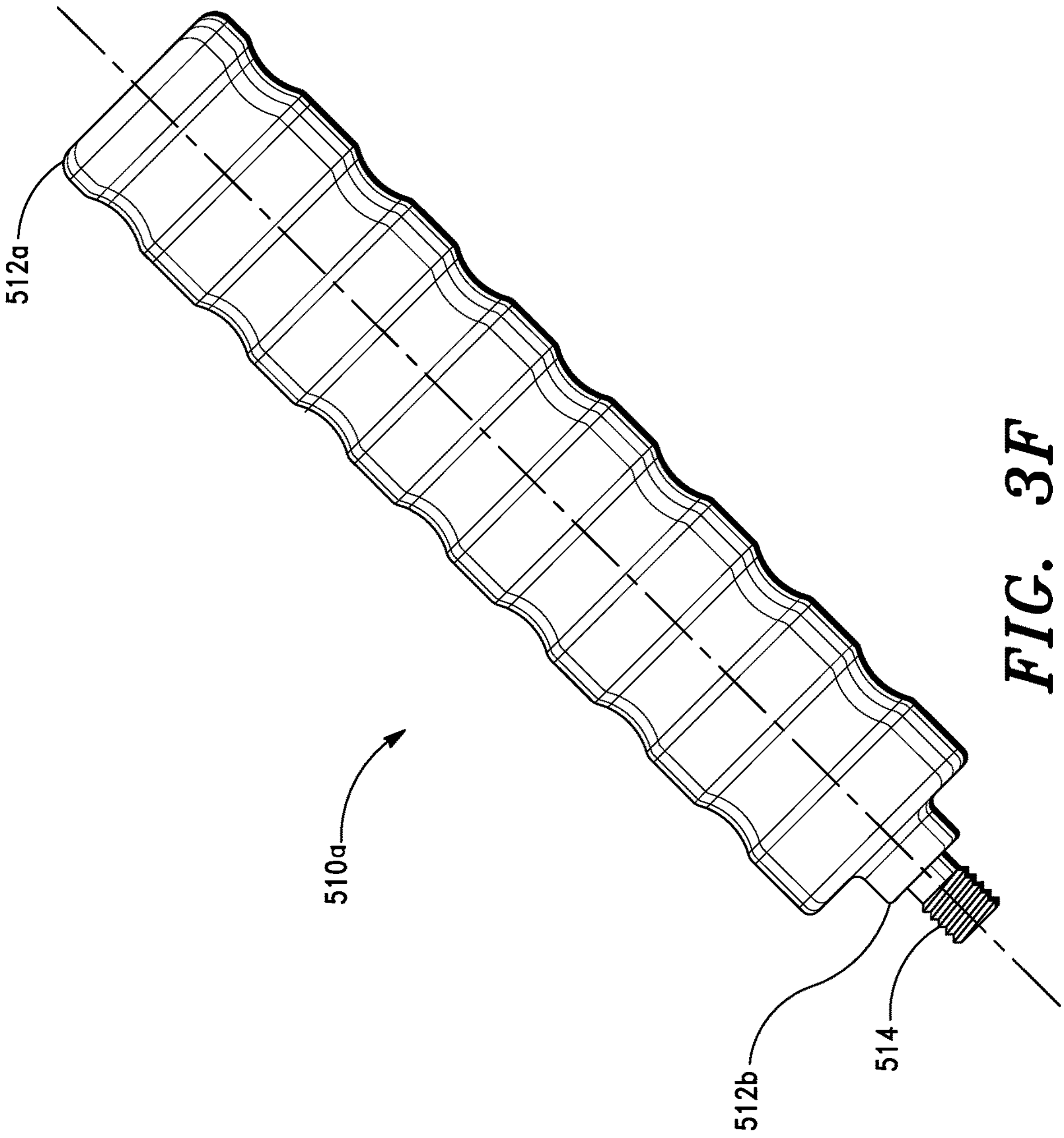
FIG. 3F is a perspective view of one embodiment of an access sleeve handle that is configured to engage the access sleeve shown in FIG. 3B, in accordance with the invention.

Referring now to FIGS. 3F and 3G, there is shown a preferred embodiment of the access sleeve handle 510*a*.

As illustrated in FIGS. 3F and 3G, the handle 510*a* preferably comprises an elongated cylindrical shaped member comprising proximal and distal ends 512*a*, 512*b*.

As further illustrated in FIG. 3F, in a preferred embodiment, the distal end 512*b* of the handle 510*a* comprises a threaded extension 514 that is sized and configured to cooperate with the threaded holes 505*a*, 505*b* of the access sleeve 502 (and threaded holes 511*a*, 511*b* of the drill guides 520*b*, 520*c*, 520*d* and 520*e*, discussed below), whereby the access sleeve handle 510*a* can be threadably engaged to the access sleeve 502 (or drill guides 520*b*, 520*c*, 520*d*, 520*e*).

Figure 3I:
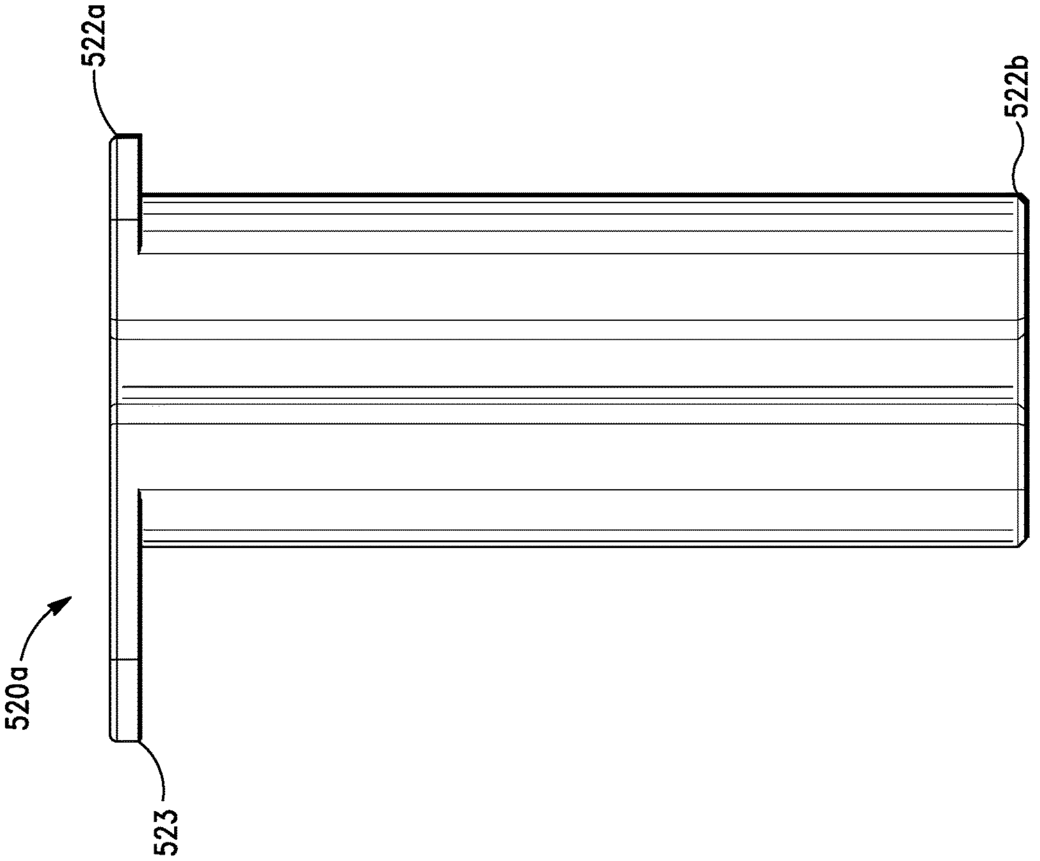
FIG. 3I is a front plan view of the drill guide shown in FIG. 3H, in accordance with the invention.
Figure 3H:
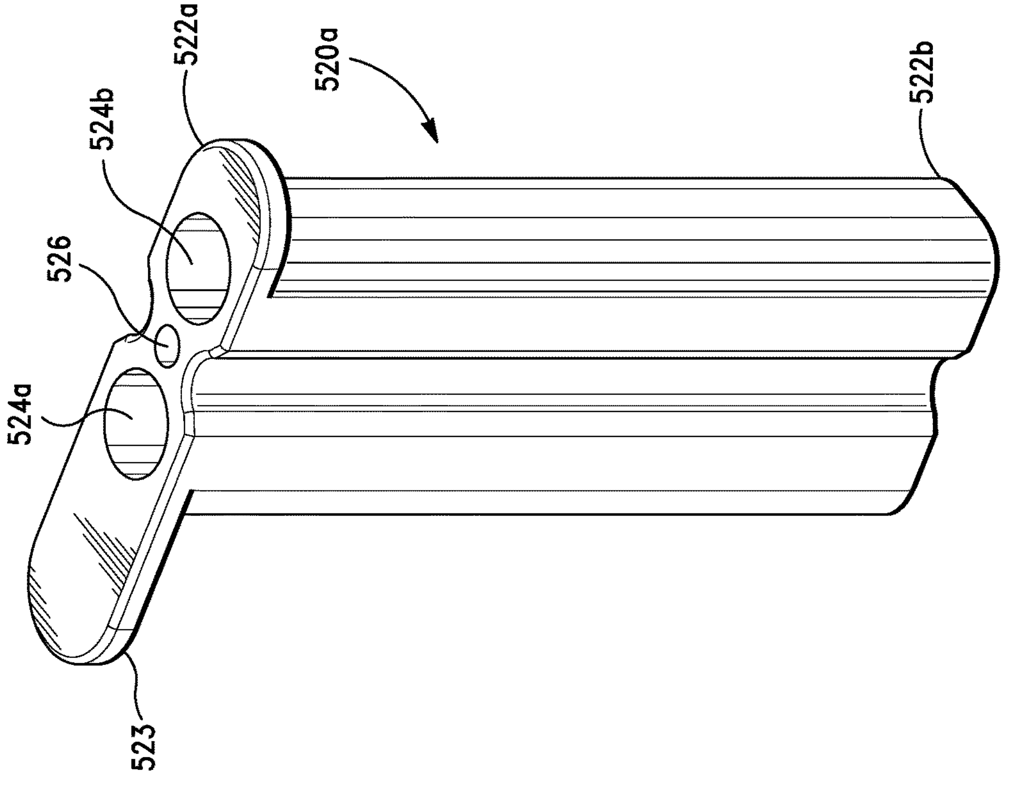
FIG. 3H is a perspective view the drill guide of the drill guide assembly shown in FIG. 3A, in accordance with the invention.

As illustrated in FIG. 3H, the drill guide 520*a* comprises proximal and distal ends 522*a*, 522*b*, a pair of drill guide lumens 524*a*, 524*b*, and a drill guide medial lumen 526; the drill guide lumens 524*a*, 524*b* and drill guide medial lumen 526 extending from the proximal end 522*a* to the distal end 522*b* of the drill guide 520*a*.

As illustrated in FIG. 3A, in a preferred embodiment, the drill guide lumens 524*a*, 524*b* are sized and configured to receive (i) the bone dislodging apparatus of the invention, i.e., drill bit 501*a*, and (ii) the drill alignment pin 530*a* shown in FIG. 3L and discussed below.

As set forth in Co-pending U.S. application Ser. No. 17/463,779, according to the invention, the drill bit 501*a* (and drill bit 501*b* shown in FIGS. 4H and 4I) can operate with various conventional manual, pneumatic, and/or electromechanical tools, such as a conventional surgical drill.

Figure 3K:
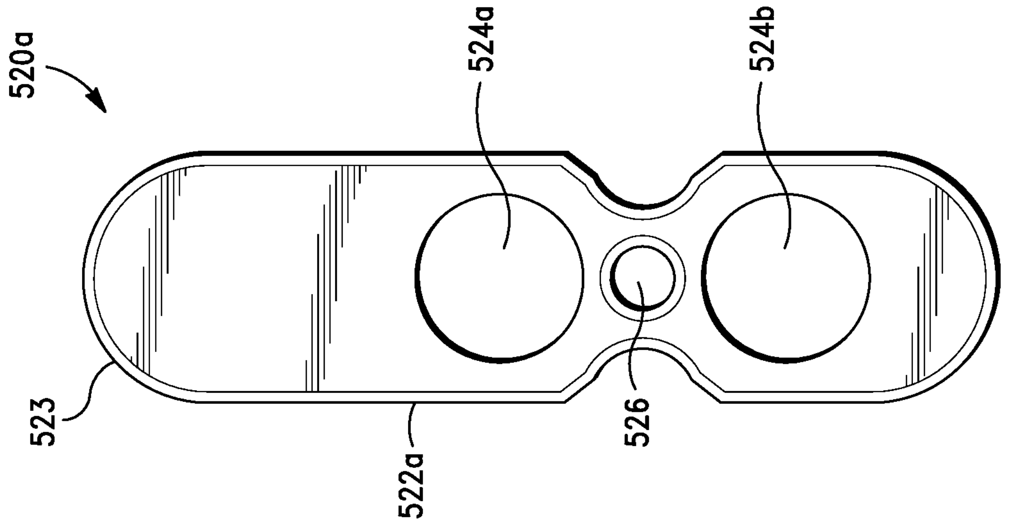
FIG. 3K is a top plan view of the drill guide shown in FIG. 3H, in accordance with the invention.
Figure 3J:
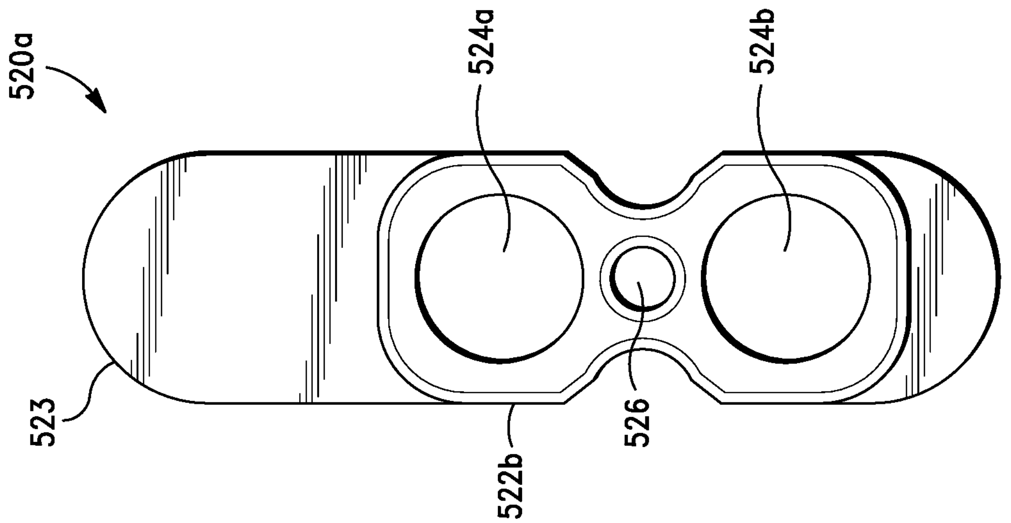
FIG. 3J is a bottom plan view of the drill guide shown in FIG. 3H, in accordance with the invention.
Figure 3L:
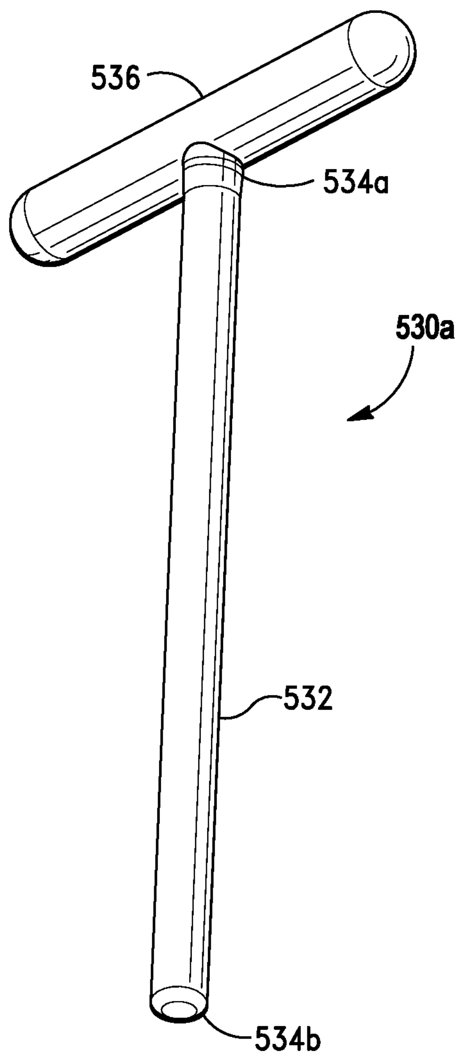
FIG. 3L is a perspective view of the embodiment of the drill alignment pin of the drill guide assembly shown in FIG. 3A, in accordance with the invention.

As illustrated in FIG. 3L, the drill alignment pin 530*a* preferably comprises an elongated guide member 532 comprising proximal and distal ends 534*a*, 534*b*. The drill alignment pin 530*a* further comprises a handle 536 that is in communication with the proximal end 534*a* of the guide member 532.

In a preferred embodiment, the drill guide medial lumen 526 is sized and configured to receive and guide the guide pin 400 of the invention.

According to the invention, the drill guide internal lumens 524*a*, 524*b* and drill guide medial lumen 526 can also be sized and configured to receive various other suitable instruments, such as surgical scopes, center punches, location pins, drill probes and drill stop assemblies, to facilitate the creation of a pilot SI joint opening.

Referring back to FIGS. 3H and 3I, in a preferred embodiment, the proximal end 522*a* of the drill guide 520*a* comprises a planar configuration comprising an extended region 523, which, as illustrated in FIG. 3A, is sized and configured to abut the proximal end 504*a* of the access sleeve 502 to position the drill guide 520*a* therein.

Figure 4A:
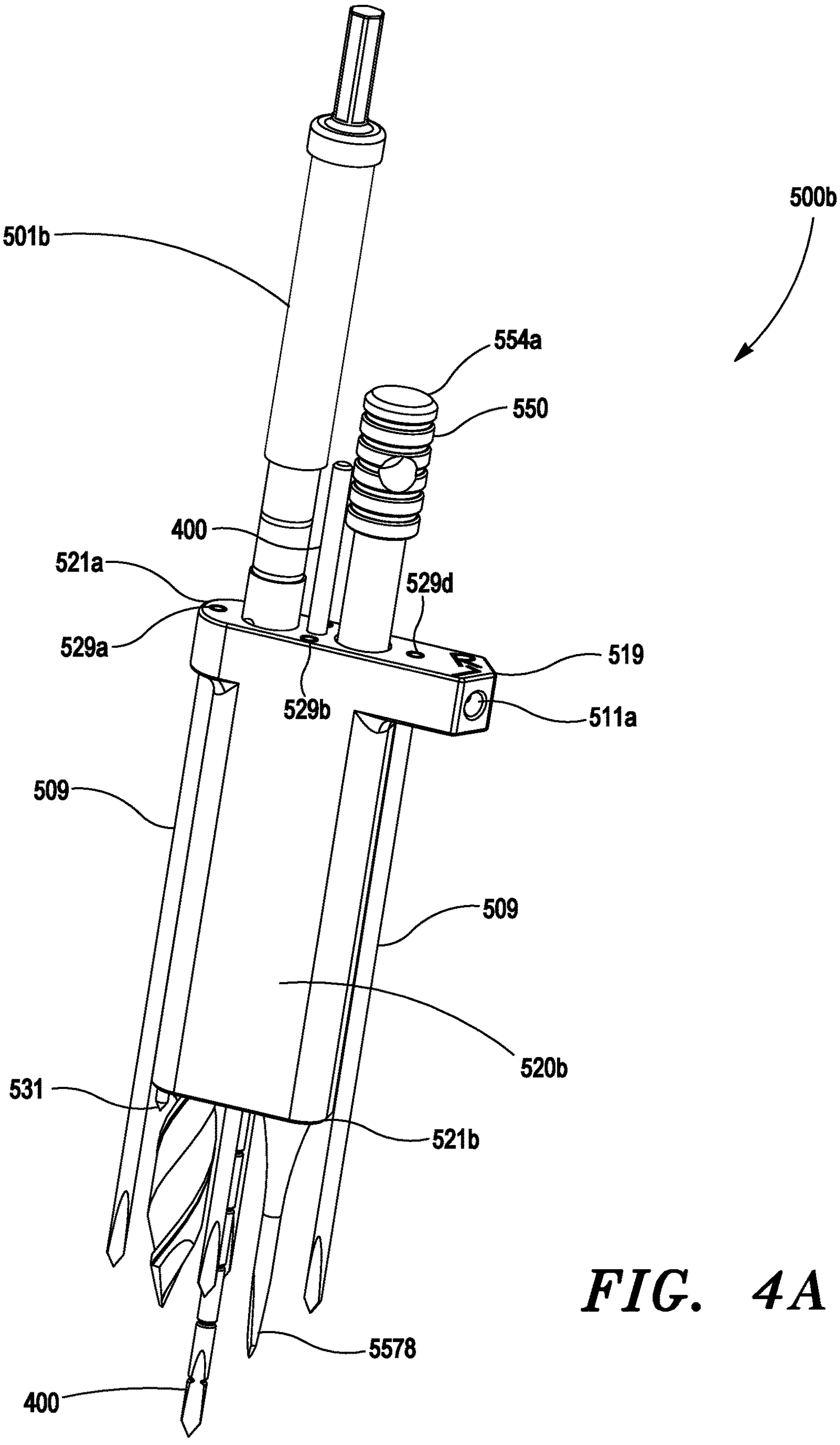
FIG. 4A is a perspective view of another embodiment of a drill guide assembly comprising another embodiment of the drill guide having a bone dislodging apparatus and a K-wire pin member disposed in the internal lumens thereof, in accordance with the invention.
Figure 4B:
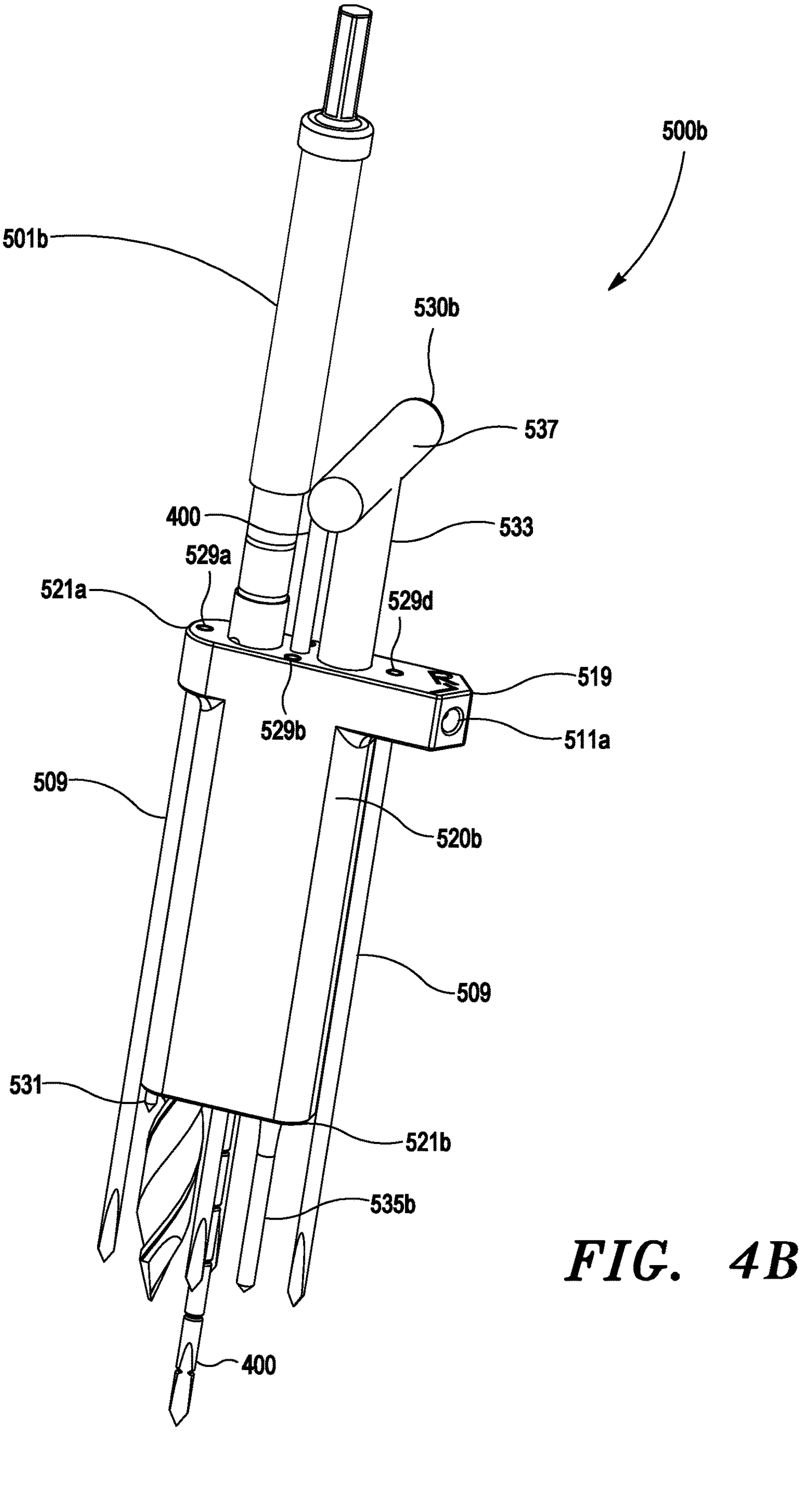
FIG. 4B is a perspective view of the drill guide assembly shown in FIG. 4A comprising the bone dislodging apparatus and a temporary fixation pin disposed in the internal lumens of the drill guide, in accordance with the invention.

Referring now to FIGS. 4A and 4B, there is shown another embodiment of a drill guide assembly of the invention (denoted "500*b*").

Figure 4D:
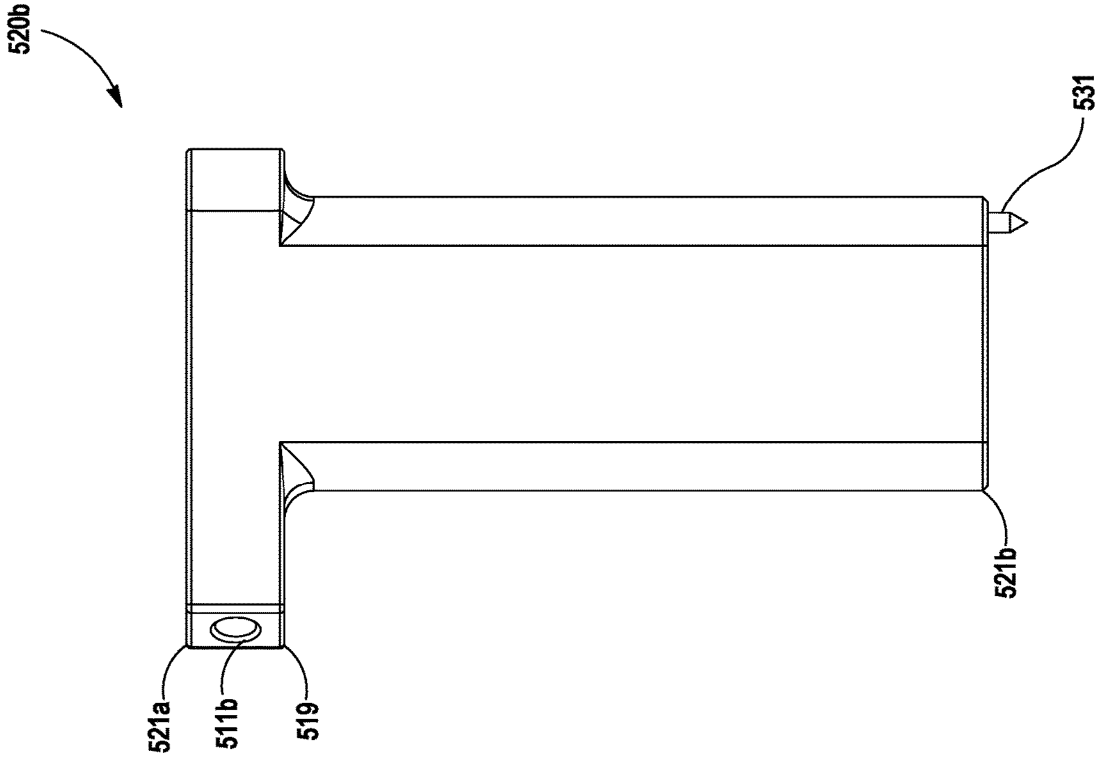
FIG. 4D is a right-side plan view of the drill guide shown in FIG. 4C, in accordance with the invention.
Figure 4C:
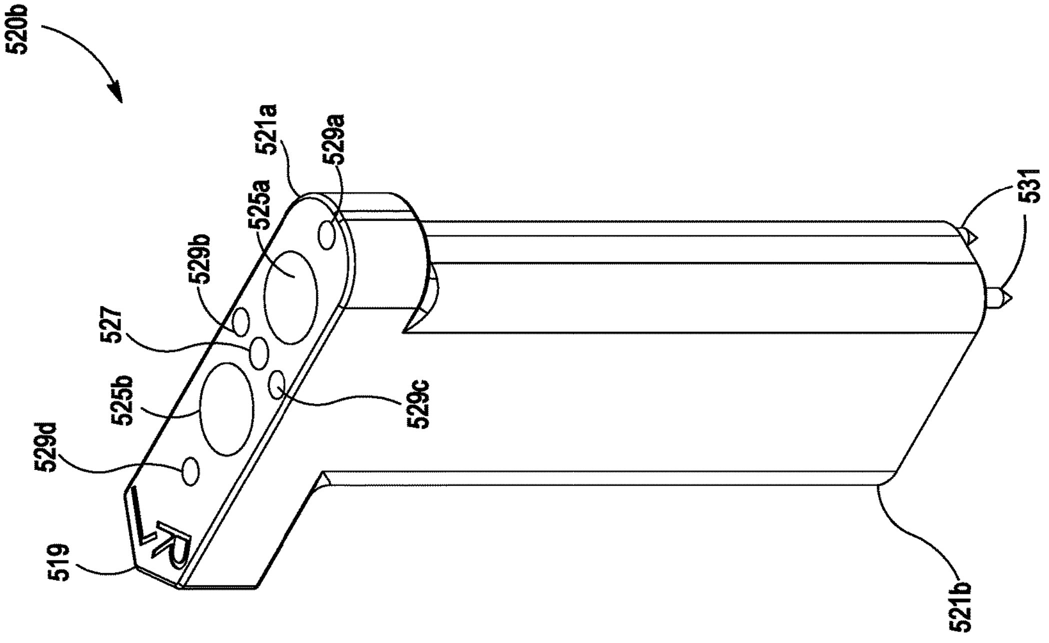
FIG. 4C is a rear perspective view of the drill guide of the drill guide assembly shown in FIGS. 4A and 4B, in accordance with the invention.
Figure 4F:
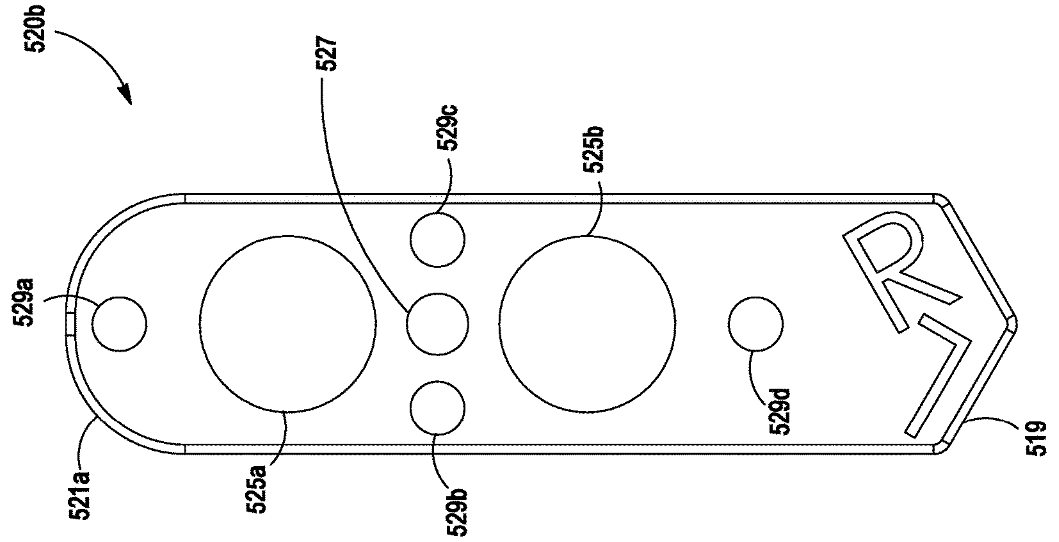
FIG. 4F is a top plan view of the drill guide shown in FIG. 4C, in accordance with the invention.
Figure 4E:
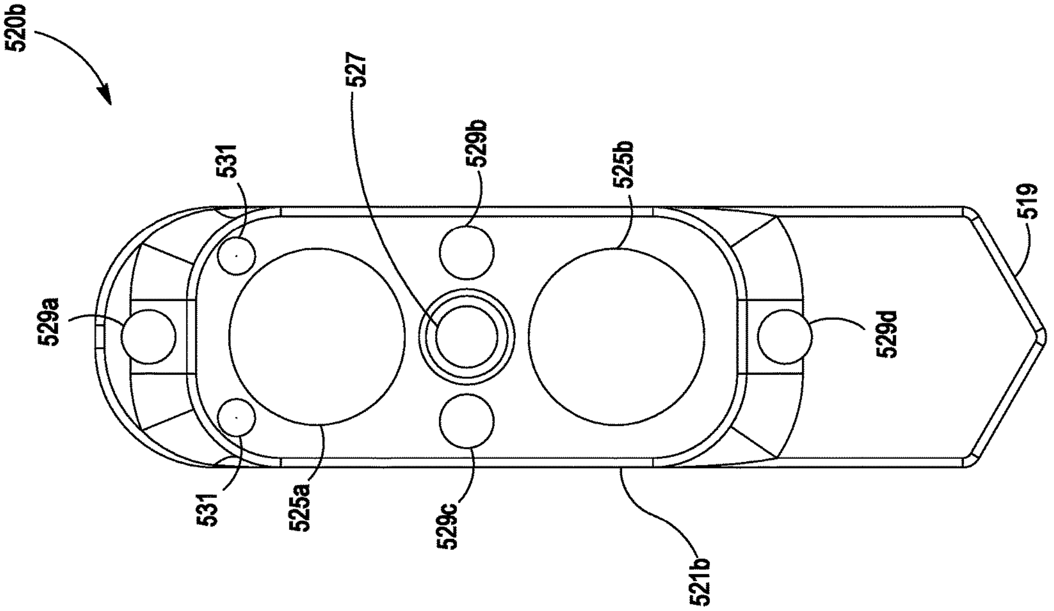
FIG. 4E is a bottom plan view of the drill guide shown in FIG. 4C, in accordance with the invention.
Figure 4G:
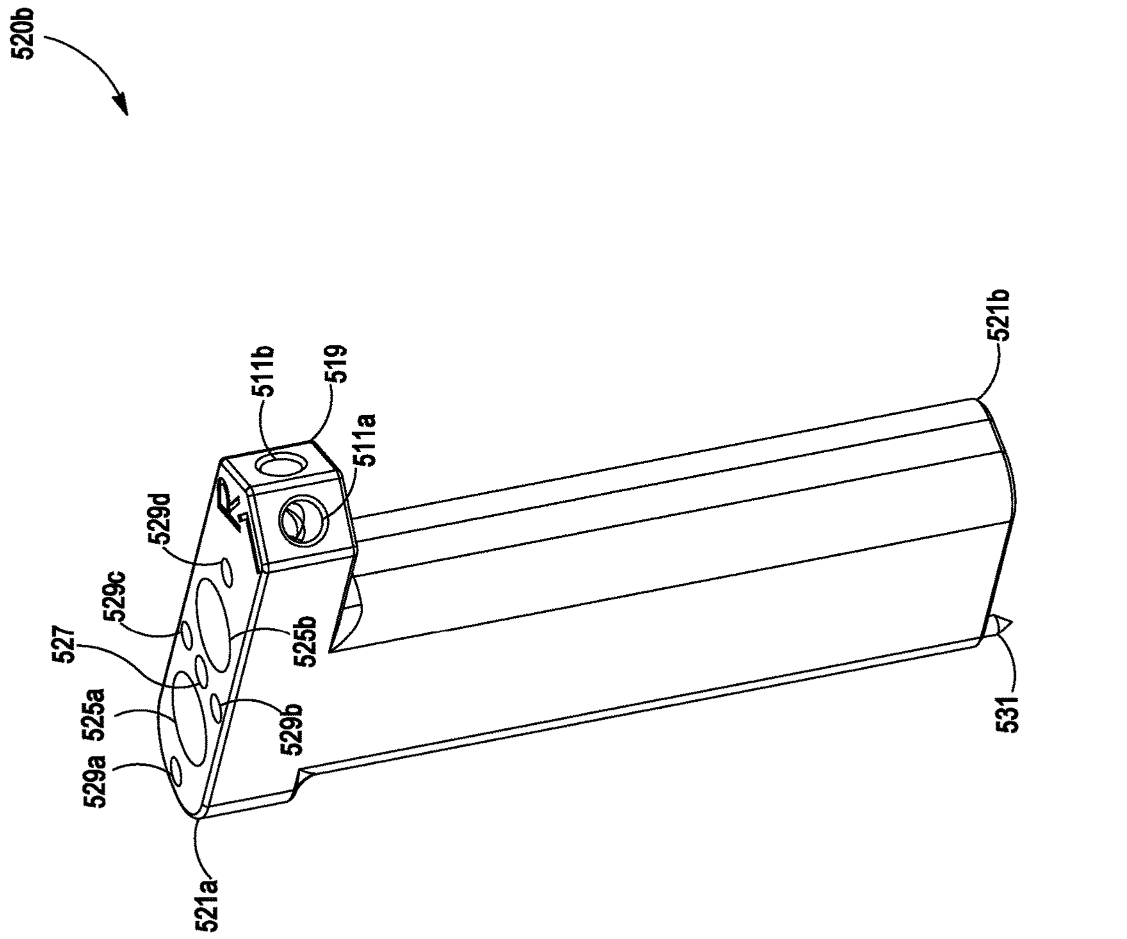
FIG. 4G is a further perspective view of the drill guide shown in FIG. 4C, in accordance with the invention.
Figure 4H:
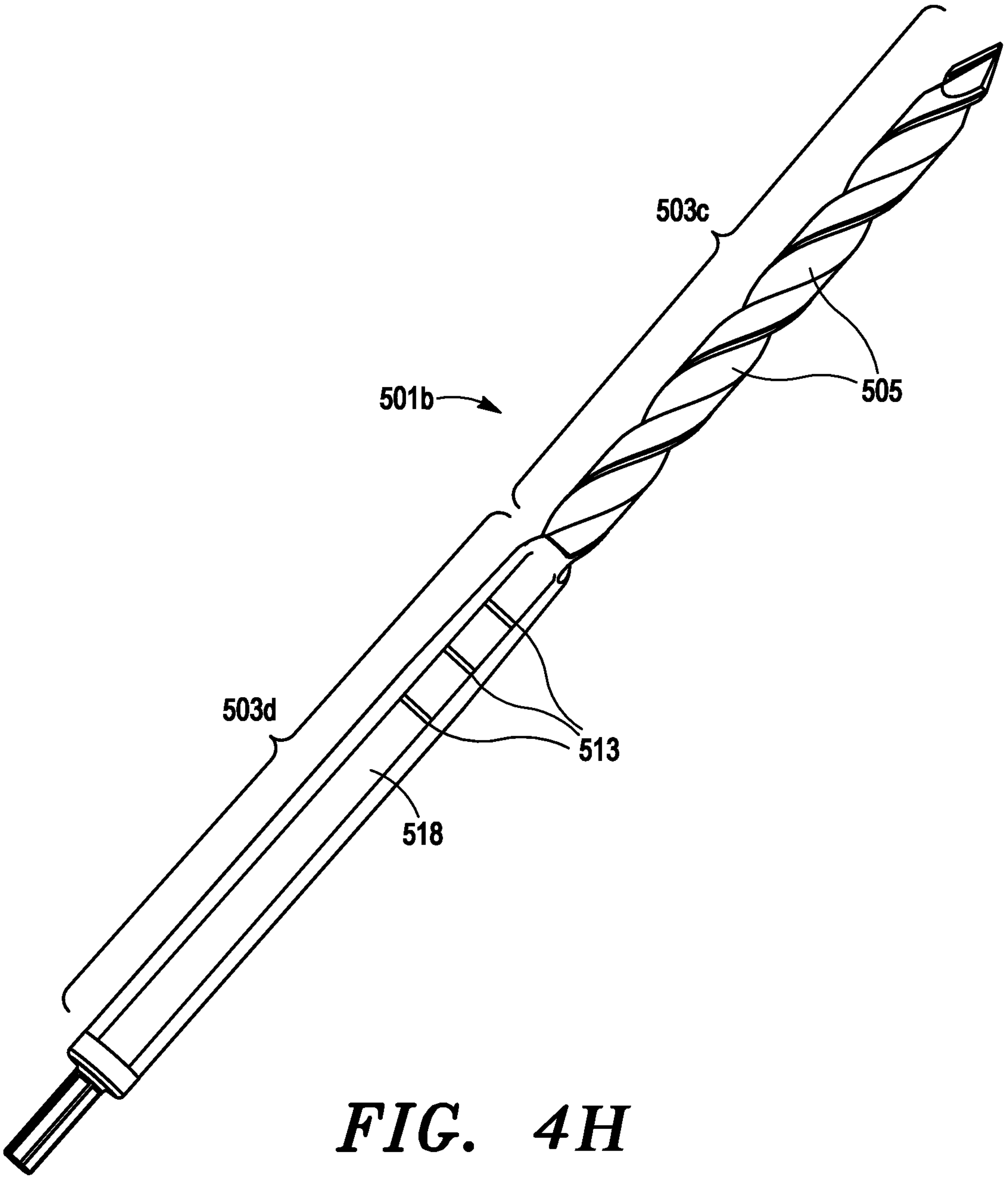
FIG. 4H is a perspective view of another embodiment of a bone dislodging apparatus, in accordance with the invention.
Figure 4I:
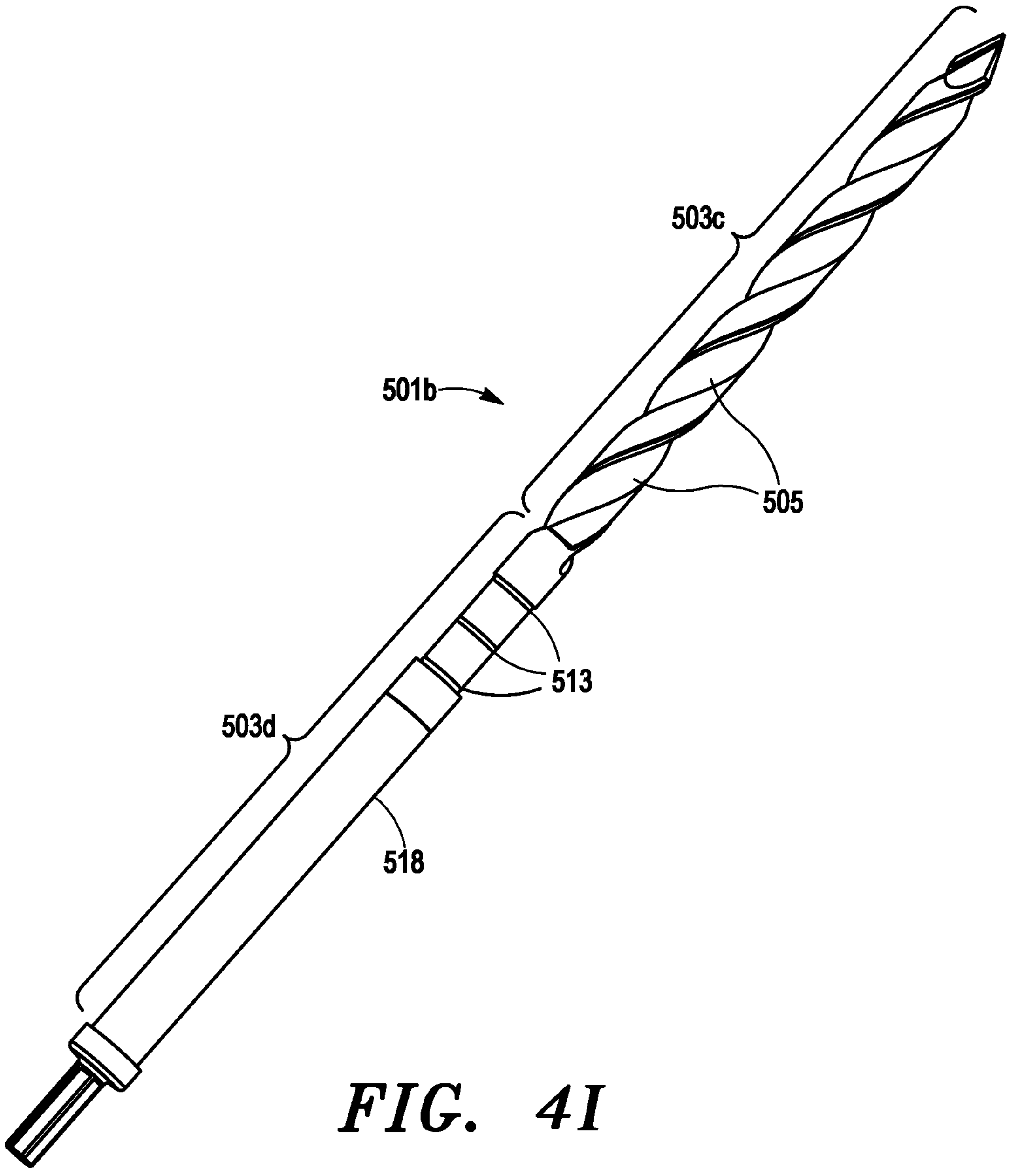
FIG. 4I is a perspective view of another embodiment of the bone dislodging apparatus shown in FIG. 4H, in accordance with the invention.
Figure 4J:
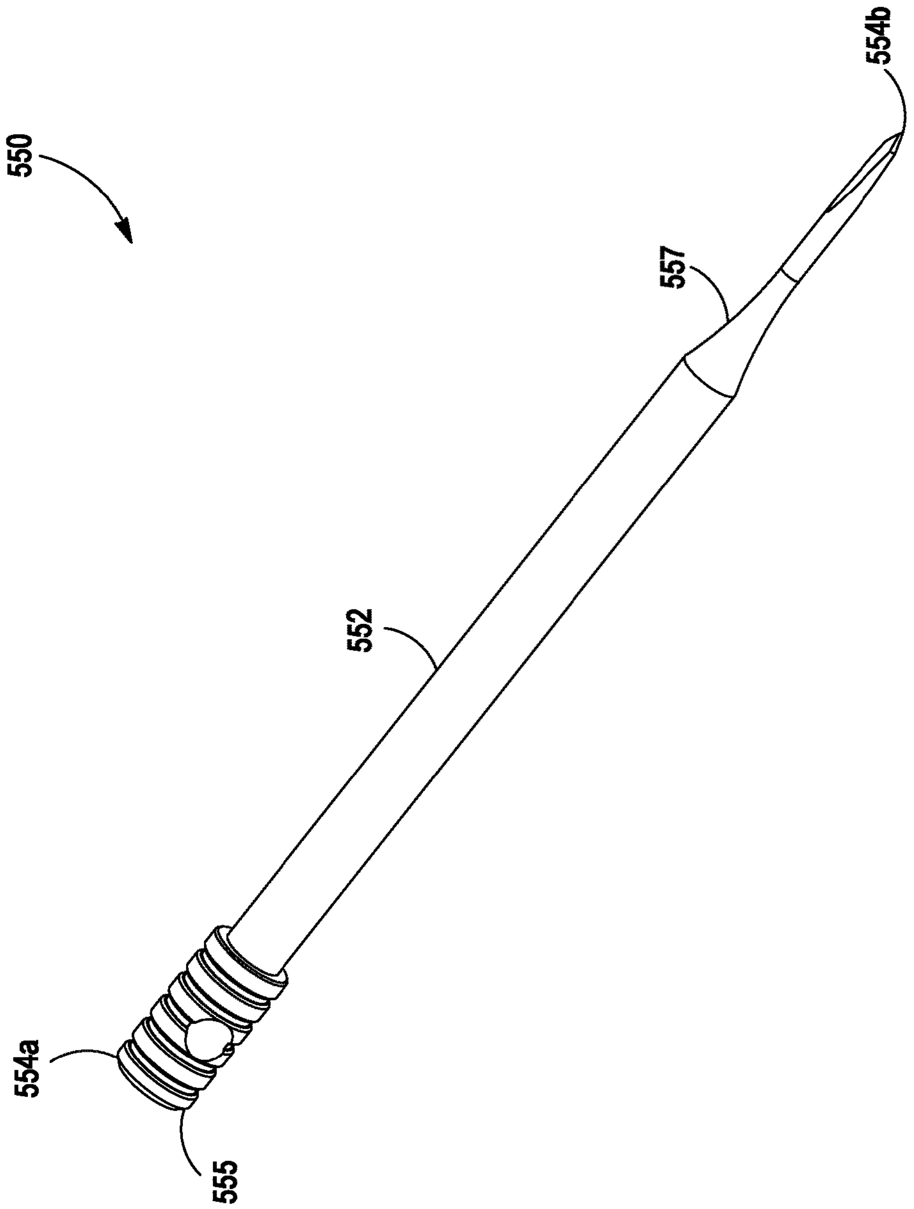
FIG. 4J is a perspective view of the K-wire member of the drill guide assembly shown in FIG. 4A, in accordance with the invention.
Figure 4K:
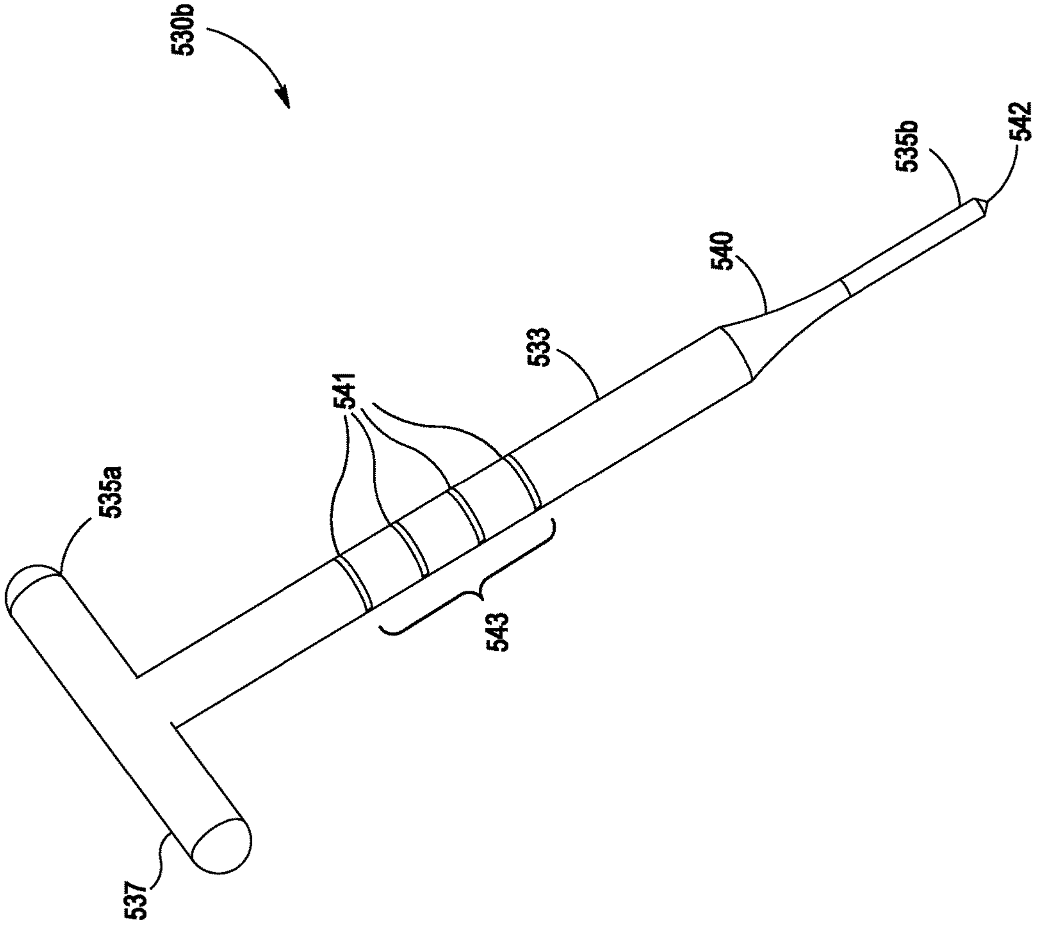
FIG. 4K is a perspective view of the temporary fixation pin of the drill guide assembly shown in FIG. 4B, in accordance with the invention.

As illustrated in FIGS. 4A and 4B, the drill guide assembly 500*b* generally comprises a drill guide 520*b*, a bone dislodging apparatus; preferably, drill bit 501*b* discussed below, a K-wire pin member 550, which is illustrated in FIG. 4J, and a drill alignment pin 530*b* (referred to herein as a "temporary fixation pin"), which is illustrated in FIG. 4K.

Referring now to FIGS. 4C-4G, there is shown a preferred embodiment of the drill guide 520*b*.

As illustrated in FIGS. 4C-4G, the drill guide 520*b* comprises proximal and distal ends 521*a*, 521*b*, a pair of drill guide lumens 525*a*, 525*b*, four (4) K-wire lumens 529*a*, 529*b*, 529*c*, 529*d*, and a drill guide medial lumen 527; the drill guide lumens 525*a*, 525*b*, four (4) K-wire lumens 529*a*,

529*b*, 529*c*, 529*d*, and drill guide medial lumen 527 extending from the proximal end 521*a* to the distal end 521*b* of the drill guide 520*b*.

As illustrated in FIG. 4B, in a preferred embodiment, the drill guide lumens 525*a*, 525*b* are similarly sized and configured to receive (i) a bone dislodging apparatus of the invention, in this instance, drill bit 501*b* shown in FIG. 4I and discussed below, and (ii) the temporary fixation pin 530*b* illustrated in FIG. 4K and discussed below.

As illustrated in FIG. 4A, in a preferred embodiment, the drill guide lumens 525*a*, 525*b* are also sized and configured to receive K-wire pin member 550 shown in FIG. 4J.

In a preferred embodiment, the drill guide medial lumen 527 is similarly sized and configured to receive and guide the guide pin 400 of the invention.

According to the invention, the drill guide lumens 525*a*, 525*b* and drill guide medial lumen 527 can similarly also be sized and configured to receive various other suitable instruments, such as surgical scopes, center punches, location pins, drill probes, and drill stop assemblies, to facilitate the creation of a pilot SI joint opening.

As illustrated in FIGS. 4C and 4D, in a preferred embodiment, the proximal end 521*a* of the drill guide 520*b* comprises an extended region 519.

As illustrated in FIGS. 4C, 4E and 4F, the proximal end 521*a* of the drill guide 520*b* comprises the four (4) K-wire lumens 529*a*, 529*b*, 529*c*, 529*d*, which extend from the proximal end 521*a* to the distal end 521*b* of the drill guide 520*b*, as illustrated in FIGS. 4E and 4F, and, as illustrated in FIG. 4A, are sized and configured to receive K-wires 509 therein.

As further illustrated in FIGS. 4E and 4F, K-wire lumens 529*a* and 529*d* are positioned on a plane that is substantially coincident with the longitudinal axis of the proximal end 521*a* of the drill guide 520*b* and K-wire lumens 529*b* and 529*c* are positioned on a plane that intersects the drill guide medial lumen 527 and is perpendicular to the plane of the K-wire lumens 529*a*, 529*d*.

As illustrated in FIG. 4G, the proximal end 521*a* of the drill guide 520*b* further comprises two (2) threaded holes 511*a*, 511*b*, which, according to the invention, are sized and configured to receive the threaded end 514 of a handle, such as the access sleeve handle 510*a* shown in FIGS. 3F and 3G (and handle 510*b* shown in FIG. 5D) and discussed above.

As further illustrated in FIGS. 4C and 4D, the distal end 521*b* of the drill guide 520*b* comprises a pair of anchor members 531 that project from the distal end 521*b* of the drill guide 520*b*. According to the invention, the anchor members 531 are designed and configured to pierce and, preferably, engage biological tissue to maintain a fixed position of the drill guide 520*b* proximate thereto.

Referring now to FIG. 4H, there is shown one embodiment of drill bit 501*b*.

As illustrated in FIG. 4H, the drill bit 501*b* similarly comprises an elongated rod structure having a proximal end region 503*d* and a bone dislodging end region 503*c*. However, as further illustrated in FIG. 4H, the proximal end region 503*d* comprises a plurality of graduated markings 513 to facilitate visual indications of the depth of the drill bit 501*b* into bone structures, i.e., SI joint bone structures, when, as discussed in detail below, the drill bit 501*b* is employed to create a SI joint pilot opening.

As further illustrated in FIG. 4H, the graduated markings 513 are thus preferably disposed on the proximal end region 503*d* of the drill bit 503*b* proximate the bone dislodging end region 503*c*.

In a preferred embodiment, the graduated markings 513 are spaced approximately 10 mm apart and, by virtue of unique configuration of the drill guide 520*b* and the location of the graduated markings 513, can be directly visualized and, hence, read during creation of pilot SI joint openings with the drill bit 501*b*.

The graduated markings 513 are also readily detectable and, hence, readable via a conventional image capture apparatus, such as a fluoroscopy and radiography system.

Referring now to FIG. 4I, there is shown a further embodiment of drill bit 501*b*. As illustrated in FIG. 4I, the drill bit 501*b* similarly comprises an elongated rod structure having the proximal end region 503*d*, bone dislodging end region 503*c* and graduated markings 513.

As further illustrated in FIG. 4I, in this embodiment, the proximal end region 503*d* of the drill bit 501*b* comprises a larger circumference than the bone dislodging end region 503*c* to enhance alignment of the drill bit 501*b* in the larger lobe portions 564*a*, 564*b* of the prosthesis internal access opening 560 in the drill guide 520*c* (and drill guides 520*d* and 520*e*, discussed below).

To abate premature wear of the graduated markings 513 and, hence, compromised detection and readability of the markings 513 when the drill bit 501*b* is repeatedly advanced into and through bone structures, the graduated markings 513 are preferably positioned on a flat region 518 on the proximal end region 503*d* of the drill bit 501*b*, whereby the graduated markings 513 are inset relative to the outer periphery of the proximal end region 503*d* of the drill bit 501*b*.

Referring now to FIG. 4J, there is shown one embodiment of a K-wire pin member 550.

As illustrated in FIG. 4J, the K-wire pin member 550 comprises an elongated cylindrical shaped member 552 comprising proximal and distal ends 554*a*, 554*b*, a head region 555 disposed on the proximal end 554*a*, and a K-wire tip 557.

As further illustrated in FIG. 4J, in some embodiments of the invention, the head region 555 of the elongated member 552 comprises a textured configuration to facilitate insertion of the K-wire pin member 550 into SI joint structures.

Referring now to FIG. 4K, there is shown another embodiment of a drill alignment pin, i.e., temporary fixation pin, 530*b* that is preferably employed with drill guide 520*b*. According to the invention, the temporary fixation pin 530*b* can also be employed with drill guide 520*a*.

As illustrated in FIG. 4K, the temporary fixation pin 530*b* preferably comprises an elongated guide member 533 comprising proximal and distal ends 535*a*, 535*b*, and a handle 537 that is disposed on the proximal end 535*a* of the guide member 533.

As further illustrated in FIG. 4K, the elongated guide member 533 of the temporary fixation pin 530*b* comprises a center region 543 similarly comprising a plurality of graduated markings 541, which preferably are readily detectable and, hence, readable via a conventional image capture apparatus, and a distal tapered end 540 that tapers to a point 542, which is adapted and configured to pierce bone structures and, as discussed below, when employed during creation of SI joint pilot openings, further supports and stabilizes the drill guide 520*b*.

According to the invention, the drill guide assembly 500*b* provides several advantages over drill guide 500*a*. Among the advantages are the following:

an access sleeve, such as access sleeve 502 shown in FIG. 3B, is not required;

only a minimal incision, i.e., an incision length in the range of 2.0 cm to 3.0 cm, is required to create the pilot openings in the SI joint structures and implant a SI joint prosthesis therein;

direct visualization of the drill bit 501*b* and, hence, markings (i.e., drill bit depth markings) 513 thereon is provided during creation of pilot SI joint openings;

direct (and optimal) visualization of the SI joint structures is provided after creation of the pilot openings in the SI joint structures; and consistent, optimal arthrodesis of the dysfunctional SI joint is achieved after placement of a SI joint prosthesis therein.

Figure 5A:
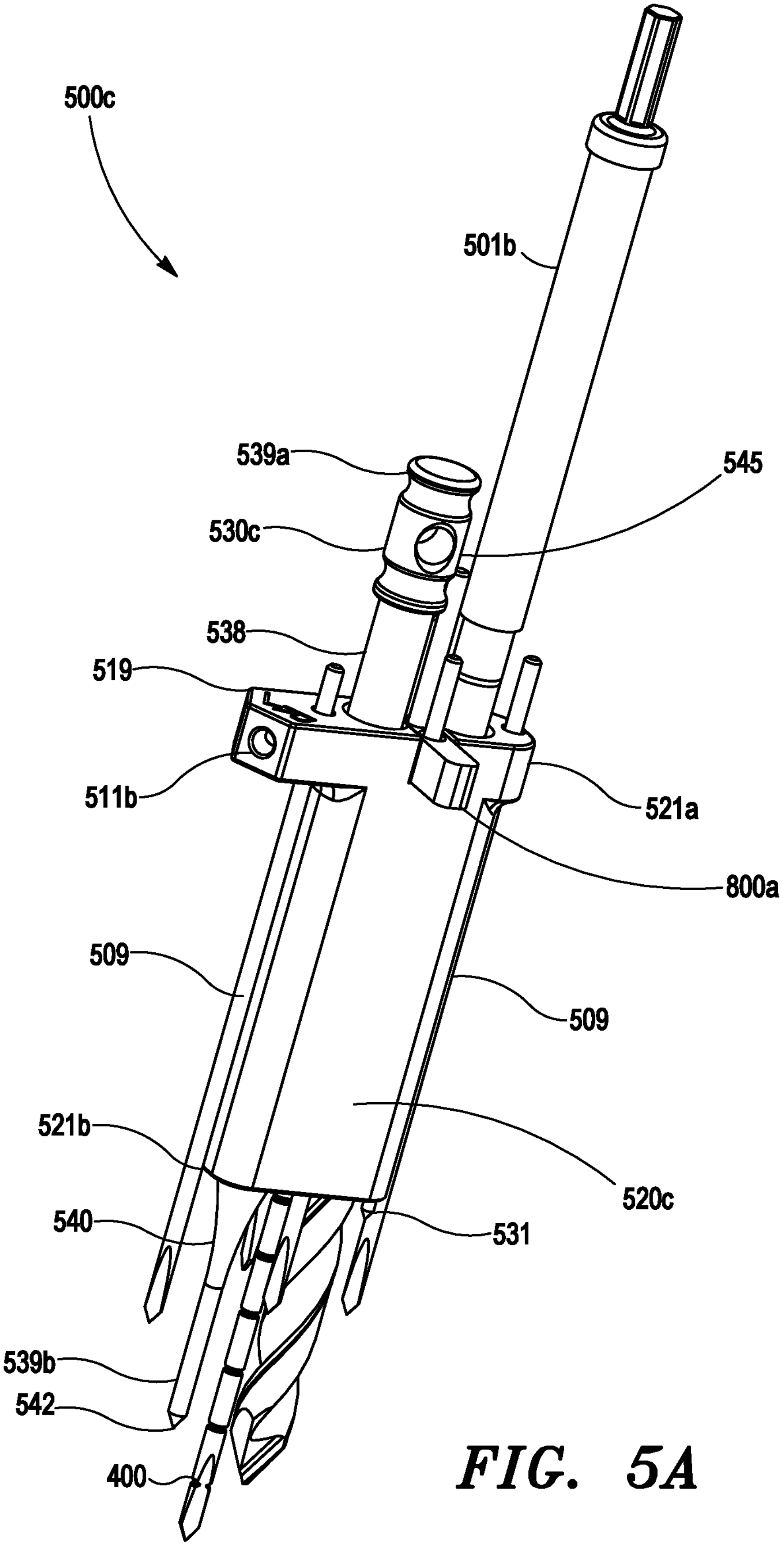
FIG. 5A is a perspective view of another embodiment of a drill guide assembly comprising yet another embodiment of the drill guide having an elongated guide member, bone dislodging apparatus, and another embodiment of a temporary fixation pin disposed in the prosthesis internal access opening thereof, in accordance with the invention.
Figure 5B:
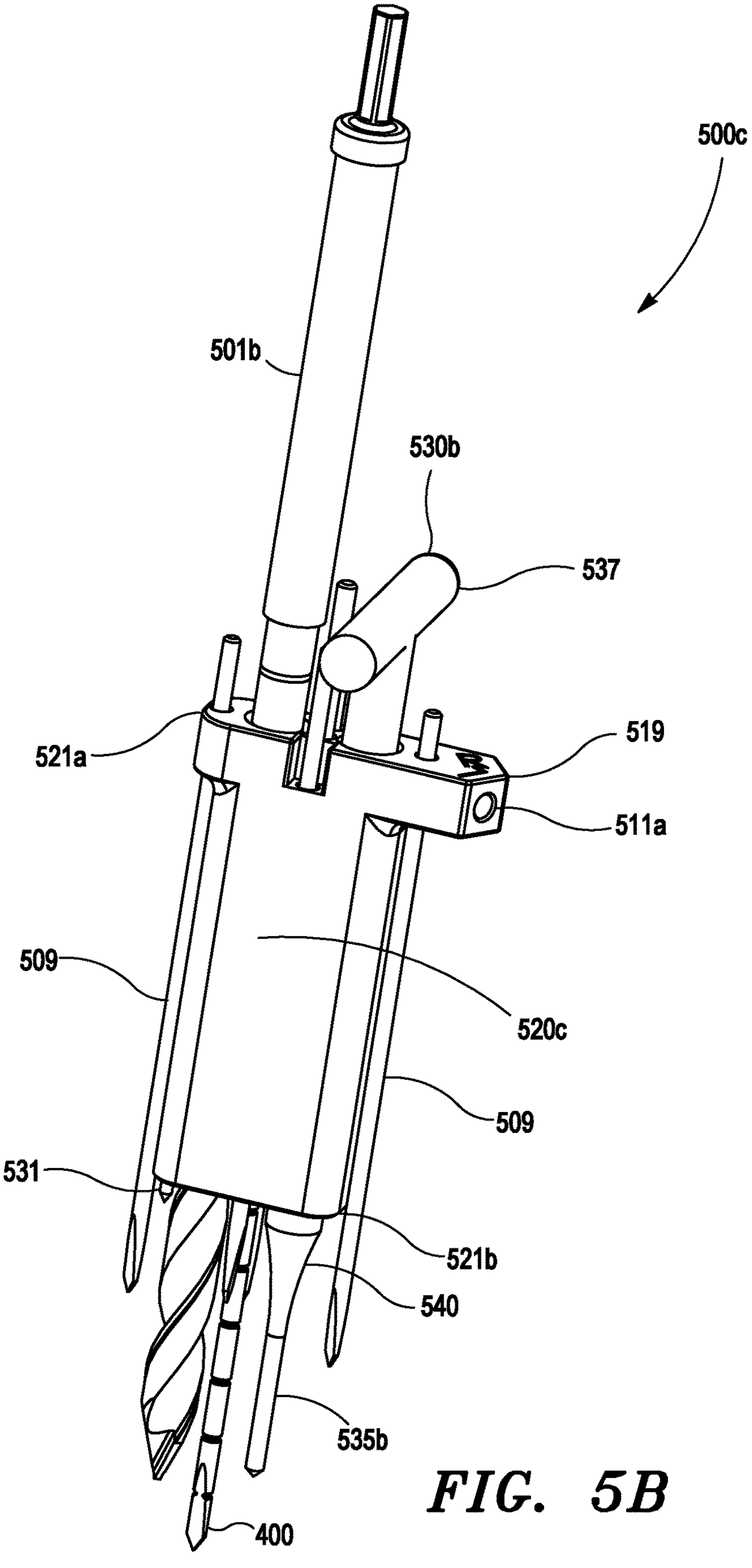
FIG. 5B is a perspective view of the drill guide assembly shown in FIG. 5A comprising the elongated guide member, bone dislodging apparatus, and the embodiment of the temporary fixation pin shown in FIG. 4K disposed in the drill guide, in accordance with the invention.
Figure 5C:
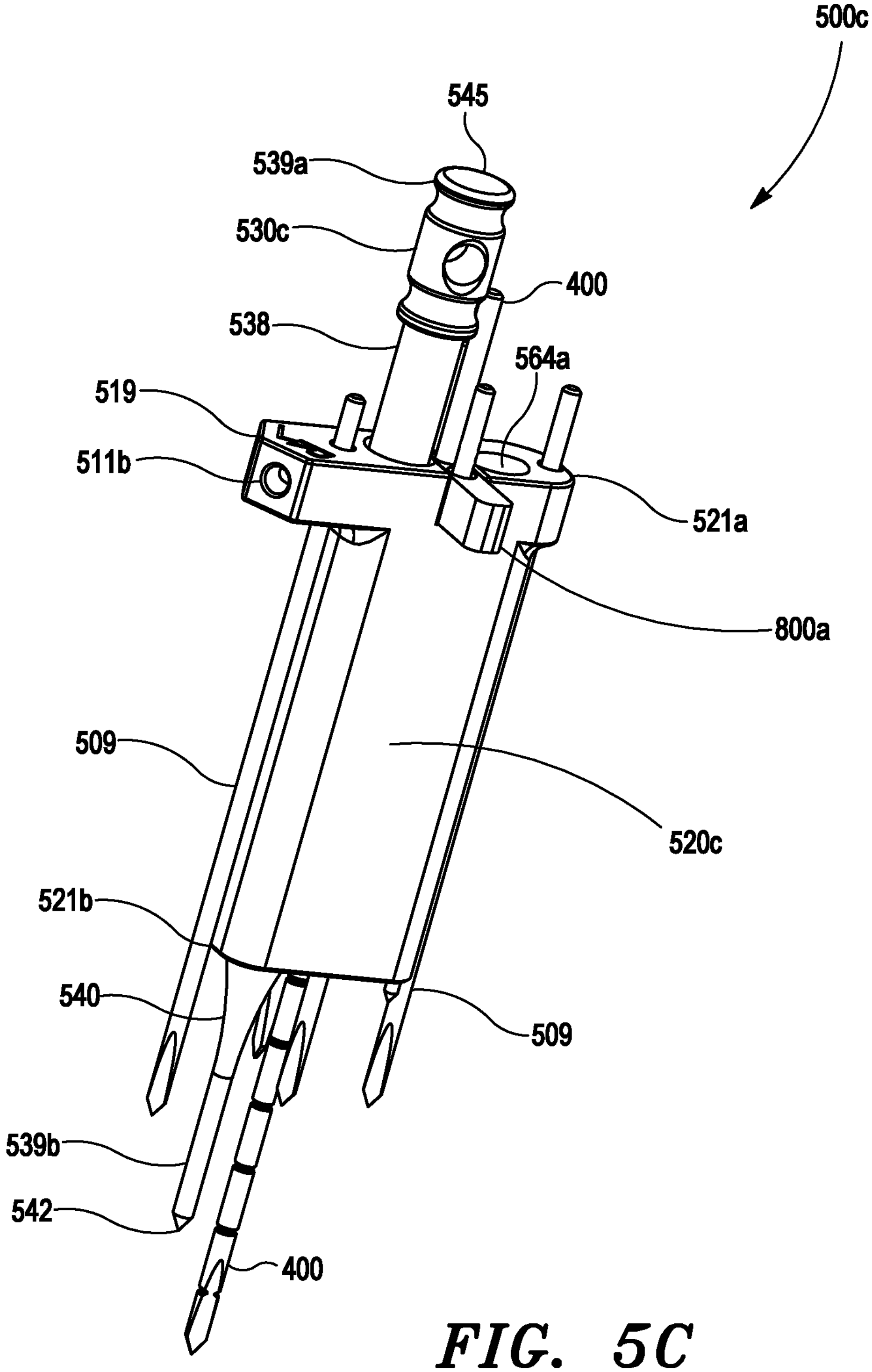
FIG. 5C is a perspective view of the drill guide assembly shown in FIG. 5A comprising the elongated guide member and temporary fixation pin shown in FIG. 4K disposed in the prosthesis internal access opening of the drill guide, in accordance with the invention.

Referring now to FIGS. 5A-5C, there is shown another embodiment of a drill guide assembly of the invention (denoted "500*c*").

As illustrated in FIGS. 5A and 5B, the drill guide assembly 500*c* generally comprises a drill guide 520*c*, a bone dislodging apparatus; preferably, drill bit 501*b* illustrated in FIG. 4I and discussed above, temporary fixation pin 530*b*, which is illustrated in FIG. 4K and also discussed above, and a temporary fixation pin 530*c*.

In some embodiments, the drill guide assembly 500*c* further comprises K-wire pin member 550, which is shown in FIG. 4J, and drill alignment pin 530*a*, which is shown in FIG. 3K.

As illustrated in FIGS. 5A and 5C, the temporary fixation pin 530*c* comprises proximal and distal ends 539*a*, 539*b*, and a similar elongated body as K-wire pin member 550 shown in FIG. 4J and a distal tapered end 540 that tapers to a point 542, which is similar to the end region of temporary fixation pin 530*b* shown in FIG. 4K.

As discussed in detail below, in some embodiments, the temporary fixation pin 530*c* is employed as a bone tamp to provide a guide recess to position or guide a bone dislodging member of the invention into a bone structure and abate undesired trajectories of the bone dislodging member.

As illustrated in FIGS. 5H-5L, the drill guide 520*c* similarly comprises proximal and distal ends 521*a*, 521*b* and the four (4) K-wire lumens 529*a*, 529*b*, 529*c*, 529*d*, which similarly extend from the proximal end 521*a* to the distal end 521*b* of the drill guide 520*c*.

As illustrated in FIG. 5A and discussed in detail below, the drill guide 520*c* further comprises an elongated guide member 800*a*.

Figure 5D:
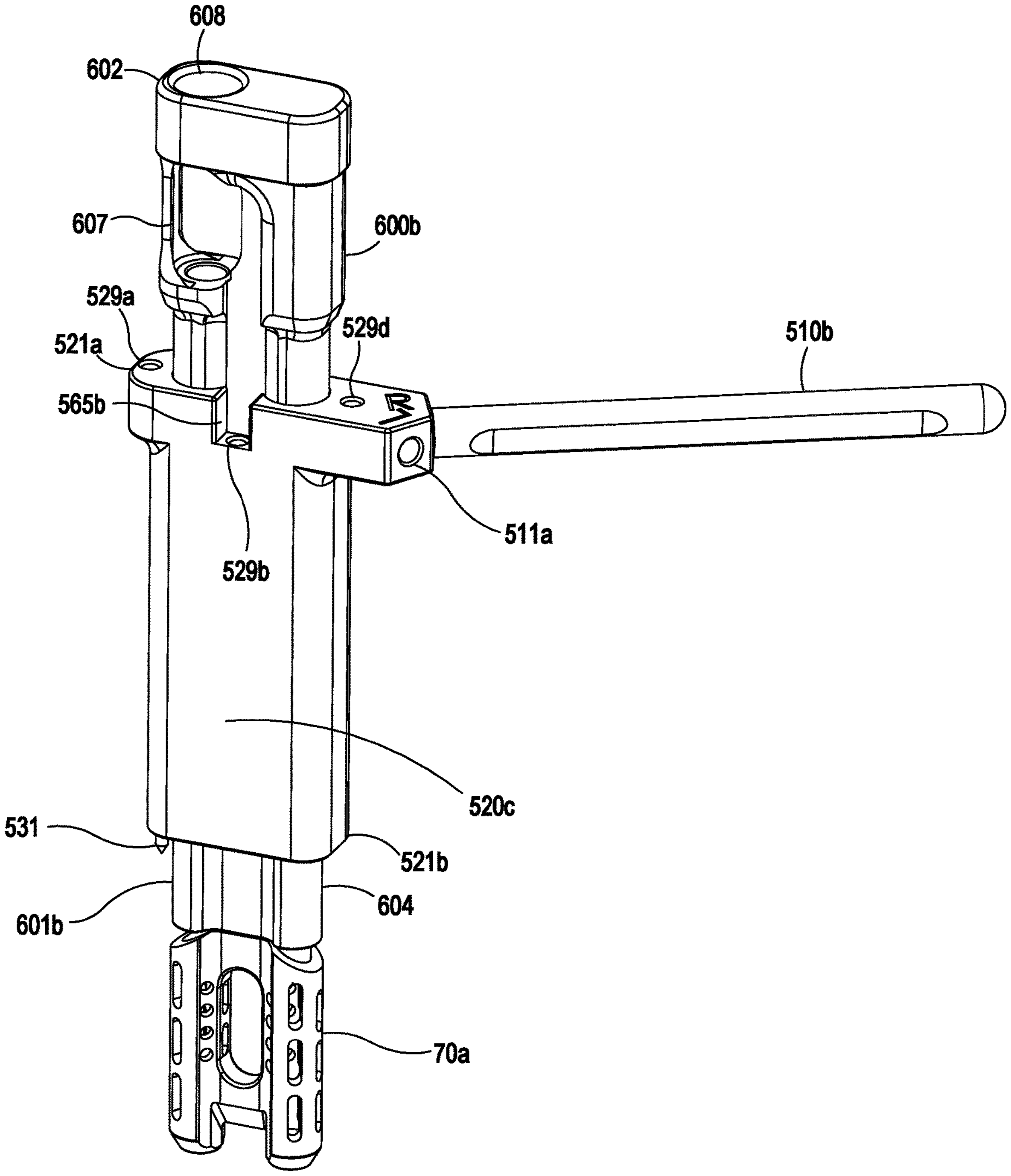
FIG. 5D is a perspective view of the drill guide shown in FIG. 5A showing a handle in communication therewith and a prosthesis deployment member with a SI joint prosthesis engaged thereto disposed in the prosthesis internal access opening of the drill guide, in accordance with the invention.
Figure 5E:
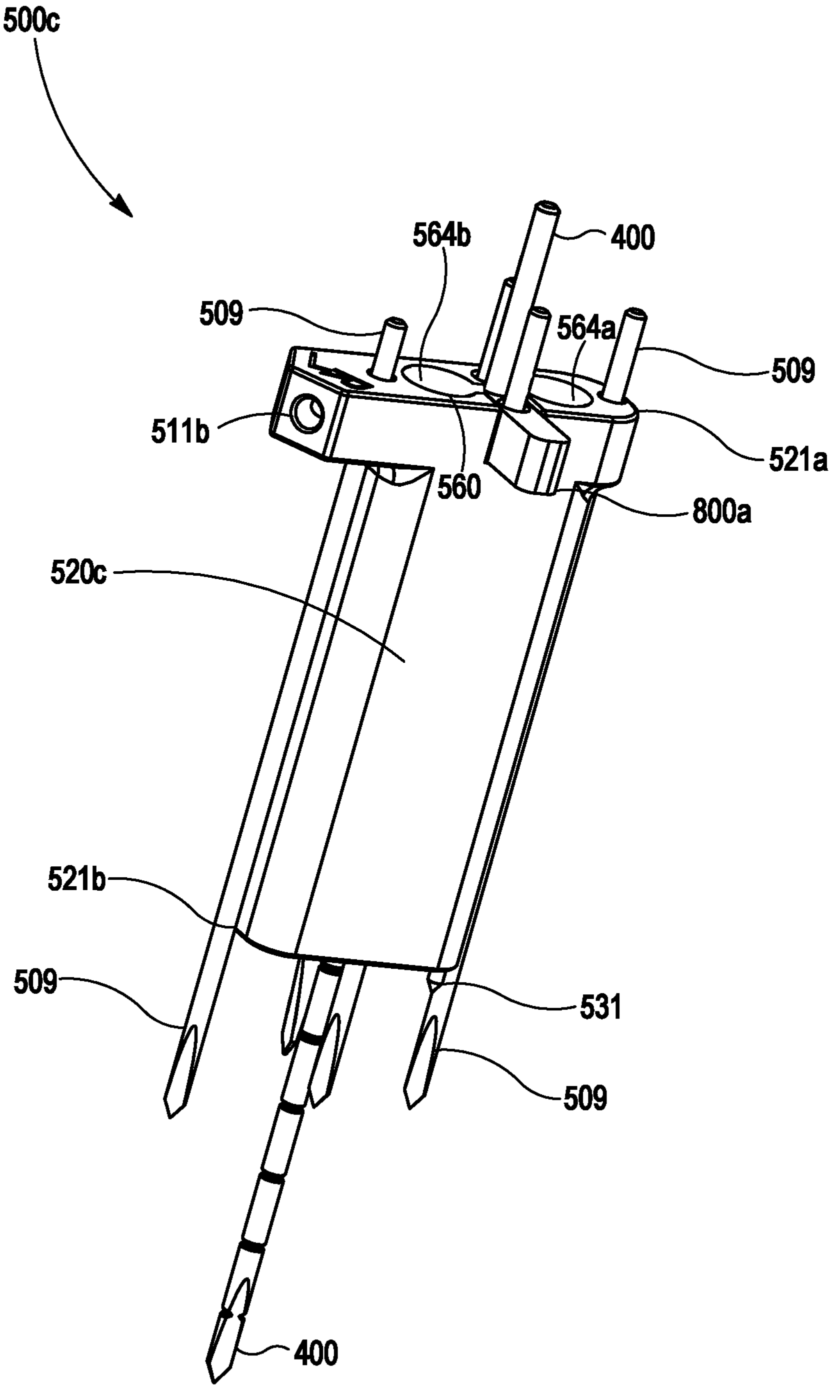
FIG. 5E is another perspective view of the drill guide shown in FIG. 5A showing the elongated guide member disposed in the prosthesis internal access opening thereof and a plurality of K-wires disposed in the K-wire lumens thereof, in accordance with the invention.
Figure 5G:
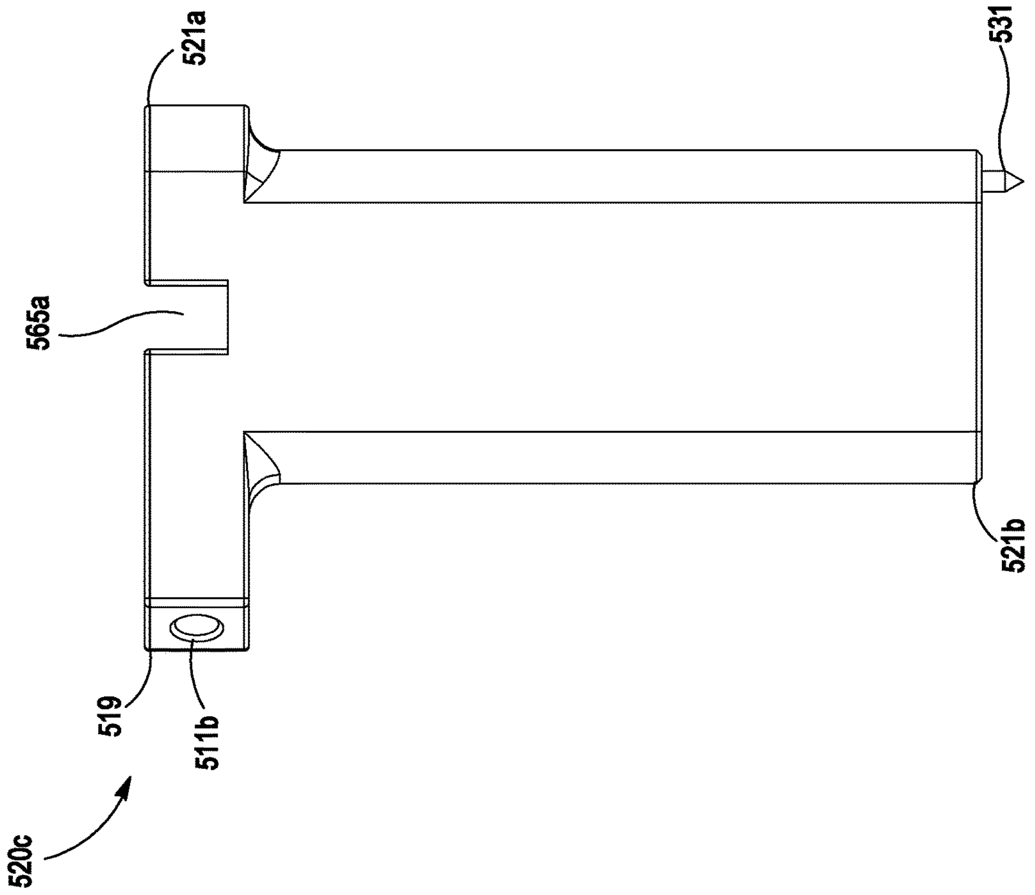
FIG. 5G is a right-side plan view of the drill guide shown in FIG. 5F, in accordance with the invention.
Figure 5F:
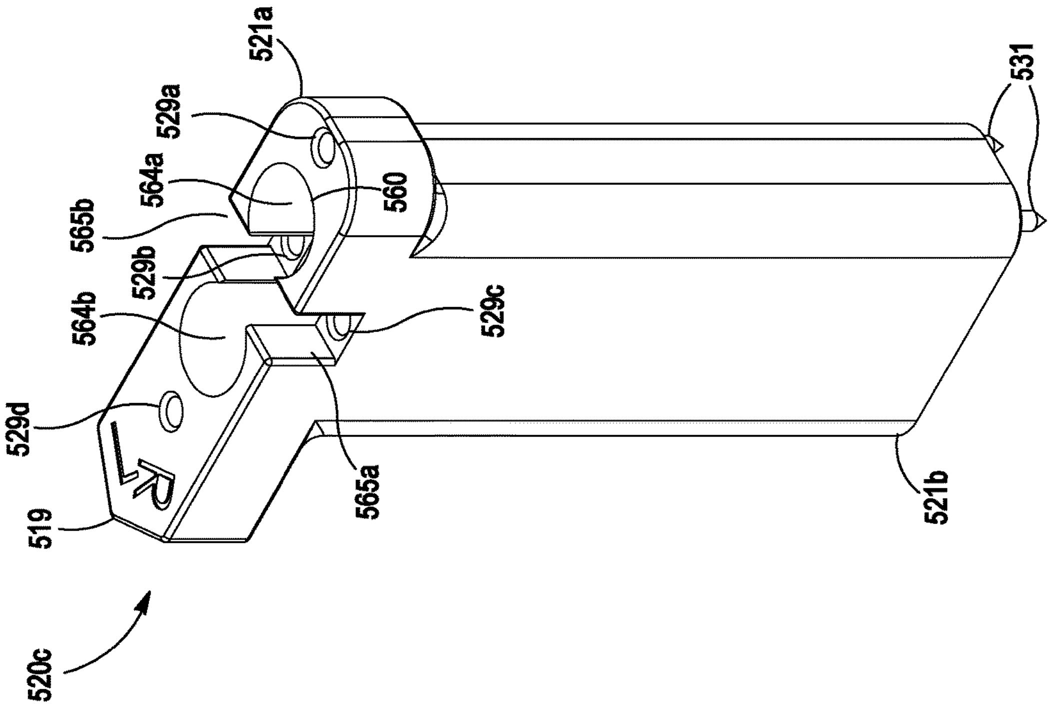
FIG. 5F is a rear perspective view of the drill guide shown in FIG. 5A, in accordance with the invention.
Figure 5I:
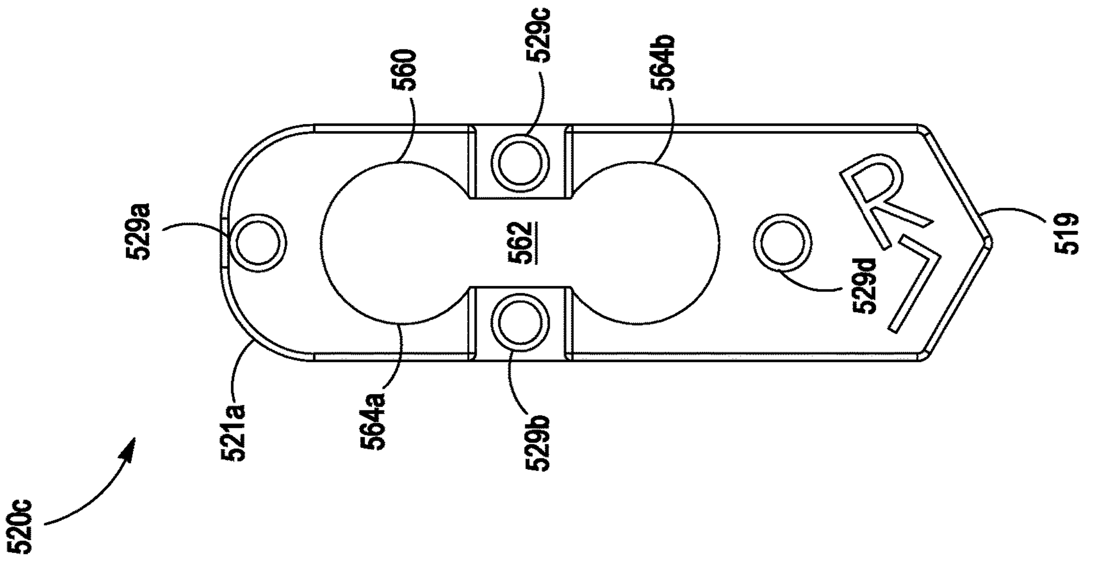
FIG. 5I is a top plan view of the drill guide shown in FIG. 5F, in accordance with the invention.
Figure 5H:
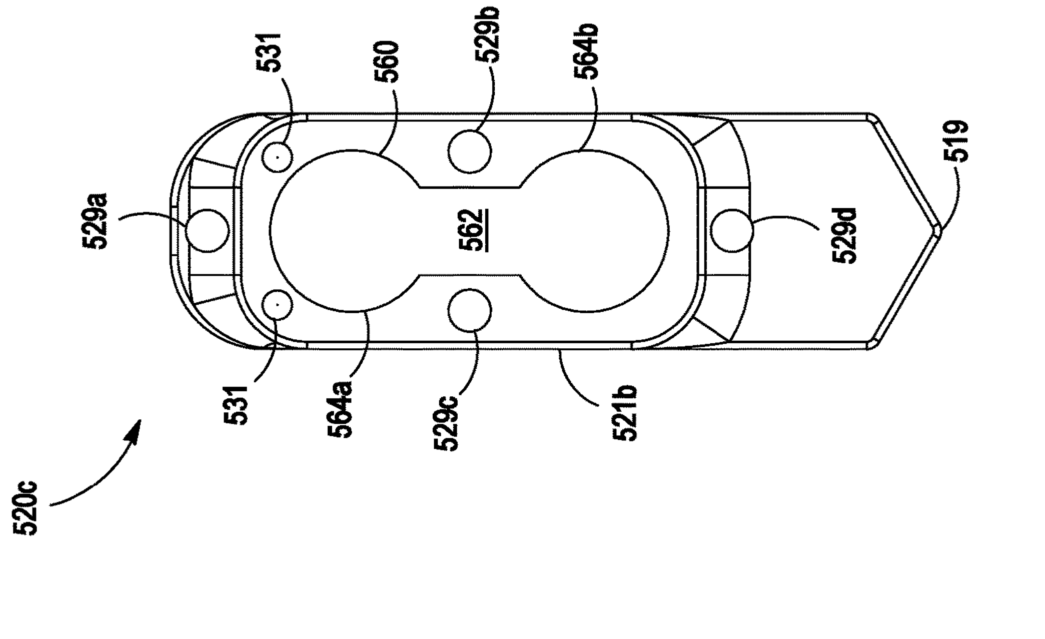
FIG. 5H is a bottom plan view of the drill guide shown in FIG. 5F, in accordance with the invention.

As illustrated in FIGS. 5H and 5I, the drill guide 520*c* comprises a prosthesis internal access opening 560, which, as discussed in detail below, is sized and configured to receive and position a SI joint prosthesis of the invention therein.

As also illustrated in FIG. 5D and discussed below, the prosthesis internal access opening 560 is also sized and configured to receive and position a prosthesis deployment assembly of the invention; particularly, prosthesis deployment assembly 600*b*, therein.

As illustrated in FIGS. 5H and 5I, the prosthesis internal access opening 560 extends from the proximal end 521*a* to the distal end 521*b* of the drill guide 520*c* and comprises a "dogbone" or "bi-lobe" cross-sectional shape comprising contiguous first and second lobe portions 564*a*, 564*b* connected by a medial portion 562.

As illustrated in FIGS. 5A and 5C, in a preferred embodiment, the medial portion 562 of the prosthesis internal access opening 560 is sized and configured to receive the elongated guide member 800*a* of drill guide 520*c*.

Figure 5K:
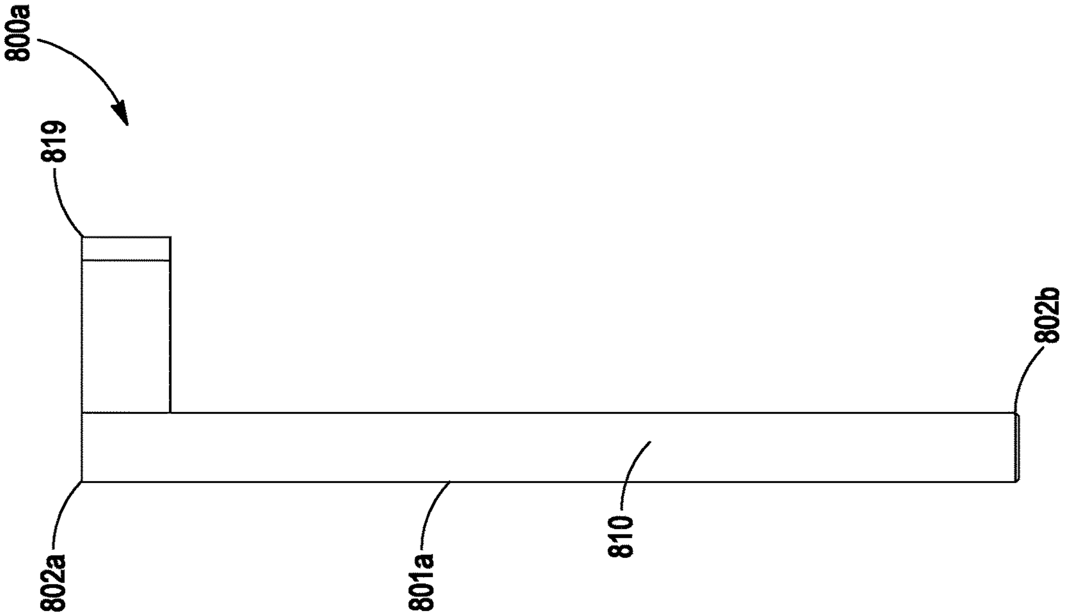
FIG. 5K is a left-side plan view of the elongated guide member shown in FIG. 5J, in accordance with the invention.
Figure 5J:
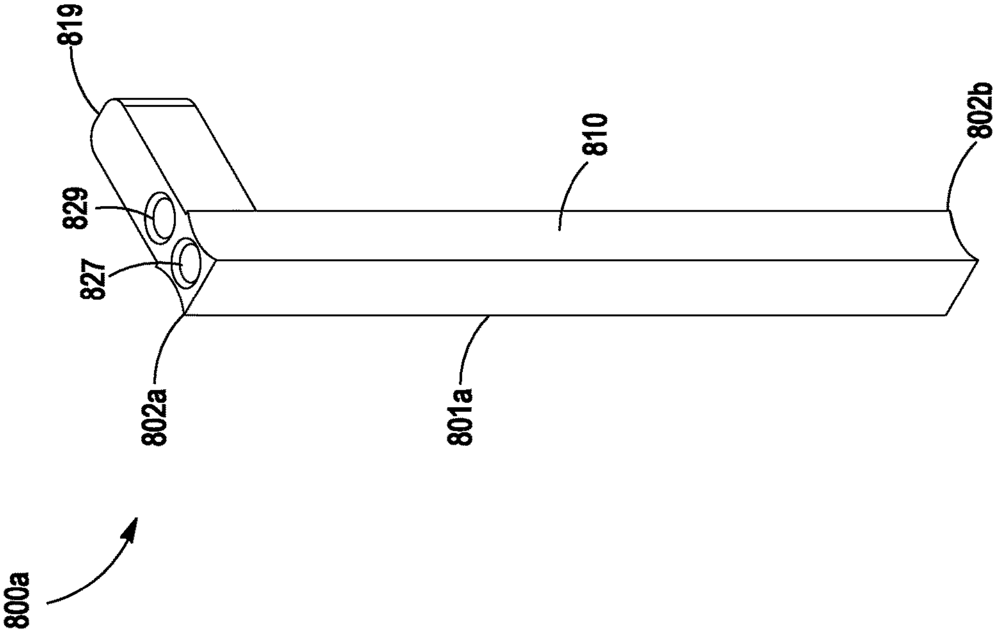
FIG. 5J is a rear perspective view of the elongated guide member shown in FIG. 5A, in accordance with the invention.

Referring now to FIGS. 5J and 5K, there is shown one embodiment of elongated guide member 800*a*.

As illustrated in FIGS. 5J and 5K, the elongated guide member 800*a* preferably comprises an elongated body 801*a* comprising proximal and distal ends 802*a*, 802*b* and an extended, substantially perpendicular end region 819 that is disposed on the proximal end 802*a* of the guide member 800*a*.

As further illustrated in FIGS. 5J and 5K, the elongated body 801*a* of the guide member 800*a* preferably comprises opposed concave regions 810 having a curvature substantially similar to the outer periphery of the first and second lobe portions 564*a*, 564*b* of the prosthesis internal access opening 560 of the drill guide 520*c*.

As additionally illustrated in FIGS. 5J and 5K, in a preferred embodiment, the elongated guide member 800*a* further comprises a guide member lumen 827 that extends through the guide member 800*a*, i.e., the elongated body 801*a* thereof, and is sized and configured to receive a guide pin of the invention, such as guide pin 400 shown in FIGS. 2A and 2B, and a guide member K-wire lumen 829 disposed on the extended end region 819 of the guide member 800*a* that is sized and configured to receive a K-wire of the invention, such as K-wires 509 shown in FIGS. 5A and 5B.

According to the invention, the guide member lumen 827 of the elongated guide member 800*a* can similarly also be sized and configured to receive various other suitable instruments, such as surgical scopes, center punches, location pins, drill probes, and drill stop assemblies, to facilitate the creation of a pilot SI joint opening.

As illustrated in FIGS. 5A and 5E, the elongated guide member 800*a* is sized and configured to slidably translate into the medial portion 562 of the prosthesis internal access opening 560.

As further illustrated in FIGS. 5A and 5E, and the extended region 819 is also sized and configured to slidably translate into one of the two (2) guide member receiving slots 565*a*, 565*b* disposed on the proximal end 521*a* of the drill guide 520*c*.

In a preferred embodiment, the first and second lobe portions 564*a*, 564*b* of the prosthesis internal access opening 560 of the drill guide 520*c* are similarly sized and configured to receive (i) a bone dislodging apparatus of the invention; particularly, drill bit 501*b*, and (ii) drill alignment pin 530*a*, temporary fixation pins 530*b*, 530*c*, and, if employed, K-wire pin member 550.

In a preferred embodiment, the opposed concave regions 810 of the elongated guide member 800*a* are sized and configured to allow slidable translation of a bone dislodging apparatus of the invention, e.g., drill bit 501*c*, and drill alignment pin 530*a*, temporary fixation pins 530*b*, 530*c*, and/or K-wire pin member 550 into and through the first and second lobe portions 564*a*, 564*b* when the elongated guide member 800*a* is positioned in the medial portion 562 of the prosthesis internal access opening 560.

As will readily be appreciated by one having ordinary skill in the art, the first and second lobe portions 564*a*, 564*b* and medial portion 562 can also readily accommodate various other suitable instruments, such as surgical scopes, center punches, location pins, drill probes, and drill stop assemblies.

Referring back to FIGS. 5A and 5B, in a preferred embodiment, the proximal end 521*a* of the drill guide 520*c* similarly comprises an extended region 519, which similarly comprises two (2) threaded holes 511*a*, 511*b*.

According to the invention, the threaded holes 511*a*, 511*b* are similarly sized and configured to receive the threaded end of a handle, such as the threaded end 514 of access sleeve handle 510*a* shown in FIGS. 3F and 3G, and the handle 510*b* illustrated in FIG. 5D and discussed above.

As illustrated in FIGS. 5F and 5G, the distal end 521*b* of the drill guide 520*c* similarly comprises anchor members 531 that project from the distal end 521*b* of the drill guide 520*c*. As indicated above, the anchor members 531 are designed and configured to pierce and, preferably, engage biological tissue to maintain a fixed position of the drill guide 520*c* proximate thereto.

According to the invention, the drill guide assembly 500*c* also provides all the aforementioned seminal advantages provided by drill guide assembly 500*b*.

Referring now to FIGS. 6A-6F, there is shown another embodiment of a drill guide (denoted "520*d*") that can also be employed with the drill guide assembly 500*c* (now denoted drill guide assembly "500*d*").

As illustrated in FIGS. 6A-6F, the drill guide 520*d* similarly comprises proximal and distal ends 521*a*, 521*b* and four (4) K-wire lumens 529*a*, 529*b*, 529*c*, 529*d*; the four (4) K-wire lumens 529*a*, 529*b*, 529*c*, 529*d* extending from the proximal end 521*a* to the distal end 521*b* of the drill guide 520*d*.

Figure 5M:
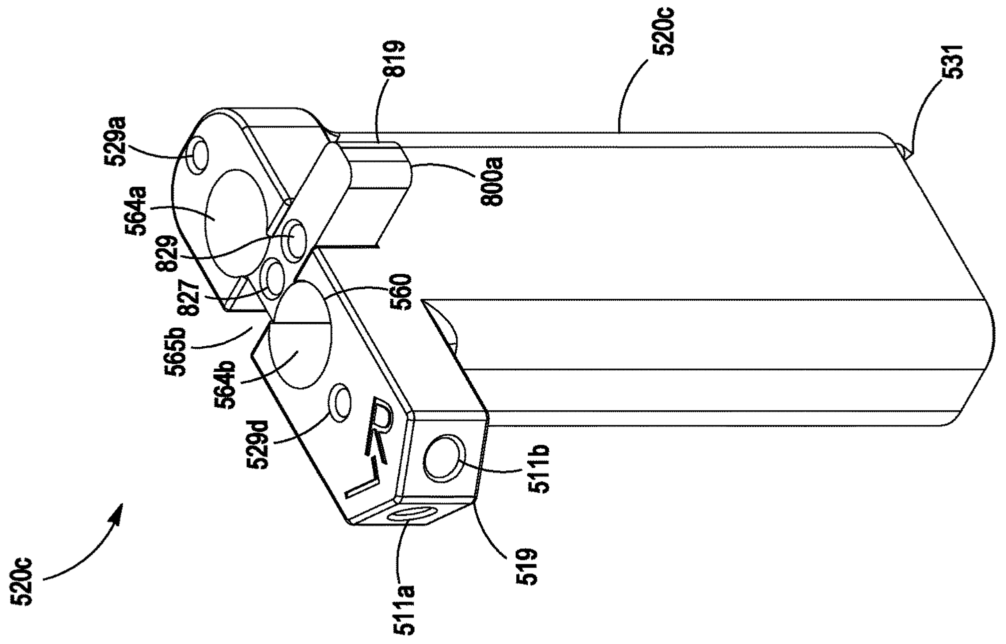
FIG. 5M is a front perspective view of the drill guide shown in FIG. 5F showing the elongated guide member shown in FIG. 5J fully disposed in the prosthesis internal access opening thereof, in accordance with the invention.
Figure 5L:
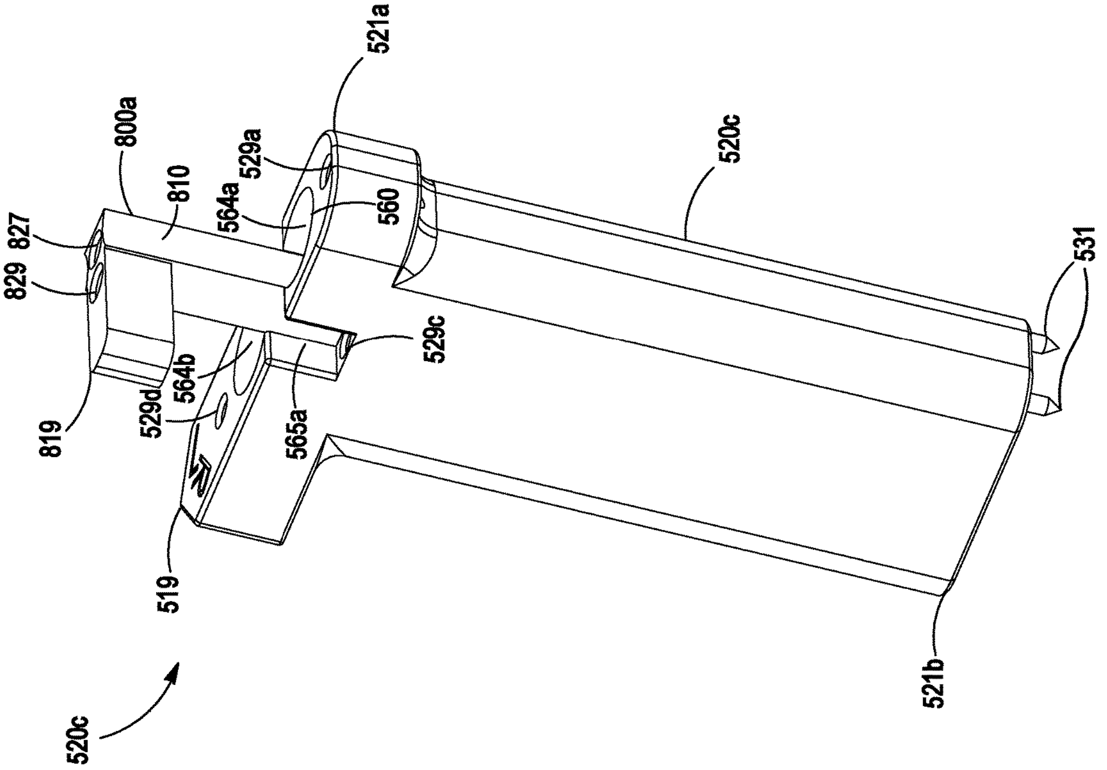
FIG. 5L is another rear perspective view of the drill guide shown in FIG. 5F showing the elongated guide member shown in FIG. 5J partially disposed in the prosthesis internal access opening thereof, in accordance with the invention.

As discussed in detail below, the drill guide 520*d* also comprises elongated guide member 800*a* illustrated in FIGS. 5L and 5M.

Figure 6B:
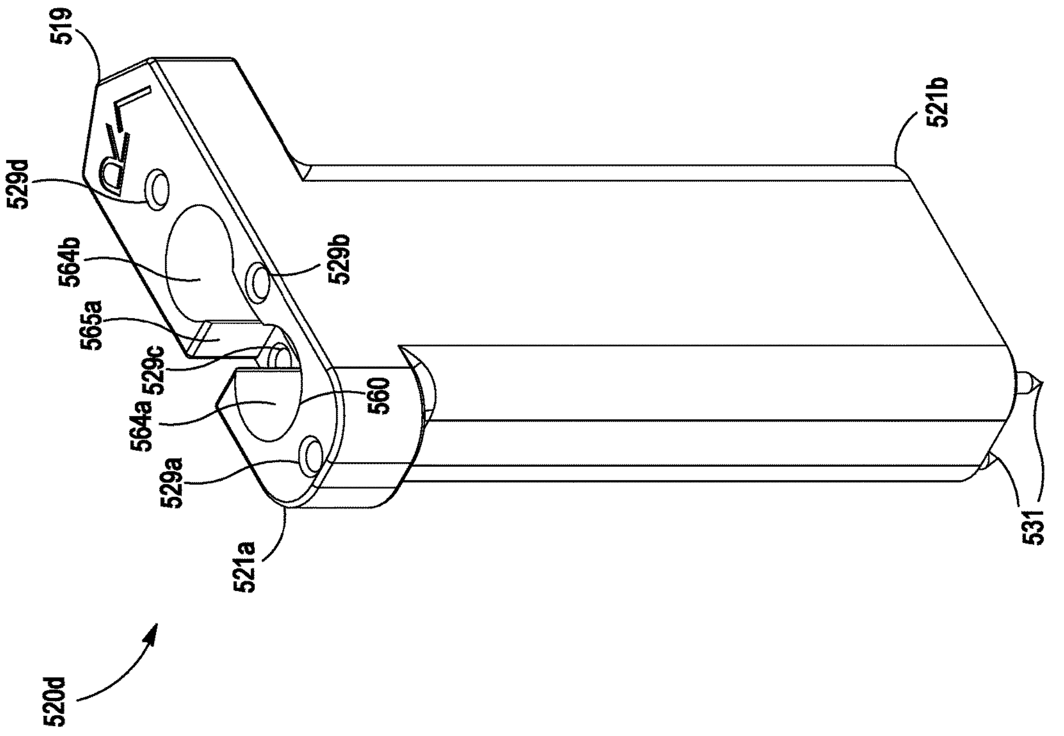
FIG. 6B is another rear perspective view of the drill guide shown in FIG. 6A, in accordance with the invention.
Figure 6A:
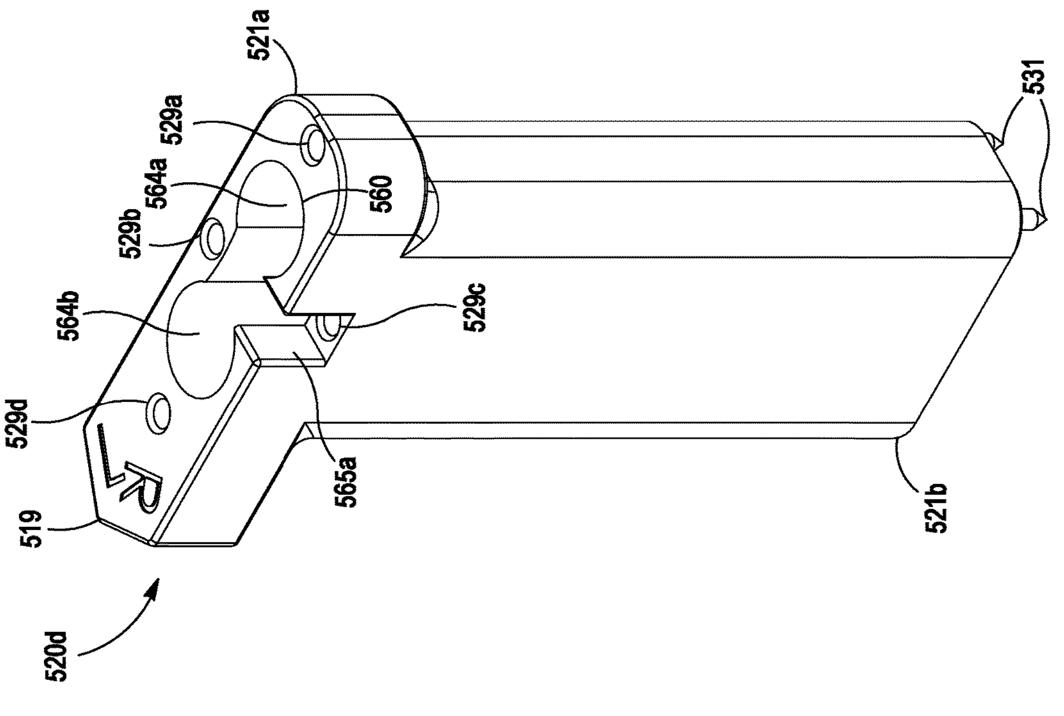
FIG. 6A is a rear perspective view of another embodiment of a drill guide, in accordance with the invention.

As illustrated in FIGS. 6A and 6B, the drill guide 520*d* similarly comprises prosthesis internal access opening 560, which, as discussed in detail below, is also sized and configured to receive and position a SI joint prosthesis of the invention therein.

Figure 6D:
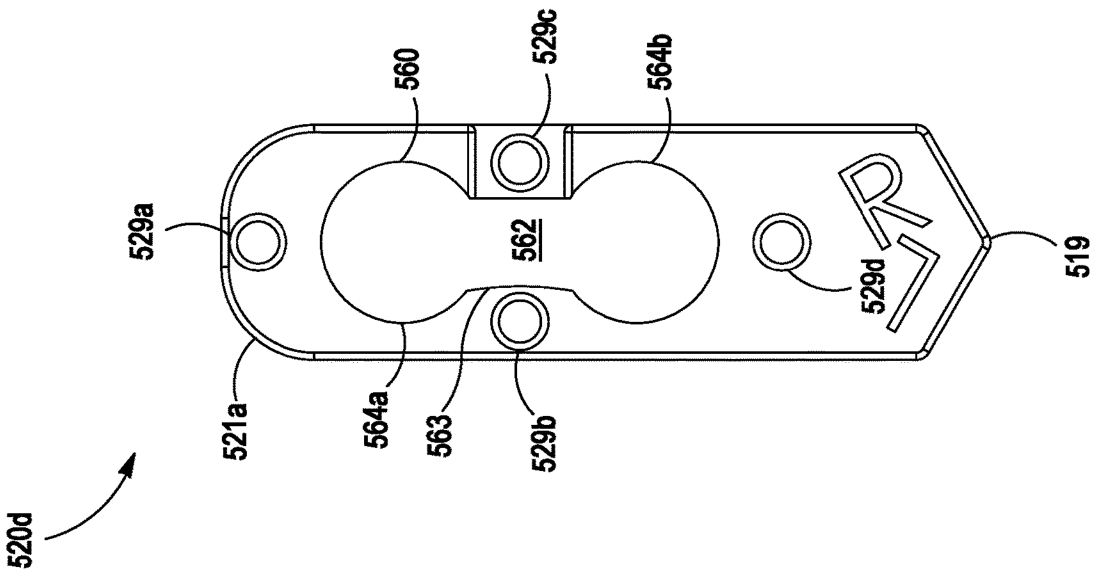
FIG. 6D is a top plan view of the drill guide shown in FIG. 6A, in accordance with the invention.
Figure 6C:
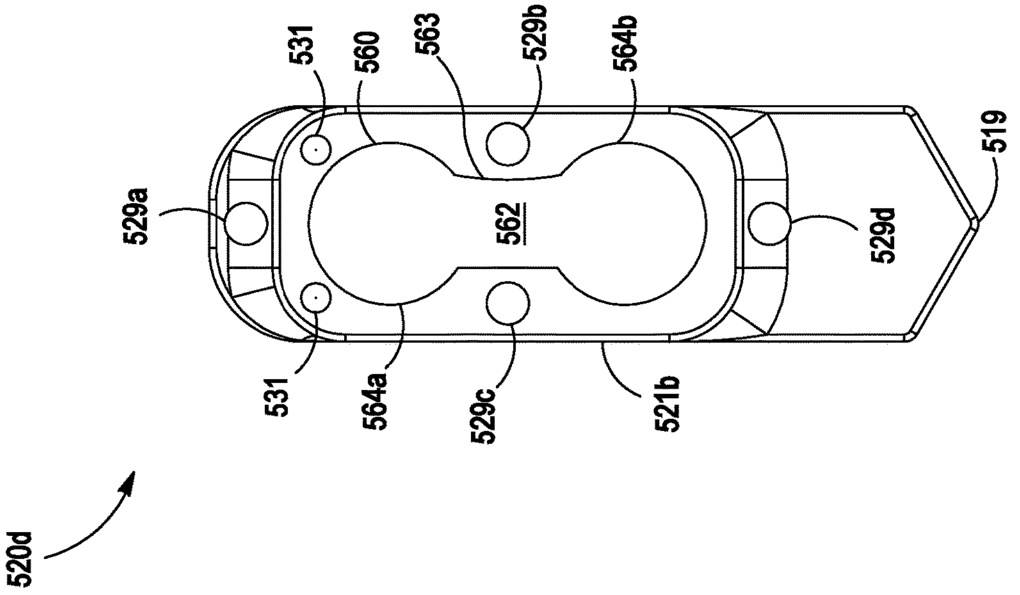
FIG. 6C is a bottom plan view of the drill guide shown in FIG. 6A, in accordance with the invention.

As illustrated in FIGS. 6C and 6D, the prosthesis internal access opening 560 similarly comprises a "dogbone" or "bi-lobe" cross-sectional shape comprising contiguous first and second lobe portions 564*a*, 564*b* connected by a medial portion 562.

As illustrated in FIGS. 6C and 6D, in a preferred embodiment, the medial portion 562 of the prosthesis internal access opening 560 is similarly sized and configured to receive the elongated guide member 800*a* therein.

As further illustrated in FIGS. 6C and 6D, the medial portion 562 of the prosthesis internal access opening 560 comprises a convex portion 563 that is similarly sized and configured to allow elongated guide member 800*a* to be advanced into the prosthesis internal access opening 560.

As illustrated in FIG. 5J and discussed above, the elongated guide member 800*a* comprises a guide member lumen 827, which is sized and configured to receive a guide pin of the invention, such as guide pin 400 shown in FIGS. 2A and 2B, and a guide member K-wire lumen 829 disposed on the extended end region 819 of the guide member 800*a*.

The extended region 819 of the elongated guide member 800*a* is also sized and configured to slidably translate into the guide member receiving slot 565*a* disposed on the proximal end 521*a* of the drill guide 520*d*.

Referring back to FIG. 6A, in a preferred embodiment, the first and second lobe portions 564*a*, 564*b* of the prosthesis internal access opening 560 of the drill guide 520*d* are similarly sized and configured to receive (i) a bone dislodging apparatus of the invention, such as drill bit 501*b* illustrated in FIG. 4I, and (ii) drill alignment pin 530*a*, temporary fixation pins 530*b*, 530*c*, and, if employed, K-wire pin member 550.

In a preferred embodiment, the opposed concave regions 810 of the elongated guide member 800*a* are similarly sized and configured to allow slidable translation of a bone dislodging apparatus of the invention, e.g., drill bit 501*b*, and drill alignment pin 530*a*, temporary fixation pins 530*b*, 530*c*, and/or K-wire pin member 550 into and through the first and second lobe portions 564*a*, 564*b* when the elongated guide member 800*a* is positioned in the medial portion 562 of the prosthesis internal access opening 560.

Figure 6F:
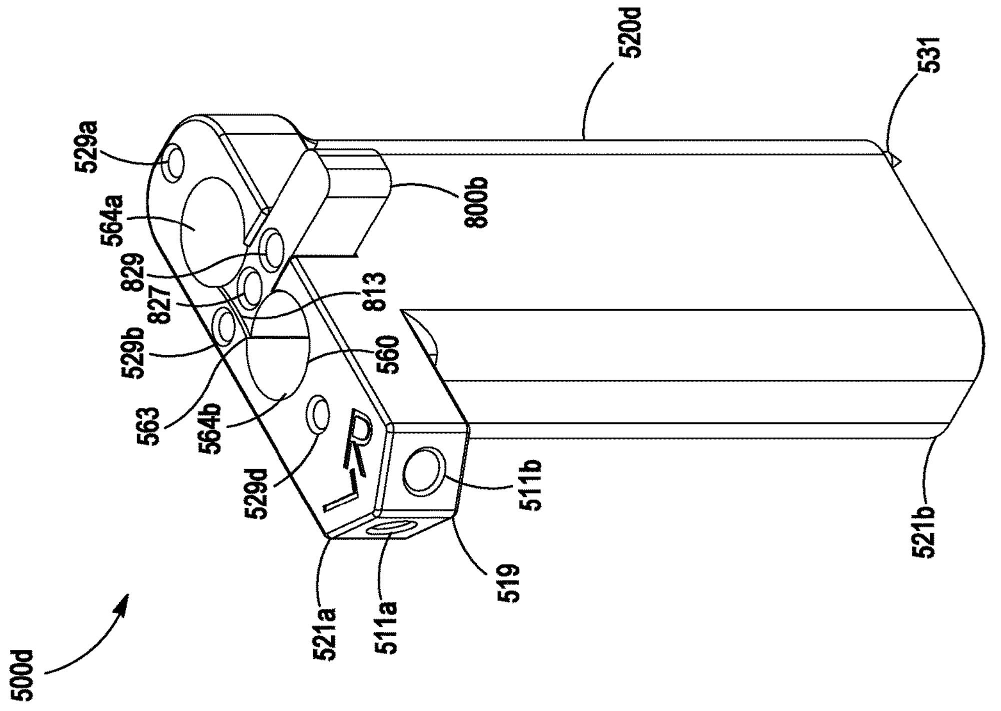
FIG. 6F is a front perspective view of the drill guide shown in FIG. 6A showing the elongated guide member shown in FIG. 5J fully disposed in the prosthesis internal access opening thereof, in accordance with the invention.

Referring now to FIG. 6F, in a preferred embodiment, the proximal end 521*a* of the drill guide 520*d* similarly comprises an extended region 519. As illustrated in FIG. 6F, the proximal end 521*a* of the drill guide 520*d* similarly comprises threaded holes 511*a*, 511*b*, which are similarly sized and configured to receive the threaded end of a handle, such as the threaded end 514 of access sleeve handle 510*a* shown in FIGS. 3F and 3G, and handle 510*b* shown in FIG. 5D, and discussed above.

As illustrated in FIGS. 6A, 6B, and 6C, the distal end 521*b* of the drill guide 520*d* similarly comprises anchor members 531 that project from the distal end 521*b* of the drill guide 520*d*, which, as indicated above, are designed and configured to pierce and, preferably, engage biological tissue to maintain a fixed position of the drill guide 520*d* proximate thereto.

According to the invention, the drill guide assembly 500*d* similarly provides all the aforementioned seminal advantages provided by drill guide assemblies 500*b* and 500*c*.

Referring now to FIGS. 7A-7L, there is shown another embodiment of a drill guide (denoted "520*e*") that can also be employed with the drill guide assembly 500*c* (now denoted drill guide assembly "500*e*").

Figure 7B:
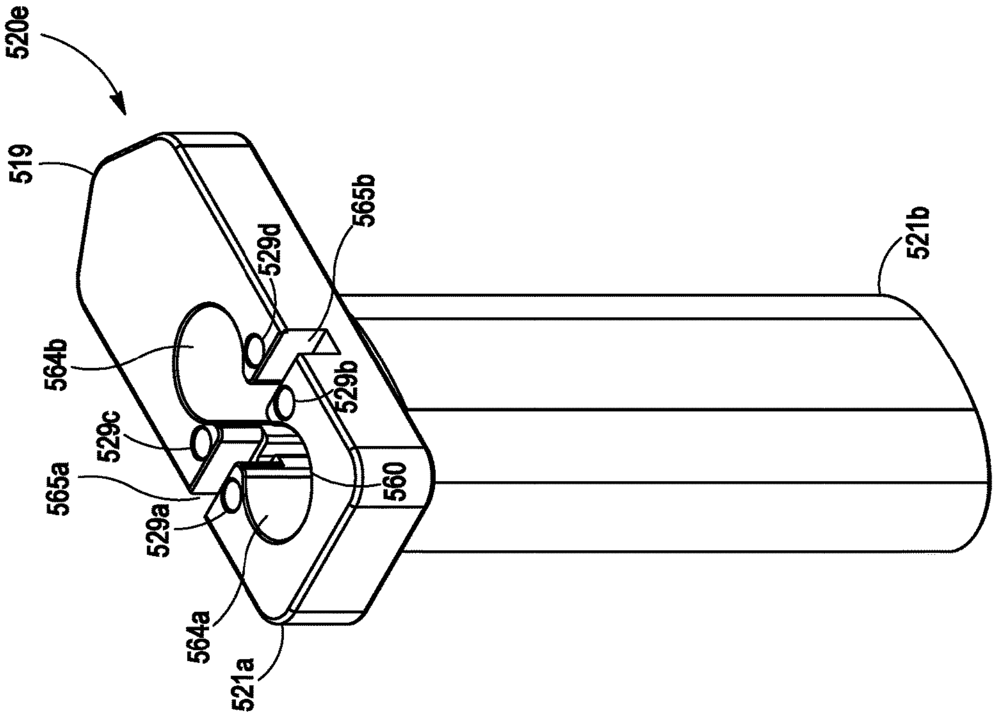
FIGS. 7A and 7B are perspective views of another embodiment of a drill guide, in accordance with the invention.
Figure 7A:
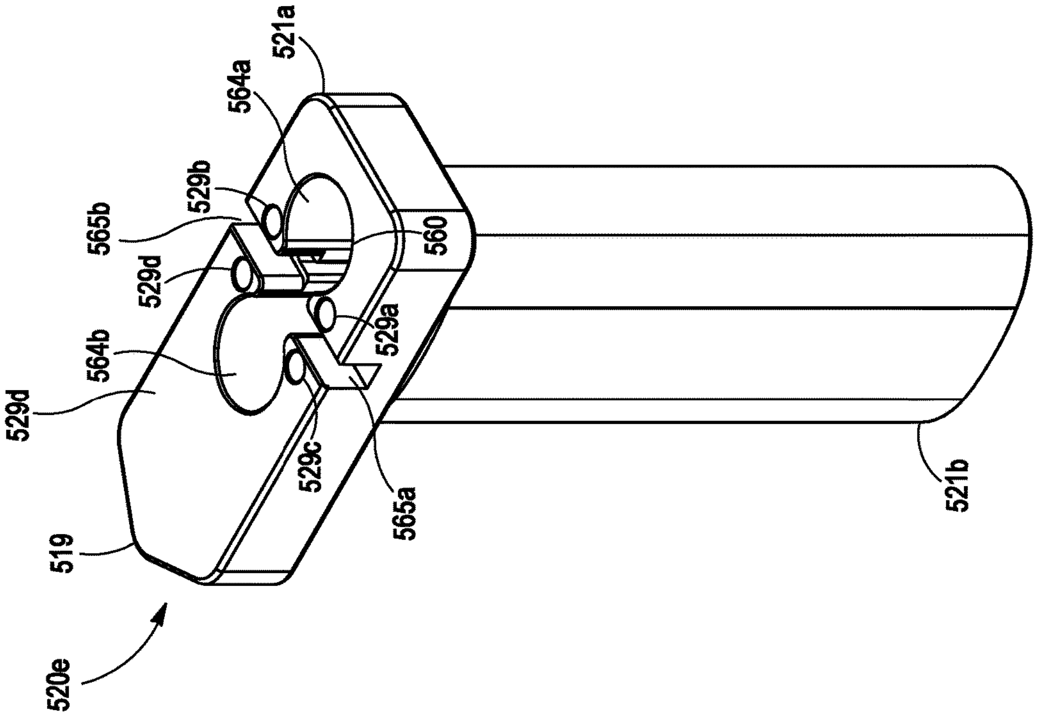
Figure 7D:
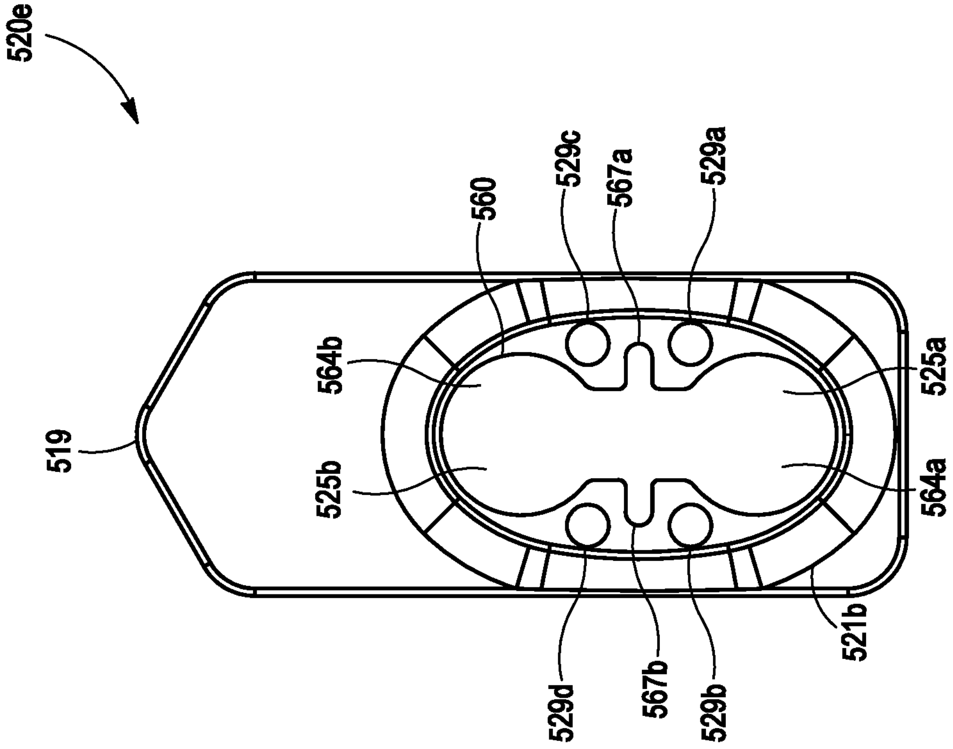
FIG. 7D is a bottom plan view of the drill guide shown in FIG. 7B, in accordance with the invention.
Figure 7C:
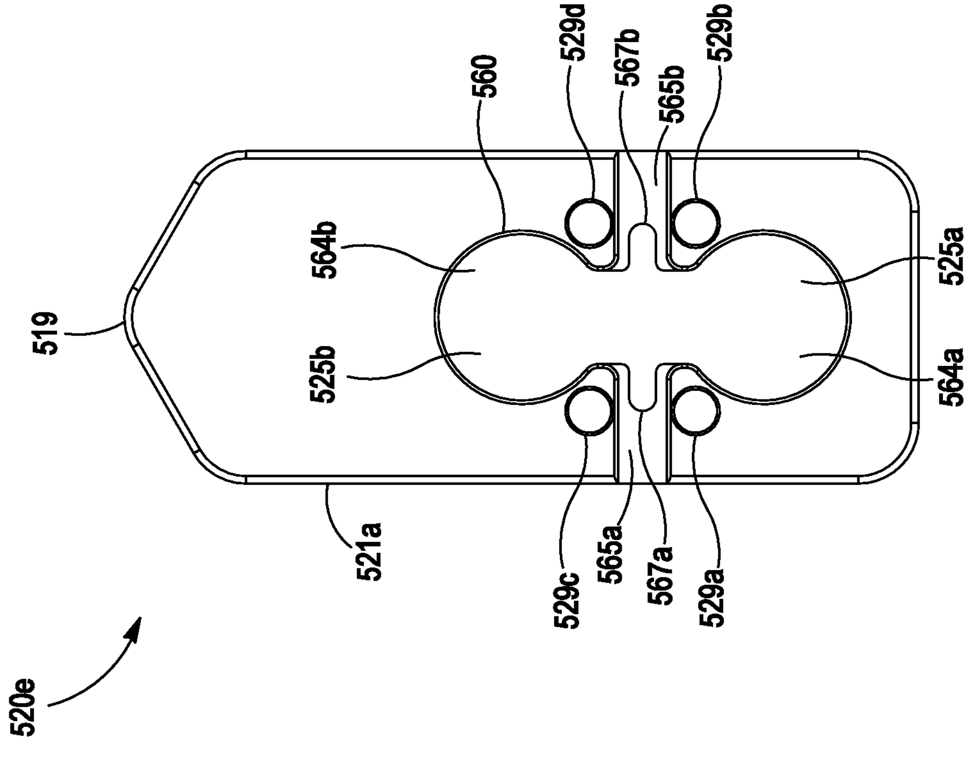
FIG. 7C is a top plan view of the drill guide shown in FIG. 7B, in accordance with the invention.

As illustrated in FIGS. 7A and 7B, the drill guide 520*e* similarly comprises proximal and distal ends 521*a*, 521*b*, the two (2) guide member receiving slots 565*a*, 565*b*, which are disposed on the proximal end 521*a* of the drill guide 520*e*, and the four (4) K-wire lumens 529*a*, 529*b*, 529*c*, 529*d*, which similarly extend from the proximal end 521*a* to the distal end 521*b* of the drill guide 520*e*, and two (2) drill guide insert channels 567*a*, 567*b*.

Figure 6E:
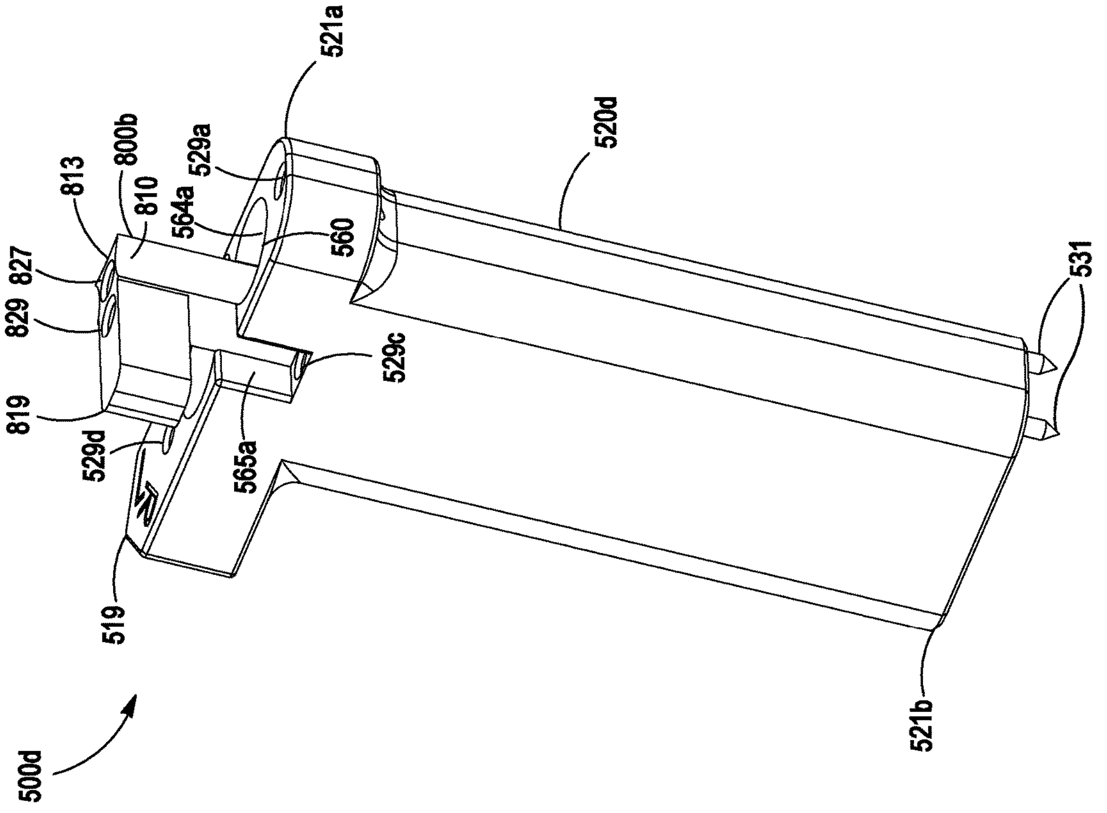
FIG. 6E is another rear perspective view of the drill guide shown in FIG. 6A showing the elongated guide member shown in FIG. 5J partially disposed in the prosthesis internal access opening thereof, in accordance with the invention.

In some embodiments of the invention, the drill guide also comprises the drill guide anchors 531 of drill guide 520*d* illustrated in FIG. 6E.

Figure 7E:
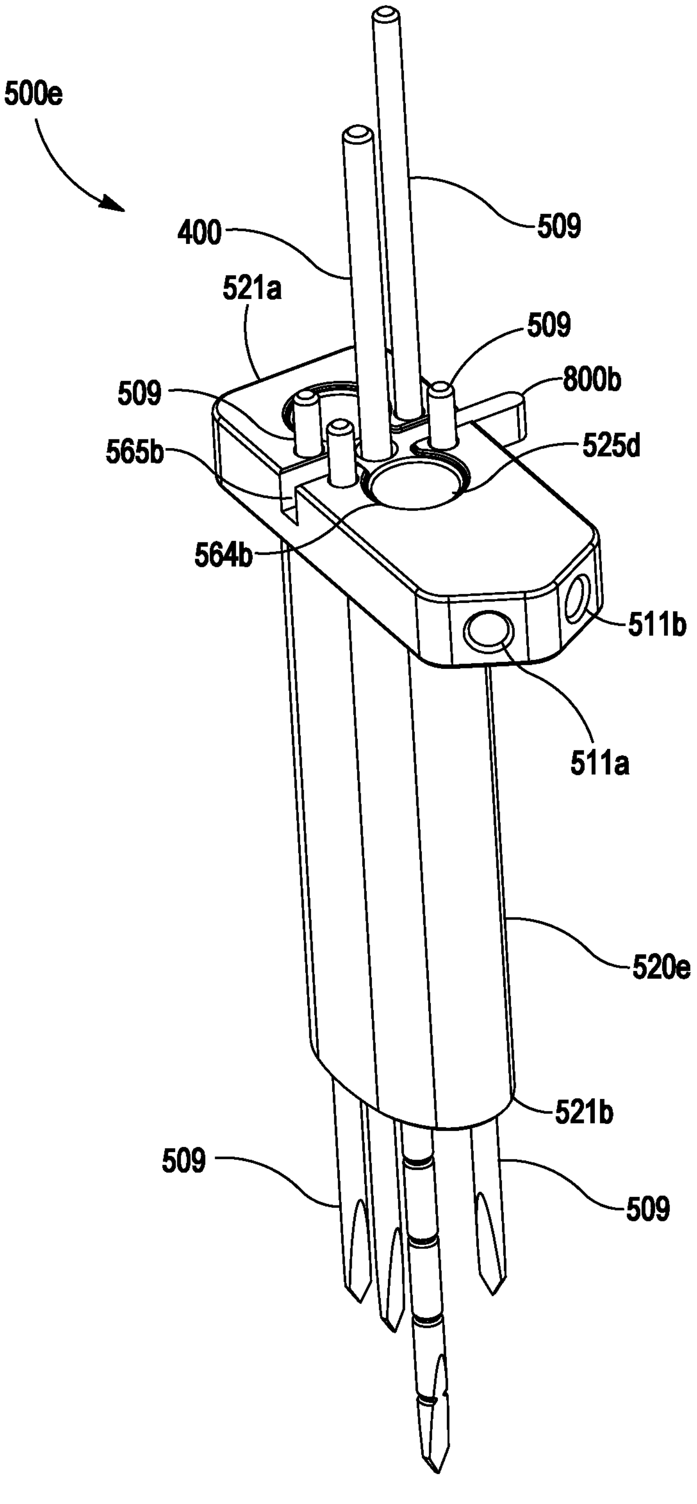
FIG. 7E is a further perspective view of the drill guide shown in FIG. 7B, showing K-wires and a guide pin positioned therein, in accordance with the invention.
Figure 7G:
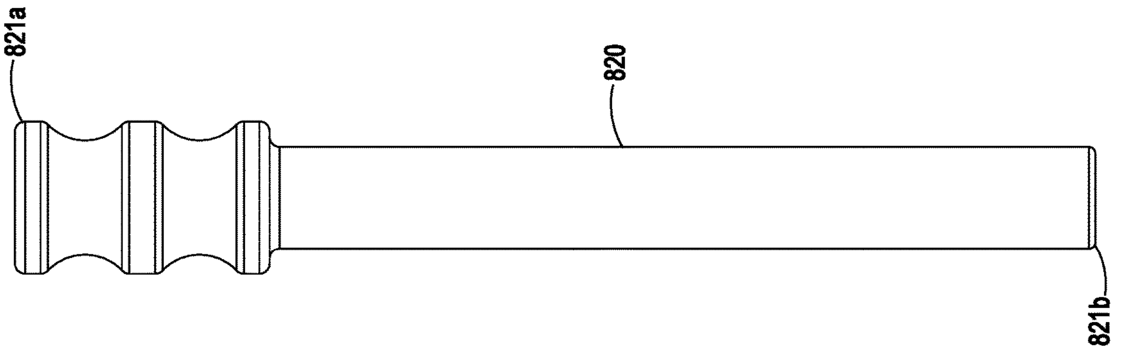
FIG. 7G is a side plan view of the K-wire driver shown in FIG. 7F, in accordance with the invention.
Figure 7F:
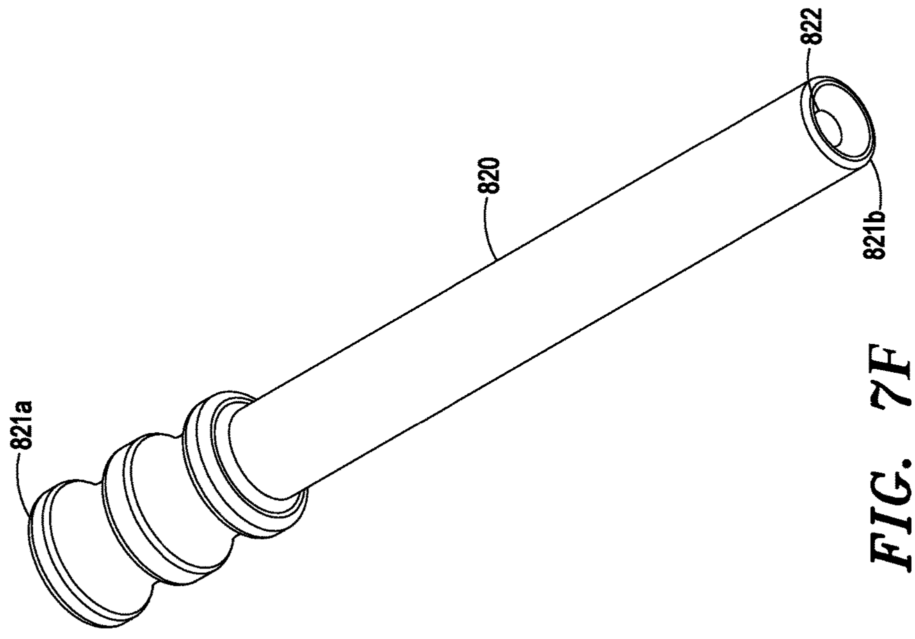
FIG. 7F is a perspective view of a K-wire driver, in accordance with the invention.
Figure 7H:
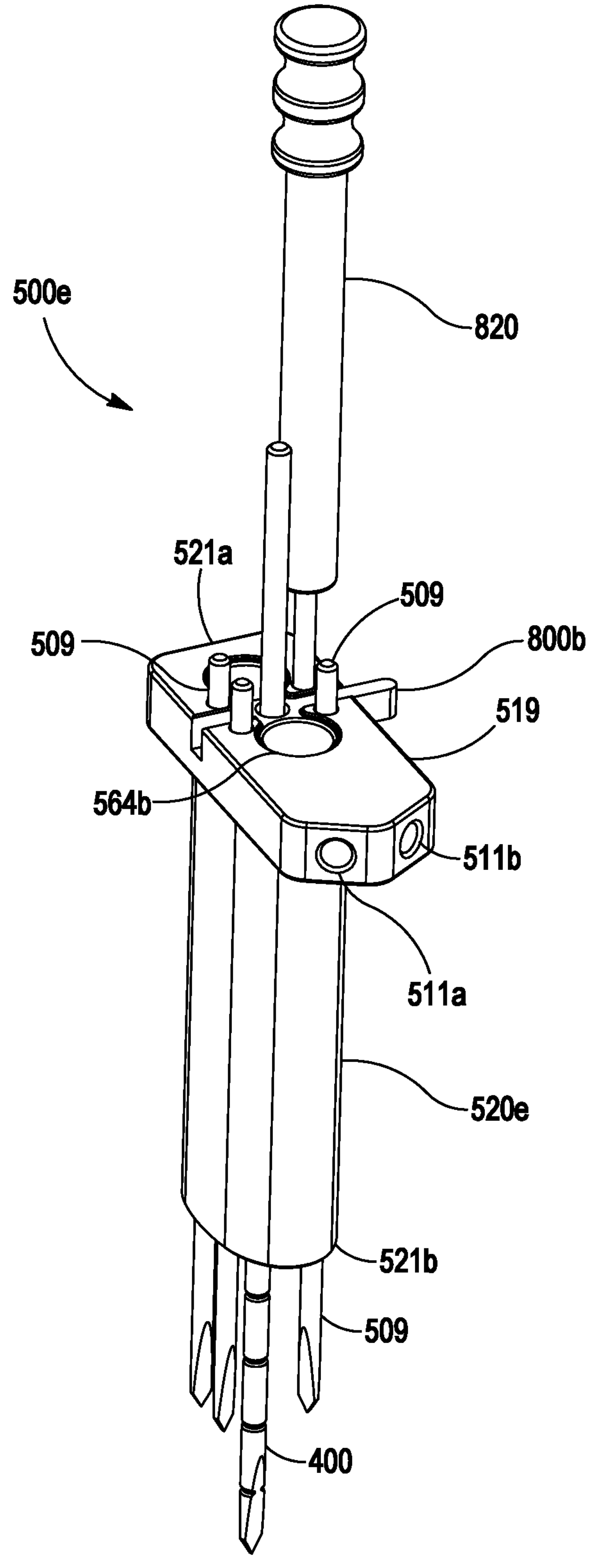
FIGS. 7H and 7I are further perspective views of the drill guide shown in FIG. 7B, showing K-wires positioned therein and the K-wire driver shown in FIGS. 7F and 7G positioned on one of the K-wires, in accordance with the invention.
Figure 7I:
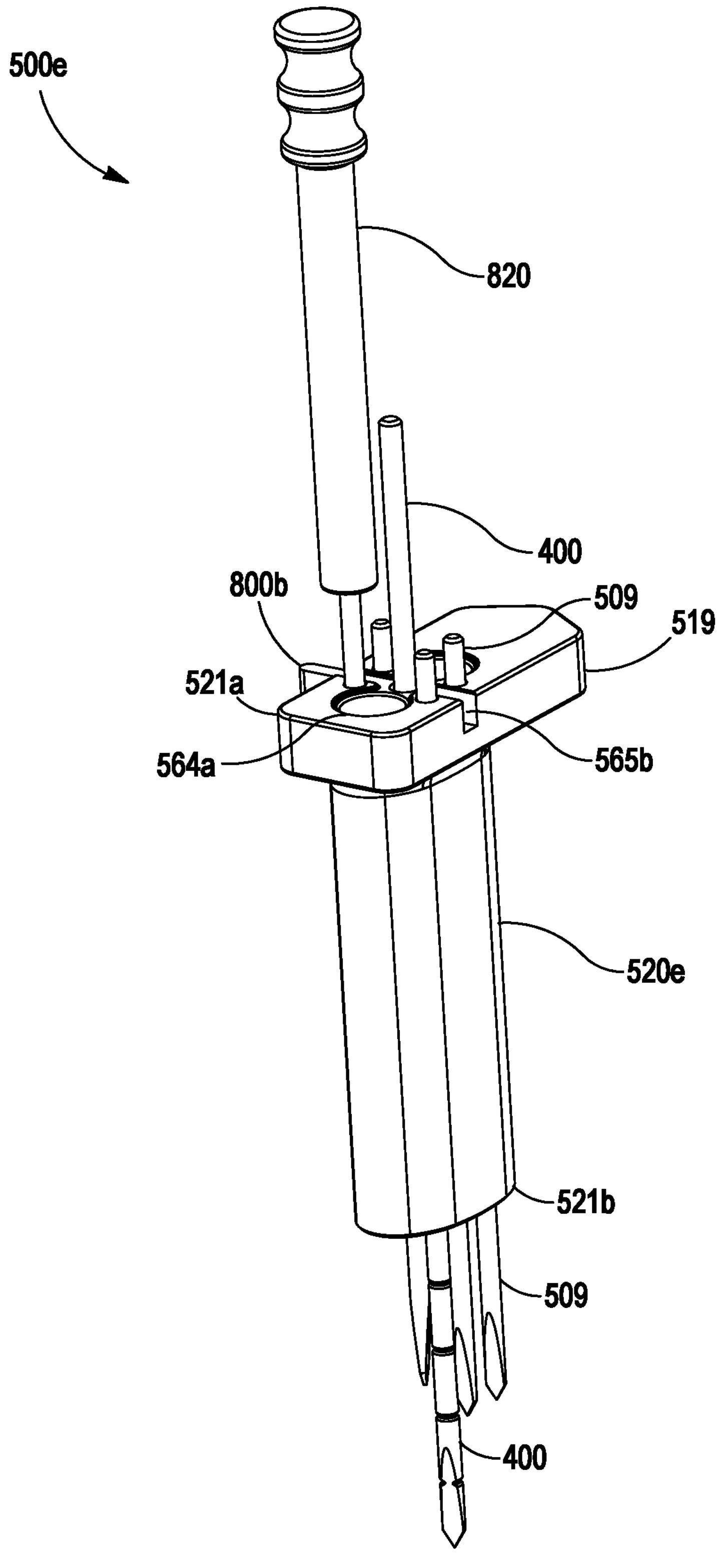
Figure 7K:
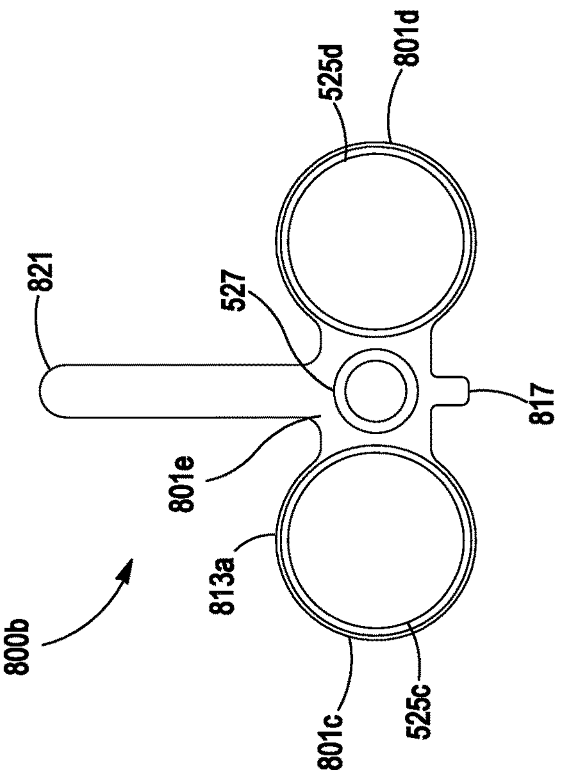
FIG. 7K is an end plan view of the drill guide insert shown in FIG. 7J, in accordance with the invention.
Figure 7J:
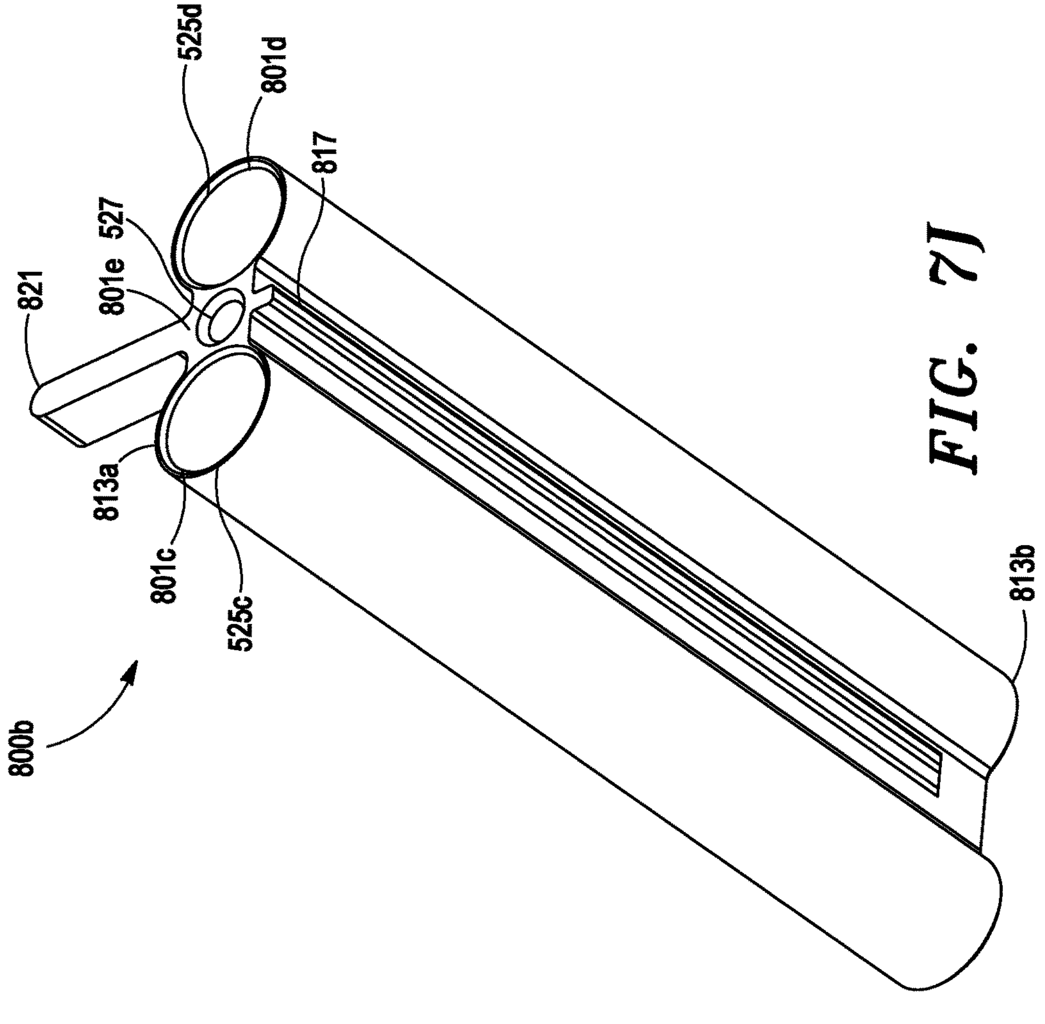
FIG. 7J is a perspective view of a drill guide insert, in accordance with the invention.

As illustrated in FIG. 7J and discussed in detail below, the drill guide 520*e* further comprises a further drill guide or insert (denoted "800*b*").

As illustrated in FIGS. 7A and 7B, the drill guide 520*e* similarly comprises a prosthesis internal access opening 560, which, as discussed in detail below, is sized and configured to receive the drill guide insert 800*b* therein.

As further illustrated in FIGS. 7A and 7B, the prosthesis internal access opening 560 similarly comprises first and second lobe portions 564*a*, 564*b*.

As also illustrated in FIGS. 7A and 7B, in this instance, K-wire lumens 529*a* and 529*b* are disposed proximate the first lobe portion 564*a* and guide member receiving slots 565*a*, 565*b* on a plane that is perpendicular to the longitudinal axis of the proximal end 521*a* of the drill guide 520*b*, and K-wire lumens 529*c* and 529*d* disposed proximate the second lobe portion 564*b* and guide member receiving slots 565*a*, 565*b* on a plane that is parallel to the plane of K-wire lumens 529*a* and 529*b* and, hence, also perpendicular to the longitudinal axis of the proximal end 521*a* of the drill guide 520*b*.

As indicated above and illustrated in FIG. 7E, the K-wire lumens 529*a*, 529*b*, 529*c*, 529*d* are sized and configured to receive K-wires 509 therein.

Referring now to FIGS. 7F-7I, to facilitate advancement of the K-wires into bone structures; particularly, bone structures of a SI joint (as discussed in detail below), in a preferred embodiment of the invention, the drill guide 520*e* further comprises a K-wire driver 820.

As illustrated in FIGS. 7F and 7G, the K-wire driver 820 comprises an elongated member comprising proximal and distal ends 821*a*, 821*b*.

As illustrated in FIG. 7F, the distal end 821*b* of the K-wire driver 820 comprises an internal K-wire seat 822 that is sized and configured to receive a proximal end of a K-wire 509 therein, as illustrated in FIGS. 7G and 7H.

In a preferred embodiment, the K-wire seat 822 has a predetermined depth (into the K-wire driver 820) to facilitate a desired advancement of the K-wires 509 into bone structures.

Referring now to FIGS. 7J and 7K, there is shown a preferred embodiment of the drill guide insert 800*b*.

As illustrated in FIGS. 7J and 7K, the drill guide insert 800*b* comprises an elongated member comprising proximal and distal ends 813*a*, 813*b*, first and second elongated cylindrical regions 801*c*, 801*d*, and a mid-region 801*e* disposed therebetween.

As further illustrated in FIGS. 7J and 7K, the first cylindrical region 801*c* comprises a first drill guide lumen 525*c* and the second cylindrical region 801*d* comprises a second drill guide lumen 525*d*, each of the drill guide lumens extending from the proximal end 813*a* to the distal end 813*b* of the drill guide insert 800*b*.

In a preferred embodiment, the drill guide lumens 525*c*, 525*d* are sized and configured to receive (i) a bone dislodging apparatus of the invention; preferably, drill bit 501*b*, and (ii) the drill alignment pin 530*a*, temporary fixation pins 530*b*, 530*c*, and, if employed, K-wire pin member 550.

As also illustrated in FIG. 7K, the mid-region 801*e* of the drill guide insert 800*b* also comprises a drill medial lumen (similarly denoted "527"), which is similarly sized and configured to receive and guide the guide pin 400 of the invention.

According to the invention, the drill guide medial lumen 527 can similarly be sized and configured to receive various other suitable instruments, such as surgical scopes, center punches, location pins, drill probes, and drill stop assemblies, to facilitate the creation of a pilot SI joint opening.

Figure 7L:
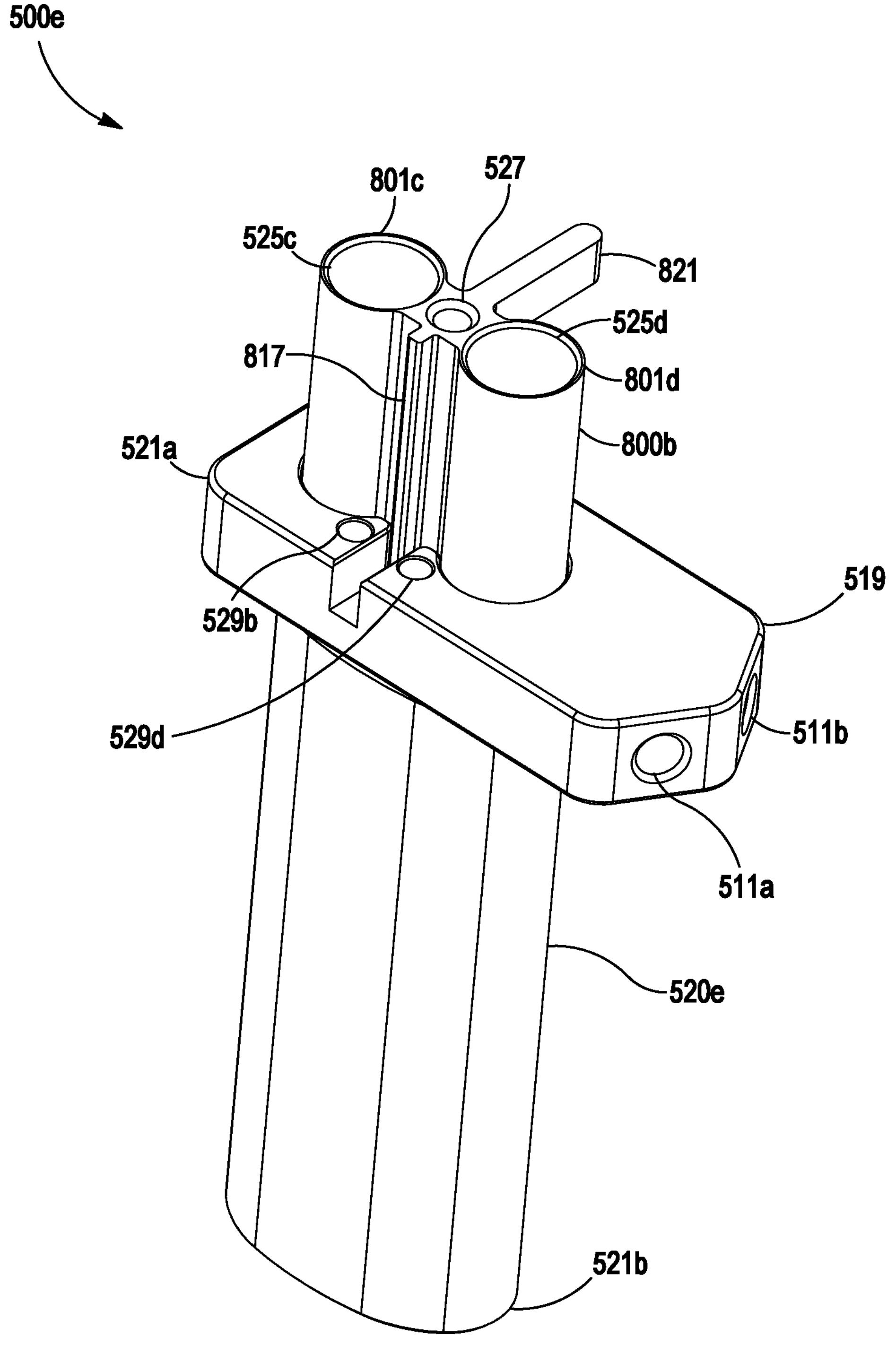
FIG. 7L is a perspective view of a drill guide assembly having the drill guide shown in FIG. 7B with the drill guide insert shown in FIGS. 7J and 7K positioned therein, in accordance with the invention.

As further illustrated in FIGS. 7J and 7K, the drill guide insert 800*b* further comprises an extended, substantially perpendicular end region 821 that is disposed on the proximal end 813*a* of the drill guide insert 800*b*, which is sized and configured to seat in the two (2) guide member receiving slots 565*a*, 565*b* of the drill guide 520*e*, and a raised elongated region 817 disposed opposite the end region 821, which is sized and configured to be received in the drill guide insert channels 567*a*, 567*b* of the drill guide 520*e*, as illustrated in FIG. 7L, and guide the drill guide insert 800*b* into the drill guide 520*e*.

According to the invention, the drill guide assembly 500*e* similarly provides all the aforementioned seminal advantages provided by drill guide assemblies 500*b*, 500*c* and 500*d*, including:

- an access sleeve, such as access sleeve 502 shown in FIG. 3B, is not required;
- only a minimal incision, i.e., an incision length in the range of 2.0 cm to 3.0 cm, is required to create the pilot openings in the SI joint structures and implant a SI joint prosthesis therein;
- direct visualization of the drill bit 501*c* (or drill bit 501*b*, if employed) and, hence, markings (i.e., drill bit depth markings) 513 thereon is provided during creation of pilot SI joint openings;
- direct (and optimal) visualization of the SI joint structures is provided after creation of the pilot openings in the SI joint structures; and
- consistent, optimal arthrodesis of the dysfunctional SI joint is achieved after placement of a SI joint prosthesis therein.

The drill guide assembly 500*e* also provides consistent, optimal guidance of (i) the bone dislodging apparatus of the invention; particularly, drill bit 501*b*, during creation of the SI joint openings in bone structures; particularly, SI joint bone structures, therewith, and (ii) the SI joint prostheses of the invention into the pilot SI joint openings.

As indicated above, in a preferred embodiment, the drill guide assemblies 500*a*, 500*b*, 500*c*, 500*d* and 500*e* are configured and adapted to create pilot SI joint openings in SI joint bone structures to accommodate placement of a SI joint prosthesis of the invention therein.

Figure 8A:
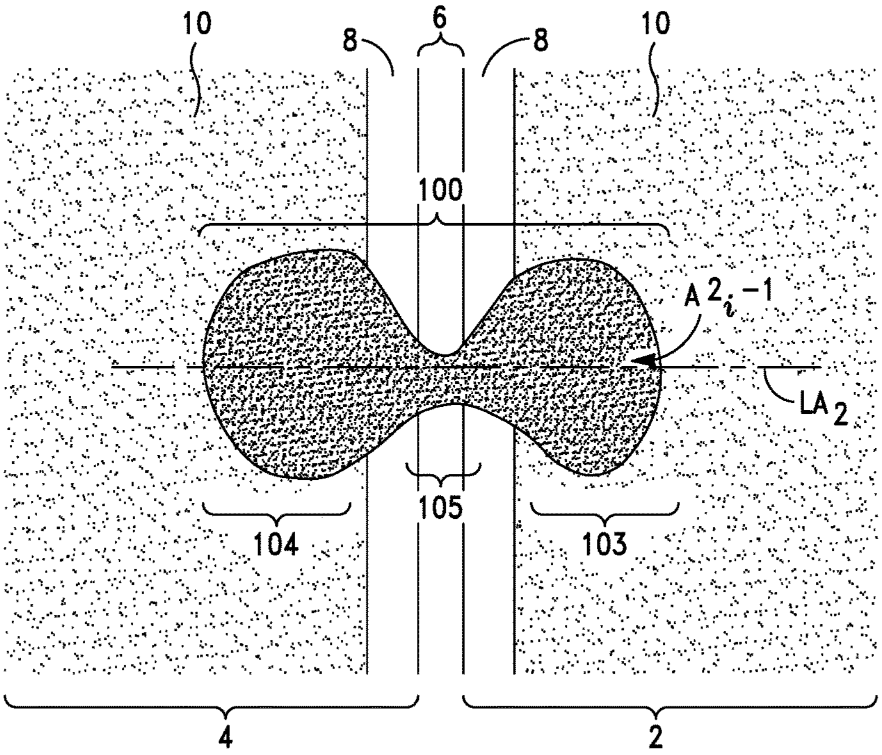
FIG. 8A is an illustration of one embodiment of a pilot SI joint opening, in accordance with the invention.

Referring now to FIG. 8A, there is shown one embodiment of a pilot SI joint opening of the invention (denoted "100") that can be created with drill guide assemblies 500*a*, 500*b*, 500*c*, 500*d*, and 500*e*.

As illustrated in FIG. 8A, the pilot SI joint opening 100 comprises a three-dimensional opening comprising first and second lobe regions 103, 104; the first lobe region 103 being disposed in the sacrum 2 and comprising a sacrum opening three-dimensional shape, and the second lobe region 104 being disposed in the ilium 4 and comprising an ilium opening three-dimensional shape.

As further illustrated in FIG. 8A, the three-dimensional pilot SI joint opening 100 further comprises an SI joint opening cross-sectional shape in a plane that intersects the sacrum 2 and ilium 4; the plane being substantially perpendicular to the longitudinal axis of the drill guide assemblies 500*a*, 500*b*, 500*c*, 500*d*, and 500*e* when the drill guide assemblies 500*a*, 500*b*, 500*c*, 500*d*, and 500*e* and, hence, drill bits 501*a* and 501*b* are disposed in a pilot opening creation position in the dysfunctional SI joint. The three-dimensional pilot SI joint opening cross-sectional shape thus comprises the sacrum opening three-dimensional shape and ilium opening three-dimensional shape.

In some embodiments, the pilot SI joint opening cross-sectional shape (i.e., pilot SI joint opening 100) is defined in part by at least one noncircular cross-sectional shaped region (denoted "105") in the noted plane.

As additionally illustrated in FIG. 8A, the three-dimensional pilot SI joint opening 100, i.e., cross-sectional shape thereof, also defines a cross-sectional area of the three-dimensional pilot SI joint opening cross-sectional shape (denoted "$A^2_i$-1").

The three-dimensional pilot SI joint opening 100, i.e., cross-sectional shape thereof, also comprises a longitudinal axis (denoted "$LA_2$") in the plane that intersects the sacrum 2 and ilium 4 and an initial pilot SI joint opening length along the axis $LA_2$.

Figure 8B:
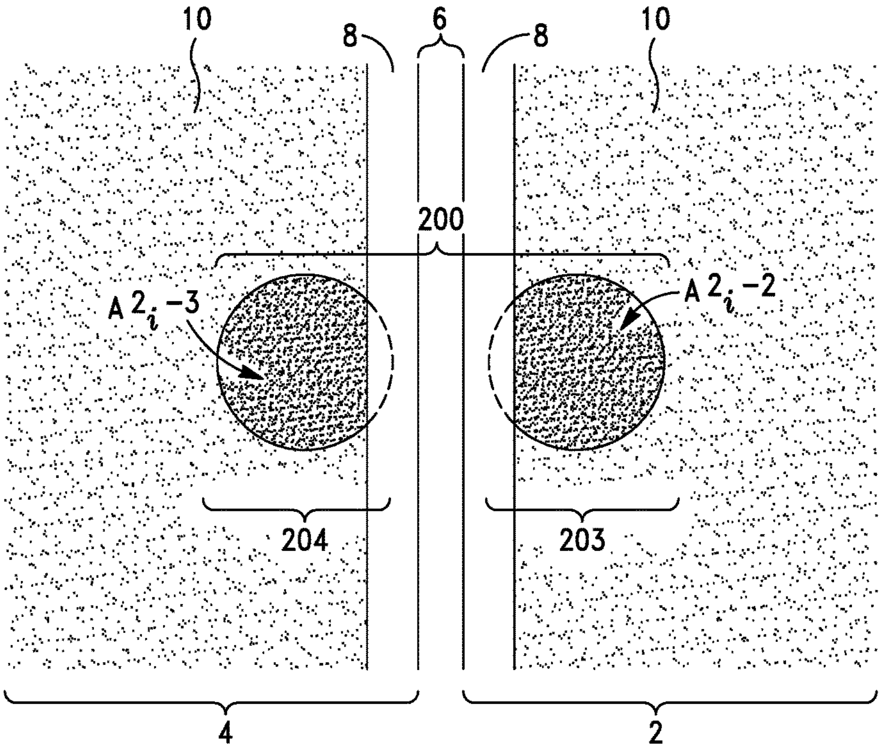
FIGS. 8B and 8C are illustrations of further embodiments of SI joint openings, in accordance with the invention.

Referring now to FIG. 8B, there is shown a further pilot SI joint opening of the invention (denoted "200") that can be created with a defect creation assembly of the invention. As illustrated in FIG. 8B, the pilot SI joint opening 200 comprises two three-dimensional pilot or guide portions or regions 203, 204; the first guide portion 203 being disposed in the sacrum 2 and the second guide portion 204 being disposed in the ilium 4.

According to the invention, the sacrum and ilium guide portions 203, 204 can comprise various configurations, e.g., cross-sectional shapes, and sizes to, as discussed in detail below, accommodate insertion of defined regions of a prosthesis of the invention therein and transition of the sacrum and ilium guide portions 203, 204 from pilot or first configurations and sizes to expanded second configurations and sizes when the prosthesis is inserted therein.

According to the invention, the sacrum and ilium guide portions 203, 204 can also be disposed at various locations in the sacrum 2 and ilium 4.

In some embodiments, the sacrum and ilium guide portions 203, 204 are disposed in the sacrum 2 and ilium 4 such that at least a portion of the sacrum and ilium guide portions 203, 204 extends into the cortical bone 8 of the SI joint structures, i.e., sacrum 2 and ilium 4, as shown in FIG. 8B, or the juncture between the sacrum 2 and ilium 4.

Figure 8C:
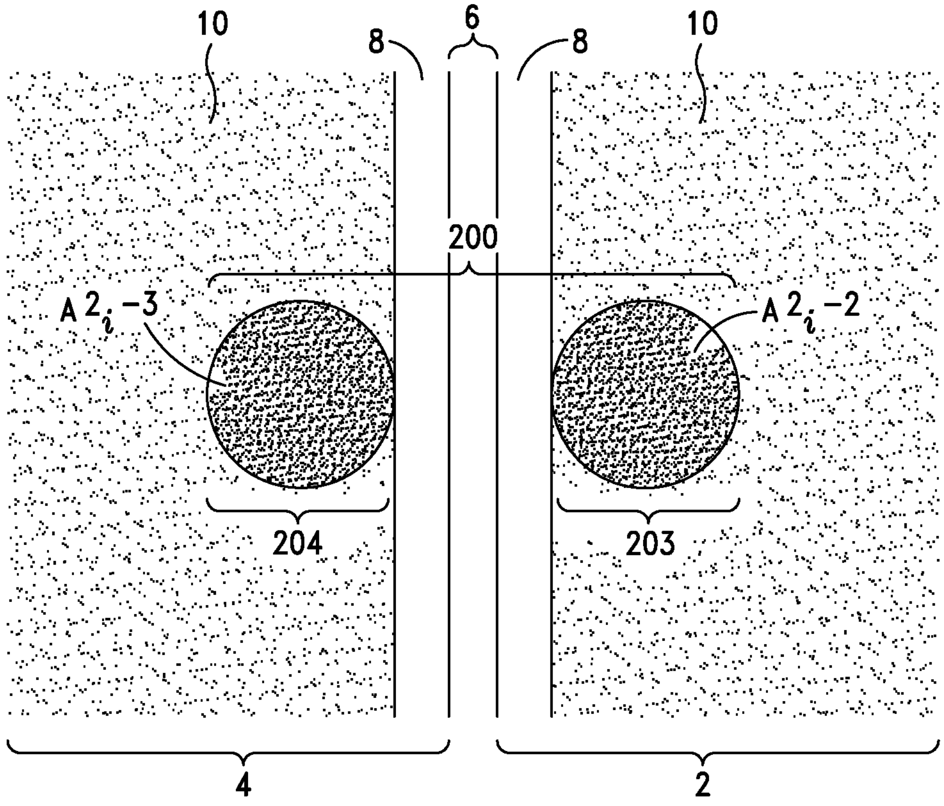

In some embodiments, the sacrum and ilium guide portions 203, 204 are solely disposed in the sacrum 2 and ilium 4, as shown in FIG. 8C.

As illustrated in FIG. 8B, in one preferred embodiment, the sacrum and ilium guide portions 203, 204 comprise substantially circular cross-sectional shapes.

As further illustrated in FIG. 8B, the sacrum and ilium guide portions 203, 204 of the pilot SI joint opening 200, i.e., cross-sectional shape thereof, define cross-sectional areas of the sacrum and ilium guide portions 203, 204 (denoted "$A^2_i$-2" and "$A^2_i$-3", respectively).

In a preferred embodiment, the sacrum and ilium guide portions 203, 204 of the pilot SI joint opening 200 are disposed on a plane that similarly intersects the sacrum 2 and ilium 4.

SI Joint Prostheses

According to the invention, various suitable SI joint prostheses, such as the prostheses illustrated in FIGS. 12A-12C, 13A-13B, 14A-14C and 15A-15D of Co-pending U.S. application Ser. No. 13/857,977, are suitable for insertion into pilot SI joint openings of the invention (i.e., SI joint openings 100, 200 described above) in a SI joint created by the drill guide assemblies 500*a*, 500*b*, 500*c*, 500*d*, and 500*e* and into and through articular cartilage and cortical bone 8 (and trabecular bone 10), which define the SI joint.

Referring now to FIGS. 9A-9I, there is shown one embodiment of a SI joint prosthesis of the invention that is particularly suitable for placement in pilot SI joint openings of the invention in a SI joint, and into and through articular cartilage and bone structures (i.e., cortical and trabecular bone 8, 10), which define the SI joint.

Figure 9A:
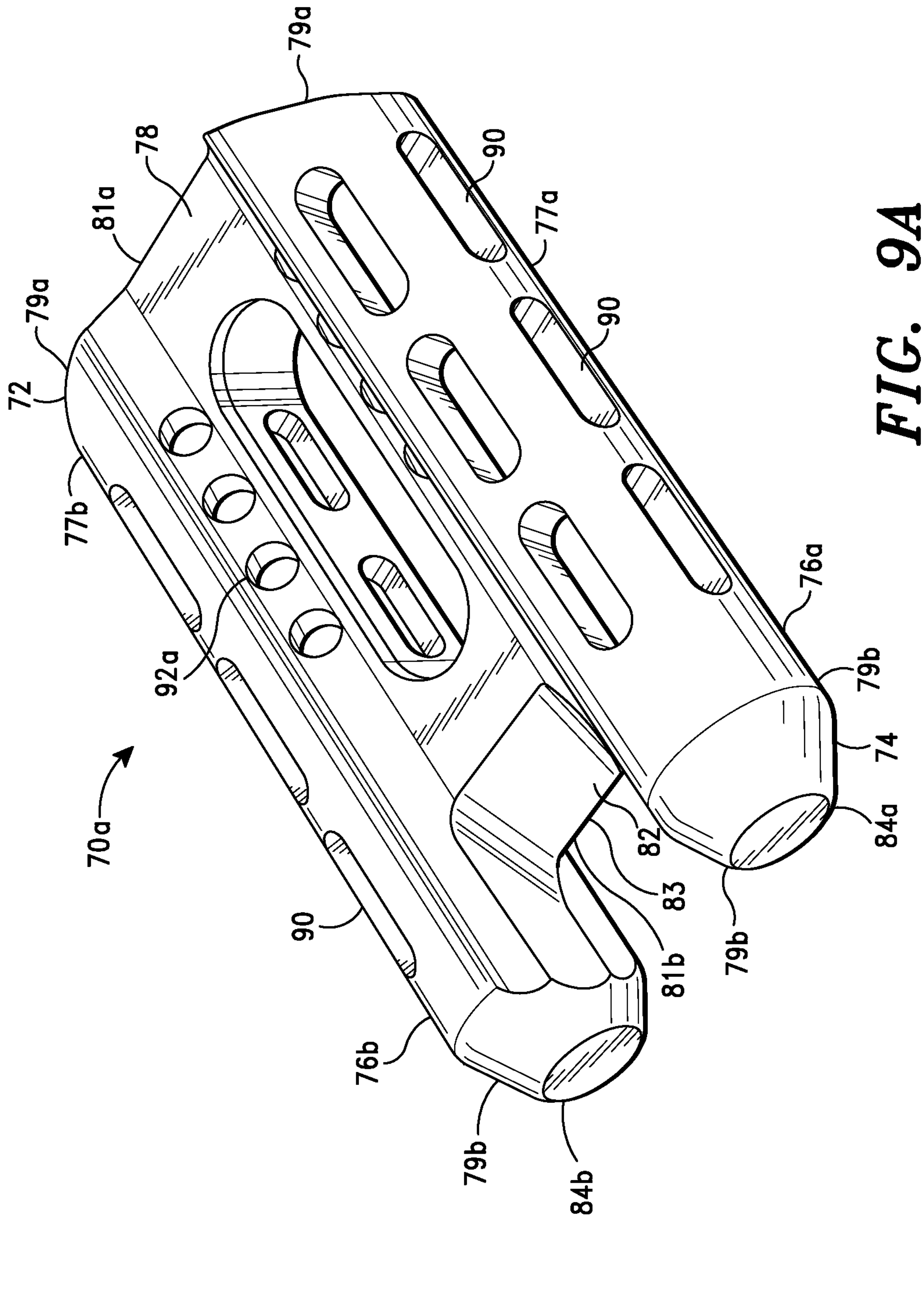
FIG. 9A is a perspective view of one embodiment of a SI joint prosthesis, in accordance with the invention.
Figure 9B:
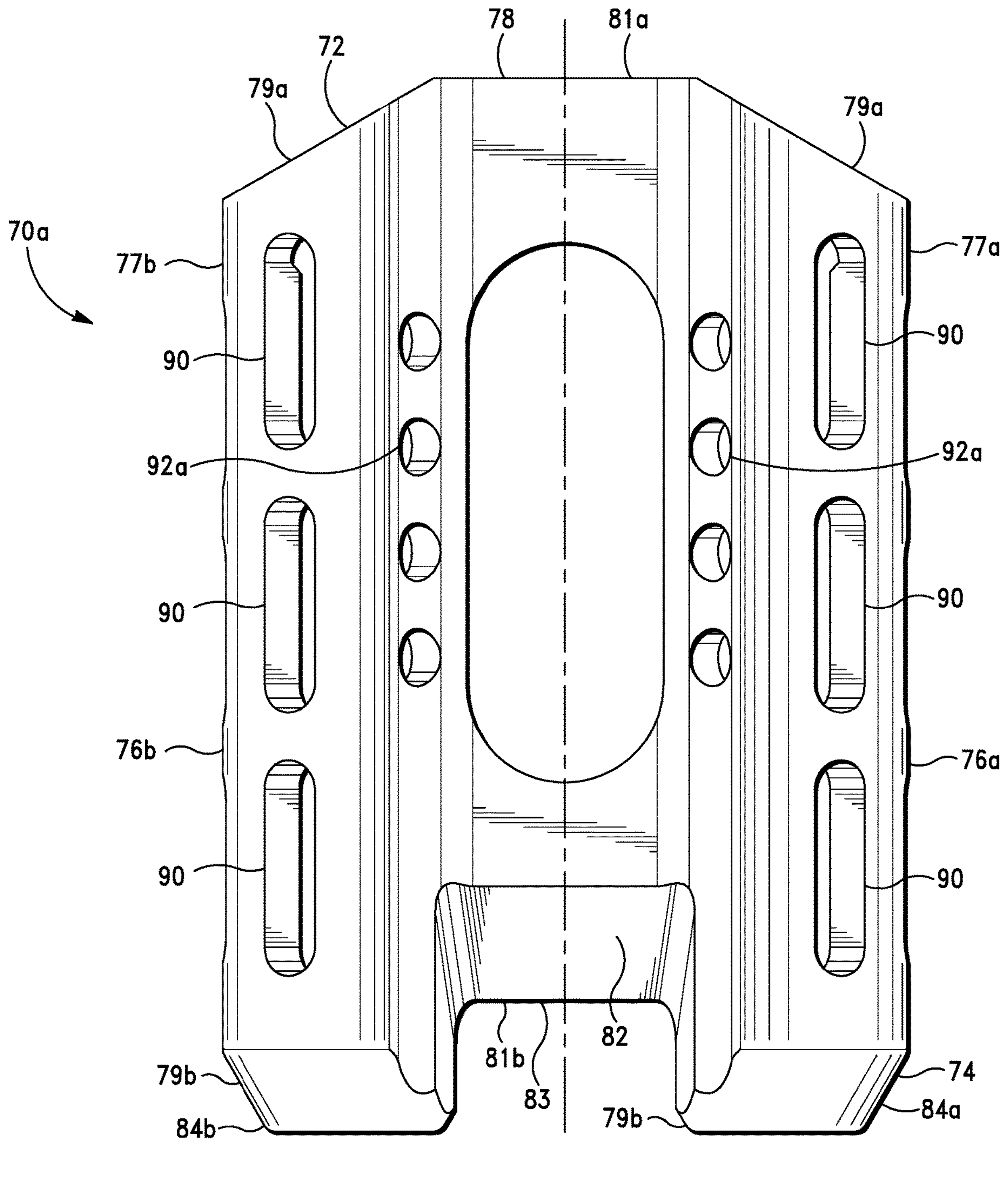
FIG. 9B is a top plan view of the SI joint prosthesis shown in FIG. 9A, in accordance with the invention.
Figure 9C:
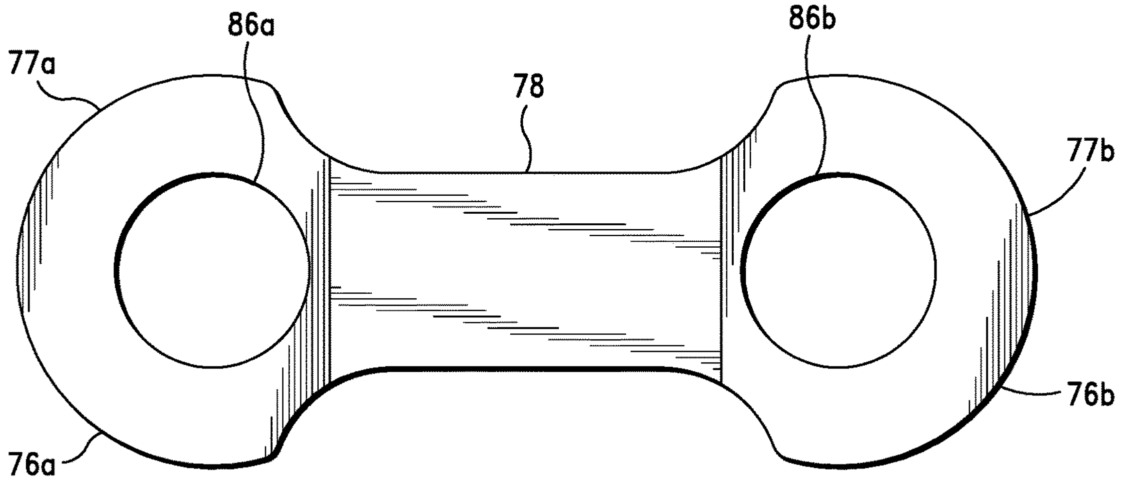
FIG. 9C is a left-side (end) view of the SI joint prosthesis shown in FIG. 9A, in accordance with the invention.
Figure 9D:
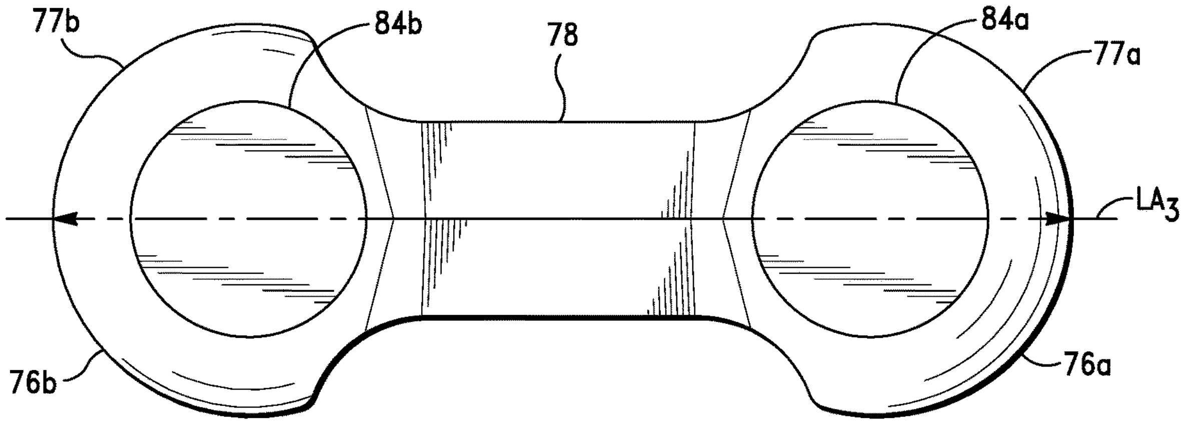
FIG. 9D is a right-side (end) view of the SI joint prosthesis shown in FIG. 9A, in accordance with the invention.
Figure 9E:
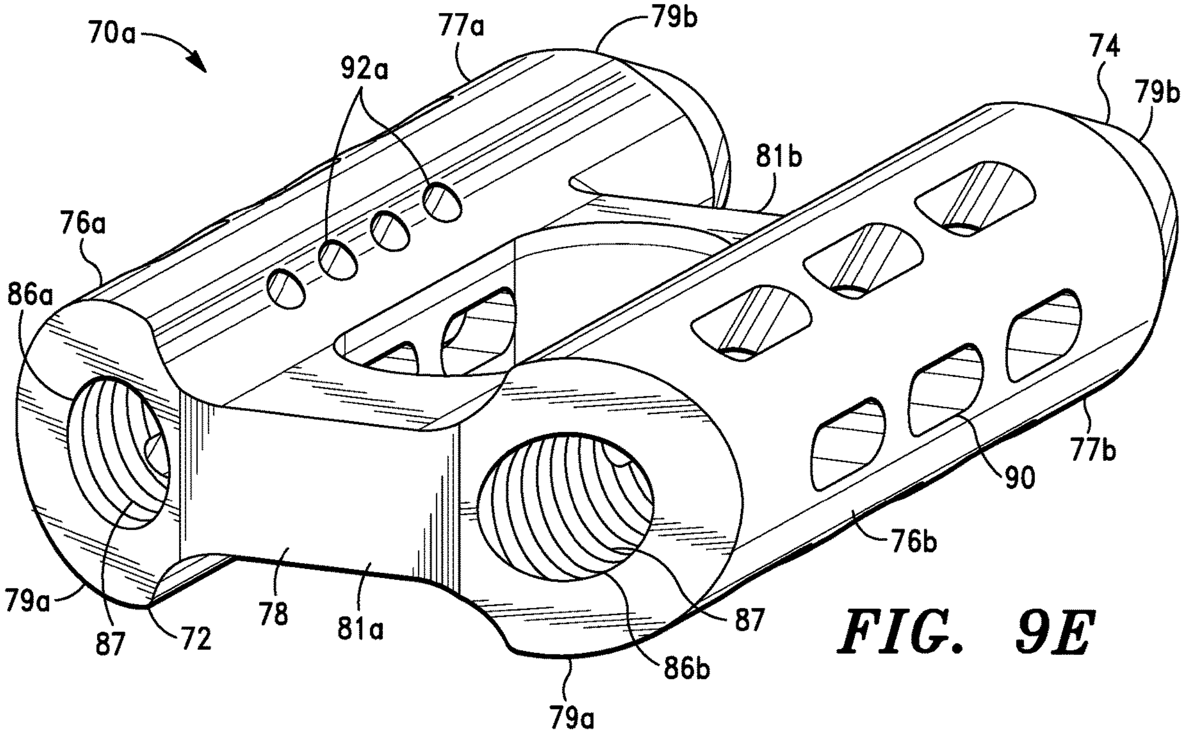
FIG. 9E is a rear perspective view of the SI joint prosthesis shown in FIG. 9A, in accordance with the invention.
Figure 9F:
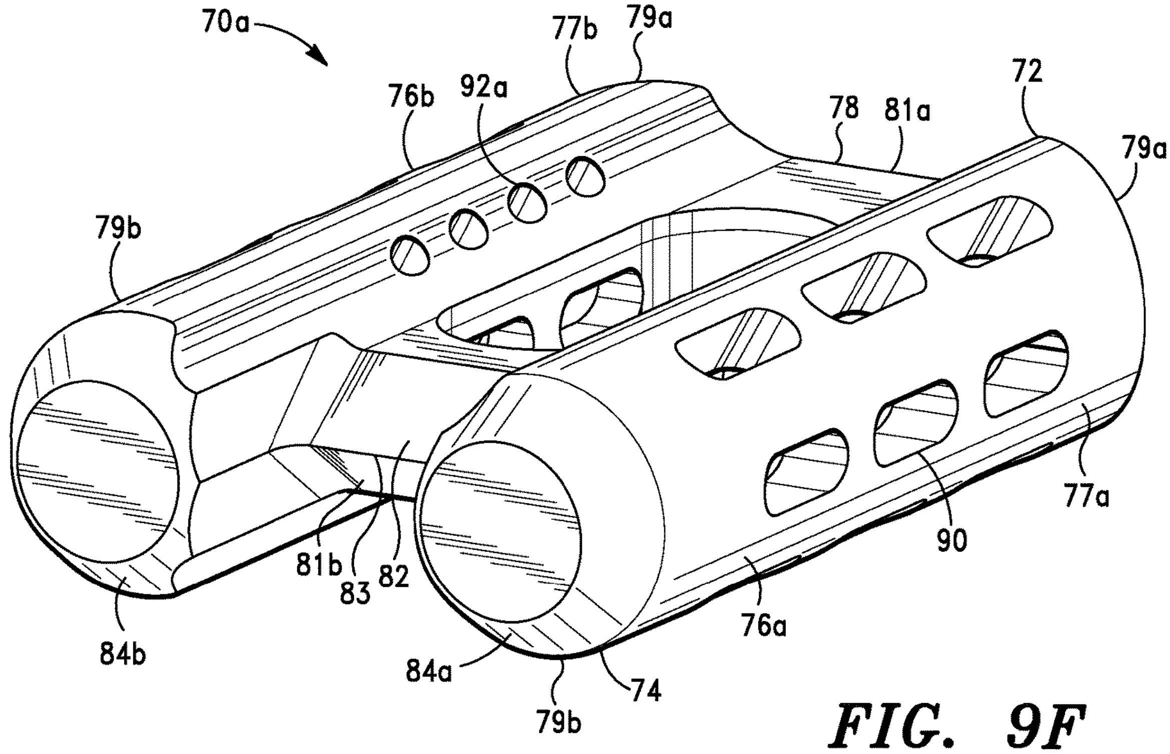
FIG. 9F is a front perspective view of the SI joint prosthesis shown in FIG. 9A, in accordance with the invention.

As illustrated in FIGS. 9A, 9E, and 9F, the SI joint prosthesis (denoted "70*a*") comprises a biocompatible and, hence, implantable member comprising proximal and distal ends 72, 74, and first and second elongated partially cylindrical sections 76*a*, 76*b* connected to a bridge section 78, whereby the SI joint prosthesis 70*a* comprises a continuous exterior surface comprising first and second partially cylindrical surface regions 77*a*, 77*b*.

As further illustrated in FIGS. 9A, 9E, and 9F, the first and second partially cylindrical sections 76*a*, 76*b* comprise proximal and distal ends 79*a*, 79*b*. The bridge section 78 similarly comprises proximal and distal ends 81*a*, 81*b*.

As set forth in Applicant's Co-Pending U.S. application Ser. Nos. 17/463,779, 17/468,811 and 18/107,563, the SI joint prosthesis 70*a* can comprise any suitable length from the proximal ends 79*a* to the distal ends 79*b* of the partially cylindrical sections 76*a*, 76*b*.

In some embodiments, the SI joint prosthesis 70*a* (and 70*b* discussed below) comprises a length in the range of 20-50 mm, more preferably, a length in the range of 30-40 mm.

As illustrated in FIGS. 9A and 9B, in some embodiments of the invention, the partially cylindrical sections 76*a*, 76*b* comprise equal lengths. In some embodiments, the partially cylindrical sections 76*a*, 76*b* comprise unequal lengths.

As illustrated in FIGS. 9A and 9C, in some embodiments, the first partially cylindrical surface region 77*a* preferably comprises a partially cylindrical surface region shape that corresponds to at least a portion of the first lobe region 103 of the pilot SI joint opening 100 and/or the sacrum guide portion 203 of the pilot SI joint opening 200, and/or the second lobe region 104 of the pilot SI joint opening 100 and/or the ilium guide portion 204 of the pilot SI joint opening 200, depending on the entry position of the prosthesis 70*a* into the pilot SI joint openings 100, 200.

The second partially cylindrical surface region 77*b* similarly preferably comprises a partially cylindrical surface region shape that corresponds to at least a portion of the first lobe region 103 of the pilot SI joint opening 100 and/or the sacrum guide portion 203 of the pilot SI joint opening 200, or the second lobe region 104 of the pilot SI joint opening 100 and/or the ilium guide portion 204 of the pilot SI joint opening 200, again depending on the entry position of the prosthesis 70*a* into the pilot SI joint openings 100, 200.

As illustrated in FIGS. 9A, 9B, and 9F-9H, in a preferred embodiment, the distal end 81*b* of the bridge section 78 comprises a taper region 82, which is configured and adapted to disrupt, i.e., cut into and through, articular cartilage and cortical bone 8 (and, in some aspects, trabecular bone 10), which define a SI joint.

In some embodiments of the invention, the taper region 82 comprises two angled regions that intersect at a central point 83, i.e., pointed proximate the mid-region of the bridge section 78, such as shown in FIGS. 9A and 9F.

In some embodiments, the taper region 82 comprises a single angled or sloped region defining a plane that intersects the plane defined by the bottom surface of the SI joint prosthesis 70*a*, i.e., wedge shaped or bevel configuration.

In a preferred embodiment, the distal ends 79*b* of the first and second elongated partially cylindrical sections 76*a*, 76*b* also comprise tapered regions 84*a*, 84*b*, which facilitate (i) insertion of the distal ends 79*b* of the first and second elongated partially cylindrical sections 76*a*, 76*b* into the first and second lobe regions 103, 104 of the pilot SI joint opening 100 and/or the sacrum and ilium guide portions 203, 204 of the pilot SI joint opening 200, and (ii) as discussed in detail below, in some embodiments, transition of the pilot SI joint opening 100 from a first configuration and size (and, hence, cross-sectional area, i.e., $A^2$-1 shown in FIG. 12A of priority U.S. application Ser. No. 17/903,527) to a second expanded configuration and size (and, hence, cross-sectional area, i.e., $A^2$-2 shown in FIG. 12B of priority U.S. application Ser. No. 17/903,527) when the SI joint prosthesis 70*a* is inserted therein.

Figure 9G:
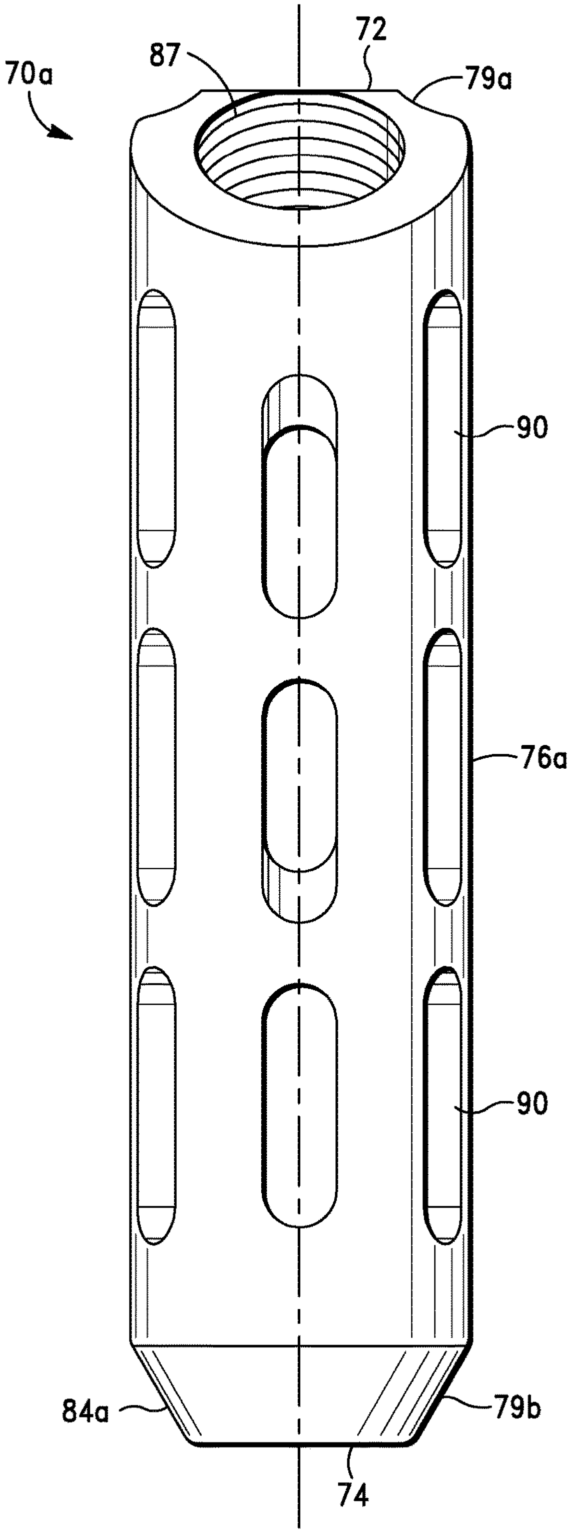
FIG. 9G is a right-side plan view of the SI joint prosthesis shown in FIG. 9A, in accordance with the invention.
Figure 9H:
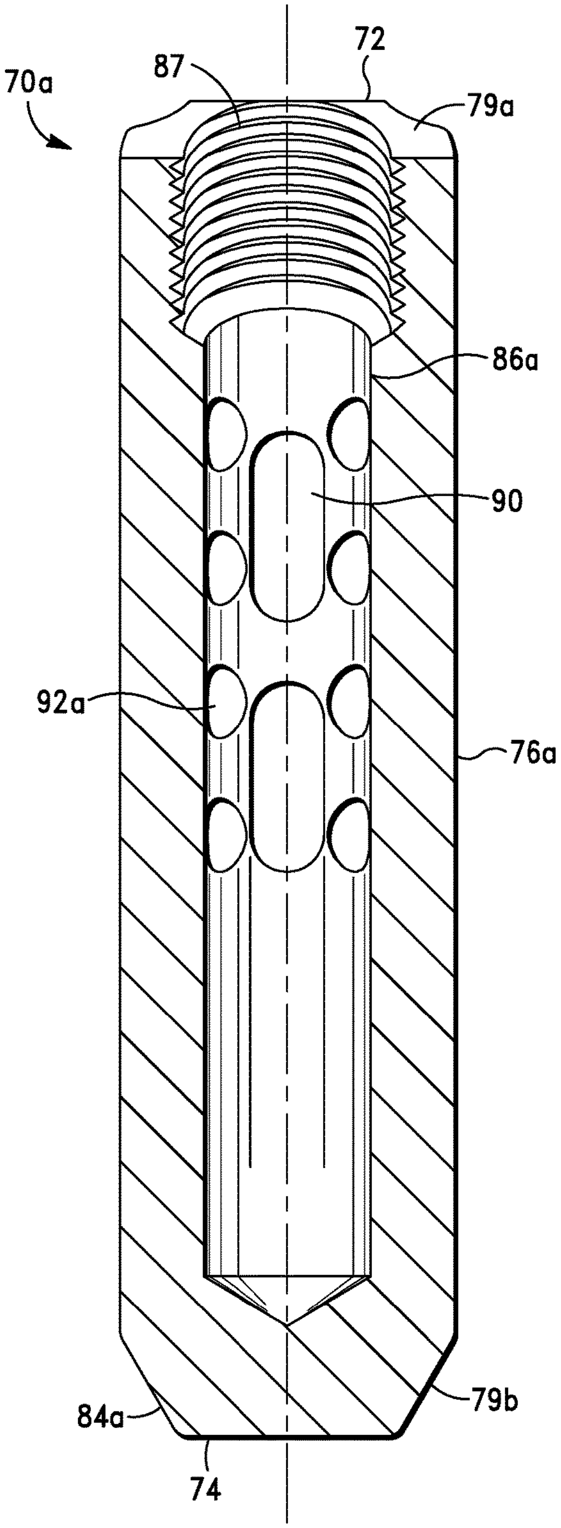
FIG. 9H is a right-side sectional plan view of the SI joint prosthesis shown in FIG. 9A, in accordance with the invention.
Figure 9I:
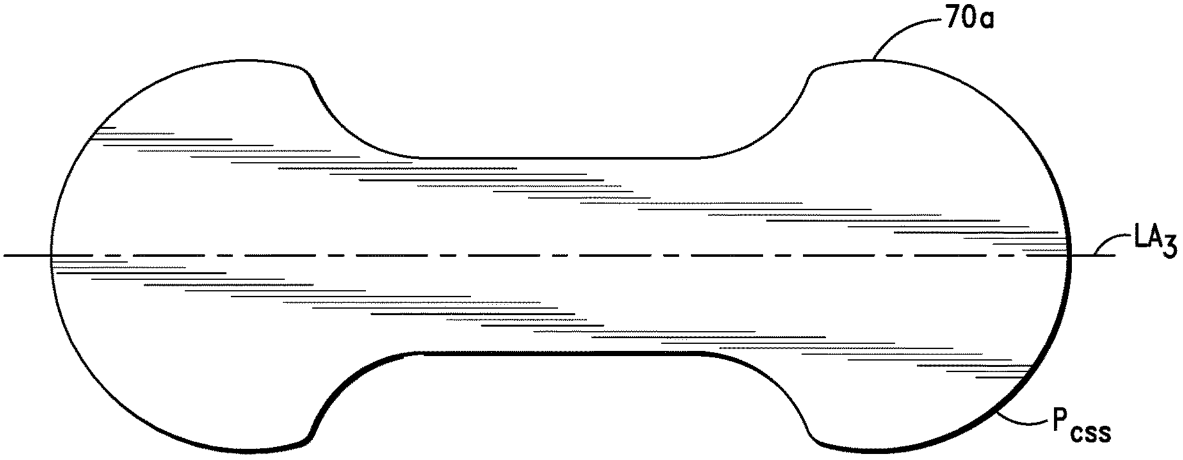
FIG. 9I is another rear plan view of the SI joint prosthesis shown in FIG. 9A showing the cross-sectional shape defined by the outer surface of the prosthesis, in accordance with the invention.

As illustrated in FIGS. 9C, 9E, and 9H, in a preferred embodiment, the first elongated partially cylindrical section 76*a* of the SI joint prosthesis 70*a* comprises an internal prosthesis engagement member lumen 86*a* that extends from the proximal end 79*a* of the first elongated partially cylindrical section 76*a*.

As illustrated in FIGS. 9C and 9E, the second elongated partially cylindrical section 76*b* of the SI joint prosthesis 70*a* also comprises an internal prosthesis engagement member lumen 86*b* that extends from the proximal end 79*a* of the first elongated partially cylindrical section 76*b*.

In a preferred embodiment, the internal prosthesis engagement member lumens 86*a*, 86*b* of the SI joint prosthesis 70*a* are sized and configured to receive the prosthesis guide pins 606 of the prosthesis deployment assemblies 600*a*, 600*b*, discussed below, and the prosthesis engagement rod 700 of the prosthesis deployment assemblies 600*a*, 600*b*.

As illustrated in FIGS. 9E and 9G, in a preferred embodiment, the internal prosthesis engagement member lumens

86*a*, 86*b* of the first and second elongated partially cylindrical sections 76*a*, 76*b* comprise a threaded region 87 proximate the proximal end 79*a* that is sized and configured to receive and threadably engage the threaded distal end 704 of the prosthesis engagement rod 700 of the prosthesis deployment assemblies 600*a*, 600*b*, discussed below (see FIG. 16B).

In a preferred embodiment, the internal prosthesis engagement lumens 86*a*, 86*b* are also configured to receive agents and compositions that further facilitate adhesion of the SI joint prosthesis 70*a* to the pilot SI openings 100, 200 of the invention and, thereby, sacrum and/or ilium, and bone material, e.g., autograft bone, and the aforementioned biologically active agents and compositions, including osteogenic agents and compositions, and pharmacological agents and compositions that facilitate osseous or bone tissue ingrowth into the SI joint prosthesis 70*a* and healing of the SI joint bone structures.

Referring back to FIGS. 9A and 9B, in a preferred embodiment, the SI joint prosthesis 70*a* further comprises an open or hollow bridge section 78 and a plurality of slots 90 and apertures (or holes) 92*a* disposed in the first and second elongated partially cylindrical sections 76*a*, 76*b*, which preferably are in communication with the internal prosthesis engagement member lumens 86*a*, 86*b*.

Figure 10A:
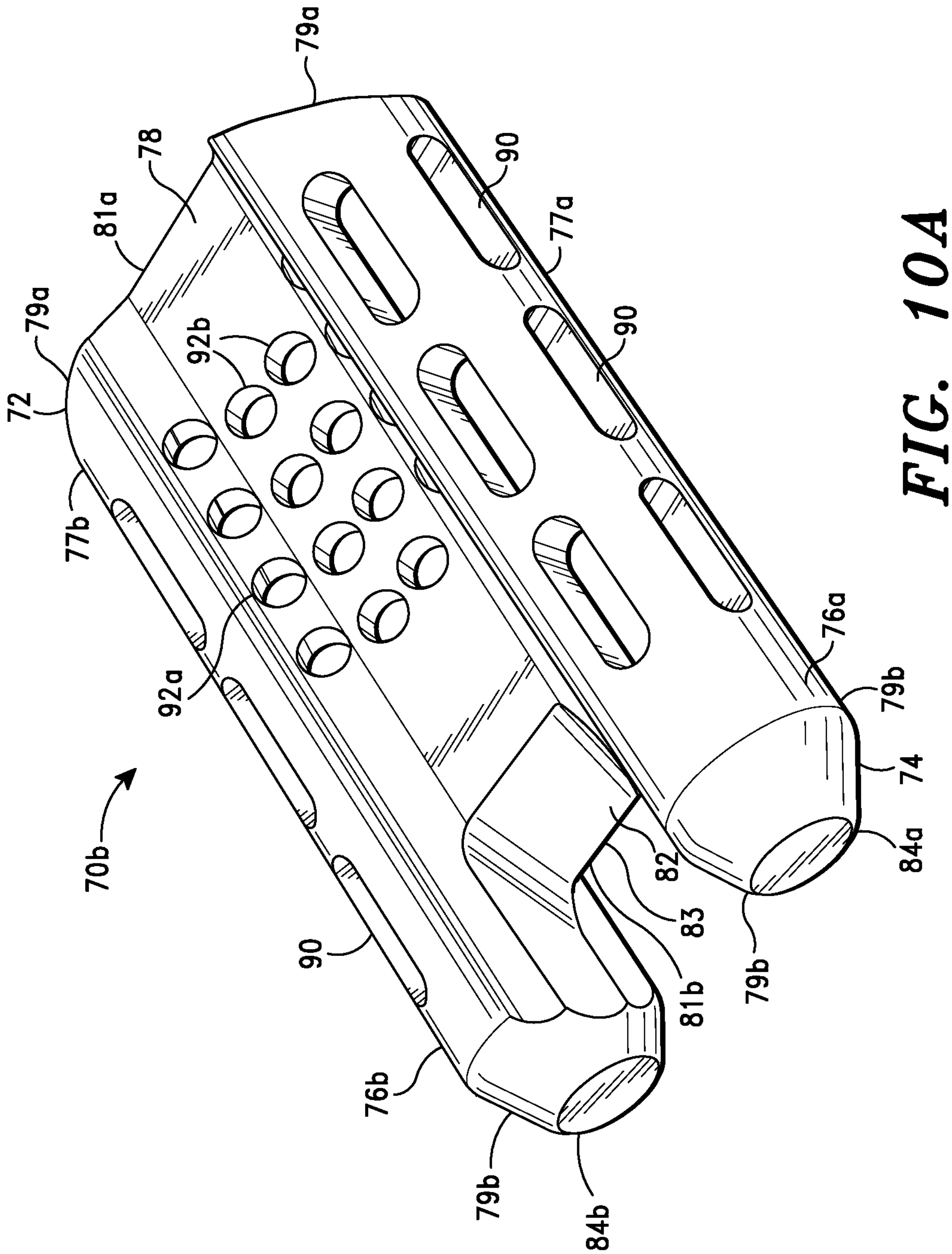
FIG. 10A is a perspective view of another embodiment of a SI joint prosthesis, in accordance with the invention.
Figure 10B:
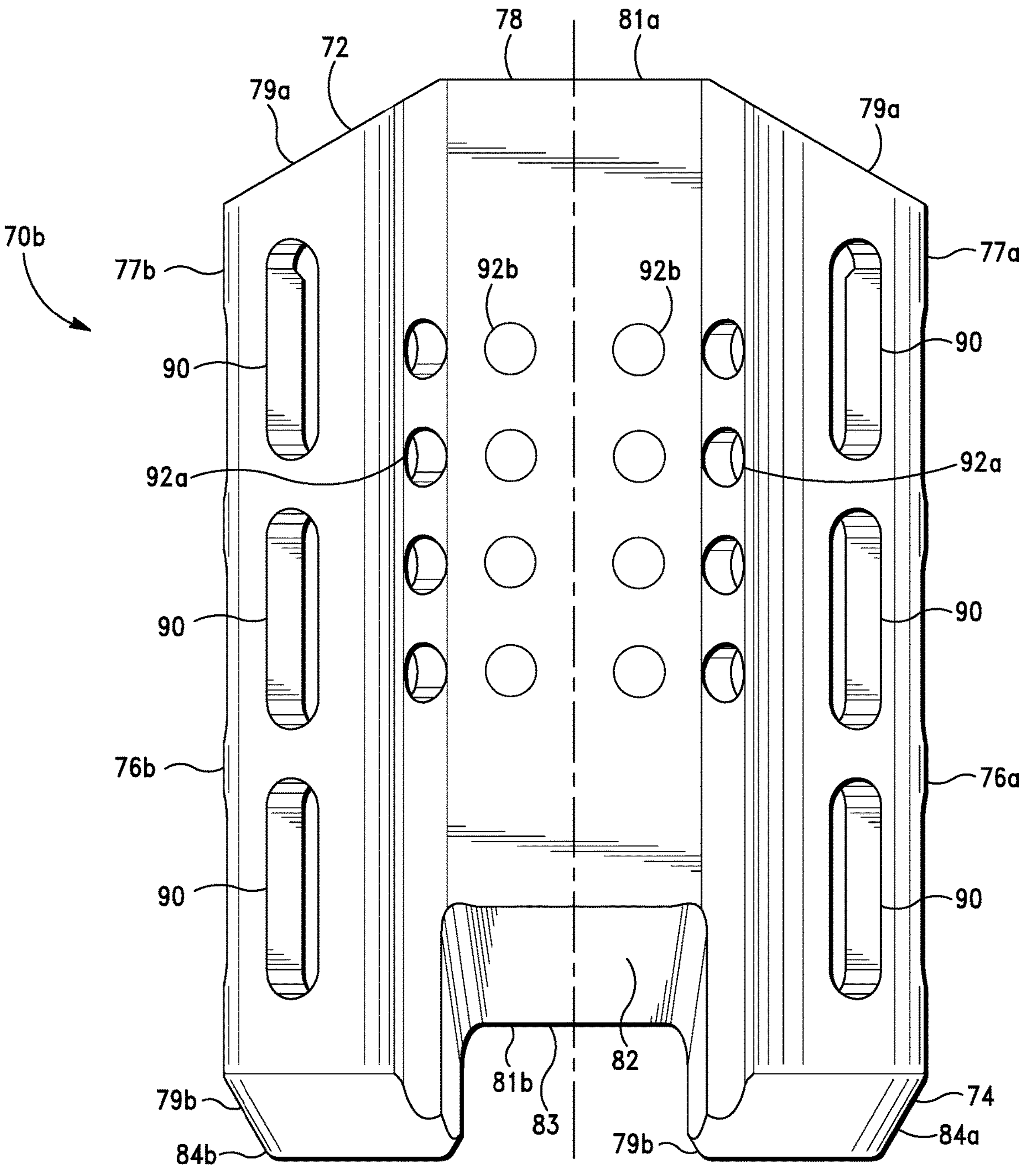
FIG. 10B is a top plan view of the SI joint prosthesis shown in FIG. 10A, in accordance with the invention.

Referring now to FIGS. 10A and 10B, there is shown another embodiment of the SI joint prosthesis illustrated in FIGS. 9A-9I. As illustrated in FIGS. 10A and 10B, the SI joint prosthesis (now denoted "70*b*") comprises all of the features of SI joint prosthesis 70*a*, with the exception of the bridge section 78 now comprises a plurality of apertures (or holes) 92*b*. In some embodiments, the bridge section 78 comprises a plurality of slots 90.

In some embodiments of the invention, the bridge section comprises a hollow structure, e.g., further comprises at least one internal passageway that is adapted to also receive the bone material, agents and compositions referenced above.

In a preferred embodiment, the bone material, agents and compositions referenced above are adapted to extrude through the slots 90 and apertures 92*a*, 92*b* of the SI joint prostheses 70*a*, 70*b* when the SI joint prostheses 70*a*, 70*b* are inserted in a pilot SI joint opening (i.e., pilot SI joint openings 100 or 200), to, as indicated above, (i) further facilitate adhesion of the SI joint prostheses 70*a*, 70*b* to the pilot SI openings 100, 200 of the invention and, thereby, sacrum and/or ilium, and (ii) facilitate osseous or bone tissue ingrowth into the SI joint prostheses 70*a*, 70*b* and healing of the SI joint bone structures.

Figure 11A:
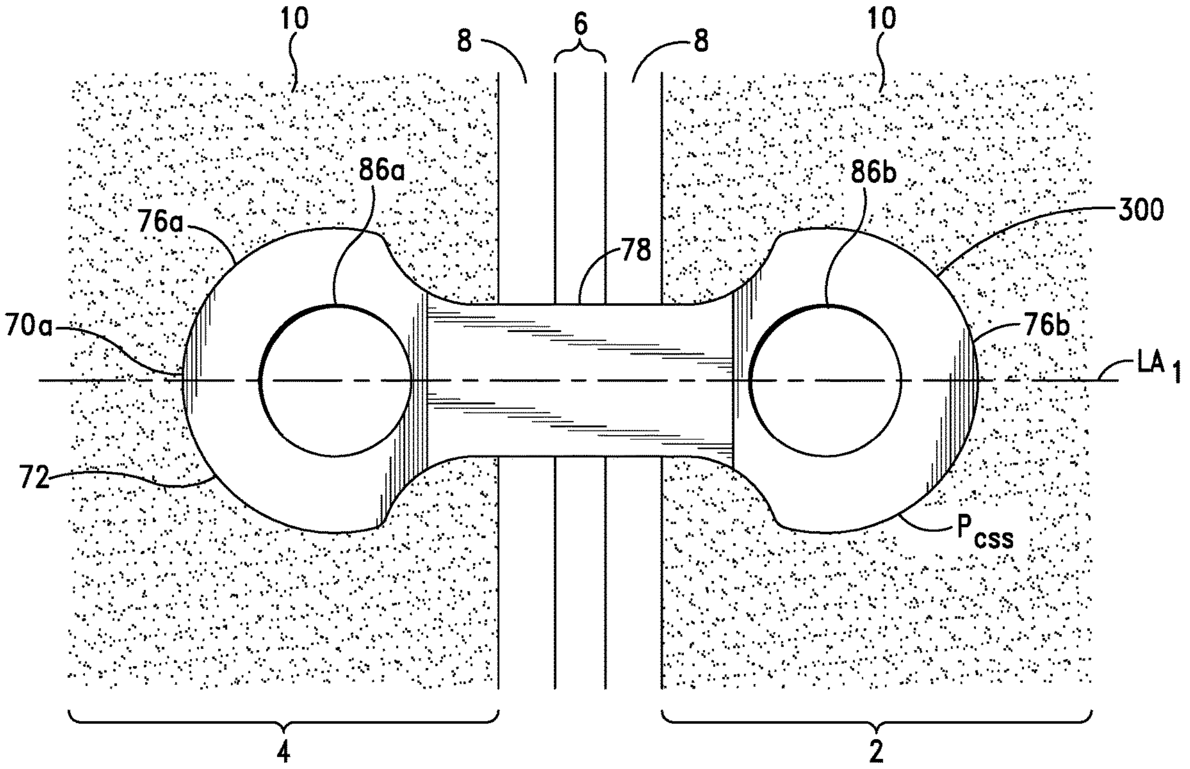
FIG. 11A is an illustration of the SI joint prosthesis shown in FIG. 9A inserted into the pilot SI joint opening shown in FIG. 8A and the resulting or induced post-prosthesis insertion SI joint opening, in accordance with the invention.
Figure 11B:
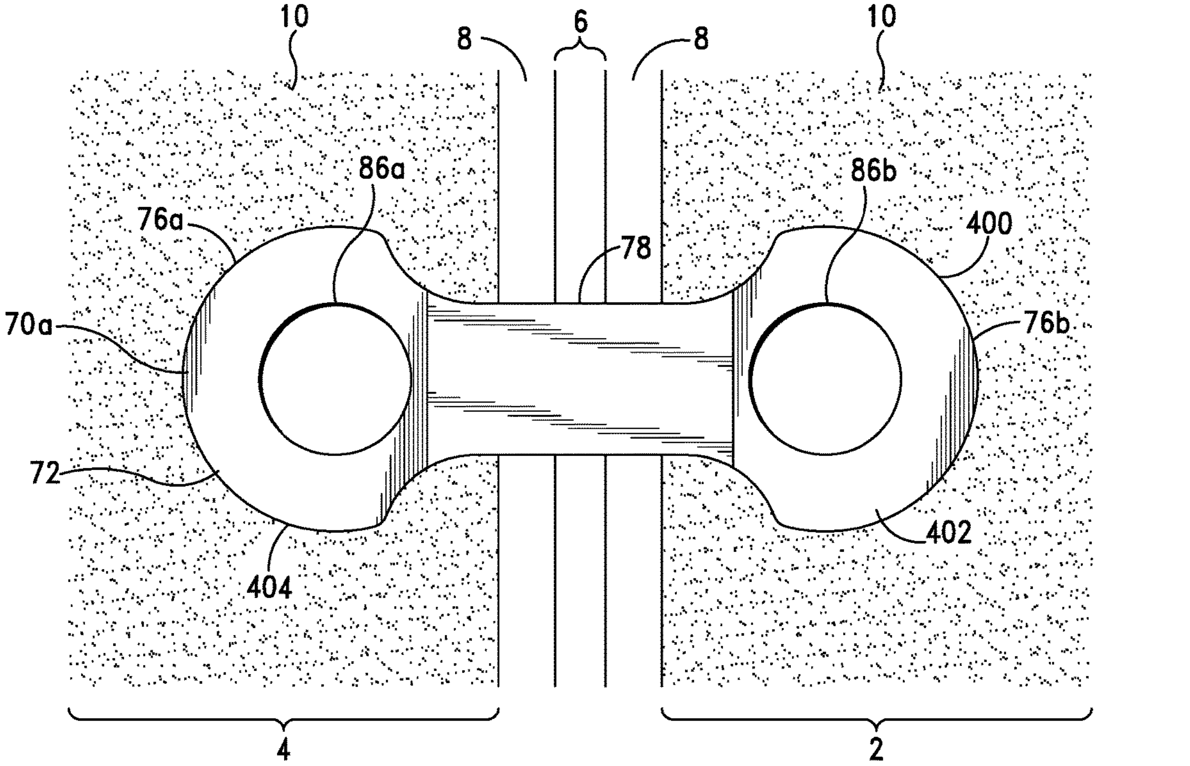
FIG. 11B is an illustration of the SI joint prosthesis shown in FIG. 10A inserted in the pilot SI joint opening shown in FIG. 8B and the resulting or induced post-prosthesis insertion SI joint opening, in accordance with the invention.

Referring now to FIG. 11A, according to the invention, the continuous exterior surface of the SI joint prostheses 70*a*, 70*b* defines a substantially bi-lobe prosthesis cross-sectional shape (denoted "$P_{CSS}$") having a longitudinal axis $LA_1$.

As set forth in Co-pending U.S. application Ser. Nos. 17/463,779 and 17/468,811, according to one embodiment of the invention, the length of the prosthesis cross-sectional shape $P_{CCS}$ along longitudinal axis $LA_1$ is greater than the length of the pilot SI joint opening 100 illustrated in FIG. 8A along the longitudinal axis $LA_1$, whereby, when the SI joint prostheses 70*a*, 70*b* are inserted into pilot SI joint opening 100, the pilot SI opening 100 transitions to a post-prosthesis insertion SI joint opening 300 illustrated in FIG. 12, which comprises a larger cross-sectional length shape that corresponds to the length of the prosthesis cross-sectional shape $P_{CCS}$.

Figure 12:
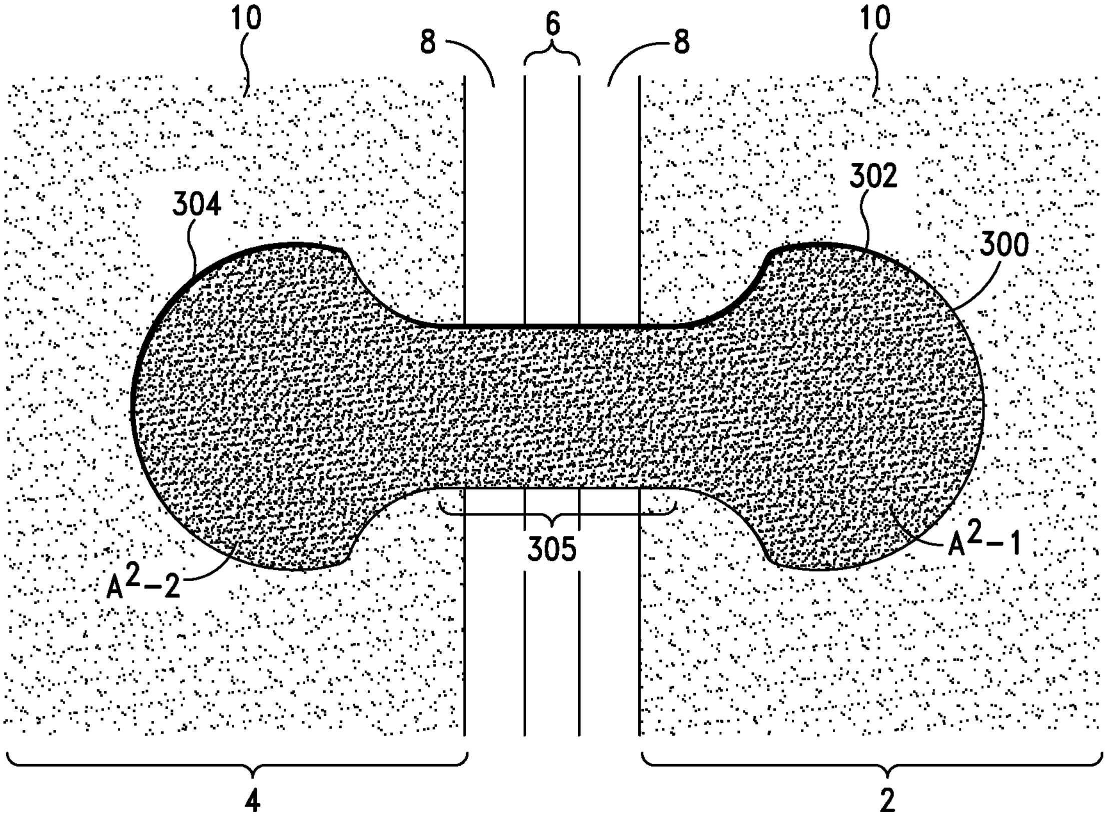
FIG. 12 is an illustration of the post-prosthesis insertion SI joint opening generated or induced when the SI joint prosthesis shown in FIG. 9A is inserted in the pilot SI joint opening shown in FIG. 8A, in accordance with the invention.

As further illustrated in FIG. 12, the cross-sectional areas of the post-prosthesis sacrum and ilium guide portions of the post-prosthesis insertion SI joint opening 300 (now denoted "302" and "304", respectively) also comprise greater cross-sectional areas (denoted "$A^2$-1" and "$A^2$-2").

As further illustrated in FIG. 12, the mid-region 105 of pilot SI joint opening 100 also transitions to a much larger region (denoted "305"), which is achieved by virtue of the tapered bridge section 78 of the SI joint prostheses 70*a*, 70*b* cutting into and through the articular cartilage and cortical bone 8, which define the SI joint 6, and the trabecular bone 10 proximate the SI joint 6.

In a preferred embodiment of the invention, to achieve sufficient expansion of the pilot SI joint openings 100, 200 when the SI joint prostheses 70*a*, 70*b* are inserted therein, preferably, the cross-sectional areas of the regions defined by the first and second elongated partially cylindrical sections 76*a*, 76*b* of the SI joint prostheses 70*a*, 70*b* are at least 0.05% greater than the cross-sectional areas defined by the first and second lobe regions 103, 104 of the pilot SI joint opening 100, and the cross-sectional areas defined by the sacrum and ilium guide portions 203, 204 of pilot SI joint opening 200.

In some embodiments of the invention, the cross-sectional areas of the regions defined by the first and second elongated partially cylindrical sections 76*a*, 76*b* of the SI joint prostheses 70*a*, 70*b* are substantially equal to or slightly smaller, e.g., <0.05%, than the cross-sectional areas defined by the first and second lobe regions 103, 104 of the pilot SI joint opening 100, and the cross-sectional areas defined by the sacrum and ilium guide portions 203, 204 of pilot SI joint opening 200.

According to the invention, the SI joint prostheses 70*a*, 70*b* can comprise various biocompatible materials, including metals and metal alloys, such as titanium, stainless-steel, cobalt-chromium alloys and nickel-titanium alloys, and various biocompatible polymers, including, without limitation, reinforced polymers, such as carbon fiber reinforced polymers and metal-framed polymers.

The SI joint prostheses 70*a*, 70*b* can additionally comprise a porous structure to facilitate (i) adhesion of the prostheses 70*a*, 70*b* to post-prosthesis insertion SI joint openings of the invention and, thereby, to SI joint bone structures, i.e., sacrum and ilium bone structures, and (ii) bone or osseous tissue ingrowth into the prostheses 70*a*, 70*b*.

The SI joint prostheses 70*a*, 70*b* can further comprise various exterior surface textures and roughness to facilitate or enhance engagement of the prosthesis to post-prosthesis insertion SI joint openings, and, thereby, to SI joint bone structures, i.e., sacrum and ilium bone structures, and/or maintain engagement thereto and positioning therein.

According to the invention the SI joint prostheses 70*a*, 70*b* can further comprise an outer coating.

In some embodiments, the outer coating comprises one of the aforementioned osteogenic compositions.

In some embodiments, the osteogenic composition comprises a demineralized bone matrix, autograft bone material, allograft bone material, xenograft bone material, polymethyl-methacrylate or calcium-based bone material.

In some embodiments, the osteogenic composition comprises a bone morphogenic protein (BMP).

In some embodiments, the BMP comprises BMP-1, BMP2a, BMP2b, BMP3, BMP4, BMP5, BMP6, BMP7, or BMP8a.

In some embodiments, the outer coating comprises one of the aforementioned biologically active agents.

In some embodiments, the biologically active agent comprises a basic fibroblast growth factor (bFGF), a transforming growth factor-β (TGF-β), a vascular endothelial growth factor (VEGF), a platelet derived growth factor (PDGF), an insulin-like growth factor (IGF), an epidermal growth factor (EGF), or a growth and differentiation factor-5 (GDF-5).

In some embodiments, the outer coating comprises one of the aforementioned pharmacological agents.

In some embodiments of the invention, the outer coating comprises a biocompatible adhesive composition.

According to the invention, suitable adhesive compositions include, without limitation, poly(L-glutamic acid)-based compositions, poly(γ-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol and combinations thereof; fibrin-based compositions, collagen-based compositions, including collagen and poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and OctylSeal); poly(ethylene glycol) (PEG) based compositions, including FocalSeal®, Progel™, Duraseal™, DuraSeal™ Xact, Coseal® and ReSure Sealant; polysaccharide-based compositions, polypeptide-based compositions, and radiation curable materials, such as poly (glycerol-co-sebacate) acrylate (PGSA), discussed below.

In some embodiments, the outer coating comprises one of the aforementioned polymers and/or compositions comprising same.

In some embodiments of the invention, the polymer comprises poly(glycerol sebacate) (PGS) or a derivative thereof, including, without limitation, poly(glycerol-co-sebacate) acrylate (PGSA) and PGS co-polymers, such as poly(glycerol sebacate)-co-poly(ethylene glycol) (PGS-PEG); and/or composites thereof, e.g., PGS-hydroxyapatite (HA) composites and PGS-poly(ε-caprolactone) (PGS-PCL) composites, and compositions comprising same.

Exemplar PGS coated SI joint prostheses are described in detail in Applicant's Co-Pending U.S. application Ser. Nos. 17/463,779, 17/468,811, and 17/469,132, which are expressly incorporated herein in its entirety.

As set forth in Co-Pending U.S. application Ser. Nos. 17/463,779, 17/468,811, and 17/469,132, PGS and derivatives thereof possess a unique property of inducing remodeling of damaged osseous or bone tissue, such as at pilot SI joint openings, and, hence, healing of the associated bone structures when disposed proximate thereto.

As further set forth in Co-Pending U.S. application Ser. Nos. 17/463,779, 17/468,811, and 17/469,132, in some embodiments, the PGS based outer coatings comprise a degree of esterification in the range of ~76%-83%, whereby the PGS exhibits adhesive properties, which will enhance engagement of prostheses 70*a*, 70*b* to the post-prosthesis insertion SI joint openings 300, 400 and, thereby, to the SI joint bone structures, i.e., sacrum and ilium bone structures.

As additionally set forth in Co-pending U.S. application Ser. Nos. 17/463,779, 17/468,811, and 17/469,132, PGS and its derivatives; particularly, PGSA are also excellent platforms for delivery and, hence, administration of biologically active agents and pharmacological agents to mammalian tissue, including osseous or bone tissue. Thus, in some embodiments of the invention, the PGS outer coatings and PGS and PGSA based compositions further comprise one or more of the aforementioned biologically active or pharmacological agents.

Bone Harvesting Assemblies

As indicated above, in a preferred embodiment of the invention, the tool assemblies of the invention further comprise a bone harvesting assembly adapted to extract and contain bone material from the bone dislodging apparatus, i.e., drill bit, after creating the SI joint opening or a portion thereof.

Referring now to FIGS. 13A-13E, there is shown one embodiment of a bone harvesting assembly of the invention (denoted "900").

Figure 13A:
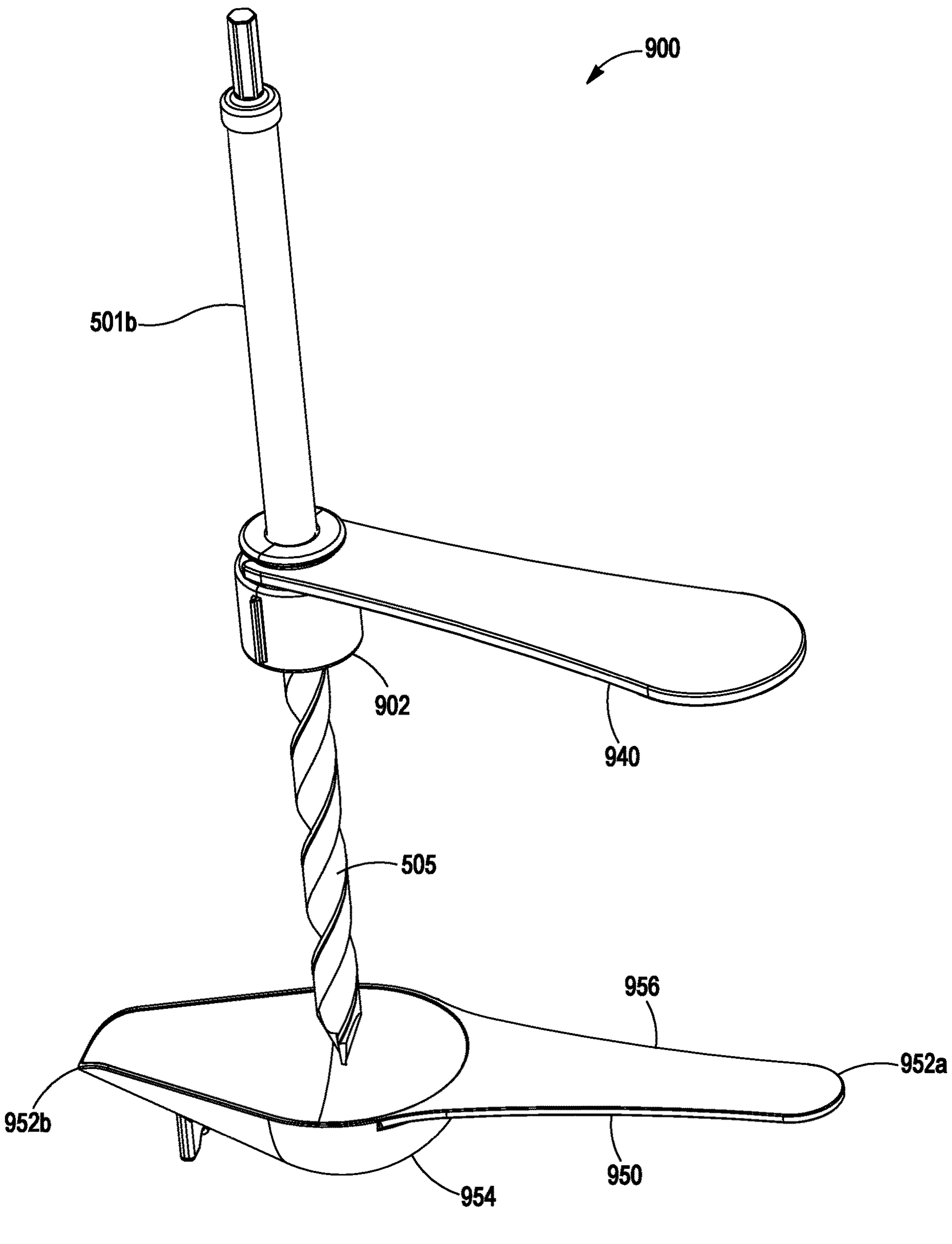
FIG. 13A is a perspective view of one embodiment of a bone harvester assembly, in accordance with the invention.
Figure 13B:
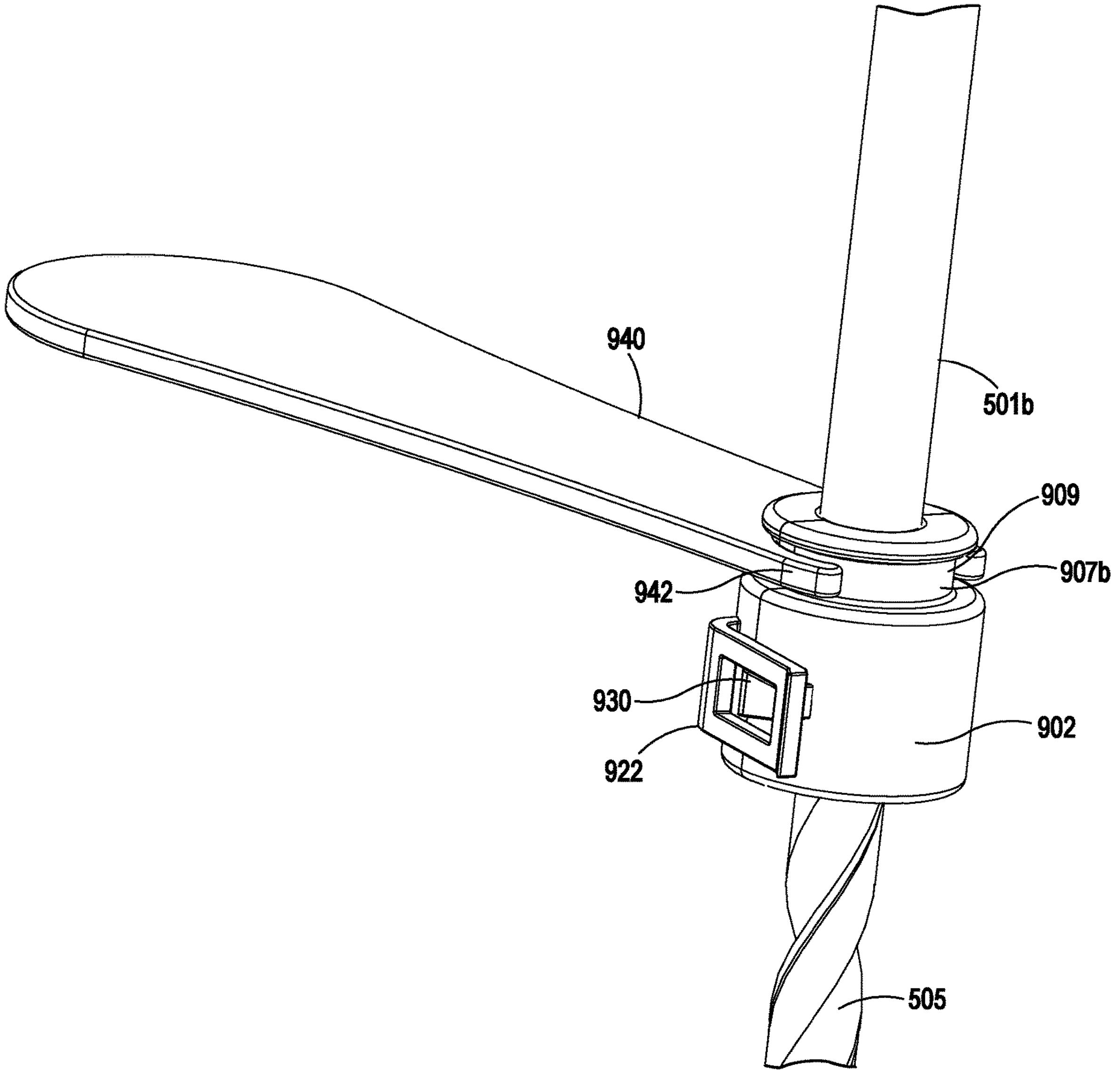
FIG. 13B is a partial further perspective view of the bone harvester assembly shown in FIG. 13A, in accordance with the invention.

As illustrated in FIGS. 13A and 13B, the bone harvesting assembly 900 generally comprises a bone retraction sleeve 902, which, as discussed below, is adapted to directly remove (or extract) bone material from the drill bit; particularly, drill bits 501*a*, 501*b* or 501*c* of the invention, and a handle 940.

Figure 13C:
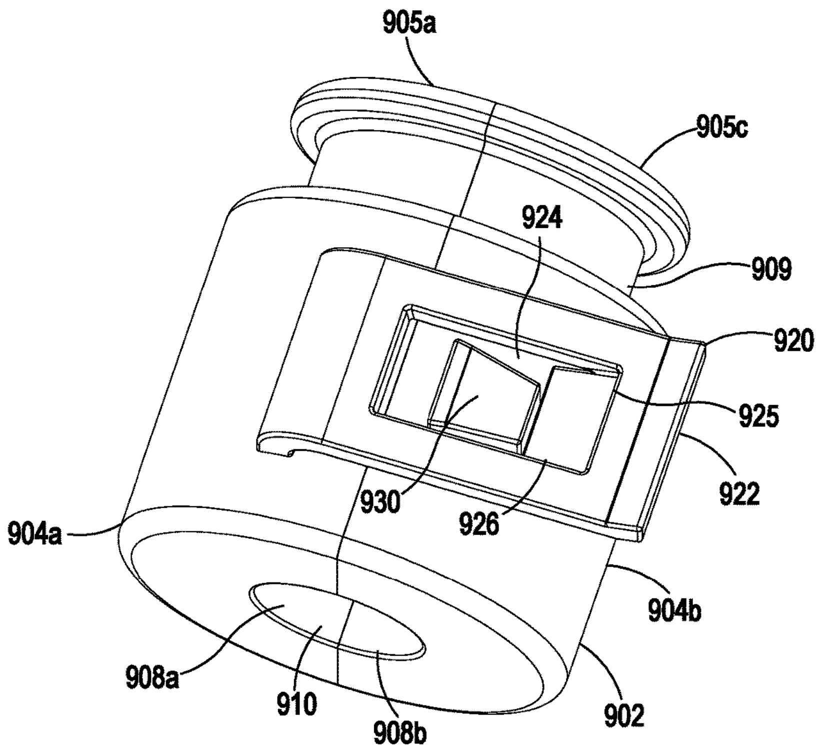
FIG. 13C is a perspective view of the bone retraction sleeve of the bone harvester assembly shown in FIG. 13A, in accordance with the invention.
Figure 13D:
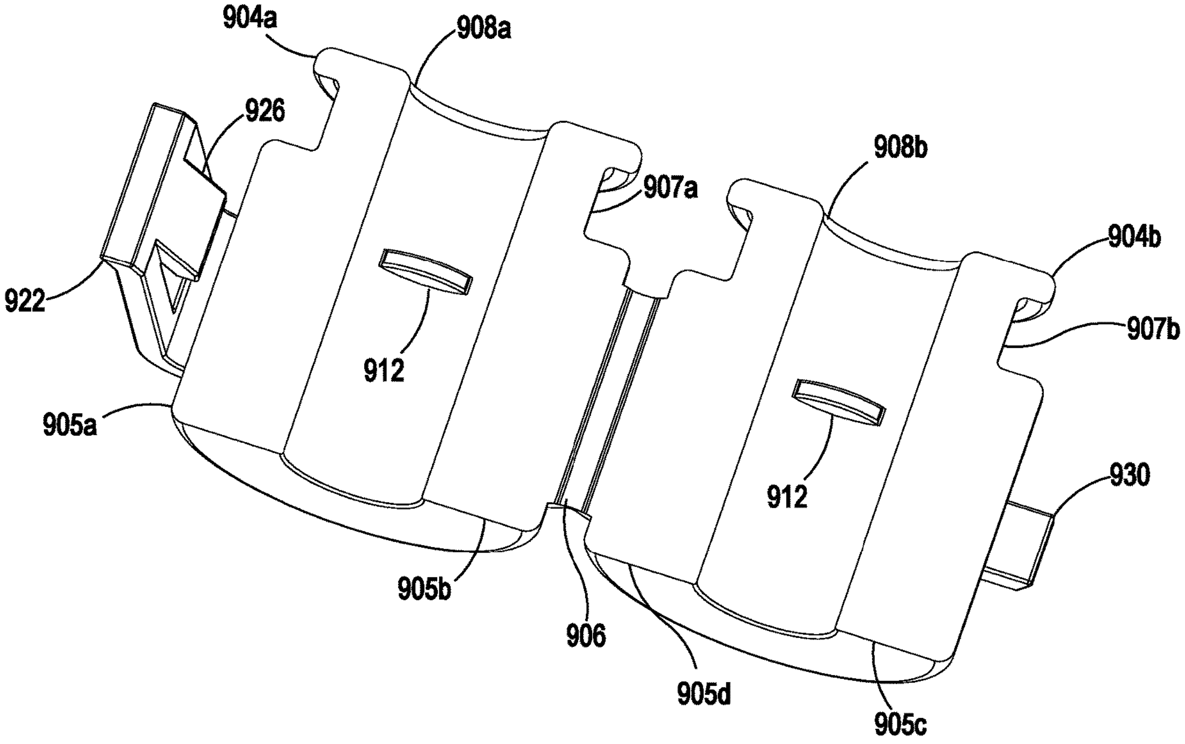
FIG. 13D is a perspective view of the bone retraction sleeve shown in FIG. 13C in an open configuration, in accordance with the invention.

As illustrated in FIG. 13D, in a preferred embodiment of the invention, the bone retraction sleeve 902 comprises two (2) corresponding shaped bone harvesting members 904*a*, 904*b*; bone harvesting member 904*a* comprising first and second edge regions 905*a*, 905*b* and bone harvesting member 904*b* comprising first and second edge regions 905*c*, 905*d*.

As further illustrated in FIG. 13D, the bone harvesting assembly 900 further comprises a hinge assembly 906, which is adapted to engage the second edge region 905*b* of bone harvesting member 904*a* and the second edge region 905*d* of bone harvesting member 904*b* to allow translation of the bone harvesting assembly 900 from an open configuration, as illustrated in FIG. 13D, to a closed configuration, as illustrated in FIG. 13C, whereby the bone harvesting assembly 900 comprises a substantially uniform cylindrical shape, and vice versa, i.e., from the closed configuration to the open configuration.

As further illustrated in FIG. 13D, each bone harvesting member 904*a*, 904*b* further comprises a correspondingly shaped and sized drill bit seat 908*a*, 908*b*. In a preferred embodiment, the drill bit seats 908*a*, 908*b* are aligned and positioned in the bone harvesting members 904*a*, 904*b*, whereby, when the bone harvesting assembly 900 is in the closed configuration illustrated in FIG. 13C, the drill bit seats 908*a*, 908*b* form a uniform drill bit guide lumen 910 that is sized and configured to receive a drill bit; preferably, drill bits 501*a*, 501*b* and 501*c* of the invention, therein, as illustrated in FIG. 13A.

As additionally illustrated in FIG. 13D, each bone harvesting member 904*a*, 904*b* further comprises a correspondingly shaped handle seat 907*a*, 907*b*.

As illustrated in FIGS. 13B and 13C, when the bone collection assembly 900 is in the closed configuration, handle seats 907*a*, 907*b* of the bone harvesting members 904*a*, 904*b* form a bone harvesting assembly seat 909 that is sized and configured to receive and seat the bone harvesting assembly handle 940 thereon.

To secure the bone harvesting members 904*a*, 904*b* in the closed configuration illustrated in FIG. 13C and, hence, secure the drill bit in the drill bit guide lumen 910, the bone harvesting assembly 900 further comprises assembly securing means 920.

As illustrated in FIGS. 13C and 13D, in a preferred embodiment, the assembly securing means 920 comprises a securing arm 922 and engagement member 930.

In a preferred embodiment, the securing arm 922 is connected proximate to the first edge region 905*a* of bone harvesting member 904*a* and the engagement member 926 is connected proximate the first edge region 905*c* of bone harvesting member 904*b*.

As further illustrated in FIGS. 13C and 13D, in a preferred embodiment, the securing arm 922 is rotatably connected proximate to the first edge region 905*a* of bone harvesting member 904*a* to allow translation of the securing arm 922 from a closed or engaged configuration, i.e., engaged to the engagement member 930, as discussed below, to an open configuration, i.e., disengaged from the engagement member 930, as illustrated in FIG. 13D.

According to the invention, the securing arm 922 can also be adapted to flex from the closed configuration to the noted open configuration and vice versa when engaged to the bone harvesting member 904*a*. Such arm flexure can be provided and/or achieved via the securing arm composition, i.e., comprising a flexible material, or securing arm configuration.

As illustrated in FIG. 13C, in a preferred embodiment, the securing arm 922 comprises an engagement member receiving slot 924 that is adapted to receive the engagement member 930 therein when the securing arm 922 is in the closed configuration illustrated in FIG. 13B.

In a preferred embodiment, the securing arm 922 further comprises a retainer flap 926 disposed on the distal end 925 of the engagement member receiving slot 924 that is sized and configured to releasably engage the engagement member 930 when the engagement member 930 is positioned in the receiving slot 924 and the securing arm 922 is in the closed configuration.

Referring now to FIG. 13D, in a preferred embodiment, each bone harvesting member 904*a*, 904*b* further comprises at least one bone extracting tab (or projection) 912 disposed on and extending from each drill bit seat 908*a*, 908*b*. In a preferred embodiment, the bone extracting tabs 912 are sized, positioned and configured to seat in a flute (or flutes) of a drill bit of the invention; particularly, flutes 505 of drill bits 501*a*, 501*b* and 501*c* (see FIGS. 3E, 4H and 4I), when the drill bit is seated in drill bit guide lumen 910 and the bone harvesting assembly 900 is in the closed configuration illustrated in FIG. 13B.

In a preferred embodiment, the bone extracting tabs 912 are sized, positioned and configured to extract bone material from the drill bit flute (or flutes) when the bone collection assembly 900 is in the closed configuration and the bone retraction sleeve 902 is translated linearly over the drill bit.

According to the invention, the bone extracting tabs 912 can be disposed at any position on the drill bit seats 908*a*, 908*b*, e.g., mid-regions, proximal end regions, distal end regions, combinations thereof, etc.

As indicated above, one or both of the drill bit seats 908*a*, 908*b* can also comprise a plurality of bone extracting tabs 912.

In an alternative embodiment, one or both of the drill bit seats 908*a*, 908*b* comprises a brush apparatus that is similarly sized and adapted to seat in the drill bit flute(s) and extract bone material from the drill bit flute(s) when the bone retraction sleeve 902 is translated linearly over the drill bit.

As indicated above and illustrated in FIGS. 13A and 13B, in a preferred embodiment, the bone harvesting assembly 900 further comprises a handle 940.

Figure 13E:
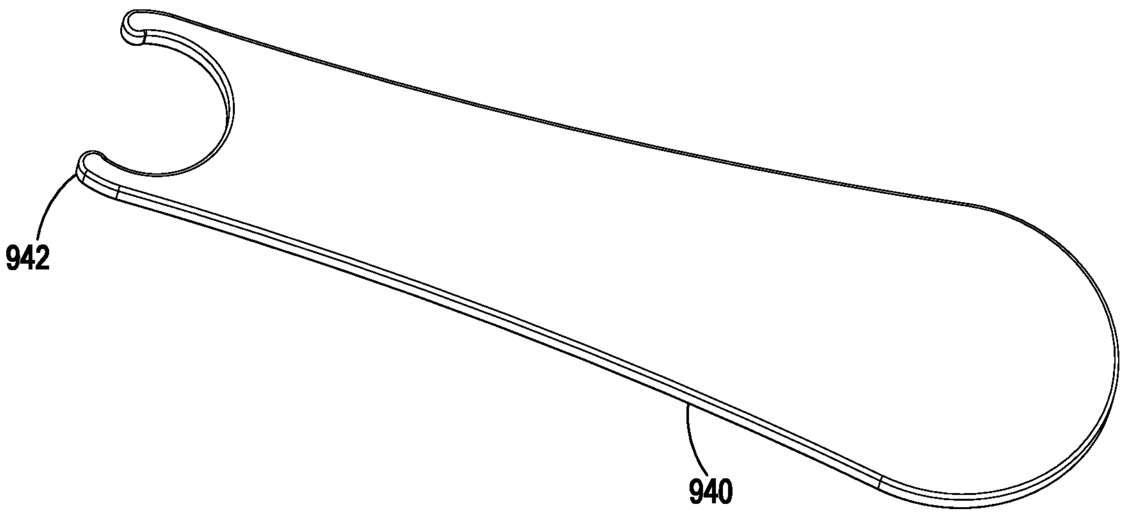
FIG. 13E is a perspective view of the handle of the bone harvester assembly shown in FIG. 13A, in accordance with the invention.

As illustrated in FIG. 13E, in a preferred embodiment, the handle 940 comprises a sleeve engagement end 942 sized and configured to releasably engage the bone harvesting assembly seat 909 of the bone retraction sleeve 902, and allow the bone retraction sleeve 902 to rotate during linear translation of the bone retraction sleeve 902 over the drill bit.

According to the invention, the handle 940 facilitates manual linear translation of the bone retraction sleeve 902 over a drill bit and rotation thereof during the linear translation, and, hence, bone material extraction from the drill bit.

In some envisioned embodiments, powered translation means are employed to induce linear translation of the bone retraction sleeve 902 over the drill bit to extract bone material therefrom.

According to the invention, various means and apparatus can be employed to harvest or capture the bone material that is extracted from the drill bit by the bone retraction sleeve 902.

Referring again to FIG. 13A, in one embodiment, the bone harvesting assembly 900 further comprises a bone material receiving member 950, comprising proximal and distal ends 952*a*, 952*b*, a recessed region 954 disposed on the distal end 952*b*, which is sized and configured to capture and retain bone material therein, and a handle 956.

Figure 13F:
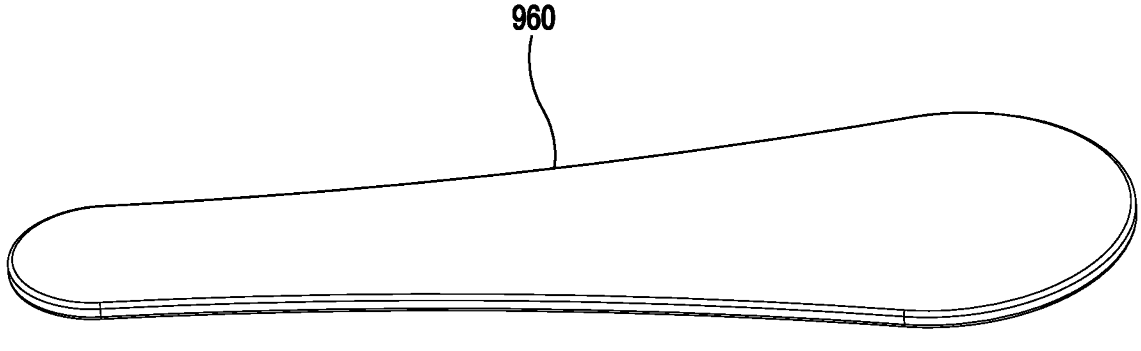
FIG. 13F is a perspective view of one embodiment of a bone material extractor, in accordance with the invention.

As illustrated in FIG. 13F, in some embodiments, the bone harvesting assembly 900 further comprises a bone material extractor 960 that is adapted to facilitate transfer the bone material from the bone material receiving member 950 to a storage container, e.g., vial, or an agent delivery system that is adapted to deliver the bone material (and/or an osteogenic composition thereof) directly to SI joint prostheses 70*a* and 70*b*.

Referring now to FIGS. 14A-14K, there is shown a further embodiment of a bone harvesting assembly of the invention that is adapted to extract and contain bone material from a bone dislodging apparatus of the invention, i.e., drill bit, after creating a SI joint opening or a portion thereof.

As illustrated in FIGS. 14A-14H, in a preferred embodiment, the harvesting assembly comprises a bone material extractor member 1002, a prosthesis holder 1020, and a bone tamp or compactor 1040.

Figure 14B:
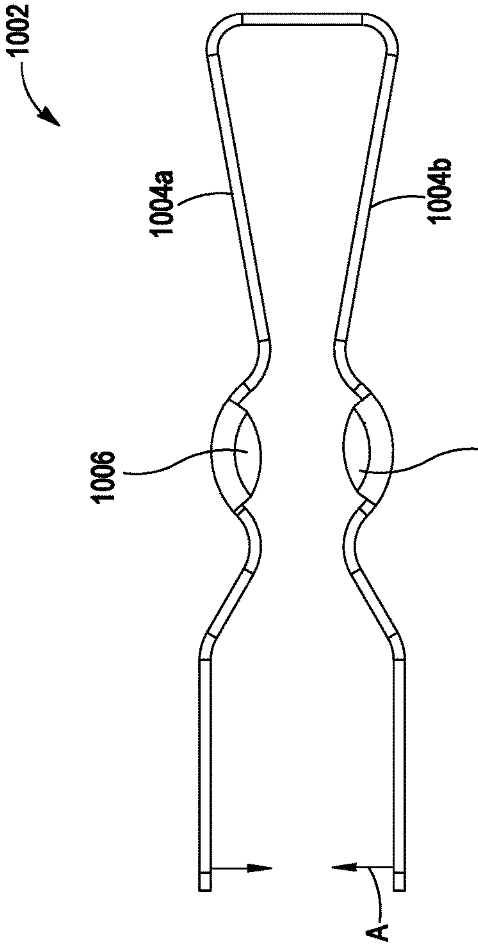
FIG. 14B is a bottom plan view of the tong member shown in FIG. 14A, in accordance with the invention.
Figure 14A:
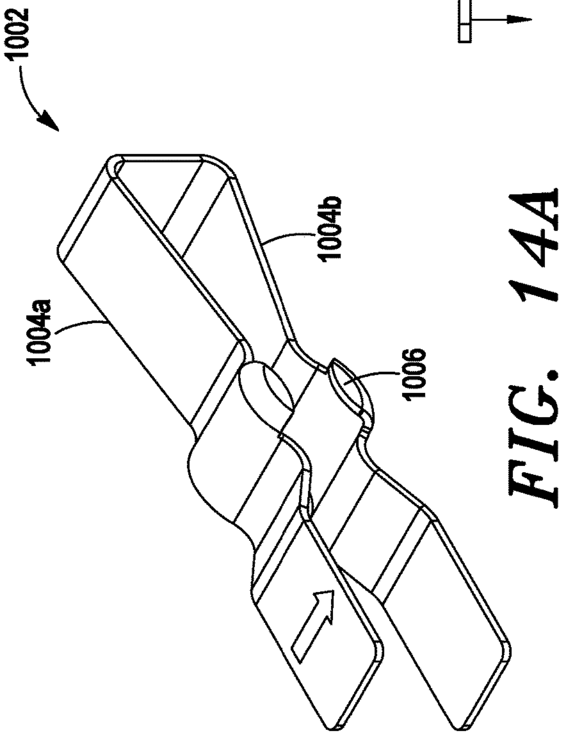
FIG. 14A is a perspective view of a tong member of a further bone harvesting assembly, in accordance with the invention.
Figure 14C:
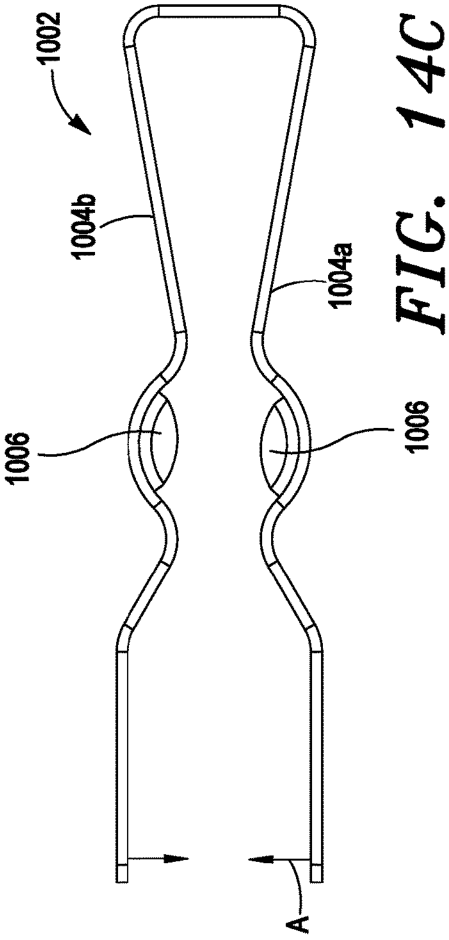
FIG. 14C is a top plan view of the tong member shown in FIG. 14A, in accordance with the invention.

As illustrated in FIGS. 14A-14C, the bone material extractor member 1002 preferably comprises a tong member 1002 comprising two (2) interconnected arms 1004*a*, 1004*b*.

As further illustrated in FIGS. 14A-14C, each of the tong member arms 1004*a*, 1004*b* comprises at least one bone extracting tab (or projection) 1006, which, according to the invention, is sized, positioned, and configured to seat in a flute (or flutes) of a drill bit of the invention; particularly, flutes 505 of drill bits 501*a* and 501*b* (see again FIGS. 5C and 5D).

According to the invention, the bone extracting tabs 1006 are also sized and configured to extract bone material from the drill bit, i.e., flute (or flutes) thereof, when the tong member 1002 is contracted in a direction denoted by Arrow "A", whereby the tong member 1002 is in a closed configuration, and the drill bit, i.e., drill bit 501*a* and/or 501*b* is rotated, whereby the tong member 1002 and, hence, bone material extracting tabs 1006 translate linearly down the drill bit in a helical fashion.

Figure 14D:
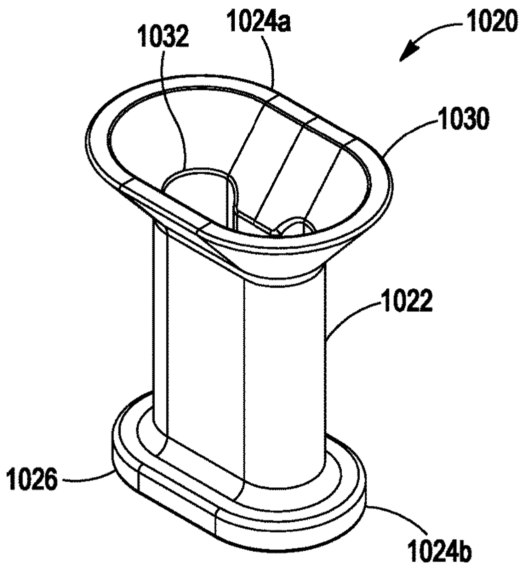
FIG. 14D is a perspective view of a prosthesis holder, in accordance with the invention.
Figure 14E:
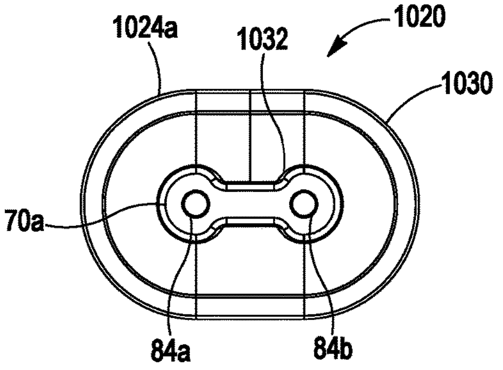
FIG. 14E is a top plan view of the prosthesis holder shown in FIG. 14D, showing a SI joint prosthesis seated therein, in accordance with the invention.
Figure 14F:
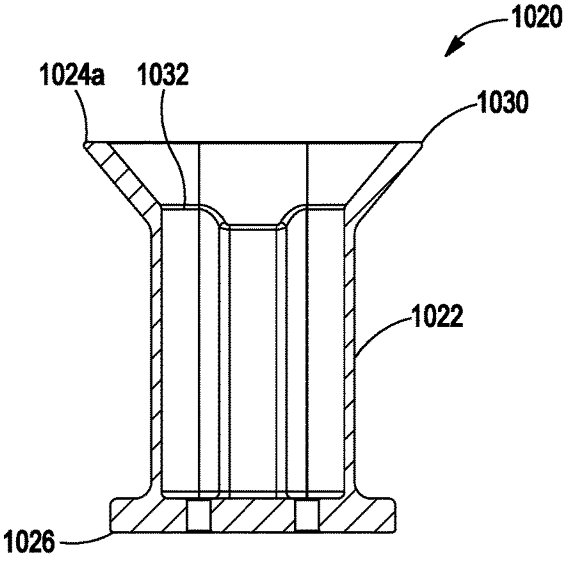
FIG. 14F is a front sectional plan view of the prosthesis holder shown in FIG. 14D, in accordance with the invention.

Referring now to FIGS. 14D-14F, there is shown one embodiment of a prosthesis holder 1020.

As illustrated in FIGS. 14D and 14F, in a preferred embodiment, the prosthesis holder 1020 comprises an elongated body 1022 comprising proximal and distal ends 1024*a*, 1024*b*, a flanged seat 1026 disposed on the distal end 1024*b*, and a bone material receiving region 1030 disposed on the proximal end 1024*a* of the prosthesis holder 1020.

As further illustrated in FIGS. 14D and 14F, in a preferred embodiment, the bone material receiving region 1030 comprises a concave cup-shaped region that is thus configured to receive and contain extracted bone material therein.

As further illustrated in FIGS. 14D and 14F, in a preferred embodiment, the bone material receiving region 1030 comprises a prosthesis internal access opening 1032, i.e., prosthesis seat, which, as illustrated in FIG. 14E, is sized and configured to receive and position a SI joint prosthesis of the invention therein.

According to the invention, when bone material is extracted from a bone dislodging member, i.e., drill bit, and deposited into the bone material receiving region 1030 of the prosthesis holder 1020, the extracted bone material is delivered into the internal lumens of the SI joint prosthesis, e.g., internal lumens 86*a*, 86*b* of SI joint prostheses 70*a*, 70*b*, when seated in the prosthesis seat 1032.

To facilitate compaction of the bone material into the SI joint prosthesis, the harvesting assembly further comprises a bone tamp or compactor 1040.

Figure 14G:
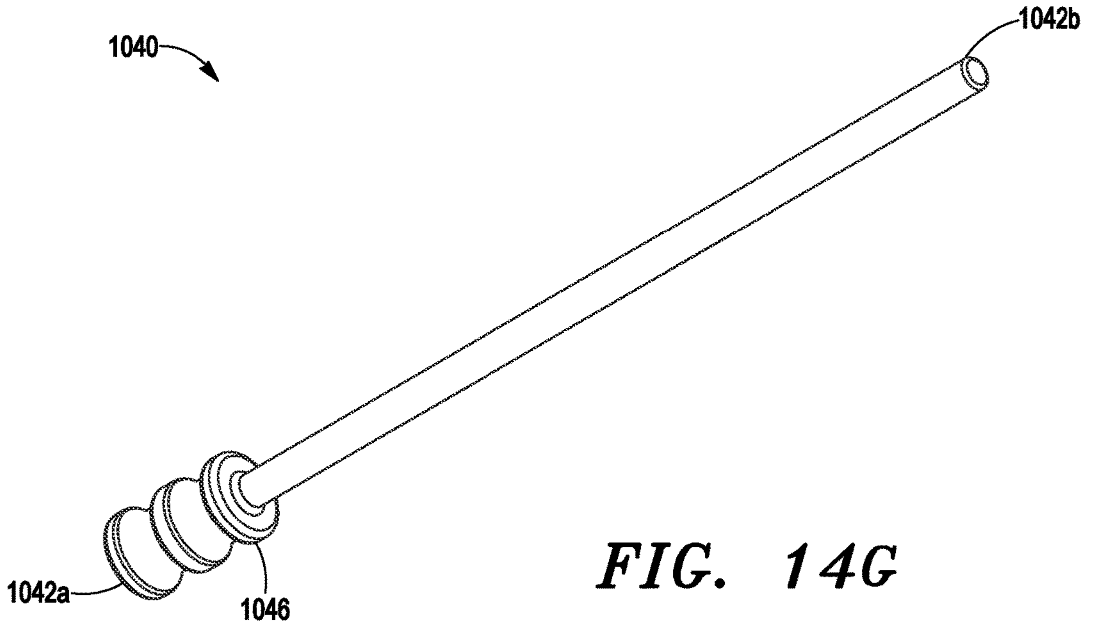
FIG. 14G is a perspective view of a bone material compactor, in accordance with the invention.
Figure 14H:
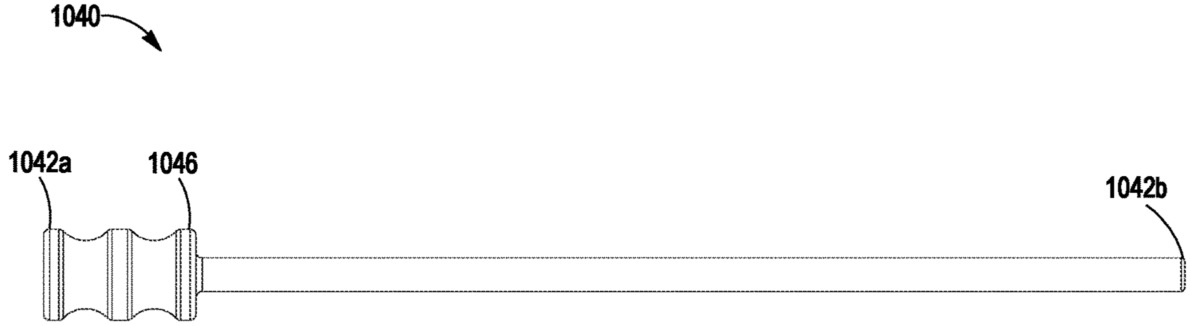
FIG. 14H is a side plan view of the bone material compactor shown in FIG. 14G, in accordance with the invention.

Referring now to FIGS. 14G and 14H, in a preferred embodiment, the bone tamp (or compactor) 1040 comprises an elongated rod member comprising proximal and distal ends 1042*a*, 1042*b*, and a handle region 1046 disposed on the proximal end 1042*b*.

In a preferred embodiment, the distal end 1042*b* of the bone tamp 1040 is sized and configured to be received in the internal lumens of the SI joint prostheses to, as indicated above, compact the bone material delivered thereto.

In some embodiments of the invention, the bone harvesting assembly further comprises a bone material delivery apparatus, which, as discussed in detail below, is configured and adapted to delivery bone material extracted from the bone dislodging apparatus directly into the internal lumens of SI joint prostheses 70*a*, 70*b*.

Figure 14I:
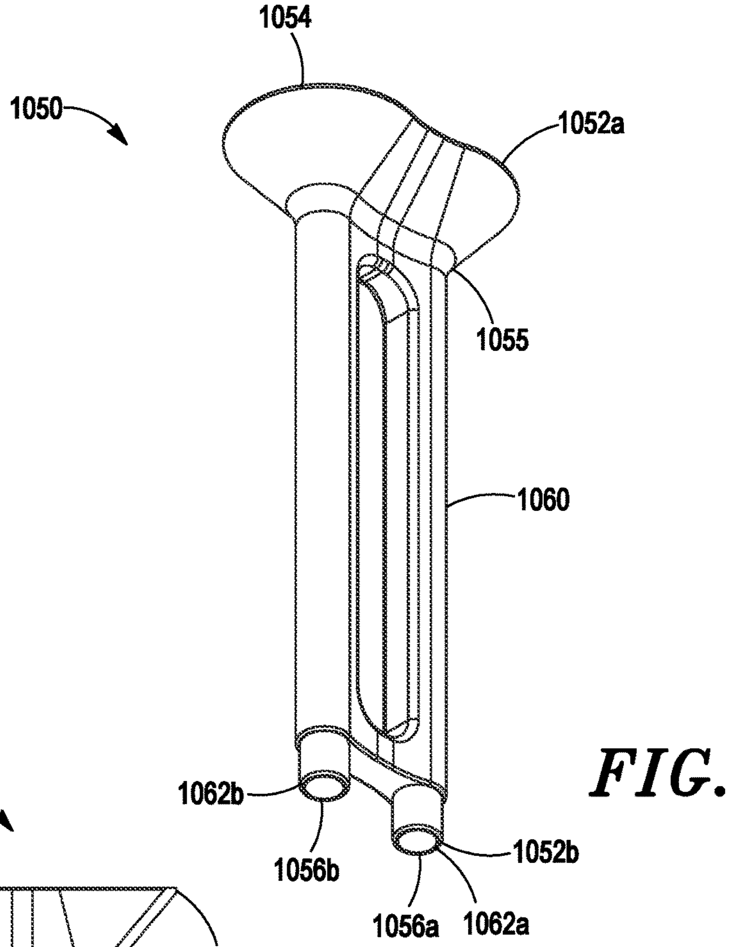
FIG. 14I is a perspective view of a bone material delivery apparatus, in accordance with the invention.
Figure 14J:
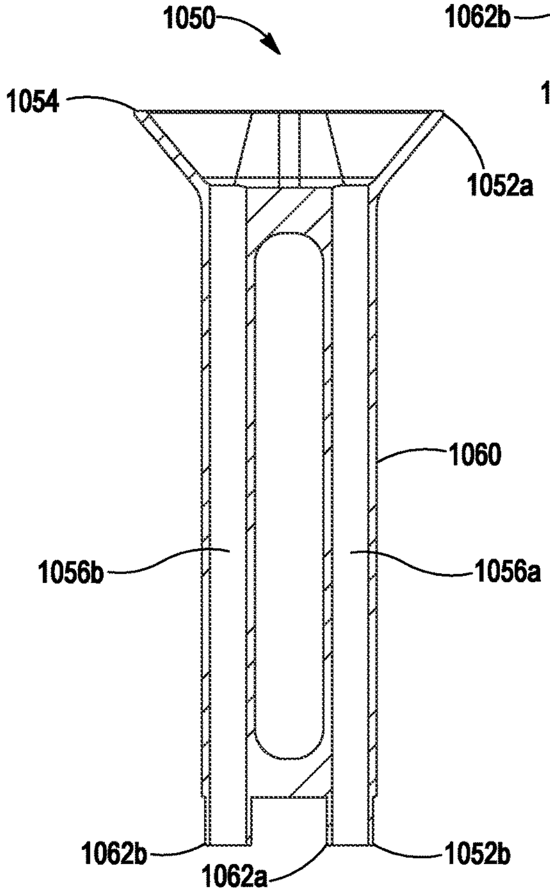
FIG. 14J is a front sectional plan view of the bone material delivery apparatus shown in FIG. 14I, in accordance with the invention.
Figure 14K:
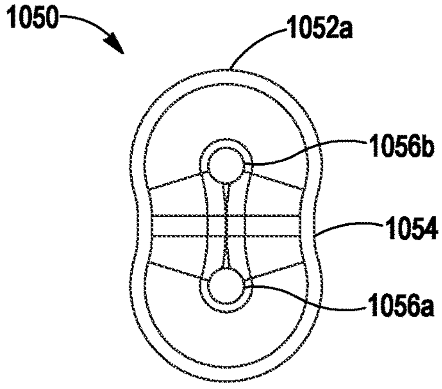
FIG. 14K is a top plan view of the bone material delivery apparatus shown in FIG. 14I, in accordance with the invention.

Referring now to FIGS. 14I-14K, there is illustrated one embodiment of a bone material delivery apparatus of the invention.

As illustrated in FIGS. 14I and 14J, the bone material delivery apparatus 1050 comprises proximal and distal ends 1052*a*, 1052*b* and a similar bone material receiving region 1054 disposed on the proximal end 1052*a*.

As illustrated in FIGS. 14J and 14K, in a preferred embodiment, the bone material receiving region 1054 similarly comprises a concave cup-shaped region that is thus configured to receive and contain extracted bone material therein.

As further illustrated in FIGS. 14J and 14K, in a preferred embodiment, the bone material receiving region 1054 comprises two (2) bone delivery lumens 1056*a*, 1056*b*, which extend through the bone material delivery apparatus 1050.

As further illustrated in FIGS. 14I and 14J, the bone material delivery apparatus 1050 further comprises an elongated body region 1060 that is in communication with the base 1055 of the bone material receiving region 1054; the body region 1060 also comprising the two (2) bone delivery lumens 1056*a*, 1056*b*, as illustrated in FIGS. 14I and 14J.

In a preferred embodiment, the length of the elongated body region (and, hence, bone delivery lumens 1056*a*, 1056*b*) is sufficient to receive and, hence, deliver a sufficient amount of bone material to SI joint prostheses 70*a*, 70*b* to substantially fill the internal lumens 86*a*, 86*b* of SI joint prostheses 70*a*, 70*b*.

As further illustrated in FIGS. 14I and 14J, the distal end 1052*b* of the bone material delivery apparatus 1050 (and, hence, body region 1060) comprises first and second prosthesis engagement regions 1062*a*, 1062*b* that extend from the distal end 1052*b* of the bone material delivery apparatus 1050 (and, hence, body region 1060).

In a preferred embodiment, the first and second prosthesis engagement regions 1062*a*, 1062*b* are sized and configured to be received into the internal lumens of the SI joint prosthesis, e.g., internal lumens 86*a*, 86*b* of SI joint prostheses 70*a*, 70*b*, and, hence, deliver bone material extracted from the bone dislodging apparatus directly into the internal lumens 86*a*, 86*b* of SI joint prostheses 70*a*, 70*b*.

Prosthesis Deployment Assembly

Referring now to FIGS. 15A-15G, there is shown one embodiment of a prosthesis deployment assembly of the invention (denoted "600*a*").

Figure 15A:
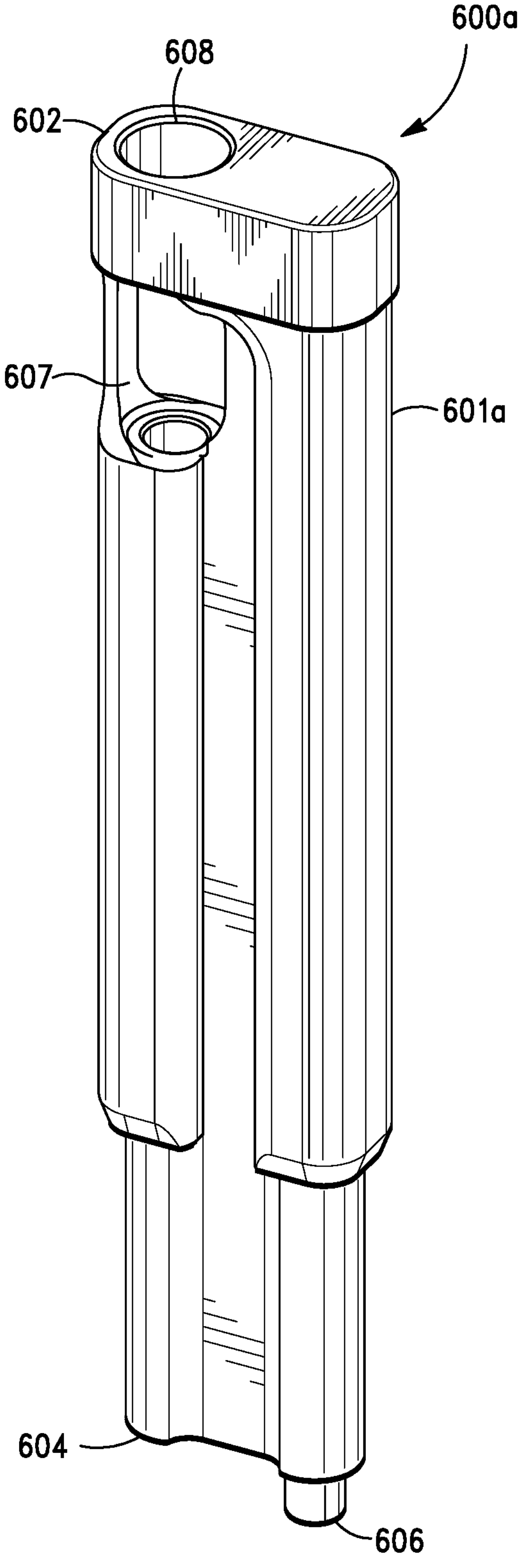
FIG. 15A is a perspective view of one embodiment of a prosthesis deployment assembly, in accordance with the invention.
Figure 15B:
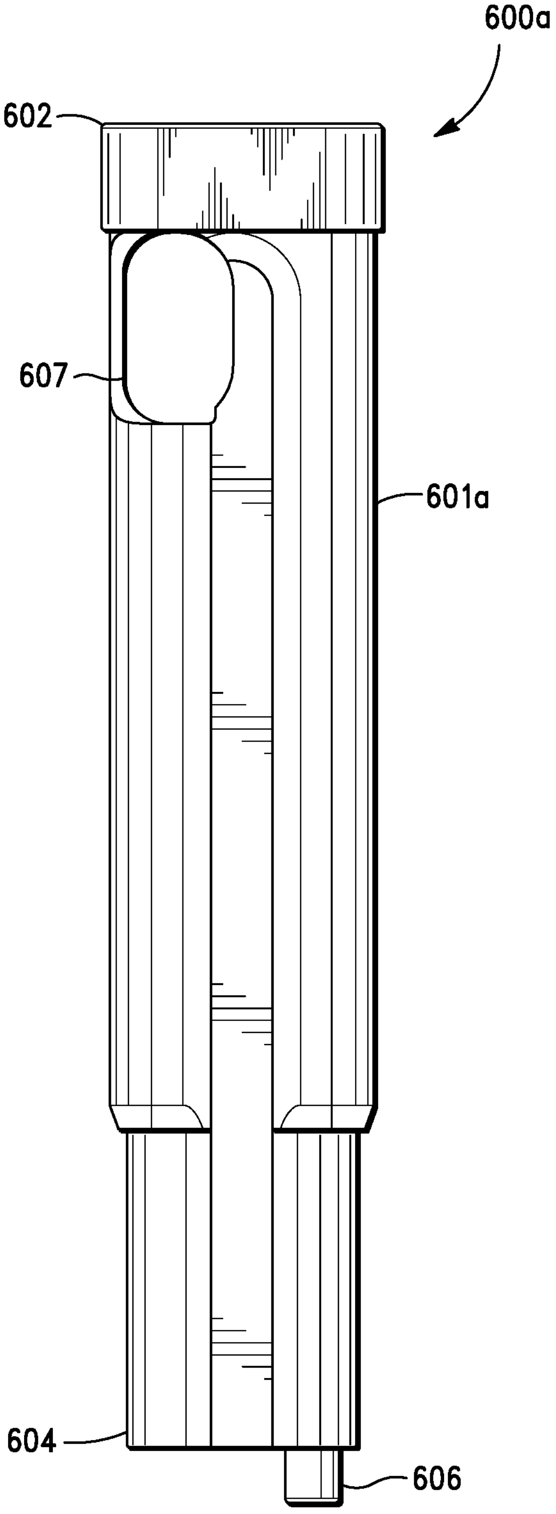
FIG. 15B is a front plan view of the prosthesis deployment assembly shown in FIG. 15A, in accordance with the invention.
Figure 15C:
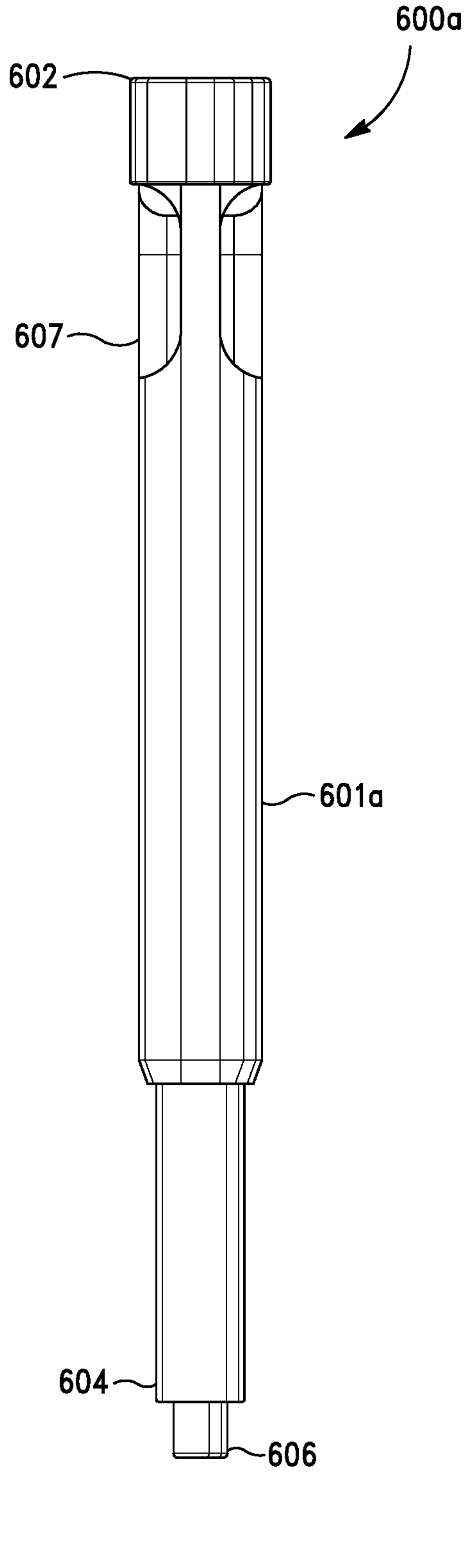
FIG. 15C is a left-side plan view of the prosthesis deployment assembly shown in FIG. 15A, in accordance with the invention.
Figure 15D:
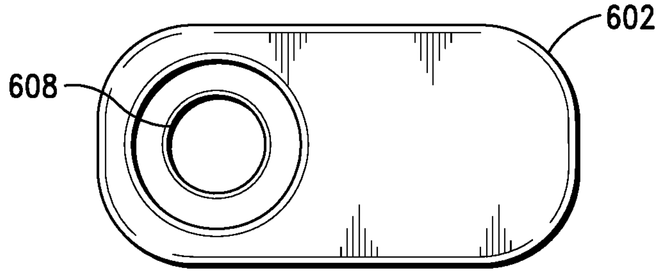
FIG. 15D is a top plan view of the prosthesis deployment assembly shown in FIG. 15A, in accordance with the invention.
Figure 15E:
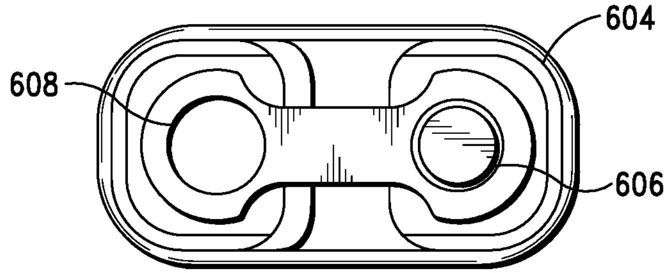
FIG. 15E is a bottom plan view of the prosthesis deployment assembly shown in FIG. 15A, in accordance with the invention.
Figure 15F:
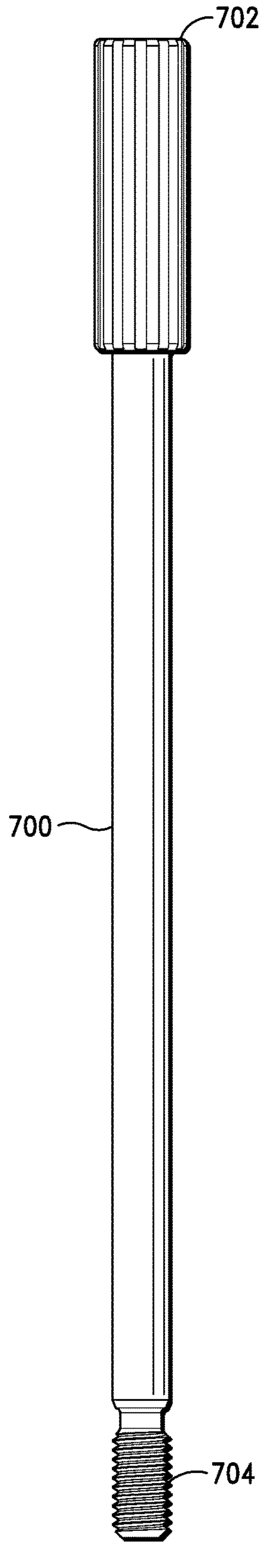
FIG. 15F is a front plan view of a prosthesis engagement rod of the prosthesis deployment assembly shown in FIG. 15A, in accordance with the invention.
Figure 15G:
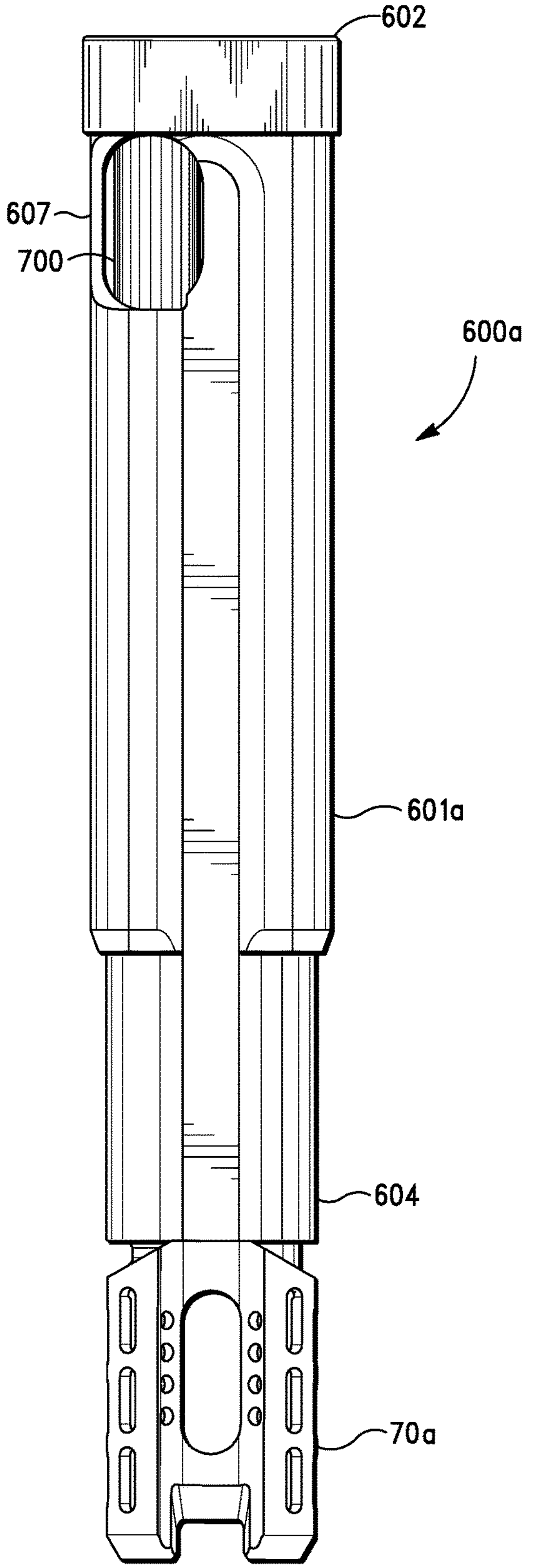
FIG. 15G is a perspective view of the prosthesis deployment assembly shown in FIG. 15A engaged to a SI joint prosthesis of the invention, in accordance with the invention.

As illustrated in FIG. 15G, in a preferred embodiment, the prosthesis deployment assembly 600*a* comprises prosthesis engagement means that is configured and adapted to connect the prosthesis deployment assembly 600*a* to SI joint prostheses 70*a*, 70*b*, and guide the prostheses 70*a*, 70*b* into pilot SI joint openings created by the drill guide assemblies 500*a*, 500*b*, 500*c*, 500*d*, and 500*e*.

As illustrated in FIGS. 15A-15C, the prosthesis deployment assembly 600*a* comprises an elongated guide member 601*a* comprising proximal and distal ends 602, 604.

As further illustrated in FIGS. 15B and 15E, the elongated guide member 601*a* further comprises a prosthesis guide pin 606 that extends from the guide member distal end 604. As indicated above and shown in FIG. 15G, the prosthesis guide pin 606 is sized and configured to seat in an internal prosthesis engagement member lumen 86*a* and 86*b* of SI joint prostheses 70*a*, 70*b*.

As illustrated in FIGS. 15A, 15D, and 15E, the elongated guide member 601*a* further comprises an internal lumen 608 that extends from the proximal end 602 of the elongated guide member 601 to the distal end 604 of the elongated guide member 601*a*.

As illustrated in FIG. 15G, in a preferred embodiment of the invention, the internal lumen 608 is sized and configured to receive the prosthesis engagement rod 700 (i.e., prosthesis engagement means) of the prosthesis deployment assembly 600*a* (and prosthesis deployment assembly 600*b*, discussed below).

Referring now to FIG. 15F, there is shown a preferred embodiment of a prosthesis engagement rod 700 of the invention. As illustrated in FIG. 15F, the prosthesis engagement rod 700 comprises a proximal end 702 and a threaded distal end 704, which is sized and configured to threadably engage an internal prosthesis engagement member lumen of SI joint prostheses 70*a*, 70*b*, e.g., internal prosthesis engagement member lumens 86*a* and/or 86*b* of prosthesis 70.

As further illustrated in FIG. 15F, in a preferred embodiment, the proximal end 702 of the prosthesis engagement rod 700 comprises a knurled configuration to facilitate threading the prosthesis engagement rod 700 into an internal prosthesis engagement member lumen of SI joint prostheses 70*a*, 70*b*.

Referring back to FIGS. 15A and 15B, to further facilitate threading the prosthesis engagement rod 700 into an internal prosthesis engagement member lumen of SI joint prostheses 70*a*, 70*b*. In a preferred embodiment, the elongated guide member 600*a* (and prosthesis deployment assembly 600*b*) further comprises an access port 607 that provides access to the knurled proximal end 602 of the prosthesis engagement rod 700 when positioned in the internal lumen 608 of the elongated guide member 601*a*, as shown in FIG. 15G, and elongated guide member 601*b*.

Figure 16B:
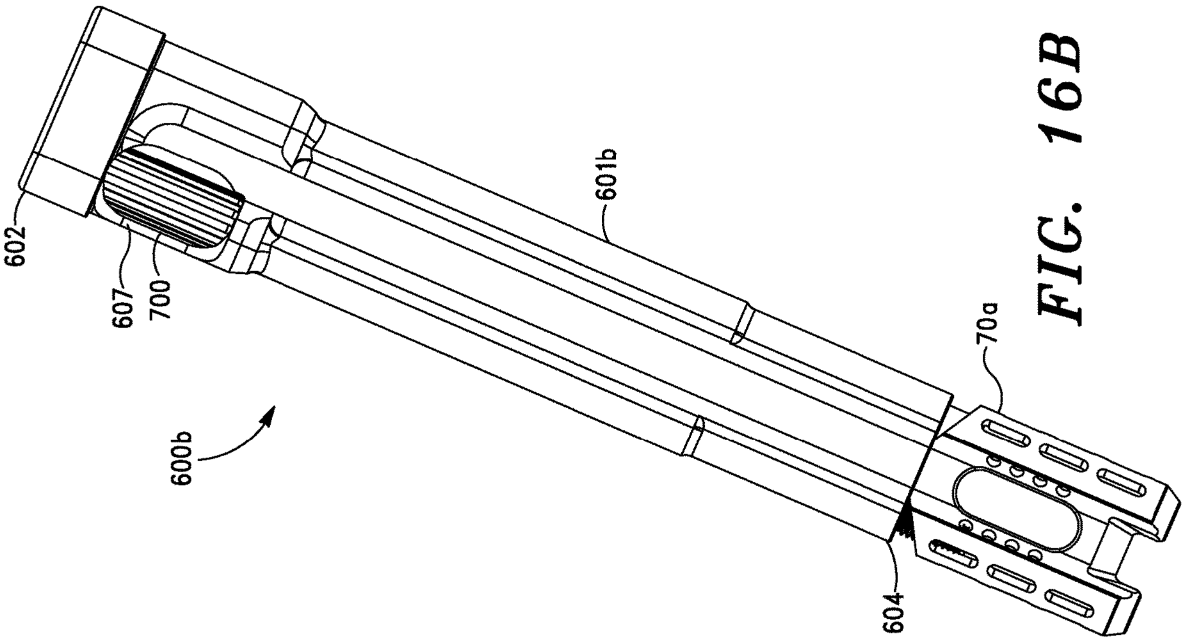
FIG. 16B is a perspective view of the prosthesis deployment assembly shown in FIG. 16A engaged to a prosthesis of the invention, in accordance with the invention.
Figure 16A:
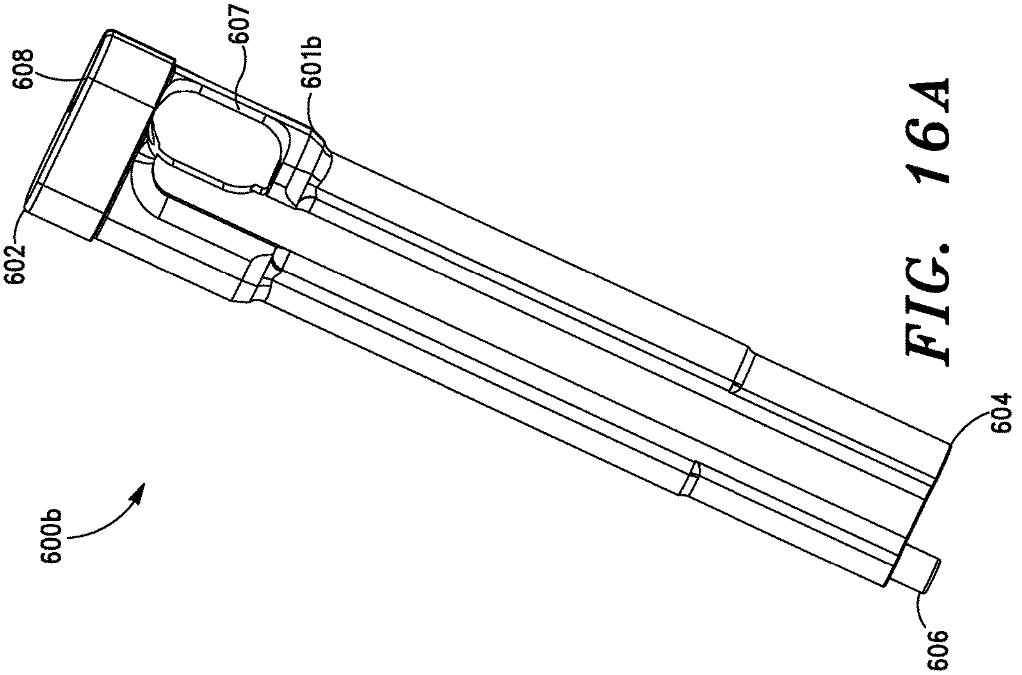
FIG. 16A is a perspective view of another embodiment of a prosthesis deployment assembly, in accordance with the invention.

Referring now to FIGS. 16A and 16B, there is shown another embodiment of a prosthesis deployment assembly of the invention (denoted "600*b*").

As illustrated in FIG. 16A, in a preferred embodiment, the prosthesis deployment assembly 600*b* is similarly configured and adapted to connect to SI joint prostheses 70*a*, 70*b*, and guide the prostheses 70*a*, 70*b* into pilot SI joint openings created by the drill guide assemblies 500*a*, 500*b*, 500*c*, 500*d*, and 500*e*.

As illustrated in FIGS. 16A and 16B, the prosthesis deployment assembly 600*b* similarly comprises an elongated guide member (denoted 601*b* in this embodiment) comprising proximal and distal ends 602, 604, prosthesis guide pin 606, internal lumen 608, access port 607, and prosthesis engagement rod 700.

As illustrated in FIGS. 16A and 16B, in this embodiment, the elongated guide member 601*b* has a narrower body that preferably comprises a cross-sectional shape that corresponds to the cross-sectional shapes of SI joint prostheses 70*a*, 70*b* and the prosthesis internal access opening 560 in the drill guide assembly 500*c*, whereby the elongated guide member 601*b* (and, hence, prosthesis 70 engaged thereto) can be readily received and positioned in the prosthesis internal access opening 560 in the drill guide assemblies 500*c*, 500*d* and 500*e*.

Figure 17A:
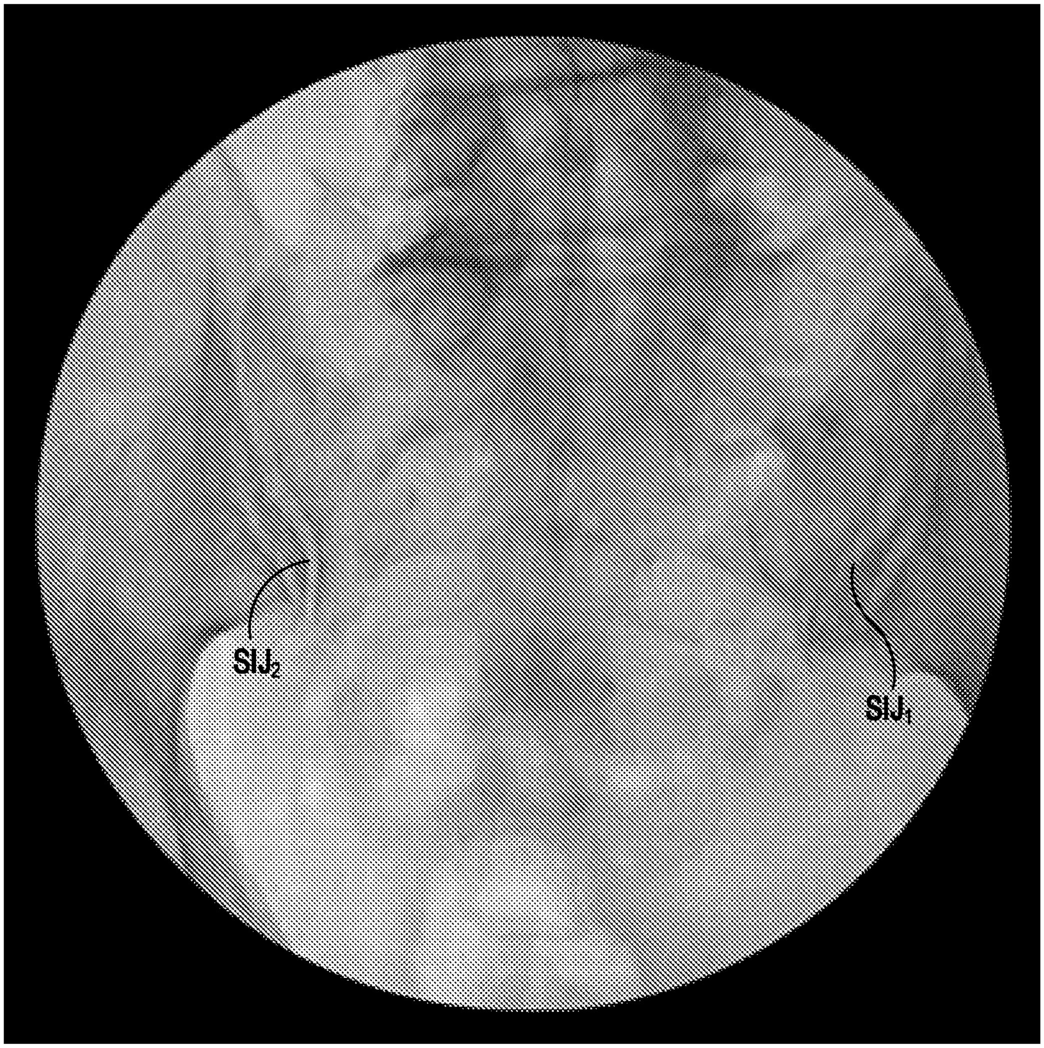
FIG. 17A is a conventional computed tomography (CT) scan image showing an anteroposterior (AP) view of a pelvic structure and SI joints associated therewith.
Figure 17B:
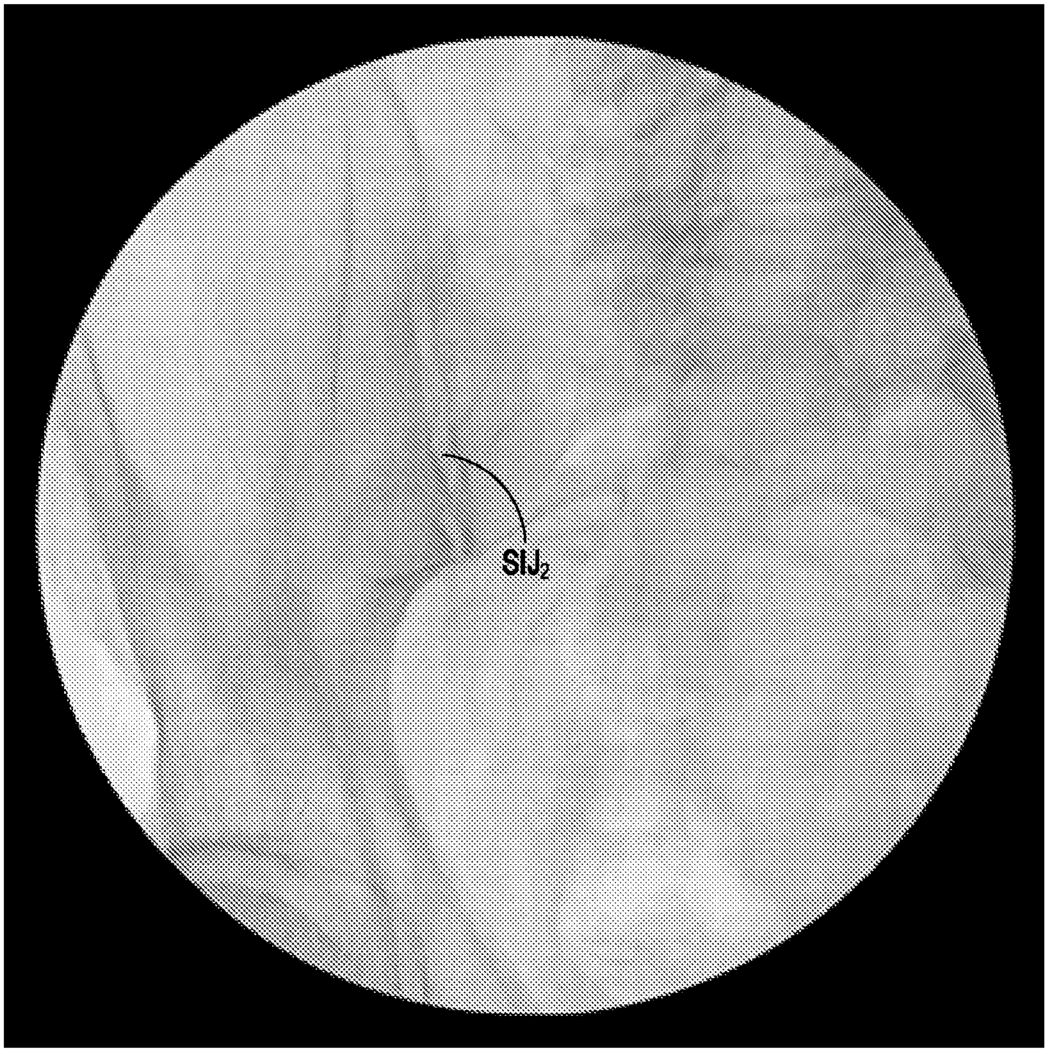
FIG. 17B is a CT scan image showing a modified AP view of a dysfunctional SI joint, in accordance with the invention.
Figure 17C:
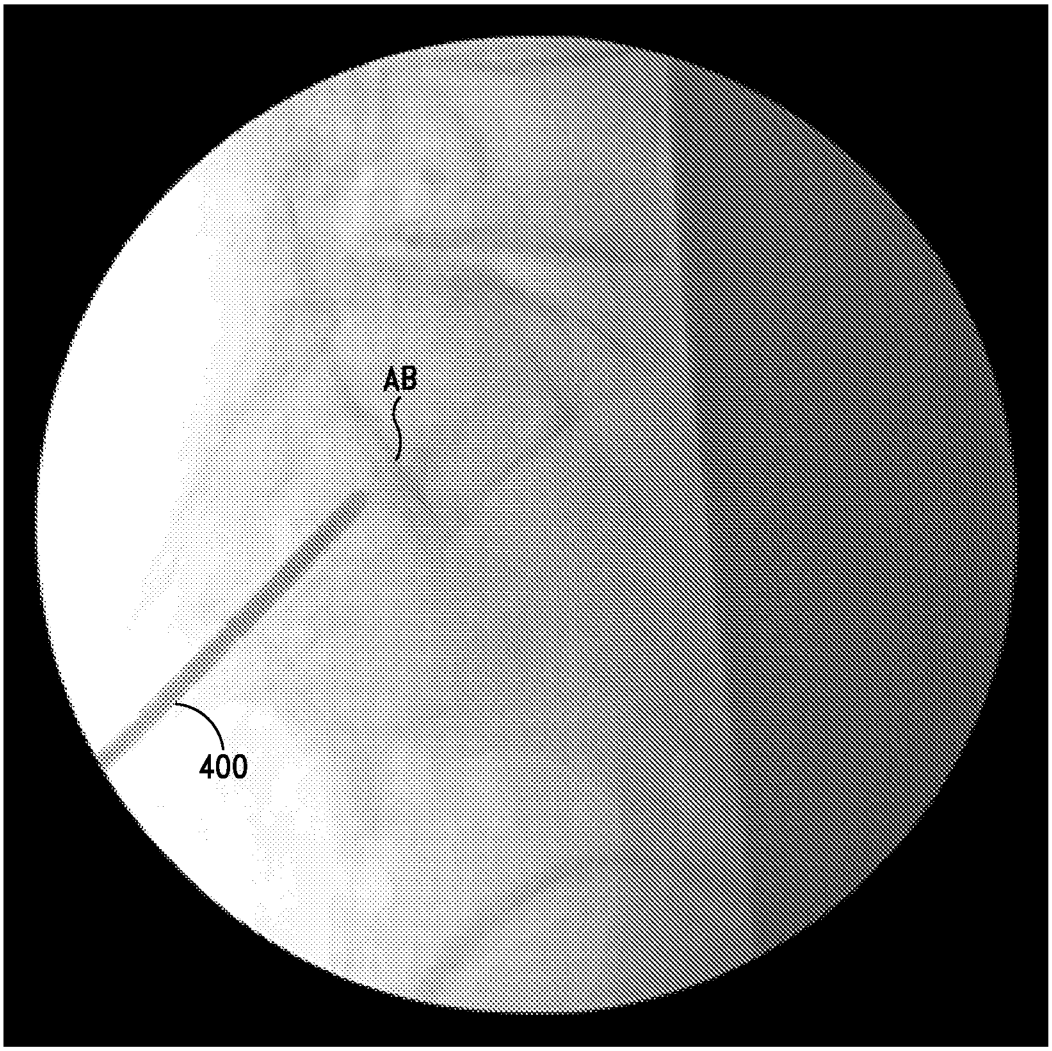
FIG. 17C is a CT scan image showing a tangent lateral view of the dysfunctional SI joint shown in FIG. 17B, showing a guide pin properly positioned therein, in accordance with the invention.
Figure 17D:
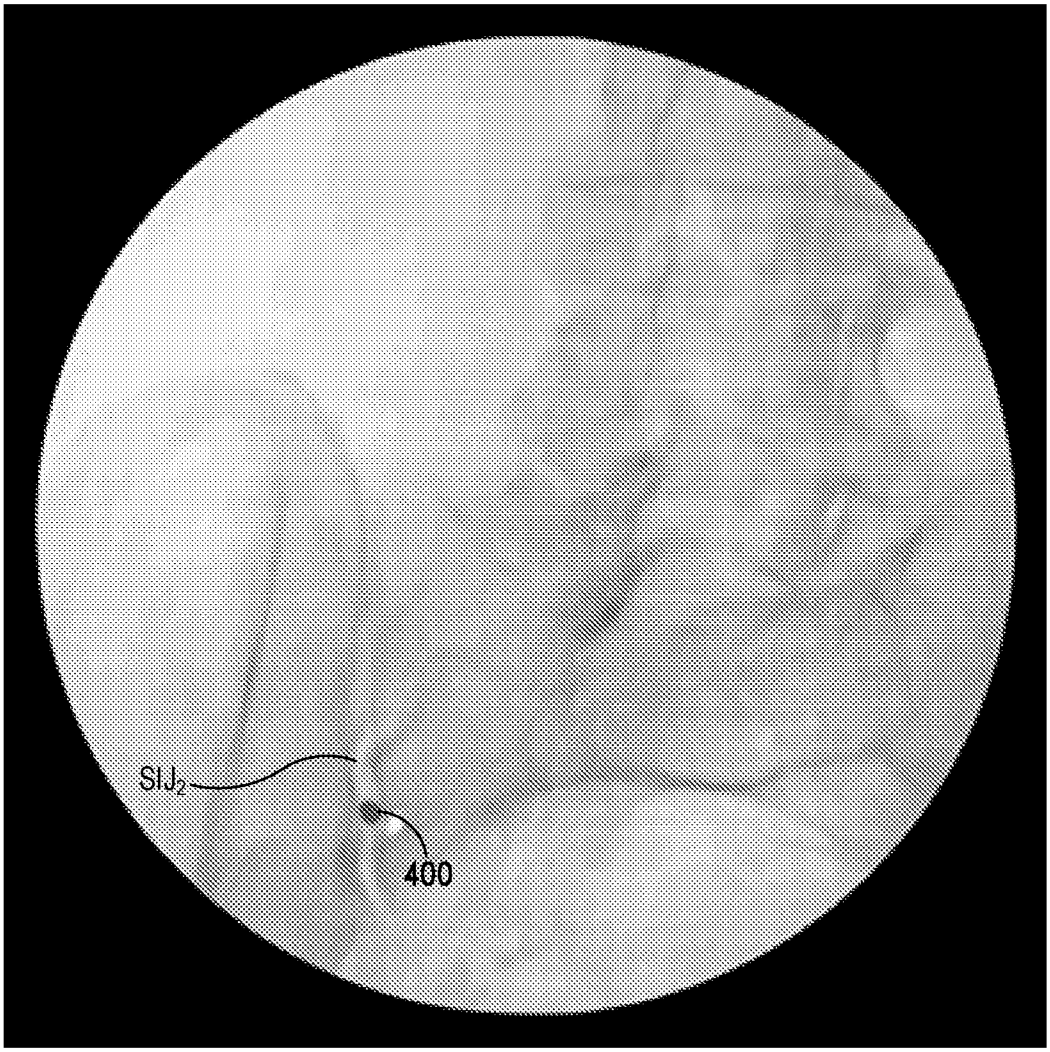
FIG. 17D is a CT scan image showing a trajectory inlet view of the dysfunctional SI joint shown in FIG. 17B, showing a guide pin properly positioned therein, in accordance with the invention.
Figure 17E:
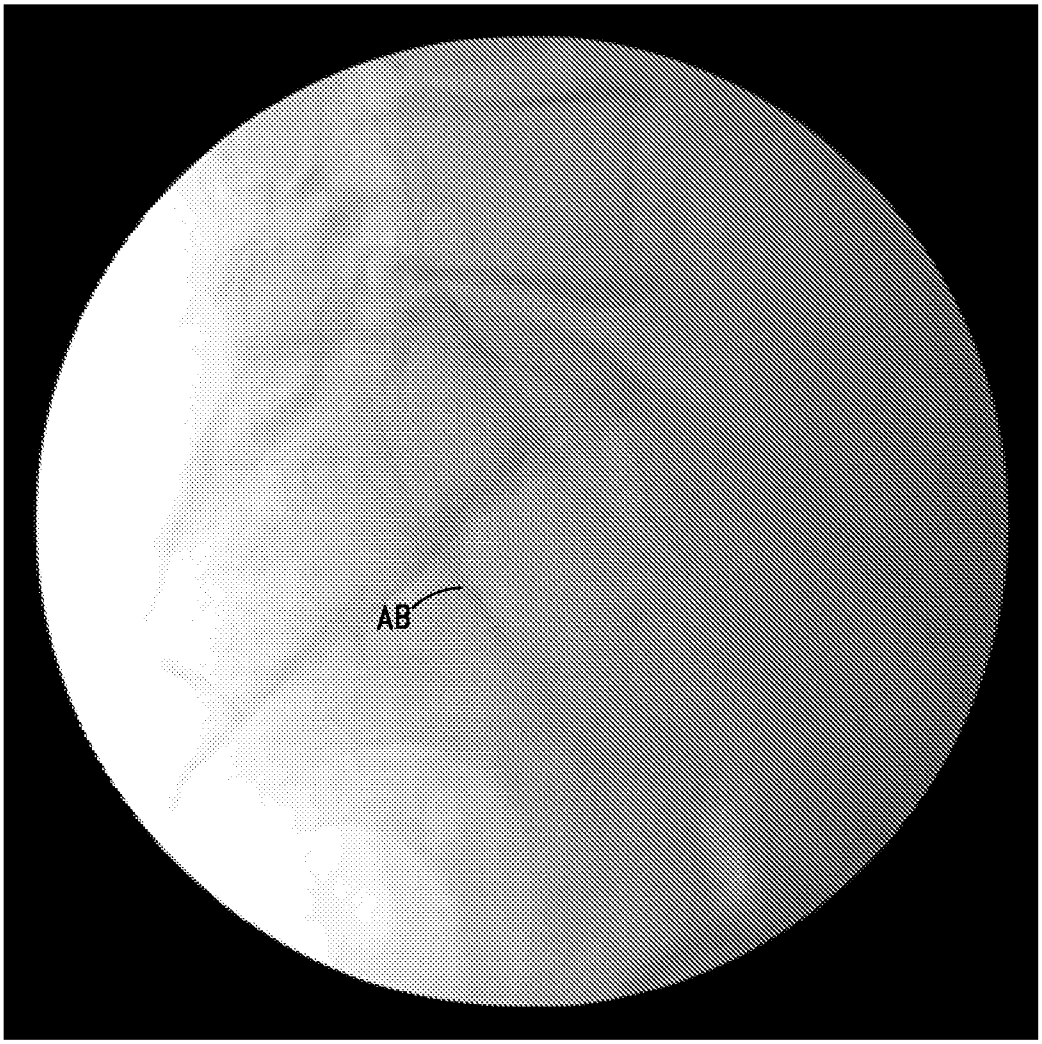
FIG. 17E is a CT scan image showing a lateral view of the dysfunctional SI joint shown in FIG. 17B, showing the alar boundary thereof, in accordance with the invention.
Figure 17F:
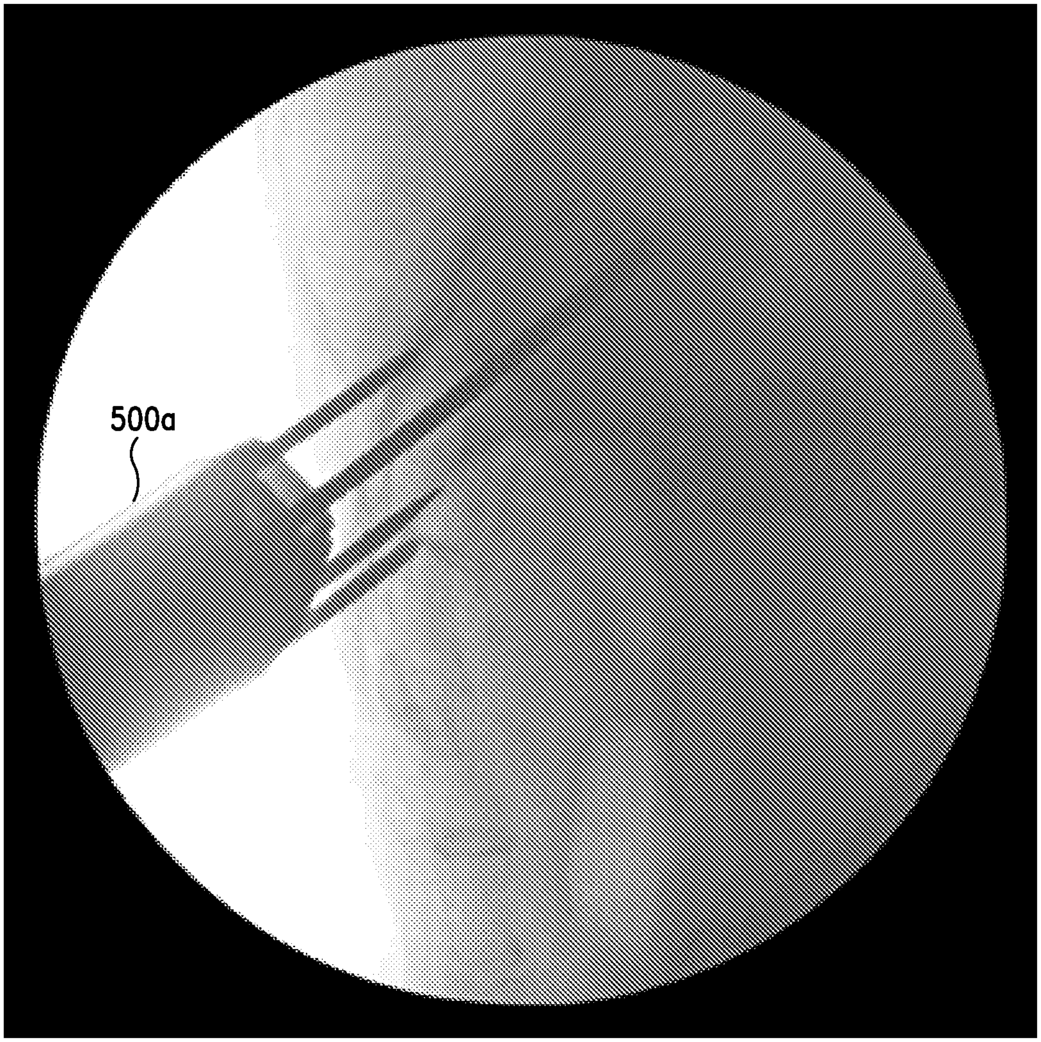
FIG. 17F is a CT scan image showing a lateral view of a drill guide assembly disposed proximate a dysfunctional SI joint, in accordance with the invention.
Figure 17G:
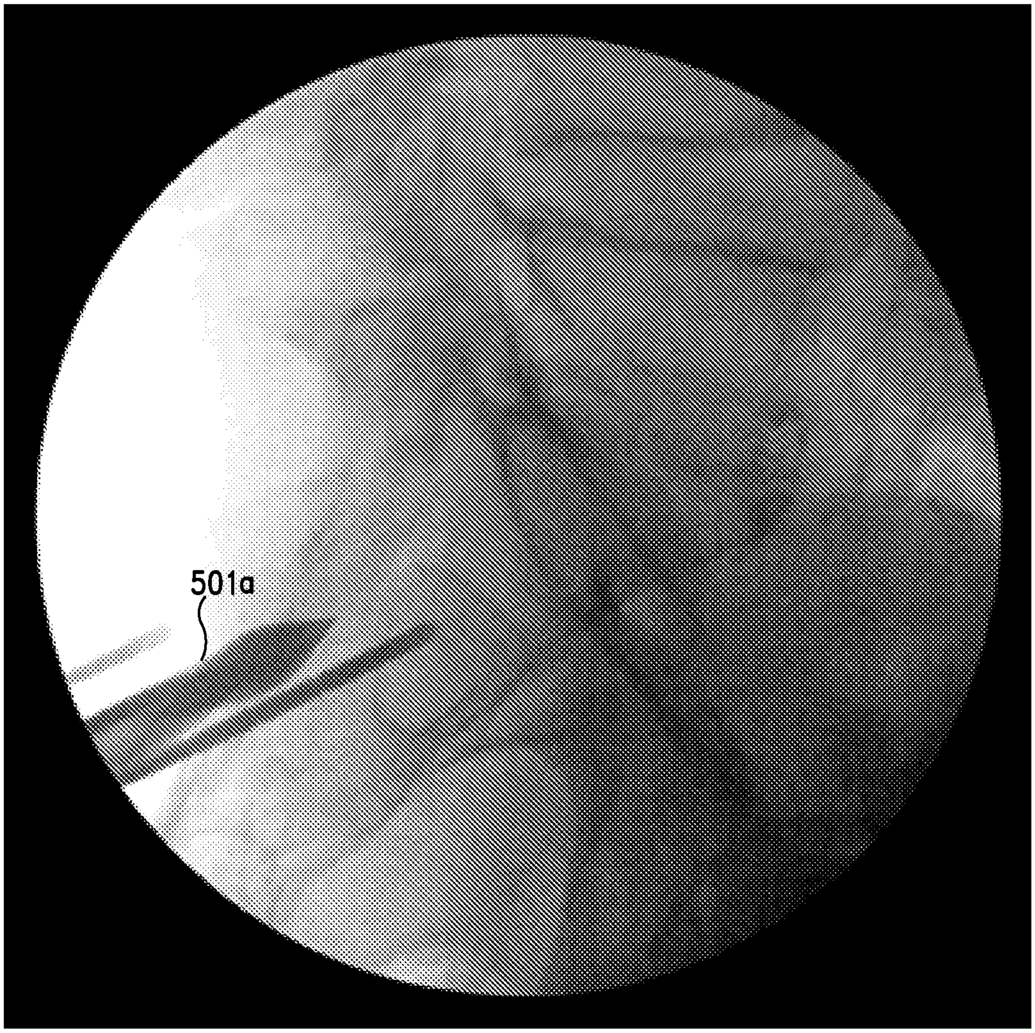
FIG. 17G is a CT scan image showing a further lateral view of the drill guide assembly disposed proximate a dysfunctional SI joint, in accordance with the invention.
Figure 17H:
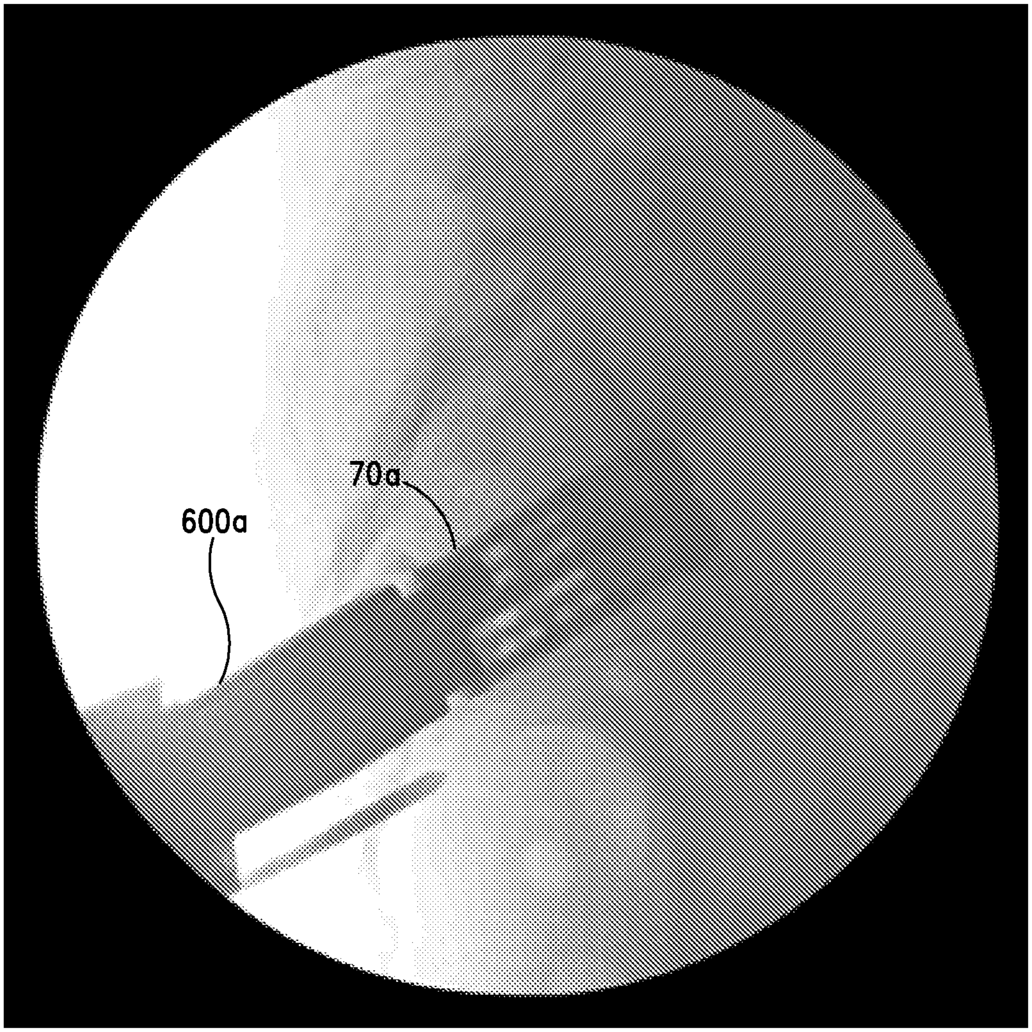
FIG. 17H is a CT scan image showing a lateral view of the prosthesis deployment assembly with a SI joint prosthesis engaged thereto disposed proximate a dysfunctional SI joint, in accordance with the invention.
Figure 17I:
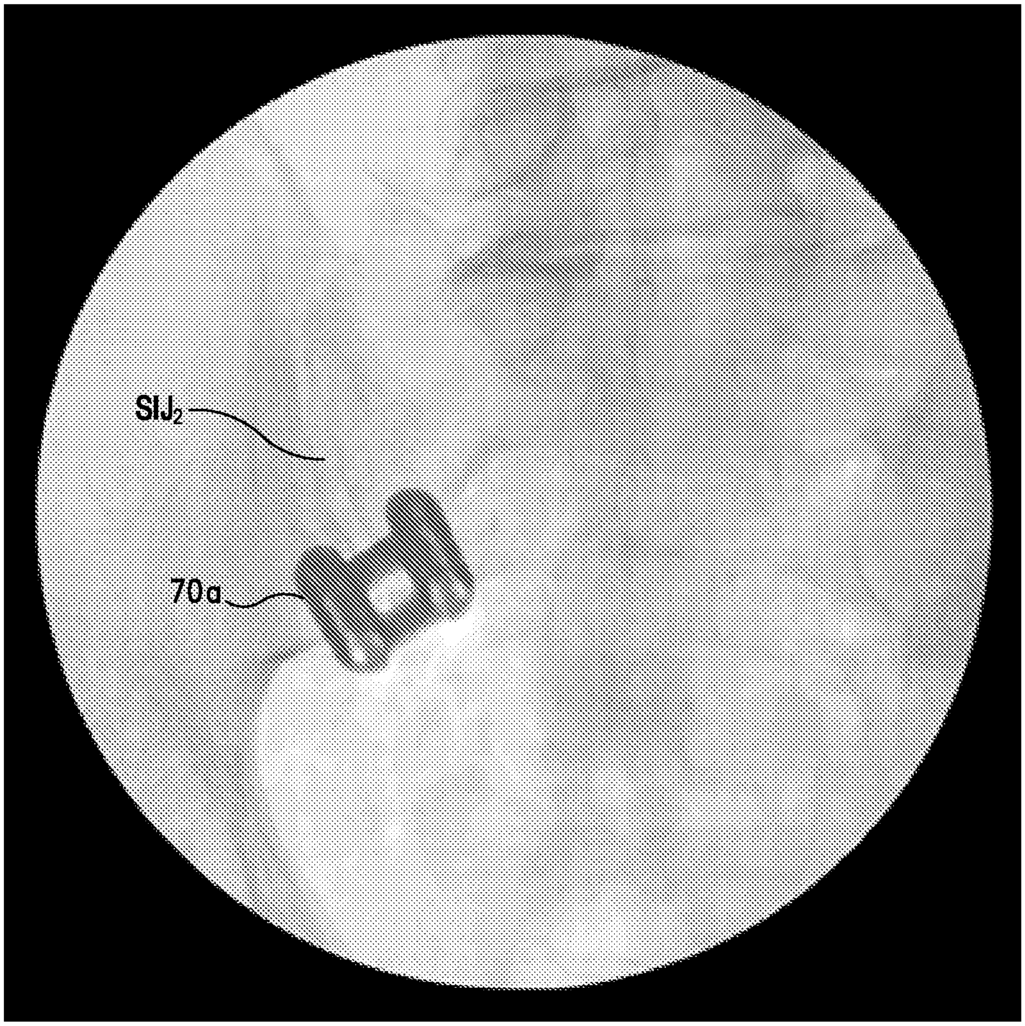
FIG. 17I is a CT scan image showing a modified AP view of the dysfunctional SI joint shown in FIG. 17B, showing a SI joint prosthesis properly positioned therein, in accordance with the invention.
Figure 17J:
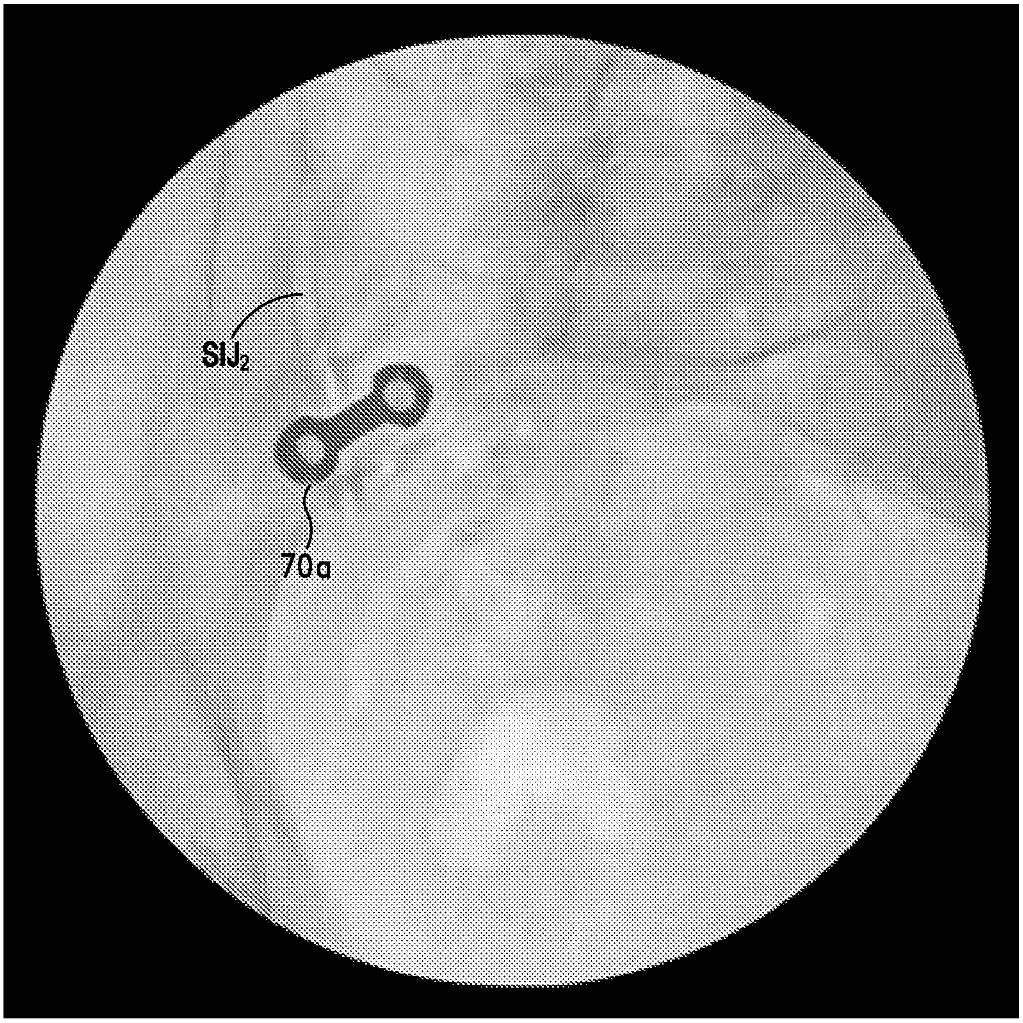
FIG. 17J is a CT scan image showing a trajectory inlet view of the dysfunctional SI joint shown in FIG. 17B, showing a SI joint prosthesis properly positioned therein, in accordance with the invention.
Figure 18A:
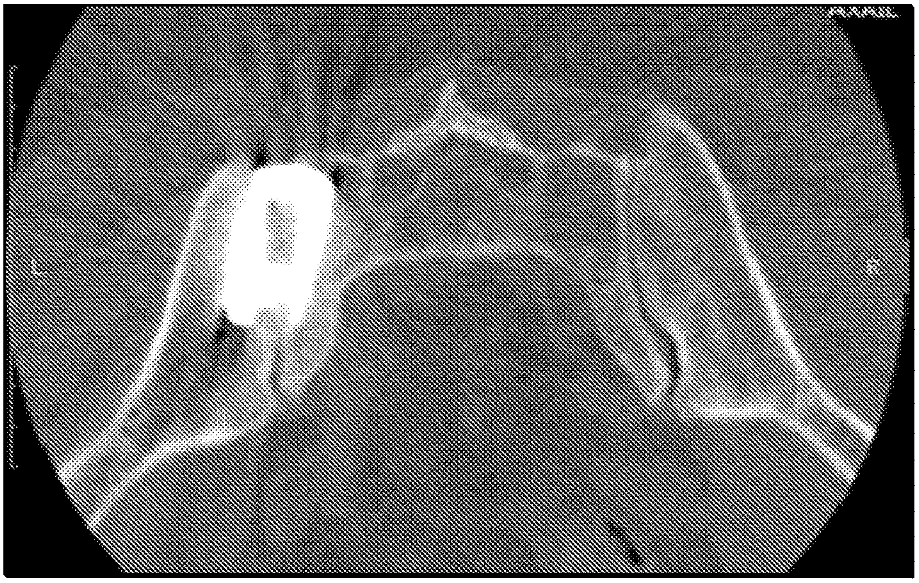
FIGS. 18A and 18B are further CT scan images of the SI joint prosthesis shown in FIG. 9A properly positioned in a dysfunctional SI joint, in accordance with the invention.
Figure 18B:
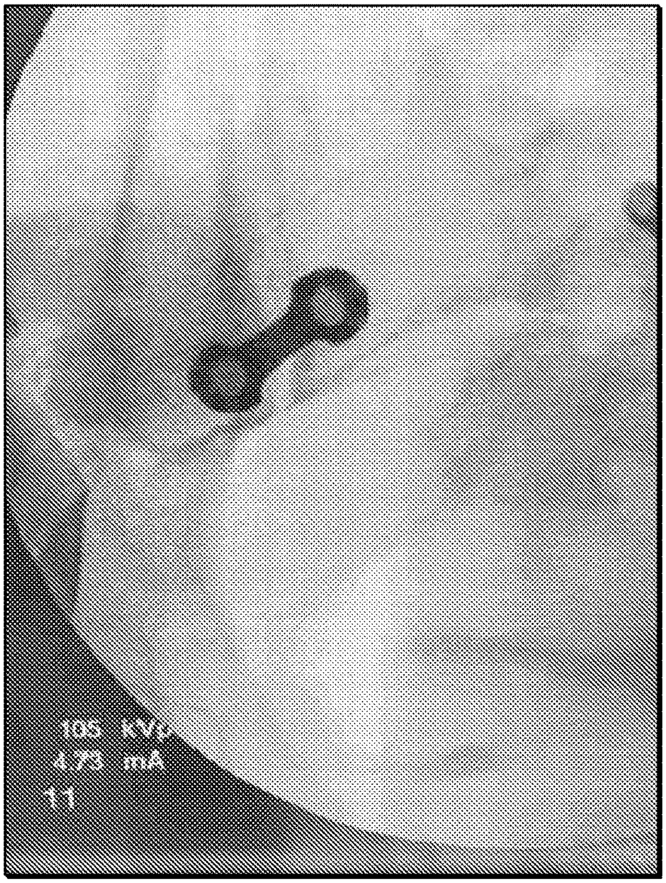

In accordance with the one embodiment of the invention, there is thus provided a method of stabilizing a dysfunctional SI joint comprising the following steps:

- providing a tool assembly of the invention, in this instance, a tool assembly comprising drill guide assembly 500*e;*
- providing a SI joint prosthesis of the invention, in this instance, SI joint prosthesis 70*a;*
- providing a prosthesis deployment assembly of the invention, in this instance prosthesis deployment assembly 600*a;*
- making an incision in and through tissue of the subject to provide posterior access to the subject's dysfunctional SI joint; preferably, a 2.0 cm to 3.0 cm incision;
- advancing the guide pin 400 of the tool assembly 500*e* with an inferior-posterior trajectory in and through the incision, and into the dysfunctional SI joint;
- attaching a drill guide handle, i.e., handle 510*a* shown in FIGS. 3F and 3G or handle 510*b* shown in FIG. 5D, to the drill guide 520*e*, as described above;
- positioning the drill guide insert 800*b* in the drill guide 520*e;*
- inserting the guide pin 400 into and through the drill guide medial lumen 527 of the drill guide insert 800*b;*
- advancing the drill guide assembly 500*e* with a posterior trajectory in and through the incision site and, thereby positioning the drill guide assembly 500*e* proximate the dysfunctional SI joint;
- inserting K-wires 509 into and through K-wire lumens 529*a*, 529*b*, 529*c*, 529*d* of the drill guide assembly 500*e* and into dysfunctional SI joint structures, e.g., soft and hard skeletal tissue, to position and stabilize the drill guide assembly 500*e* proximate the dysfunctional SI joint;
- advancing the bone dislodging apparatus, in this instance, drill bit 501*b*, through drill guide internal lumen 525*d* of the drill guide insert 800*b* and to the first bone structure, i.e., ilium or sacrum, of the dysfunctional SI joint;
- creating a first portion of a pilot SI joint opening in the first bone structure with the drill bit 501*b;*
- retracting the drill bit 501*b* out of the first bone structure and the drill guide internal lumen 525*d* of the drill guide insert 800*b;*
- inserting the drill alignment pin 530*a* into and through the drill guide internal lumen 525*d* of the drill guide insert 800*b* and into the first portion of the pilot SI joint opening to further stabilize the drill guide assembly 500*e* proximate the dysfunctional SI joint;
- advancing the drill bit 501*b* through drill guide internal lumen 525*c* of the drill guide insert 800*b* to the second (or opposing) bone structure of the dysfunctional SI joint;
- creating a second portion of the pilot SI joint opening in the second bone structure with the drill bit 501*b;*
- retracting the drill bit 501*b* out of the second bone structure and drill guide internal lumen 525*c* of the drill guide insert 800*b;*
- retracting the drill alignment pin 530*a* out of the first portion of the pilot SI joint opening and drill guide internal lumen 525*d* of the drill guide insert 800*b;*
- removing the drill guide insert 800*b* from the drill guide 520*e;*
- retracting the guide pin 400 out of the dysfunctional SI joint;
- connecting the prosthesis deployment assembly 600*a* to the SI joint prosthesis (in this instance SI joint prosthesis 70*a*);
- inserting the SI joint prosthesis, i.e., SI joint prosthesis 70*a*, into and through the internal opening 560 of the drill guide 520*e* and into the pilot SI joint opening with the prosthesis deployment assembly 600*a*, wherein the SI joint prosthesis, i.e., SI joint prosthesis 70*a*, is spaced a predetermined distance away from the SI joint dorsal recess (such as shown in FIG. 17H);
- retracting the prosthesis deployment assembly 600*a* out of the dysfunctional SI joint;
- retracting the K-wires 509 out of the dysfunctional SI joint structures; and
- retracting the drill guide 520*e* out of the subject's body.

In some embodiments, the method further comprises the steps of (i) providing a bone harvesting assembly of the invention; preferably, the bone harvesting assembly illustrated in FIGS. 14A-14K and described above, (ii) extracting bone material from drill bit 501*b* with the harvesting assembly after the first portion of the pilot SI joint opening is created in the first bone structure with the drill bit 501*b*, and (iii) extracting bone material from drill bit 501*b* with the harvesting assembly after the second portion of the pilot SI joint opening is created in the second bone structure with the drill bit 501*b*.

As indicated above, in a preferred embodiment, when the SI joint prosthesis, i.e., SI joint prosthesis 70*a* (and, hence, SI joint prosthesis 70*b* when employed), is advanced into the pilot SI joint opening with the prosthesis deployment assembly 600*a*, the SI joint prosthesis, i.e., SI joint prosthesis 70*a*, is disposed at a distance in the range of at least 2.0 mm to 6.0 mm away from the SI joint dorsal recess, more preferably, a distance of at least 3.0 mm away from the SI joint dorsal recess.

In a preferred embodiment, when the SI joint prosthesis, i.e., SI joint prosthesis 70*a* or 70*b*, is advanced into the pilot SI joint opening with the prosthesis deployment assembly 600*a*, the SI joint prosthesis is preferably press-fit in the pilot SI joint opening and induces a transition of the pilot SI joint opening to a larger post-prosthesis insertion SI joint opening.

In a preferred embodiment, a further initial step in the minimally-invasive SI joint stabilization methods of the invention comprises the step of providing an image capture apparatus configured and adapted to capture images of at least the subject's anatomical structure, including the dysfunctional SI joint and the anatomic structure proximate thereto, and the guide pin 400 and SI joint prostheses 70*a*, 70*b* during advancement toward and when disposed proximate to the dysfunctional SI joint.

In a preferred embodiment, the image capture apparatus comprises a CT system. However, according to the invention, further suitable image capture apparatus comprise a fluoroscopy system, radiography system, magnetic resonance imaging system, and an ultrasound system.

In a preferred embodiment, after the step of providing the image capture apparatus, and before the step of making an incision in and through tissue of the subject, a further step in the minimally-invasive SI joint stabilization methods comprises capturing images of the subject's anatomical structure with the image capture apparatus to properly align the patient on the surgical table. According to the invention, standard or classic lateral images via CT scans can be employed to ensure proper alignment, i.e., a true prone position, of the patient.

After the step of ensuring proper alignment of the patient, a further initial step in the minimally-invasive SI joint stabilization methods of the invention comprises determining key SI joint landmarks, e.g., dogleg, dorsal recess, etc., preferably, via CT scans, to establish at least a sagittal line, incision (or skin entry) site, and guide pin trajectory and, thereby, prosthesis trajectory into the dysfunctional SI joint.

Since the SI joint comprises a unique shape and does not align with the axis of the spine (i.e., the plane of the SI joint defined by the region between the sacrum and the ilium is not aligned with (or parallel with) the sagittal plane or anteroposterior axis of the spine), as discussed in detail below, in a preferred embodiment, modified anteroposterior (AP) views or images of at least the subject's dysfunctional SI joint, and the guide pin 400 and SI joint prostheses when deployed in the subject's body are acquired via CT scans.

As discussed above, advancement of the guide pin 400 into the dysfunctional SI joint is a critical step in the methods for stabilizing a dysfunctional SI joint. The guide pin 400 ensures (i) proper trajectory of the drill guides of the invention and creation of the pilot SI joint openings, e.g., pilot SI joint opening 100, (ii) proper trajectory of the prosthesis deployment assemblies 600*a*, 600*b* and, hence, SI joint prostheses 70*a*, 70*b* engaged thereto to and into the pilot SI joint openings and, thereby, accurate and optimal placement of the SI joint prostheses 70*a*, 70*b* in the dysfunctional SI joint.

In a preferred embodiment, during the step of advancing the guide pin 400 into the dysfunctional SI joint, a further step in the minimally-invasive SI joint stabilization methods thus comprises capturing images of the guide pin 400 with the image capture apparatus to ensure proper trajectory and placement of the guide pin 400 proximate the dysfunctional SI joint.

As indicated above, since the SI joint comprises a unique shape and does not align with the axis of the spine, in a preferred embodiment, a series modified (or angled) anteroposterior (AP) images of the guide pin 400 and dysfunctional SI joint (and, if necessary, surrounding structures) during advancement of the guide pin 400 toward and, particularly, when disposed proximate to and in the dysfunctional SI joint are preferably acquired via CT scans to ensure proper trajectory and placement of the guide pin 400 proximate the dysfunctional SI joint.

Referring first to FIG. 17A there is shown a conventional AP view image of a dysfunctional SI joint. As illustrated in FIG. 17A the SI joints (denoted "$SIJ_1$" and "$SIJ_2$"), including the dysfunctional SI joint on the left side ("$SIJ_2$"), are represented by multiple non-linear lines, which reflect mis-alignment of the imaged SI joints ("$SIJ_1$" and "$SIJ_2$"). The mis-alignment of the imaged SI joints ("$SIJ_1$" and "$SIJ_2$") in the conventional AP view image makes properly aligning the guide pin 400 in a SI joint, i.e., "$SIJ_1$" or "$SIJ_2$", very difficult. Indeed, one must guess the advancement trajectory of the guide pin 400.

Referring now to FIG. 17B, there is shown a CT scan image showing a modified AP view of the left, i.e., dysfunctional, SI joint ("$SIJ_2$"). As illustrated in FIG. 17B, the dysfunctional SI joint ("$SIJ_2$") is now shown and, hence, represented by a substantially straight line indicating substantial alignment of the imaged dysfunctional SI joint ("$SIJ_2$").

The modified AP view of the dysfunctional SI joint ("$SIJ_2$") shown in FIG. 17B facilitates accurate advancement, trajectory, and positioning of the guide pin 400 in the dysfunctional SI joint ("$SIJ_2$"), as shown in the tangent lateral and trajectory inlet views shown in FIGS. 17C and 17D, respectively.

As indicated above, in a preferred embodiment, the guide pin 400 is advanced into the dysfunctional SI joint to, but no further than, the alar boundary (denoted "AB" in FIGS. 1A, 17C and 17E).

A CT scan image showing a tangent lateral view of the dysfunctional SI joint ("$SIJ_2$") also facilitates accurate advancement and, hence, depth of the guide pin 400 in the dysfunctional SI joint ("$SIJ_2$"), as shown in FIG. 17C.

In a preferred embodiment, during the step of advancing the SI joint prosthesis into the pilot SI joint opening with the prosthesis deployment assemblies 600*a*, 600*b*, a further step in the minimally-invasive SI joint stabilization methods comprises capturing images of the SI joint prosthesis with the image capture apparatus to ensure proper placement of the SI joint prostheses 70*a*, 70*b* in the dysfunctional SI joint.

In a preferred embodiment, CT scan images showing lateral views of the drill guide assemblies 500*a*, 500*b*, 500*c*, 500*d* and 500*e* and the prosthesis deployment assemblies 600*a*, 600*b* during advancement of the drill guide assemblies 500*a*, 500*b*, 500*c*, 500*d* and 500*e* and prosthesis deployment assemblies 600*a*, 600*b* toward and, particularly, when disposed proximate to the dysfunctional SI joint are acquired to ensure proper trajectory of the drill guide assemblies 500*a*, 500*b*, 500*c*, 500*d* and 500*e* and the prosthesis deployment assemblies 600*a*, 600*b*, such as shown in FIGS. 17F, 17G, and 17H.

In a preferred embodiment, CT scan images showing modified AP and/or trajectory inlet views of the SI joint prosthesis and dysfunctional SI joint (and, if necessary, surrounding structures) during advancement of the SI joint prostheses 70*a*, 70*b* toward and, particularly, when disposed proximate to and in the dysfunctional SI joint are also acquired to ensure proper trajectory and placement of the SI joint prosthesis in the dysfunctional SI joint, such as shown in FIGS. 17I, 17J, 18A, and 18B.

In some embodiments, after the step of creating the pilot SI joint opening with the drill guide assemblies 500*a*, 500*b*, 500*c*, 500*d* and 500*e*, the methods for stabilizing a dysfunctional SI joint further comprise the step of harvesting the dislodged bone material, e.g., cortical bone, trabecular bone, and bone marrow, with one of the aforediscussed bone harvesting assemblies for subsequent use in a biologically active composition of the invention and thereafter delivery to the SI joint prostheses 70*a*, 70*b*.

EXAMPLES

The following example is provided to enable those skilled in the art to more clearly understand and practice the present invention. The example should not be considered as limiting the scope of the invention, but merely as being illustrated as representative thereof.

An adult male, age 42 presented with a traumatic injury proximate the SI joint, resulting in a dysfunctional SI joint and significant pain associated therewith, i.e., a visual analog pain score (VAS) of approximately 8.0.

CT scans were initially performed to determine the full extent of the patient's injury, check for any SI joint abnormalities, and plan the SI joint stabilization procedure, including determining the incision site, guide pin trajectory, and SI joint prosthesis required to stabilize the dysfunctional SI joint.

Before proceeding with the SI joint stabilization procedure, CT scans were also performed to ensure proper alignment of the patient on the surgical table.

The SI joint stabilization procedure was performed in accord with the method that includes the drill guide assembly 500*e* summarized above. The specifics of the procedure were as follows:

SI Joint Prosthesis

The SI joint prothesis selected and, hence, provided for the stabilization procedure comprised SI joint prosthesis 70*a* illustrated in FIGS. 10A and 10B and described in detail above. The SI joint prosthesis 70*a* comprised a length of 30 mm and the elongated partially cylindrical sections, i.e., barrels, of the SI joint prosthesis 70*a* comprised a diameter of 7.5 mm. The SI joint prosthesis 70*a* was sourced from Applicant, i.e., Tenon Medical, Inc., and referred to as a CATAMARAN® SIJ Fixation System.

The SI joint prosthesis 70*a* included an autograft bone material, which was placed in the barrels of the SI joint prosthesis 70*a* after the prosthesis was implanted in the dysfunctional SI joint.

Inferior Posterior Prosthesis Trajectory

The initial incision was placed along the lateral lip of the posterior third of the iliac crest to the posterior superior spine, which provided a prosthesis entry point into the dysfunctional SI joint through the posterior ligaments at approximately the S3 level. The trajectory of the SI joint prosthesis was toward the mid-point of the S1 end plate and the sacral promontory.

Creation of Pilot SI Joint Opening

The pilot SI joint opening was created with the drill guide assembly 500*e* illustrated in FIGS. 7A-7L, and described above.

The pilot SI joint opening, which was similar to pilot SI joint opening 200 described above, was created by drilling a first opening in the sacrum bone structure and a second opening in the ilium bone structure with the drill guide assembly 500*e*.

After the first opening in the sacrum bone structure and second opening in the ilium bone structure were created with the drill guide assembly 500*e*, the dislodged bone material, i.e., autograft bone material, was harvested with the bone collection assembly illustrated in FIGS. 14A-14I.

Radiological Assessment

CT scan images of the patient's SI joint six (6) months after the SI joint stabilization procedure reflected (i) secure and proper placement of the SI joint prosthesis in the SI joint, (ii) substantial solid bridging of osseous tissue, and, hence, bone across the SI joint and, (iii) substantial ossification around the SI joint prosthesis.

Post-Procedure SI Joint Pain Relief and Function

After a recovery period of fourteen (14) days, the patient reported that the pain had been substantially reduced.

The patient was also subjected to a series of post procedure tests to determine the stability of the SI joint and mobility of the musculoskeletal structures of the pelvic and lumbar regions proximate the SI joint. The results were very favorable. The patient tested positive to the flexion abduction and external rotation (FABER) test. The patient also responded very favorably to Gaenslen, thigh thrust, compression, and distraction tests.

The tests thus confirmed that the post procedure SI joint was stabilized and that the musculoskeletal structures of the pelvic and lumbar regions proximate thereto were restored to a near normal level.

As will readily be appreciated by one having ordinary skill in the art, the present invention provides numerous advantages compared to prior art systems and methods for stabilizing dysfunctional SI joints. Among the advantages are the following:

- the provision of improved minimally-invasive SI joint stabilization systems and apparatus, and methods of using same, which facilitate posterior trajectory placement of SI joint prostheses in dysfunctional SI joints and, thereby, effective stabilization of the dysfunctional SI joints;
- the provision of improved minimally-invasive SI joint stabilization systems, which, when employed to stabilize dysfunctional SI joints, disrupt less tissue and muscles, and avoid nerves and large blood vessels;
- the provision of improved minimally-invasive SI joint stabilization systems and apparatus, including prostheses, which, when employed to stabilize dysfunctional SI joints, effectively ameliorate pain associated with SI joint dysfunction;
- the provision of improved minimally-invasive SI joint stabilization systems comprising drill guide assemblies adapted to create pilot openings in dysfunctional SI joints for placement of SI joint prostheses therein via a minimal incision, i.e., an incision length no greater than 3.0 cm;
- the provision of improved minimally-invasive SI joint stabilization systems comprising drill guide assemblies adapted to create pilot openings in dysfunctional SI joints for placement of SI joint prostheses therein, which provide optimal direct visualization of the bone dislodging member thereof and the pilot opening during and after creation of the pilot openings;
- the provision of improved minimally-invasive SI joint stabilization systems comprising drill guide assemblies adapted to receive and guide and, thereby, provide consistent, optimal placement of SI joint prostheses into dysfunctional SI joints;
- the provision of improved minimally-invasive SI joint stabilization systems comprising drill guide assemblies adapted to create pilot openings in dysfunctional SI joints for placement of SI joint prostheses therein, which provide consistent, optimal arthrodesis of the dysfunctional SI joint after placement of a SI joint prosthesis in the pilot openings;
- the provision of improved minimally-invasive SI joint stabilization systems comprising a bone harvesting assembly adapted to harvest, i.e., retract and collect, bone material, i.e., autograft bone material, directly from a drill bit after creation of SI joint pilot openings (and portions thereof) for subsequent formation of an osteogenic composition and/or direct delivery to SI joint prostheses; and
- the provision of improved SI joint prostheses that can readily be employed in minimally-invasive SI joint stabilization systems, which facilitate remodeling of damaged osseous tissue and regeneration of new osseous tissue and osseous tissue structures.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A system for stabilizing a dysfunctional sacroiliac (SI) joint, said dysfunctional SI joint comprising a sacrum bone structure and an ilium bone structure, said system comprising:

a tool assembly and a SI joint prosthesis, said tool assembly comprising a drill guide assembly adapted to create a pilot SI joint opening in said dysfunctional SI joint, said pilot SI joint opening comprising a sacrum pilot opening portion in said sacrum bone structure and an ilium pilot opening portion in said ilium bone structure, said drill guide assembly comprising a guide pin, a drill guide, a drill guide insert, a bone dislodging member and a drill alignment pin, said drill guide comprising a first proximal end, a first distal end, an internal access opening and a plurality of Kirschner (K)-wire lumens, said internal access opening and said plurality of K-wire lumens extending from said first proximal end of said drill guide to said first distal end of said drill guide, said internal access opening of said drill guide sized and configured to receive said drill guide insert and said SI joint prosthesis therein, said plurality of K-wire lumens sized and configured to receive a plurality of K-wires therein, said drill guide insert comprising a second proximal end, a second distal end, a drill guide medial lumen, a first drill guide insert lumen and a second drill guide insert lumen, said drill guide medial lumen, said first drill guide insert lumen and said second drill guide insert lumen extending from said second proximal end of said drill guide insert to said second distal end of said drill guide insert, said drill guide medial lumen sized and configured to receive said guide pin therein, said first drill guide insert lumen and said second drill guide insert lumen sized and configured to receive said bone dislodging member and said drill alignment pin therein, said bone dislodging member adapted to dislodge bone and create said pilot SI joint opening in said dysfunctional SI joint, said guide pin comprising an elongated graduated rod structure, said elongated rod structure comprising a third proximal end, a third distal end, a mid-region disposed between said third proximal end and said third distal end, and a plurality of spaced detectable markings that extend from said third distal end of said elongated rod structure to at least said mid-region of said elongated rod structure, said guide pin configured and adapted to be advanced into said dysfunctional SI joint and, when said advanced into said dysfunctional SI joint, guide said drill guide assembly to said dysfunctional SI joint and position said drill guide assembly during creation of said pilot SI joint opening by said drill guide assembly, said drill alignment pin comprising an elongated cylindrical-shaped guide member, said elongated guide member comprising a fourth proximal end, a blunt distal end and a handle that is in communication with the fourth proximal end, said drill alignment pin sized and configured to be advanced into said first drill guide insert lumen, said second drill guide insert lumen of said drill guide lumen and said pilot SI joint opening in said dysfunctional SI joint created by said bone dislodging member, said drill alignment pin further configured and adapted to stabilize said drill guide assembly during said creation of said pilot SI joint opening by said drill guide assembly when said drill guide insert is received in said drill guide, said drill alignment pin is said advanced into said first drill guide insert lumen or said second drill guide insert lumen of said drill guide insert and advanced into said pilot SI joint opening created by said bone dislodging member, said drill guide assembly adapted to be said positioned and first stabilized during said creation of said pilot SI joint opening in said dysfunctional SI joint by said drill guide assembly when said guide pin is advanced into said dysfunctional SI joint, said drill guide insert is received in said drill guide, said guide pin is received in said drill guide medial lumen of said drill guide insert, said drill guide is guided to said dysfunctional SI joint by said guide pin and disposed proximate said dysfunctional SI joint, and a plurality of K-wires is received in and extends through said plurality of K-wire lumens in said drill guide and engages said dysfunctional SI joint, said drill guide assembly further adapted to be said positioned and second stabilized during said creation of said pilot SI joint opening in said dysfunctional SI joint by said drill guide assembly when said guide pin is said advanced into said dysfunctional SI joint, said drill guide insert is said received in said drill guide, said guide pin is said received in said drill guide medial lumen of said drill guide insert, said drill guide is said guided to said dysfunctional SI joint by said guide pin and said disposed proximate said dysfunctional SI joint, said plurality of K-wires is said received in and extends through said plurality of K-wire lumens in said drill guide and said engages said dysfunctional SI joint, and said drill alignment pin is said advanced in said first drill guide insert lumen or said second drill guide lumen of said drill guide insert and advanced into said sacrum pilot opening portion or said ilium pilot opening portion of said pilot SI joint opening in said dysfunctional SI joint said created by said bone dislodging member, said SI joint prosthesis comprising a single, solid, non-bonded, indivisible member comprising a first elongated region, a second elongated region and a bridge region disposed between said first elongated region and said second elongated region, said first elongated region comprising a first length, said second elongated region comprising a second length and said bridge region comprising a third length, said third length of said bridge region being greater than 50% of said first length of said first elongated region and greater than 50% of said second length of said second elongated region, said SI joint prosthesis sized and configured to be received in said internal access opening of said drill guide and advanced into said sacrum pilot opening in said sacrum bone structure and said ilium pilot opening in said ilium bone structure prior created by said drill guide assembly.

2. The system of claim 1, wherein said detectable markings of said guide pin are detectable and readable by a conventional image capture apparatus.

3. The system of claim 1, wherein said first elongated region of said SI joint prosthesis comprises a first internal lumen and said second elongated region of said SI joint prosthesis comprises a second internal lumen, said first internal lumen of said first elongated region comprises a first internal threaded region, said second internal lumen of said second elongated region comprises a second internal threaded region.

4. The system of claim 3, wherein said first internal lumen of said first elongated region and said second internal lumen of said second elongated region are adapted to receive an osteogenic composition therein.

5. The system of claim 4, wherein said first elongated region of said SI joint prosthesis further comprises a first plurality of slots in communication with said first internal lumen of said first elongated region, said first plurality of slots sized and configured to allow said osteogenic composition, when disposed in said first internal lumen, to be dispersed out of said first internal lumen, into and through said first plurality of slots and delivered to said dysfunctional SI joint when said SI joint prosthesis is advanced into said pilot SI joint opening in said dysfunctional SI joint.

6. The system of claim 5, wherein said second elongated region further comprises a second plurality of slots in communication with said second internal lumen of said second elongated region, said second plurality of slots sized and configured to allow said osteogenic composition, when disposed in said second internal lumen, to be dispersed out of said second internal lumen, into and through said second plurality of slots and delivered to said dysfunctional SI joint when said SI joint prosthesis is said advanced into said pilot SI joint opening in said dysfunctional SI joint.

7. The system of claim 4, wherein said osteogenic composition comprises a bone-based material selected from the group consisting of a demineralized bone matrix, an autograft bone material, an allograft bone material, and a xenograft bone material.

8. The system of claim 4, wherein said osteogenic composition comprises a bone morphogenic protein (BMP) selected from the group consisting of BMP-1, BMP2a, BMP2b, BMP3, BMP4, BMP5, BMP6, BMP7, and BMP8a.

9. The system of claim 1, wherein said tool assembly further comprises a bone harvester assembly adapted to extract and collect dislodged bone material from said bone dislodging member during creation of said pilot SI joint opening in said dysfunctional SI joint.

* * * * *